US009963711B2

(12) United States Patent
Cogan et al.

(10) Patent No.: US 9,963,711 B2
(45) Date of Patent: May 8, 2018

(54) FAD2 PERFORMANCE LOCI AND CORRESPONDING TARGET SITE SPECIFIC BINDING PROTEINS CAPABLE OF INDUCING TARGETED BREAKS

(71) Applicants: Dow AgroSciences LLC, Indianapolis, IN (US); Sangamo BioSciences, Inc., Richmond, CA (US)

(72) Inventors: Noel Cogan, Macleod (AU); John Forster, Diamond Creek (AU); Matthew Hayden, Templestowe (AU); Tim Sawbridge, Coburg (AU); German Spangenberg, Bundoora (AU); Steven R. Webb, Westfield, IN (US); Manju Gupta, Carmel, IN (US); William Michael Ainley, Carmel, IN (US); Matthew J. Henry, Indianapolis, IN (US); Jeffrey C. Miller, Richmond, CA (US); Dmitry Y. Guschin, Richmond, CA (US)

(73) Assignees: Sangamo Therapeutics, Inc., Richmond, CA (US); Dow AgroSciences LLC, Indianapolis, IN (US)

( * ) Notice: Subject to any disclaimer, the term of this patent is extended or adjusted under 35 U.S.C. 154(b) by 714 days.

(21) Appl. No.: 14/019,244

(22) Filed: Sep. 5, 2013

(65) Prior Publication Data

US 2014/0090112 A1 Mar. 27, 2014

Related U.S. Application Data

(60) Provisional application No. 61/697,886, filed on Sep. 7, 2012.

(51) Int. Cl.

| | |
|---|---|
| ***C12N 15/82*** | (2006.01) |
| ***C12N 15/66*** | (2006.01) |
| ***C12N 9/22*** | (2006.01) |
| ***C12N 15/10*** | (2006.01) |
| ***C12N 15/90*** | (2006.01) |
| ***C07K 14/47*** | (2006.01) |

(52) U.S. Cl.

CPC ...... *C12N 15/8216* (2013.01); *C07K 14/4702* (2013.01); *C12N 9/22* (2013.01); *C12N 15/102* (2013.01); *C12N 15/66* (2013.01); *C12N 15/822* (2013.01); *C12N 15/8247* (2013.01); *C12N 15/902* (2013.01); *C12Y 301/00* (2013.01); *C07K 2319/81* (2013.01)

(58) Field of Classification Search

None

See application file for complete search history.

(56) References Cited

U.S. PATENT DOCUMENTS

| | | | |
|---|---|---|---|
| 4,769,061 | A | 9/1988 | Comai |
| 4,810,648 | A | 3/1989 | Stalker |
| 4,940,835 | A | 7/1990 | Fraley et al. |
| 5,789,538 | A | 8/1998 | Rebar et al. |
| 5,925,523 | A | 7/1999 | Dove et al. |
| 6,007,988 | A | 12/1999 | Choo et al. |
| 6,013,453 | A | 1/2000 | Choo et al. |
| 6,140,081 | A | 10/2000 | Barbas |
| 6,200,759 | B1 | 3/2001 | Dove et al. |
| 6,242,568 | B1 | 6/2001 | Barbas et al. |
| 6,453,242 | B1 | 9/2002 | Eisenberg et al. |
| 6,479,626 | B1 | 11/2002 | Kim et al. |
| 6,534,261 | B1 | 3/2003 | Cox et al. |
| 6,599,692 | B1 | 6/2003 | Case et al. |
| 6,689,558 | B2 | 2/2004 | Case |
| 6,794,136 | B1 | 9/2004 | Eisenberg et al. |
| 6,903,185 | B2 | 6/2005 | Kim et al. |
| 7,030,215 | B2 | 4/2006 | Liu et al. |
| 7,067,317 | B2 | 6/2006 | Rebar et al. |
| 7,070,934 | B2 | 7/2006 | Cox, III et al. |
| 7,153,949 | B2 | 12/2006 | Kim et al. |
| 7,253,273 | B2 | 8/2007 | Collingwood |
| 7,262,054 | B2 | 8/2007 | Jamieson et al. |
| 7,361,635 | B2 | 4/2008 | Miller et al. |
| 8,420,782 | B2 | 4/2013 | Bonas et al. |
| 8,440,431 | B2 | 5/2013 | Voytas et al. |
| 2003/0232410 | A1 | 12/2003 | Liljedahl et al. |
| 2005/0026157 | A1 | 2/2005 | Baltimore et al. |
| 2005/0064474 | A1 | 3/2005 | Holmes et al. |
| 2005/0208489 | A1 | 9/2005 | Carroll et al. |
| 2005/0267061 | A1 | 12/2005 | Martin |
| 2006/0188987 | A1 | 8/2006 | Guschin et al. |
| 2007/0059795 | A1 | 3/2007 | Moore et al. |

(Continued)

FOREIGN PATENT DOCUMENTS

| | | |
|---|---|---|
| EP | 0 242 246 | 11/1992 |
| EP | 1806398 A1 | 7/2007 |

(Continued)

OTHER PUBLICATIONS

Okuley et al 1994 (The Plant Cell, 6: p. 147-158.*
Ainley et al., "Trait Stacking Via Targeted Genome Editing," *Plant Biotechnol. J.* 11(9):1126-1134 (2013).
ATCC 39256.
ATCC 53435.
ATCC 67441.
ATCC 67442.
Beerli et al., Toward Controlling Gene Expression at Will: Specific Regulation of the ERBB-2/HER-2 Promoter by Using Polydactyl Zinc Finger Proteins Constructed From Modular Building Blocks, *PNAS USA* 95(25):14628-14633 (1998).
Beerli et al., "Engineering Polydactyl Zinc-Finger Transcription Factors," *Nature Biotechnol.* 20:135-141(2002).

(Continued)

*Primary Examiner* — Matthew R Keogh
(74) *Attorney, Agent, or Firm* — Dahna S. Pasternak; Pasternak Patent Law

(57) ABSTRACT

A method of gene editing or gene stacking within a FAD2 loci by cleaving, in a site directed manner, a location in a FAD2 gene in a cell, to generate a break in the FAD2 gene and then ligating into the break a nucleic acid molecule associated with one or more traits of interest is disclosed.

5 Claims, 25 Drawing Sheets

(56) References Cited

U.S. PATENT DOCUMENTS

| | | | | |
|---|---|---|---|---|
| 2007/0134796 | A1 | 6/2007 | Holmes et al. | |
| 2007/0218528 | A1 | 9/2007 | Miller | |
| 2008/0131962 | A1 | 6/2008 | Miller | |
| 2008/0168586 | A1 * | 7/2008 | Laga .................. | C12N 15/8247 800/306 |
| 2008/0182332 | A1 | 7/2008 | Cai | |
| 2009/0111119 | A1 | 4/2009 | Doyon et al. | |
| 2009/0117617 | A1 | 5/2009 | Holmes et al. | |
| 2009/0205083 | A1 | 8/2009 | Gupta et al. | |
| 2009/0263900 | A1 | 10/2009 | DeKelver et al. | |
| 2010/0047805 | A1 | 2/2010 | Wang | |
| 2010/0199389 | A1 | 8/2010 | Butler et al. | |
| 2011/0041195 | A1 | 2/2011 | Doyon | |
| 2011/0123509 | A1 | 5/2011 | Jantz et al. | |
| 2011/0145940 | A1 | 6/2011 | Voytas et al. | |
| 2011/0159541 | A1 | 6/2011 | Collingwood et al. | |
| 2011/0167521 | A1 * | 7/2011 | DeKelver .......... | C12N 15/8216 800/298 |
| 2011/0189775 | A1 | 8/2011 | Ainley et al. | |
| 2011/0201055 | A1 | 8/2011 | Doyon et al. | |
| 2011/0207221 | A1 | 8/2011 | Cost et al. | |
| 2011/0239315 | A1 | 9/2011 | Bonas et al. | |
| 2011/0281361 | A1 | 11/2011 | DeKelver et al. | |
| 2011/0293785 | A1 | 12/2011 | Franklin et al. | |
| 2011/0301073 | A1 | 12/2011 | Gregory et al. | |
| 2012/0102587 | A1 | 4/2012 | Anai | |
| 2013/0326645 | A1 | 12/2013 | Cost et al. | |

FOREIGN PATENT DOCUMENTS

| | | | |
|---|---|---|---|
| EP | 1862551 | A1 | 12/2007 |
| GB | 2338237 | | 8/1998 |
| WO | WO 93/19181 | | 9/1993 |
| WO | WO 95/19431 | | 7/1995 |
| WO | WO 96/06166 | | 7/1995 |
| WO | WO 96/30517 | | 2/1996 |
| WO | WO 98/53057 | | 8/1998 |
| WO | WO 98/53058 | | 11/1998 |
| WO | WO 98/53059 | | 11/1998 |
| WO | WO 98/53060 | | 11/1998 |
| WO | WO 98/54311 | | 11/1998 |
| WO | 98/56239 | A1 | 12/1998 |
| WO | WO 00/27878 | | 12/1998 |
| WO | WO 01/60970 | | 8/2001 |
| WO | WO 01/88197 | | 11/2001 |
| WO | WO 02/016536 | | 2/2002 |
| WO | WO 02/077227 | | 10/2002 |
| WO | WO 02/099084 | | 12/2002 |
| WO | WO 03/016496 | | 2/2003 |
| WO | 2003080802 | A2 | 10/2003 |
| WO | 2004/072259 | A2 | 8/2004 |
| WO | WO 05/012515 | | 2/2005 |
| WO | 2005028630 | A2 | 3/2005 |
| WO | WO 05/107437 | | 11/2005 |
| WO | 2006/079567 | A2 | 8/2006 |
| WO | WO 07/014275 | | 2/2007 |
| WO | WO 07/053482 | | 5/2007 |
| WO | 2008/084107 | A1 | 7/2008 |
| WO | 2011005998 | A1 | 1/2011 |
| WO | 2011049627 | A1 | 4/2011 |
| WO | 2011146121 | A1 | 11/2011 |
| WO | 2014039702 | A2 | 3/2014 |
| WO | 2014141147 | A1 | 9/2014 |

OTHER PUBLICATIONS

Bibikova et al., "Stimulation of Gomologous Recombination Through Targeted Cleavage by Chimeric Nucleases," *Mol. Cell. Biol.* 21(1):289-297 (2001).

Bibikova et al., "Enhancing Gene Targeting With Designed Zinc Finger Nucleases," *Science* 300(5620):764 (2003).

Bitinate et al., "Foki Dimerization is Required for DNA Cleavage," *PNAS USA* 95:10570-10575 (1998).

Bonas et al., "Genetic and Structural Characterization of the Avirulence Gene AVRBS3 From Xanthomonas Campestris PV. Vesicatori"*Mol. Gen. Genet.* 218:127-136 (1989).

Cai et al., Targeted Transgene Integration in Plant Cells Using Designed Zinc Finger Nucleases, *Plant Mol. Biol.* 69(6):699-709 (2009).

Choo et al., Advances in Zinc Finger Engineering, *Curr. Opin. Struct. Biol.* 10:411-416 (2000).

Curtin et al., "Targeted Mutagenesis of Duplicated Genes in Soybean With Zinc-Finger Nucleases," *Plant Physiology* 156:466-473 (2011).

D'Halluin et al., "Homologous Recombination: A Basis for Targeted Genome Optimization in Crop Species Such as Maize," *Plant Biotechnology Journal* 6(1):93-102 (2008).

DeGreef et al., "Evaluation of Herbicide Resistance in Transgenic Crops Under Field Conditions," *Nat Biotechnology* 7:61-64 (1989).

Doyon et al., "Heritable Targeted Gene Disruption in Zebrafish Using Designed Zinc-Finger Nucleases," *Nat. Biotechnol.* 26:702-708 (2008).

Elliott et al., "Isolation and Characterization of Fruit Vacuolar Invertase Genes From Two Tomato Species and Temporal Differences in MRNA Levels During Fruit Ripening," *Plant Molec. Biol.* 21:515-524 (1993).

Fisher et al., Starch Branching Enzyme II From Maize Endosperm , *Plant Physiol.* 102:1045-1046 (1993).

Geiser et al., "The Hypervariable Region in the Genes Coding for Entomopathogenic Crystal Proteins of Bacillus Thuringiensis: Nucleotide Sequence of the KURHD1 Gene of Subsp. Kurstaki HD1," *Gene* 48:109-118 (1986).

Guerts et al., Knockout Rats Via Embryo Microinjection of Zinc-Finger Nucleases, *Science* 325(5939):433 (2009).

Haft et al., "A Guild of 45 CRISPR-Associated (CAS) Protein Families and Multiple CRISPR/CAS Subtypes Exist in Prokaryotic Genomes," *PLoS Comput. Biol.* 1:e60 (2005) <http://www.jcvi.org/cms/nc/publications/listing/browse/3/article//Haft/#sthash.bXXP6pOi.dpuf>.

Hayes et al., "Molecular Cloning and Heterologous Expression of a CDNA Encoding a Mouse Glutathione S-Transferase YC Subunit Possessing High Catalytic Activity for Aflatoxin B1-8,9-Epdxide," *Biochem. J.* 285:173-180 (1992).

Heuer et al., "Repeat Domain Diversity of AVRBS3-Like Genes in *Ralstonia solanacearum* Strains and Association With Host Preferences in the Field," *Appl. and Envir. Micro.* 73(13):4379-4384 (2007)

Isalan et al., "A Rapid, Generally Applicable Method to Engineer Zinc Fingers Illustrated by Targeting the HIV-1 Promoter," *Nature Biotechnol.* 19:656-660 (2001).

Jansen et al., "Identification of Genes That Are Associated With DNA Repeats in Prokaryotes," *Mol. Microbiol.* 43:1565-1575 (2002).

Jones et al., "Isolation of the Tomato CF-9 Gene for Resistance to Cladosporium Fulvum by Transposon Tagging," *Science* 266:789-793 (1994).

Kay et al., "A Bacterial Effector Acts as a Plant Transcription Factor and Induces a Cell Size Regulator," *Science* 318:648-651 (2007).

Kim et al., "Chimeric Restriction Enzyme:GAL4 Fusion to FOKL Cleavage Domain," *J. Biol. Chem.* 379:489-495 (1998).

Kim et al., "Getting a Handhold on DNA: Design of Poly-Zinc Finger Proteins With Femtomolar Dissociation Constants," *PNAS USA* 95:2812-2817 (1998).

Kim et al., "Design of TATA Box-Binding Proteinyzinc Finger Fusions for Targeted Regulation of Gene Expression," *PNAS* 94:3616-3620 (1997).

Kim et al., "Site-Specific Cleavage of DNA-RNA Hybrids by Zinc Finger/Foki Cleavage Domain Fusions," *Gene* 203:43-49 (1997).

Kim et al., "Construction of a Z-DNA-Specific Restriction Endonuclease," *PNAS* 94:12875-12879 (1997).

Kim et al., "Hybrid Restriction Enzymes: Zinc Finger Fusions to Fok I Cleavage Domain," *PNAS* 93:1156-1160 (1996).

Kim et al., "Chimeric Restriction Endonuclease," *PNAS* 91:883-887 (1994).

(56) References Cited

OTHER PUBLICATIONS

Knutson et al., "Modification of *Brassica* Seed Oil by Antisense Expression of a Stearoyl-Acyl Carrier Protein Desaturase Gene," *Proc. Natl. Acad. Sci. U.S.A.*, 89:2624-2628 (1992).
Kumar et al., "Controlling Transgene Integration in Plants," *Trends Plant Sci.* 6:155-159 (2001).
Le et al., "Simultaneous Generation and Germline Transmission of Multiple Gene Mutations in Rat Using CRISPR-CAS Systems," *Nature Biotechnology* 31:684-686 (2013).
Lee et al., "The Molecular Basis of Sulfonylurea Herbicide Resistance in Tobacco," *EMBO J.* 7(5):1241 (1988)
Liu et al., "Design of Polydactyl Zinc-Finger Proteins for Unique Addressing Within Complex Genomes," *PNAS USA* 94:5525-5530 (1997).
Makarova et al., "A Putative RNA-Interference-Based Immune System Inprokaryotes: Computational Analysis of the Predicted Enzymatic Machinery, Functional Analogies With Eukaryotic RNAI, and Hypothetical Mechanisms of Action," *Biol. Direct.* 1:7 (2006).
Makarova et al., "A DNA Repair System Specific for the Thermophilic Archaea and Bacteria Predicted by Genomic Context Analysis," *Nucleic Acids Res.* 30:482-496 (2002).
Mani et al., "Binding of Two Zinc Finger Nuclease Monomers to Two Specific Sites is Required for Effective Double-Strand DNA Cleavage," *Biochem. Biophys. Res. Commun.* 334:1191-1197 (2005).
Marshall et al., "Allelic Mutations in Acetyl-Coenzyme a Carboxylase Confer Herbicide Tolerance in Maize," *Theor. Appl. Genet.* 83:435-442 (1992).
Martin et al., "Map-Based Cloning of a Protein Kinase Gene Conferring Disease Resistance to Tomato," *Science* 262:1432-1436 (1993).
Miki et al., "Transformation of *Brassica napus* Canola Cultivars With *Arabidopsis thaliana* Acetohydroxyacid Synthase Genes and Analysis of Herbicide Resistance," *Theor. Appl. Genet.* 80:449 (1990).
Mindrinos et al., "The *A. thaliana* Disease Resistance Gene RPS2 Encodes a Protein Containing a Nucleotide-Binding Site and Leucine-Rich Repeats," *Cell* 78:1089 (1994).
Moehle et al., "Targeted Gene Addition Into a Specified Location in the Human Genome Using Designed Zinc Finger Nucleases," *Proc. Natl. Acad. Sci. USA* 104(9):3055-3060 (2007).
Nekrasov et al., "Targeted Mutagenesis in the Model Plant *Nicotiana benthamiana* Using CAS9 RNA-Guided Endonuclease," *Nature Biotechnology* 31:691-693 (2013).
Pabo et al., "Design and Selection of Novel CYS2HIS2 Zincfinger Proteins," *Ann. Rev. Biochem* 70:313-340 (2001).
Paszkowski et al., "Gene Targeting in Plants," *EMBO J.* 7:4021-4026 (1988).
Pen et al., "Production of Active Bacillus Licheniformis Alpha-Amylase in Tobacco and Its Application in Starch Liquefaction," *BioTechnology* 10:292 (1992).
Przibilla et al., "Site-Specific Mutagenesis of the D1 Subunit of Photosystem II in Wild-Type Chlamydomona," Plant Cell 3:169-174 (1991).
Puchta et al., "Homologous Recombination in Plant Cells is Enhanced by in Vivo Induction of Double Strand Breaks Into DNA by a Site-Specific Endonuclease," *Nucleic Acid Research* 21:5034-5040 (1993).
Raboy et al., "A Survey of Maize Kernel Mutants for Variation in Phytic Acid," *Maydica* 35:383-390 (1990).
Roberts et al., "Rebase: Restriction Enzymes and Methyltransferases," *Nucleic Acids Res.* 31:418-420 (2003).
Scheffler et al., "Desaturase Multigene Duplication Families of *Brassica napus* Arose Through Genome Duplicatiom," *TAG* 94(5):583-591 (1997).
Schierholt et al., "Mapping a High Oleic Acid Mutation in Winter Oilseed Rape (*Brassica napus* L.)" *TAG* 101(5-6):897-901 (2000).
Schierholt et al., "Inheritance of High Oleic Acid Mutations in Winter Oilseed Rape (*Brassica napus* L.)" *Crop Sci.* 41:1444-1449 (2001).
Schornack et al., "Gene-For-Gene-Mediated Recognition of Nuclear-Targeted AVRBS3-Like Bacterial Effector Proteins," *J. Plant Physiol.* 163(30:256-272 (2006).
Segal, "Custom DNA-Binding Proteins Come of Age: Polydactyl Zinc-Finger Proteins," *Curr. Opin. Biotechnol.* 12:632-637 (2001).
Shan et al., "Targeted Genome Modification of Crop Plants Using a CRISPR-CAS System," *Nature Biotechnology* 31:686-680 (2013).
Shiroza et al., "Sequence Analysis of the *Streptococcus* Mutans Fructosyltransferase Gene and Flanking Regions," *J. Bacteriol.* 170(21:810-816 (1988).
Shukla et al., "Precise Genome Modification in the Crop Species *Zea mays* Using Zinc-Finger Nucleases," *Nature* 459:437-441 (2009).
Siebert et at., "Efficient Repair of Genomic Double-Strand Breaks by Homologous Recombination Between Directly Repeated Sequences in the Plant Genome," *Plant Cell* 14:1121-1131 (2002).
Smith et al., "A Detailed Study of the Substrate Specificity of a Chimeric Restriction Enzyme," *Nucleic Acids Res.* 27:674-681 (1999).
Smith et al., "Requirements for Double-Strand Cleavage by Chimeric Restriction Enzymes With Zinc Finger DNA-Recognition Domains," *Nucleic Acids Res.* 28:3361-3369 (2000).
Sogaard et al., "Site-Directed Mutagenesis of Histidine 93, Aspartic Acid 180, Glutamic Acid 205, Hisitidine 290, and Aspartic Acid 291 at the Active Site and Tryptophan 279 at the Raw Starch Binding Site in Barley A-Amylase 1," *J. Biol. Chem.* 268:22480 (1993).
Steinmetz et al., "The DNA Sequence of the Gene for the Secreted *Bacillus subtilis* Enzyme Levansucrase and Its Genetic Control Sites," *Mol. Gen. Genet.* 20:220 (1985).
Tanhuanpaa et al., "Mapping and Cloning of FAD2 Gene to Develop Allele-Specific PCR for Oleic Acid in Spring Turnip Rape (*Brassica rapa* SSP. *oleifera* ),"*Mol. Breed.* 4:543-550 (1998).
Terada et al., "Efficient Gene Targeting by Homologous Recombination in Rice," *Nat. Biotechnol.* 20(10):1030 (2002).
Terada et al., "Gene Targeting by Homologous Recombinationas a Biotechnological Tool for Rice Functional Genomics," *Plant Physiol.* 144(2):846 (2007).
Umov et al., "Genome Editing With Engineered Zinc Finger Nucleases," *Nature Reviews* 11:636-546(2010).
Umov et al., "Highly Efficient Endogenous Human Gene Correction Using Designed Zinc-Finger Nucleases," *Nature* 435:646-651 (2005).
Van Hartingsveldt et al., "Cloning, Characterization and Overexpression of the Phytase-Encoding Gene (PHYA) of Aspergillus Niger," *Gene* 127:87-94 (1993).
Wah et al., "Structure of Foki Has Implications for DNA Cleavage," *PNAS USA* 95:10564-10569 (1998).
Wu et al., "Custom-Designed Zinc Finger Nucleases: What Is Next?," *Cell. Mol. Life Sci.* 64:2933-2944 (2007).
Yang et al., "Identification of FAD2 and FAD3 Genes in *Brassica napus* Genome and Development of Allele-Specific Markers for High Oleic and Low Linolenic Acid Contents," *Theory App. Genet.* 125:715-729 (2012).
Wang, et al., "Application of Zinc Finger Nucleases in Genome Targeting Modification," Chinese Journal of Biochemistry and Molecular Biology 25:(7):585-589 (English translation of Abstract only).
Alt, et al., "Phenotypic and Molecular Analysis of Oleate Content in the Mutant Soybean Line M23," Crop Science: A Journal Serving the International Community of Crop Scientists, Crop Science Society of America 45(5):1997-2000 (2005).
Buhr, et al., "Ribozyme Termination of RNA Transcripts Down-Regulate Seed Fatty Acid Genes in Transgenic Soybean," The Plant Journal 30(2):155-163 (2002)
Curtin, et al., "Text S1 Supplemental Methods Hairy Root Transformation of Soybean Cotyledons," Plant Physiology (2011) http://plantphysiol.org/content/suppl/2011/04.04/pp.111.172981.dc2/172981supplemental_methods.pdf.

(56) References Cited

OTHER PUBLICATIONS

Dierking, et al., "New Sources of Soybean Seed Meal and Oil Composition Traits Identified Through Tilling," BMC Plant Biology 9(1):89 (2009).

Heppard, "Developmental and Growth Temperature Regulation of Two Different Microsomal Omega-6 Desaturase Genes in Soybeans," Plant Physiology 110(1):311-319 (1996).

Pham, et al., "Mutant Alleles of FAD2-1A and FAD2-1B Combine to Produce Soybeans With the High Oleic Seed Oil Trait," BMC Plant Biology 10(1)195 (2010).

Sandhu, et al., "Enhanced Oleic Acid Content in the Soybean Mutant M23 is Associated With the Deletion in the FAD2-LA Gene Encoding a Fatty Acid Desaturase," Journal of the American Oil Chemists Society 84(3):229-235 (2007).

Jinek, et al., "A Programmable Dual-RNA-Guided DNA Endonuclease in Adaptive Bacterial Immunity," Science 337:816-821 (2012).

Barkley, et al., "A Real-Time PCR Genotyping Assay to Detect FAD2A SNPS in Peanuts (Arachis Hypogaea L.)", Electronic Journal of Biotechnology 14(1) ISSN:0717-3458 (2001).

* cited by examiner

FIG1A

| | | |
|---|---|---|
| | | 1 40 |
| FAD2-3 (SEQ ID NO:8) | (1) | ATGGGTGCAGGTGGAAGAATGCAAGTGTCTCCTCCCTCCA |
| FAD2A (SEQ ID NO:5) | (1) | ATGGGTGCAGGTGGAAGAATGCAAGTGTCTCCTCCCTCCA |
| FAD2-2 (SEQ ID NO:7) | (1) | ATGGGCGCAGGTGGAAGAATGCAAGTCTCTCCTCCCTCCA |
| FAD2-1 (SEQ ID NO:6) | (1) | ATGGGTGCAGGTGGAAGAATGCAAGTCTCTCCTCCCTCCA |
| | | 41 80 |
| FAD2-3 (SEQ ID NO:8) | (41) | AGAAGTCTGAAACCGACACCATCAAGCGCGTACCCTGCGA |
| FAD2A (SEQ ID NO:5) | (41) | AAAAGTCTGAAACCGACAACATCAAGCGCGTACCCTGCGA |
| FAD2-2 (SEQ ID NO:7) | (41) | GCTGCCCCGAAACCAAAACCCTCAAACGCGTGCCCTGCGA |
| FAD2-1 (SEQ ID NO:6) | (41) | GCTGCCCCGGAACCAACACCCTCAAACGCGTGCCCTGCGA |
| | | 81 120 |
| FAD2-3 (SEQ ID NO:8) | (81) | GACACCGCCCTTCACTGTCGGAGAACTCAAGAAAGCAATC |
| FAD2A (SEQ ID NO:5) | (81) | GACACCGCCCTTCACTGTCGGAGAACTCAAGAAAGCAATC |
| FAD2-2 (SEQ ID NO:7) | (81) | GACACCACCCTTCACTCTCGGAGAGCTCAAGAAAGCAATC |
| FAD2-1 (SEQ ID NO:6) | (81) | GACACCACCATTCACTCTCGGAGAGCTCAAGAAAGCAATC |
| | | 121 160 |
| FAD2-3 (SEQ ID NO:8) | (121) | CCACCGCACTGTTTCAAACGCTCGATCCCTCGCTCTTTCT |
| FAD2A (SEQ ID NO:5) | (121) | CCACCGCACTGTTTCAAACGCTCGATCCCTCGCTCTTTCT |
| FAD2-2 (SEQ ID NO:7) | (121) | CCACCTCACTGCTTCAAACGCTCCATCCCTCGCTCCTTCT |
| FAD2-1 (SEQ ID NO:6) | (121) | CCACCTCACTGCTTCAAACGCTCCATCCCACGCTCCTTCT |
| | | 161 200 |
| FAD2-3 (SEQ ID NO:8) | (161) | CCTACCTCATCTGGCACAT--CATCATAGCCTCCTGCTTC |
| FAD2A (SEQ ID NO:5) | (161) | CCTACCTCATCTGGCACAT--CATCATAGCCTCCTGCTTC |
| FAD2-2 (SEQ ID NO:7) | (161) | CCTACCTCCTCTTCGACAT--CCTCGTCTCCTCCTCCCTC |
| FAD2-1 (SEQ ID NO:6) | (161) | CCT-CTTCGACATCATCATCTCCTCCTCGGCTCCTCCCTC |
| | | 201 240 |
| FAD2-3 (SEQ ID NO:8) | (199) | TACTACGTGGCCACCACTTACTTCCCTCTCCTCCCTCACC |
| FAD2A (SEQ ID NO:5) | (199) | TACTACGTGGCCACCACTTACTTCCCTCTCCTCCCTCACC |
| FAD2-2 (SEQ ID NO:7) | (199) | TACCACCTCTCCACAGCCTACTTCCCTCTCCTCCCCCACC |
| FAD2-1 (SEQ ID NO:6) | (200) | TACCACCTCTCCACAGCCTACTTCCCTCTCC--------- |

FIG 1B

```
                                 241                                    280
FAD2-3 (SEQ ID NO:8)    (239)   CTCTCTCCTACTTCGCCTGGCCTCTCTACTGGGCCTGCCA
FAD2A (SEQ ID NO:5)     (239)   CTCTCTCCTACTTCGCCTGGCCTCTCTACTGGGCCTGCCA
FAD2-2 (SEQ ID NO:7)    (239)   CTCTCCCTTACCTCGCCTGGCCCCTCTACTGGGCCTGCCA
FAD2-1 (SEQ ID NO:6)    (231)   ------CTTACCTCGCCTGACCCCTCTACTGGGCCTGCCA
                                 281                                    320
FAD2-3 (SEQ ID NO:8)    (279)   AGGGTGCGTCCTAACCGGCGTCTGGGTCATAGCCCACGAG
FAD2A (SEQ ID NO:5)     (279)   GGGCTGCGTCCTAACCGGCGTCTGGGTCATAGCCCACGAG
FAD2-2 (SEQ ID NO:7)    (279)   AGGCTGCGTCCTAACGGGCCTCTGGGTCATCGCCCACGAA
FAD2-1 (SEQ ID NO:6)    (265)   AGGCTGCGTCCTAACGGGCCTCTGGGTCATAGCCCACGAG
                                 321                                    360
FAD2-3 (SEQ ID NO:8)    (319)   TGCGGCCACCACGCCTTCAGCGACTACCAGTGGCTTGACG
FAD2A (SEQ ID NO:5)     (319)   TGCGGCCACCACGCCTTCAGCGACTACCAGTGGCTGGACG
FAD2-2 (SEQ ID NO:7)    (319)   TGCGGCCACCACGCCTTCAGCGACCACCAGTGGCTGGACG
FAD2-1 (SEQ ID NO:6)    (305)   TGCGGCCACCACGCCTTCAGCGACCACCAGTGGCTGGACG
                                 361                                    400
FAD2-3 (SEQ ID NO:8)    (359)   ACACCGTCGGTCTCATCTTCCACTCCTTCCTCCTCGTCCC
FAD2A (SEQ ID NO:5)     (359)   ACACCGTCGGCCTCATCTTCCACTCCTTCCTCCTCGTCCC
FAD2-2 (SEQ ID NO:7)    (359)   ACGCCGTGGGCCTCGTCTTCCACTCCTTCCTCCTCGTCCC
FAD2-1 (SEQ ID NO:6)    (345)   ACGCCGCCGGCCTCGTCTTCCACTCCTTCCTCCTCGTCCC
                                 401                                    440
FAD2-3 (SEQ ID NO:8)    (399)   TTACTTCTCCTGGAAGTACAGTCATCGACGCCACCATTCC
FAD2A (SEQ ID NO:5)     (399)   TTACTTCTCCTGGAAGTACAGTCATCGACGCCACCATTCC
FAD2-2 (SEQ ID NO:7)    (399)   TTACTTCTCCTGGAAGTACAGCCATCGACGCCACCATTCC
FAD2-1 (SEQ ID NO:6)    (385)   GTACTTCTCCTGGAAGTACATCCAT-GACGCCACCATTCC
                                 441                                    480
FAD2-3 (SEQ ID NO:8)    (439)   AACACTGGCTCCCTCGAGAGAGACGAAGTGTTTGTCCCCA
FAD2A (SEQ ID NO:5)     (439)   AACACTGGCTCCCTCGAGAGAGACGAAGTGTTTGTCGCCA
FAD2-2 (SEQ ID NO:7)    (439)   AACACCGGATCCCTCGAGAGGGATGAAGTGTTCGTCCCCA
FAD2-1 (SEQ ID NO:6)    (424)   AACAGCGGATCCCTCGATAGGGACGAAGTGTTCGTCCCCA
```

FIG1C

| | | 481 520 |
|---|---|---|
| FAD2-3 (SEQ ID NO:8) | (479) | AGAAGAAGTCAGACATCAAGTGGTACGGCAAGTACCTCAA |
| FAD2A (SEQ ID NO:5) | (479) | AGAAGAAGTCAGACATCAAGTGGTACGGCAAGTACCTCAA |
| FAD2-2 (SEQ ID NO:7) | (479) | AGAAGAAATCGGACATCAAGTGGTACGGAAAGTACCTCAA |
| FAD2-1 (SEQ ID NO:6) | (464) | AGAAGAAATCGGACATCAAGTGGTACGGCAAGTACCTCAA |
| | | 521 560 |
| FAD2-3 (SEQ ID NO:8) | (519) | CAACCCTTTGGGACGCACCGTGATGTTAACGGTTCAGTTC |
| FAD2A (SEQ ID NO:5) | (519) | CAACCCTTTGGCACCCACCGTGATGTTAACGGTTCAGTTC |
| FAD2-2 (SEQ ID NO:7) | (519) | CAACCCGCTAGGACGCACGGTGATGCTAACCGTCCAGTTC |
| FAD2-1 (SEQ ID NO:6) | (504) | CAACCCGCTAGGACGCACGGTGATGCTAACCGTCCAGTTC |
| | | 561 600 |
| FAD2-3 (SEQ ID NO:8) | (559) | ACTCTCGGCTGGCCGTTGTACTTAGCCTTCAACGTCTCGG |
| FAD2A (SEQ ID NO:5) | (559) | ACTCTCGGCTGGCCTTTGTACTTAGCCTTCAACGTCTCGG |
| FAD2-2 (SEQ ID NO:7) | (559) | ACGCTCGGCTGGCCGTTGTACTTAGCCTTCAACGTCTCTG |
| FAD2-1 (SEQ ID NO:6) | (544) | AAGCTCGGCTGGCCGTTGTACTTAGCCTTCAACGTCTCGG |
| | | 601 640 |
| FAD2-3 (SEQ ID NO:8) | (599) | GAAGACCTTACGACGGCGGCTTCGCTTGCCATTTCCACCC |
| FAD2A (SEQ ID NO:5) | (599) | GGAGACCTTACGACGGCGGCTTCGCTTGCCATTTCCACCC |
| FAD2-2 (SEQ ID NO:7) | (599) | GAAGACCTTACAGCGACGGTTTCGCTTGCCATTTCCACCC |
| FAD2-1 (SEQ ID NO:6) | (584) | GAAGACCTTACAGCGACGGTTTCGCTTGCCATTTCCACCC |
| | | 641 680 |
| FAD2-3 (SEQ ID NO:8) | (639) | CAACGCTCCCATCTACAACGACCGCGAGCGTCTCCAGATA |
| FAD2A (SEQ ID NO:5) | (639) | CAACGCTCCCATCTACAACGACCGTGAGCGTCTCCAGATA |
| FAD2-2 (SEQ ID NO:7) | (639) | GAACGCTCCCATCTACAACGACCGCGAGCGTCTCCAGATA |
| FAD2-1 (SEQ ID NO:6) | (624) | GAACGCTCCCATCTACAACGACCGCGAGCGTCTCCAGATA |
| | | 681 720 |
| FAD2-3 (SEQ ID NO:8) | (679) | TACATCTCCGACGCTGGCATCCTCGCCGTCTGCTACGGTC |
| FAD2A (SEQ ID NO:5) | (679) | TACATCTCCGACGCTGGCATCCTCGCCGTCTGCTACGGTC |
| FAD2-2 (SEQ ID NO:7) | (679) | TACATCTCTGACGCTGGCGTCCTCTCCGTATGTTACGGTC |
| FAD2-1 (SEQ ID NO:6) | (664) | TACATCTCTGACGCTGGCGTCCTCTCCGTATGTTACGGTC |

```
FIG1D                              721                                    760
FAD2-3 (SEQ ID NO:8)    (719)  TCTTCCGTTACGCCGCCGCGCAGGGAGTGGCCTCGATGGT
 FAD2A (SEQ ID NO:5)    (719)  TCTACCGCTACGCTGCTGTCCAAGGAGTTGCCTCGATGGT
FAD2-2 (SEQ ID NO:7)    (719)  TCTACCGCTACGCTGGTTCGCGAGGAGTGGCCTCGATGGT
FAD2-1 (SEQ ID NO:6)    (704)  TCTACCGTTACGCTGCTTCGCGAGGAGTAGCCTCTGTGGT
                               761                                    800
FAD2-3 (SEQ ID NO:8)    (759)  CTGCTTCTACGGAGTCCCGCTTCTGATTGTCAATGGTTTC
 FAD2A (SEQ ID NO:5)    (759)  CTGCTTCTACGGAGTTCCTCTTCTGATTGTCAACGGGTTC
FAD2-2 (SEQ ID NO:7)    (759)  CTGTGTCTACGGAGTTCCGCTTATGATTGTCAACTGTTTC
FAD2-1 (SEQ ID NO:6)    (744)  CTGTGTCTACGGAGTTCCGCTTCTAATTGTCAACTGTTTC
                               801                                    840
FAD2-3 (SEQ ID NO:8)    (799)  CTCGTGTTGATCACTTACTTGCAGCACACGCATCCTTCCC
 FAD2A (SEQ ID NO:5)    (799)  TTAGTTTTGATCACTTACTTGCAGCACACGCATCCTTCCC
FAD2-2 (SEQ ID NO:7)    (799)  CTCGTCTTGATCACTTACTTGCAGCACACGCACCCTTCGC
FAD2-1 (SEQ ID NO:6)    (784)  CTCGTCTTGATCACTTACTTGCAGCACACGCACCCTTCGC
                               841                                    880
FAD2-3 (SEQ ID NO:8)    (839)  TGCCTCACTACGATTCGTCCGAGTGGGATTGGTTGAGGGG
 FAD2A (SEQ ID NO:5)    (839)  TGCCTCACTATGACTCGTCTGAGTGGGATTGGTTGAGGGG
FAD2-2 (SEQ ID NO:7)    (839)  TGCCTCACTATGATTCTTCGGAGTGGGATTGGTTGAGAGG
FAD2-1 (SEQ ID NO:6)    (824)  TGCCTCACTATGATTCTTCCGAGTGGGATTGGTTGAGAGG

FAD2-3 (SEQ ID NO:8)    (879)  AGCTTTGGCTACCGTTGACAGAGACTACGGAATCTTGAAC
 FAD2A (SEQ ID NO:5)    (879)  AGCTTTGGCCACCGTTGACAGAGACTACGGAATCTTGAAC
FAD2-2 (SEQ ID NO:7)    (879)  AGCTTTGGCTACTGTGGATAGAGACTATGGAATCTTGAAC
FAD2-1 (SEQ ID NO:6)    (864)  AGCTTTGGCTACTGTGGATAGAGACTATGGAATCTTGAAC
                               921                                    960
FAD2-3 (SEQ ID NO:8)    (919)  AAGGTCTTGCACAATATTACCGACACCCACGTGGCGCATC
 FAD2A (SEQ ID NO:5)    (919)  AAGGTCTTCCACAATATCACGGACACCCACGTGGCGCATC
FAD2-2 (SEQ ID NO:7)    (919)  AAGGTGTTTCATAACATCACGGACACGCACGTGGCGCATC
FAD2-1 (SEQ ID NO:6)    (904)  AAGGTGTTCCATAACATCACGGACACGCACGTGGCGCATC
```

FIG1E

```
                                 961                                     1000
FAD2-3 (SEQ ID NO:8)    (959)   ATCTGTTCTCCACGATGCCGCATTATCACGCGATGGAAGC
 FAD2A (SEQ ID NO:5)    (959)   ACCTGTTCTCGACCATGCCGCATTATCACGCGATGGAAGC
FAD2-2 (SEQ ID NO:7)    (959)   ATCTGTTCTCGACGATGCCGCATTATAACGCGATGGAAGC
FAD2-1 (SEQ ID NO:6)    (944)   ATCTGTTCTCGACGATGCCGCATTATAACGCGATGGAAGC
                                 1001                                    1040
FAD2-3 (SEQ ID NO:8)    (999)   TACCAAGGCGATAAAGCCGATACTG-GGAGAGTATTATCA
 FAD2A (SEQ ID NO:5)    (999)   TACGAAGGCGATAAAGCCGATACTG-GGAGAGTATTATCA
FAD2-2 (SEQ ID NO:7)    (999)   GACCAAGGCGATAAAGCCGATACTT-GGAGAGTATTACCA
FAD2-1 (SEQ ID NO:6)    (984)   GACCAAGGCGATAAAGCCGATACTTTGGAGAGTATTACCA
                                 1041                                    1080
FAD2-3 (SEQ ID NO:8)   (1038)   GTTCGATGGGACGCCGGTGGTTAAGGCGATGTGGACGGAG
 FAD2A (SEQ ID NO:5)   (1038)   GTTCGATGGGACGCCGGTGGTTAAGGCGATGTGGACGGAG
FAD2-2 (SEQ ID NO:7)   (1038)   GTTTGATGGAACGCCGGTGGTTAAGGCGATGTGGACGGAG
FAD2-1 (SEQ ID NO:6)   (1024)   GTTTGATGGAACGCCGGCGGTTAAGGCGATGTGGACGGAG
                                 1081                                    1120
FAD2-3 (SEQ ID NO:8)   (1078)   GCGAAGGAGTGTATCTATGTGGAACCGGACAGGCAAGGTG
 FAD2A (SEQ ID NO:5)   (1078)   GCGAAGGAGTGTATCTATGTGGAACCGGACAGGCAAGGTG
FAD2-2 (SEQ ID NO:7)   (1078)   GCGAAGGAGTGTATCTATGTTGAACCGGATAGGCAAGGTG
FAD2-1 (SEQ ID NO:6)   (1064)   GCGAAGGAGTGTATCTATGTTGAACCGGATAGGCAAGGTG
                                 1121                                    1160
FAD2-3 (SEQ ID NO:8)   (1118)   AGAAGAAAGGTGTGTTCTGG--------------------
 FAD2A (SEQ ID NO:5)   (1118)   AGAAGAAAGGTGTGTTCTGGTACAACAATAAGTTATCTTG
FAD2-2 (SEQ ID NO:7)   (1118)   AGAAGAAAGGTGTGTTCTGGTACAACAATAAGTTATGAGG
FAD2-1 (SEQ ID NO:6)   (1104)   AGAAGAAAGGTGTGTTCTGGTACAACAATAA---------
                                 1161
FAD2-3 (SEQ ID NO:8)   (1138)   ----
 FAD2A (SEQ ID NO:5)   (1158)   CTAA
FAD2-2 (SEQ ID NO:7)   (1158)   ATGA
FAD2-1 (SEQ ID NO:6)   (1135)   ----
```

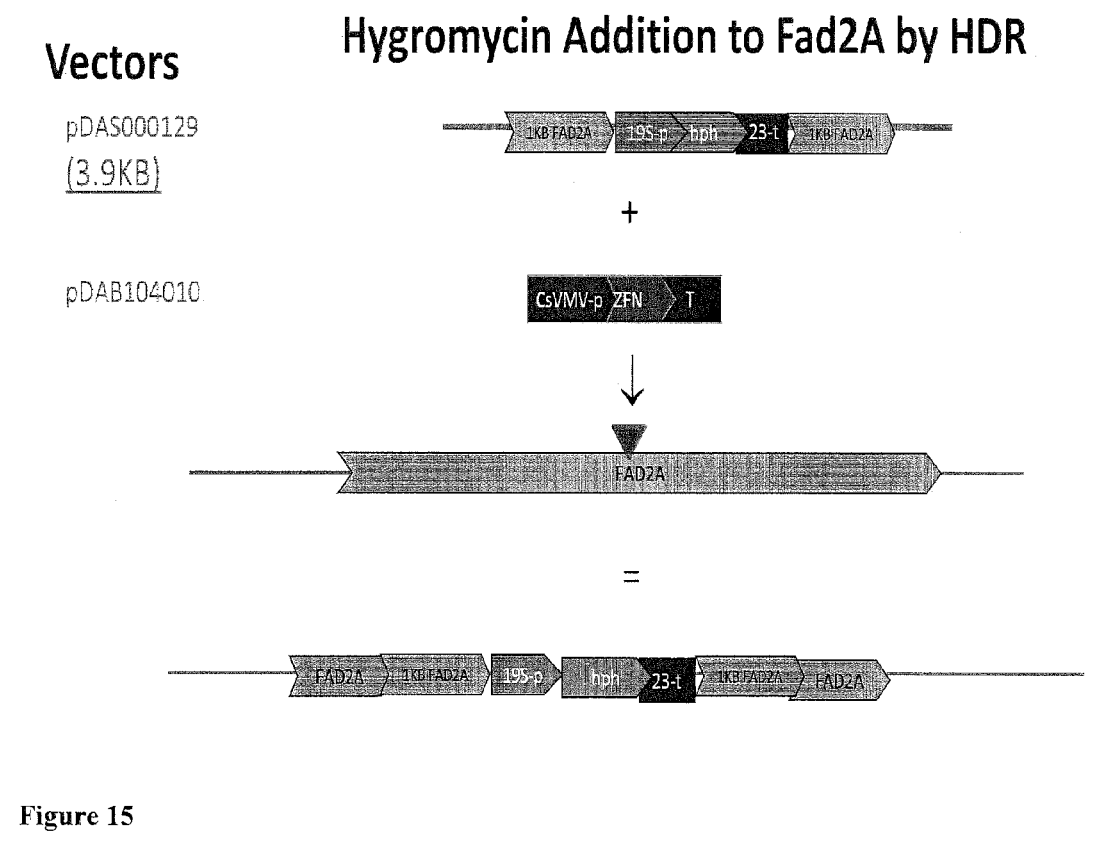

Vectors

Hygromycin Addition to Fad2A by HDR pDAS000129
(3.9KB)

1KB FAD2A | 19S-p | hph | 23-t | 1KB FAD2A

+ pDAB104010

CsVMV-p | ZFN | T

FAD2A

=

FAD2A | 1KB FAD2A | 19S-p | hph | 23-t | 1KB FAD2A | FAD2A

Figure 15

FAD2 PERFORMANCE LOCI AND CORRESPONDING TARGET SITE SPECIFIC BINDING PROTEINS CAPABLE OF INDUCING TARGETED BREAKS

CROSS-REFERENCE TO RELATED APPLICATIONS

The present application claims priority to the benefit of U.S. Provisional Patent Application No. 61/697,886, filed Sep. 7, 2012, the disclosure of which is hereby incorporated by reference in its entirety.

FIELD OF THE DISCLOSURE

The present disclosure relates generally to compositions and methods for use in recombinant plant technology (for example, for generating a transgenic plant). More specifically, the present disclosure relates to plant cells and plants including loci within their genomes that may be used for the site-specific introduction of any nucleic acid of interest.

BACKGROUND

Many plants are genetically transformed with exogenous nucleic acids (e.g., transgenes) to introduce desirable traits, for example, to improve agricultural value. Examples of improvements in agricultural value that can be achieved through genetic transformation include: improved nutritional quality, increased yield, pest or disease resistance, drought and stress tolerance, improved horticultural quality (e.g., improved pigmentation and/or growth), herbicide resistance, production of industrially useful compounds and/or materials from the plant, and/or production of pharmaceuticals. The introduction of cloned genes into plant cells and recovery of stable fertile transgenic plants can be used to make a genetic modification of a plant stable through multiple generations, and thereby allow the genetic engineering of a crop plant.

In methods for genetic transformation and transgenic plant production, exogenous DNA is typically randomly introduced into the nuclear or plastid DNA of a eukaryotic plant cell, followed by isolation of cells containing integrated exogenous DNA, and subsequent regeneration of a stably transformed plant. Transgenic plants were typically generated by *Agrobacterium*-mediated transformation technology. Successes with these techniques spurred the development of other methods to introduce a nucleic acid molecule of interest into the genome of a plant, such as PEG-mediated DNA uptake in protoplasts, microprojectile bombardment, and silicon whisker-mediated transformation.

In all of these plant transformation methods, however, the exogenous nucleic acids incorporated in the plant genome are integrated randomly in the genome of the plant cell, and in unpredictable copy number. Terada et al. (2002) *Nat Biotechnol* 20(10):1030; Terada et al. (2007) *Plant Physiol* 144(2):846; D'Halluin et al. (2008) *Plant Biotechnology J.* 6(1):93. For example, the transgenes are frequently integrated in the form of sequence repeats, either of the whole transgene or of parts thereof. Such a complex integration pattern commonly adversely impacts the expression level of the integrated nucleic acid (e.g., by destruction of transcribed RNA through post-transcriptional gene silencing mechanisms, or by inducing methylation of the integrated DNA). Also, the location of the integration site commonly influences the level of expression of the integrated nucleic acid. Moreover, the integration of the exogenous DNA may have a disruptive effect on the region of the genome where the integration occurs, and thereby influence or disturb the normal function of that target region to produce undesirable side-effects. The combination of factors including the foregoing results in a wide variation in the level of expression of transgene or exogenous DNA (and overall agronomic quality) between different transgenic plant cell and plant lines, even those created by the same methods. Because the integration is random, these effects are not able to be controlled by the practitioner while he or she attempts to produce a new plant with desirable characteristics.

The foregoing considerations necessitate that, whenever the effects of introducing a particular exogenous nucleic acid into a plant is investigated, a large number of transgenic plant lines must be generated and analyzed in order to obtain significant results. Likewise, in the generation of a transgenic plant containing a particular integrated nucleic acid so as to provide the transgenic plant with a desired phenotype, a large population of independently created transgenic plant lines must be created to allow the selection of a plant line with optimal expression of the nucleic acid, and with minimal or no side-effects on the overall phenotype and performance of the transgenic plant. These practical considerations take on added importance in transgenic plants created by inserting multiple exogenous nucleic acids (i.e., gene stacking). In such plants, phenomena such as post-transcriptional gene silencing may be amplified.

Several methods have been developed in an effort to control transgene insertion in plants. See, e.g., Kumar and Fladung (2001) Trends Plant Sci. 6:155-9. These methods rely on homologous recombination-based transgene integration, which has been successfully applied both in prokaryotes and lower eukaryotes. Paszkowski et al. (1988) EMBO J. 7:4021-6. However, until recently in plants, the predominant mechanism for transgene integration has been based on illegitimate recombination, which involves little homology between recombining DNA strands. A major challenge in this area is therefore the detection and selective generation of rare homologous recombination events, which are masked by far more efficient integration events via illegitimate recombination. Moreover, even if the selective generation and detection of targeted homologous recombination events is achieved, the event must be targeted to a desirable location in the host genome in order to realize the maximum benefit of this strategy.

For example, an assumed benefit of targeted genetic transformation is the reduction in event-to-event variability of transgene expression, as compared to transformation events that are obtained from random integration. A further assumed benefit is a significant reduction in the number of events required to screen introduced nucleic acids, sort transformation constructs, and produce events that contribute to desirable overall characteristics in the resulting transgenic plant. A critical factor required to realize these benefits is the identification of specific locations in the genome where transgene performance is consistent, and if possible, where adverse effects on the host plant are eliminated or minimized.

Recently, methods and compositions for targeted cleavage of genomic DNA have been described. Such targeted cleavage events can be used, for example, to induce targeted mutagenesis, induce targeted deletions of cellular DNA sequences, and facilitate targeted recombination and integration at a predetermined chromosomal locus. See, for example, Urnov et al. (2010) *Nature* 435(7042):646-51; United States Patent Publications 20030232410; 20050208489; 20050026157; 20050064474; 20060188987;

20090263900; 20090117617; 20100047805; 20110207221; 20110301073; 2011089775; 20110239315; 20110145940; and International Publication WO 2007/014275, the disclosures of which are incorporated by reference in their entireties for all purposes. Cleavage can occur through the use of specific nucleases such as engineered zinc finger nucleases (ZFN), transcription-activator like effector nucleases (TALENs), or using the CRISPR/Cas system with an engineered crRNA/tracr RNA ('single guide RNA') to guide specific cleavage. U.S. Patent Publication No. 20080182332 describes the use of non-canonical zinc finger nucleases (ZFNs) for targeted modification of plant genomes; U.S. Patent Publication No. 20090205083 describes ZFN-mediated targeted modification of a plant EPSPS locus; U.S. Patent Publication No. 20100199389 describes targeted modification of a plant Zp15 locus and U.S. Patent Publication No. 20110167521 describes targeted modification of plant genes involved in fatty acid biosynthesis. In addition, Moehle et al. (2007) *Proc. Natl. Acad, Sci. USA* 104(9): 3055-3060 describes using designed ZFNs for targeted gene addition at a specified locus. U.S. Patent Publication 20110041195 describes methods of making homozygous diploid organisms.

However, there remains a need for compositions and methods for modifying and/or modulating expression of FAD2 genes in plants, including generation of plants with targeted insertions of desired transgenes at the FAD2 locus.

BRIEF SUMMARY OF THE DISCLOSURE

The present disclosure describes compositions and methods for modulating expression of FAD2 genes (e.g., in plants, algae, and fungi) and the use of these loci as sites for the targeted integration of a nucleic acid sequence of interest (e.g., an exogenous nucleic acid sequence) into a host cell. In some embodiments, a host cell may contain one or more genomes with one or more FAD2 sequences (e.g., homeologues or paralogs), any or all of which may be selectively modified and/or disrupted. In specific examples, the present disclosure describes FAD2A, FAD2A', FAD2C and FAD2C' genes, as well as corresponding homeologues or paralogs, in *Brassica napus* (i.e., *B. napus* line, DH12075) and their use as loci for targeted integration of a nucleic acid sequence of interest. As described herein, though FAD2 genes are involved in fatty acid biosynthesis in the host, their modification or disruption (e.g., by integration of an exogenous nucleic acid in the FAD2 coding sequence) unexpectedly may have no or minimal adverse effects on the resultant host organism.

Also described herein is the use of one or more particular FAD2 loci in tandem with a polypeptide capable of effecting cleavage and/or integration of specific nucleic acid sequences within the FAD2 loci. Examples of the use of FAD2 loci in tandem with a polypeptide capable of effecting cleavage and/or integration of the FAD2 loci include a polypeptide selected from the group consisting of zinc finger proteins, meganucleases, TAL domains, TALENs, RNA-guided CRISPR-Cas9, recombinases, leucine zippers, CRISPr/Cas and others known to those in the art. Particular examples include a chimeric ("fusion") protein comprising a site-specific DNA binding domain polypeptide and cleavage domain polypeptide (e.g., a nuclease), such as a ZFN protein comprising a zinc-finger polypeptide and a FokI nuclease polypeptide. For example, described herein is a demonstration of the in vitro and in vivo efficacy and specificity of particular ZFNs designed to bind and induce double stranded breaks in FAD2A, FAD2A', FAD2C, FAD2C', and in combinations thereof without cleaving corresponding homeologues or paralogs. In some embodiments, particular FAD2 loci may be used with any of the foregoing polypeptides to effect site-specific integration of a nucleic acid of interest that is subsequently expressed in the host while having a minimal adverse impact on the agronomic performance of the host.

In certain aspects, described herein are polypeptides comprising a DNA-binding domain that specifically binds to a FAD2 gene. In some embodiments such a polypeptide may also comprise a nuclease (cleavage) domain or half-domain (e.g., a ZFN, a recombinase, a transposase, or a homing endonuclease, including a homing endonuclease with a modified DNA-binding domain, TAL domains, TALENs, RNA-guided CRISPR-Cas9), and/or a ligase domain, such that the polypeptide may induce a targeted double-stranded break, and/or facilitate recombination of a nucleic acid of interest at the site of the break. In particular embodiments, a DNA-binding domain that targets a FAD2 locus may be a DNA-cleaving functional domain. The foregoing polypeptides may be used in some embodiments to introduce an exogenous nucleic acid into the genome of a host organism (e.g., a plant or animal species) at one or more FAD2 loci. In certain embodiments, the DNA-binding domains comprise a zinc finger protein with one or more zinc fingers (e.g., 2, 3, 4, 5, 6, 7, 8, 9 or more zinc fingers), and can which is engineered (non-naturally occurring) to bind to any sequence within a FAD2 gene. Any of the zinc finger proteins described herein may bind to a target site within the coding sequence of the target gene or within adjacent sequences (e.g., promoter or other expression elements). In certain embodiments, the zinc finger protein binds to a target site in an FAD2 gene, for example, as shown in Table 5. The recognition helix regions of exemplary FAD2-binding zinc fingers are shown in Table 4. One or more of the component zinc finger binding domains of the zinc finger protein can be a canonical (C2H2) zinc finger or a non-canonical (e.g., C3H) zinc finger (e.g., the N-terminal and/or C-terminal zinc finger can be a non-canonical finger).

Also described herein are methods for disrupting or editing a FAD2 gene. Additionally described herein are genetically modified host organisms (e.g., transgenic plants) produced by methods according to embodiments of the invention. In particular examples, a transgenic organism produced by a method according to an embodiment of the invention may be, without limitation, algae, a fungus, a monocotyledonous plant, a dicotyledonous plant, etc.

The FAD2 genes disclosed herein may include those found in any plant, algae, or fungi that have one or more FAD2 genes.

The foregoing and other features will become more apparent from the following detailed description of several embodiments, which proceeds with reference to the accompanying figures.

BRIEF DESCRIPTION OF THE FIGURES

FIG. 1, panels A to E, show a sequence alignment of FAD2 gene sequences (SEQ ID NOs:5-8), generated using AlignX®.

FIG. 5, panels A and B, show ZFN targeting of FAD2 genes.

FIG. 15 shows a schematic for integration of pDAS000129 into the FAD2A locus.

SEQUENCES

Figure 2:
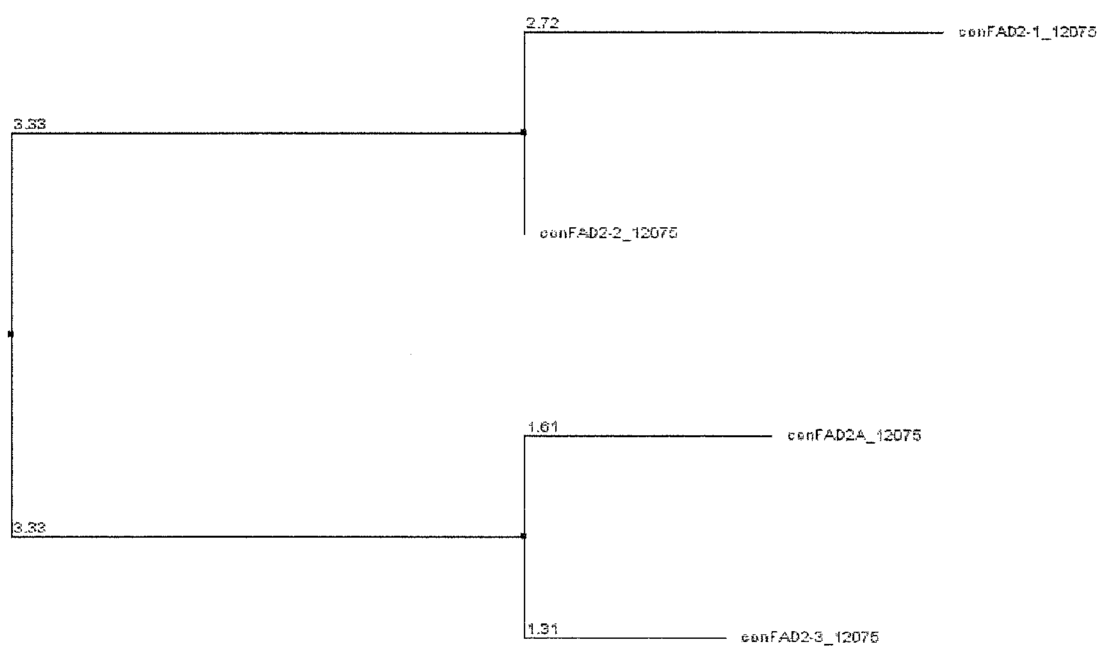
FIG. 2 is a schematic depicting a phylogenetic tree of FAD2 gene sequences generated using Jalview v 2.3 based on neighbor joining distances.

The nucleic acid sequences are shown using standard letter abbreviations for nucleotide bases, as defined in 37 C.F.R. § 1.822. Only one strand of each nucleic acid sequence is shown, but the complementary strand is understood to be included by any reference to the displayed strand.

DETAILED DESCRIPTION

I. Overview of Several Embodiments

Embodiments of the invention establish an approach for targeted integration of exogenous nucleic acids (e.g., transgenes) in a host genome without greatly adversely impacting other phenotypes of the host beyond those affected by the integrated nucleic acid. Some embodiments may be used for "stacking" multiple nucleic acids in a single host genome. Such an approach requires the development and deployment of four inter-connected technologies: targeting technologies allowing the introduction of double stranded breaks in specific genomic DNA locations (see, e.g., Puchta et al. (1993) Nucleic Acids Res. 21:5034-40; Siebert and Puchta (2002) Plant Cell 14:1121-31; D'Halluin et al. (2008) Plant Biotechnol. J. 6(1):93-102; Cai et al. (2009) Plant Mol. Biol. 69(6):699-709; Shukla et al. (2009) Nature 459(7245):437-41); Shan et al. (2103) Nature Biotechnol. 31:686-680; Le et al. (2013) Nature Biotechnol 31: 688-691; Nekrasov et al. (2013) Nature Biotechnol. 31:691-693, Ainely et al. (2013) Plant Biotechnol. J. (On Line 19 August); delivery technologies allowing the delivery of an optimized exogenous (donor) nucleic acid (Bibikova et al. (2003) Science 300(5620):764); integration technologies involving modification of the host genes (located either in the homologous recombination or NHEJ pathways) so as to increase the HDR or NHEJ frequencies for targeted donor DNA integration; analytical tools to enrich and characterize targeted integration events; and specific desired host genomic locations ("performance loci") that are genetically well-defined and that support stable gene expression across generations without greatly adversely affecting the transformed host organism. See, also, United States Patent Publications 20030232410; 20050208489; 20050026157; 20050064474; 20060188987; 20090263900; 20090117617; 20100047805; 20110207221; 20110301073; 2011089775; 20110239315; 20110145940; 20080182332; 20090205083; 20100199389; 20110167521. For example, in plants, a performance locus is a locus where the negative impact on the agronomic or quality properties of a transgenic plant wherein a transgene has been integrated at the locus is negligible or non-existent.

Embodiments described herein take advantage of the unexpected finding that plant FAD2 genes are performance loci for the targeted integration of exogenous nucleic acids (e.g., gene(s); non-coding DNA sequences, such as an Engineered Landing Pads (ELPs) (U.S. application Ser. No. 12/011,735) and Engineered Transgene Insertion Platform (ETIP) (U.S. Publication No. 20140090113); and plant transformation unit(s)). The ubiquitous nature of FAD2 loci in plants, and evidence that alteration or knock-out of FAD2 in canola, corn, sunflower, wheat, cotton, and soybean does not carry an agronomic or quality penalty, identifies FAD2 loci as a broad class of performance loci across commercially-relevant plant species.

Some embodiments utilize site-specific double-stranded DNA cleavage at a FAD2 locus, for example, resulting from the delivery and expression of a target-site specific DNA recognition and cleavage protein. In specific examples, such a FAD2-specific DNA recognition and cleavage protein may be, for example and without limitation, a ZFN; a TALEN; RNA-guided CRISPR-Cas9, a recombinase (e.g., Cre, Hin, RecA, Tre, and FLP recombinases); a meganuclease, and an engineered protein derived from any of the foregoing or their equivalents. Cleavage may also be effected using the CRISPR/Cas system with an engineered crRNA/tracr RNA ('single guide RNA') to guide specific cleavage. In some embodiments, such a double-strand break may be repaired via integration of a donor nucleic acid at the cleavage site within the FAD2 performance locus, for example, by Homology Directed Repair (HDR) or Non-Homologous End Joining (NHEJ).

This disclosure exemplifies the utility of FAD2 loci as performance loci, for example, by describing the FAD2A, 2A', 2C or 2C' locus in canola (*Brassica napus*), and corresponding FAD2-specific ZFNs that may be utilized to integrate an exogenous nucleic acid at the FAD2A, 2A', 2C or 2C' locus.

Embodiments of the present invention address many unsolved problems in the art. For example, the selectivity of the targeted integration approach described herein may reduce or eliminate the necessity of repeated field trials required for elimination of unwanted transgenic events, which trials are costly due to the resources involved and the burdensome regulatory requirements in this area. Furthermore, the targeted DNA integration approaches described herein may be particularly beneficial in the process of transgene stacking.

Although the native nucleotide sequence at an endogenous FAD2 locus may be used to directly target a nucleic acid of interest, in some embodiments, a nucleic acid may first be targeted to at least one FAD2 locus of the host, such that the integration of further nucleic acid molecules of interest into the host is facilitated. In other examples, nucleotide sequences that are not homologous to native sequences of the host organism (e.g., essentially randomly generated nucleic acid sequences) that flank a DNA recognition site (e.g., zinc finger recognition sites) may be utilized.

II. Terms

As used in this application, including the claims, terms in the singular and the singular forms, "a," "an," and "the," for example, include plural referents, unless the content clearly dictates otherwise. Thus, for example, a reference to "plant," "the plant," or "a plant" also refers to a plurality of plants. Furthermore, depending on the context, use of the term, "plant," may also refer to genetically-similar or identical progeny of that plant. Similarly, the term, "nucleic acid," may refer to many copies of a nucleic acid molecule. Likewise, the term, "probe," may refer to many similar or identical probe molecules.

Numeric ranges are inclusive of the numbers defining the range, and expressly include each integer and non-integer fraction within the defined range. Unless defined otherwise, all technical and scientific terms used herein have the same meaning as commonly understood by one of ordinary skill in the art.

In order to facilitate review of the various embodiments described in this disclosure, the following explanation of specific terms is provided:

Isolated: An "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component (e.g., a nucleic acid may be isolated from a chromosome by breaking chemical bonds connecting the nucleic acid to the remaining DNA in the chromosome). Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

Cross: As used herein in regard to plants, the term "cross" or "crossed" refers to the fusion of gametes via pollination to produce progeny (e.g., cells, seeds, and plants). This term encompasses both sexual crosses (i.e., the pollination of one plant by another) and selfing (i.e., self-pollination, for example, using pollen and ovule from the same plant).

Backcrossing: Backcrossing methods may be used to introduce a nucleic acid sequence into a plant. This technique has been widely used for decades to introduce new traits into plants. Jensen, N., Ed. *Plant Breeding Methodology*, John Wiley & Sons, Inc., 1988. In a typical backcross protocol, the original variety of interest (recurrent parent) is crossed to a second variety (non-recurrent parent) that carries a nucleic acid sequence of interest to be transferred. The resulting progeny from this cross are then crossed again to the recurrent parent, and the process is repeated until a plant is obtained wherein essentially all of the desired morphological and physiological characteristics of the recurrent plant are recovered in the converted plant, in addition to the transferred nucleic acid sequence from the non-recurrent parent.

Introgression: As used herein, the term "introgression" refers to the transmission of an allele (or modified allele comprising an exogenous nucleic acid) into a genetic background at a particular locus. In some embodiments, introgression of a specific allele at the locus may occur by transmitting the allele to at least one progeny via a sexual cross between two parents of the same species, where at least one of the parents has the specific allele form in its genome. Progeny comprising the specific allele may be repeatedly backcrossed to a line having a desired genetic background. Backcross progeny may be selected for the specific allele form, so as to produce a new variety wherein the specific allele form has been fixed in the genetic background. In some embodiments, introgression of a specific allele may occur by recombination between two donor genomes (e.g., in a fused protoplast), where at least one of the donor genomes has the specific allele form in its genome.

Introgression may involve transmission of a specific allele form that may be, for example and without limitation, a disrupted or modified allele; a transgene; a PTU; and an ELP.

Germplasm: As used herein, the term "germplasm" refers to genetic material of or from an individual plant, a group of plants (e.g., a plant line, variety, and family), and a clone derived from a plant or group of plants. A germplasm may be part of an organism or cell, or it may be separate (e.g., isolated) from the organism or cell. In general, germplasm provides genetic material with a specific molecular makeup that is the basis for hereditary qualities of the plant. As used herein, "germplasm" refers to cells of a specific plant; seed; tissue of the specific plant (e.g., tissue from which new plants may be grown); and non-seed parts of the specific plant (e.g., leaf, stem, pollen, and cells). As used herein, the term "germplasm" is synonymous with "genetic material," and it may be used to refer to seed (or other plant material) from which a plant may be propagated. A "germplasm bank" may refer to an organized collection of different seed or other genetic material (wherein each genotype is uniquely identified) from which a known cultivar may be cultivated, and from which a new cultivar may be generated.

Gene: As used herein, the term "gene" (or "genetic element") may refer to a heritable genomic DNA sequence with functional significance. A gene may be a native nucleic acid, or a nucleic acid that has been integrated into the genome. The term "gene" may also be used to refer to, for example and without limitation, a cDNA and/or an mRNA encoded by a heritable genomic DNA sequence.

Nucleic acid molecule: As used herein, the term "nucleic acid molecule" may refer to a polymeric form of nucleotides (i.e., ribonucleotides, deoxyribonucleotides, and/or a modified form of either of the foregoing). A "nucleic acid molecule" as used herein is synonymous with "nucleic acid" and "polynucleotide." The term includes both sense and anti-sense strands of RNA, cDNA, genomic DNA, and synthetic forms and mixed polymers thereof. The term includes any topological conformation, including single-stranded, double-stranded, partially duplexed, triplexed, hairpinned, circular, and padlocked conformations. A nucleic acid molecule can include either or both of naturally-occurring and modified nucleotides. Such nucleotides may be linked together by naturally-occurring and/or non-naturally-occurring nucleotide linkages.

Nucleic acid molecules may be modified chemically or biochemically, or may contain derivatized nucleotide bases, as will be readily appreciated by those of skill in the art. Such modifications include, for example and without limitation: labels; methylation; substitution of one or more of the naturally-occurring nucleotides with an analog; and internucleotide modifications (e.g., uncharged linkages, for example, methyl phosphonates, phosphotriesters, phosphoramidates, and carbamates; charged linkages, for example, phosphorothioates and phosphorodithioates; pendent moieties, for example, peptides; intercalators, for example, acridine and psoralen; chelators; alkylators; and modified linkages, for example, alpha anomeric nucleic acids).

Exogenous: An "exogenous" molecule is a molecule that is not native to a specified system (e.g., a germplasm, variety, elite variety, and/or plant) with respect to nucleotide sequence and/or genomic location (i.e., locus) for a polynucleotide (and with respect to amino acid sequence and/or cellular localization for a polypeptide). In embodiments, exogenous or heterologous polynucleotides or polypeptides may be molecules that have been artificially supplied to a biological system (e.g., a plant cell, a plant gene, a particular plant species or variety, and/or a plant chromosome) and are not native to that particular biological system. Thus, the designation of a nucleic acid as "exogenous" may indicate that the nucleic acid originated from a source other than a naturally-occurring source, or it may indicate that the nucleic acid has a non-natural configuration, genetic location, or arrangement of elements.

In contrast, for example, a "native" or "endogenous" nucleic acid is a nucleic acid (e.g., a gene) that does not contain a nucleic acid element other than those normally present in the chromosome or other genetic material on which the nucleic acid is normally found in nature. An endogenous gene transcript is encoded by a nucleotide sequence at its natural chromosomal locus, and is not artificially supplied to the cell.

Operably linked: A first nucleic acid sequence is operably linked with a second nucleic acid sequence when the first nucleic acid sequence is in a functional relationship with the second nucleic acid sequence. For instance, a promoter is operably linked with a coding sequence when the promoter affects the transcription or expression of the coding sequence. When recombinantly produced, operably linked nucleic acid sequences are generally contiguous and, where necessary to join two protein-coding regions, in the same reading frame. However, elements need not be contiguous to be operably linked.

Promoter: A promoter is a region of DNA that generally is located upstream (towards the 5' region) of a nucleic acid that enhances transcription of the nucleic acid. Promoters permit the proper activation or repression of the nucleic acid(s) with which they are operably linked. A promoter contains specific sequences that are recognized by transcription factors. These factors bind to the promoter DNA sequences and result in the recruitment of RNA polymerase, the enzyme that synthesizes the RNA from the coding region of the nucleic acid. Transformed: A vector "transforms" or "transduces" a cell when it transfers nucleic acid molecules into the cell. A cell is "transformed" by a nucleic acid molecule when the nucleic acid molecule becomes stably replicated by the cell, either by incorporation of the nucleic acid molecule into the cellular genome or by episomal replication. As used herein, the term "transformation" encompasses all techniques by which a nucleic acid molecule can be introduced into a cell. Examples include, but are not limited to: transfection with viral vectors; transformation with plasmid vectors; electroporation (Fromm et al. (1986) Nature 319:791-3); lipofection (Feigner et al. (1987) Proc. Natl. Acad. Sci. USA 84:7413-7); microinjection (Mueller et al. (1978) Cell 15:579-85); *Agrobacterium*-mediated transfer (Fraley et al. (1983) Proc. Natl. Acad. Sci. USA 80:4803-7); direct DNA uptake; and microprojectile bombardment (Klein et al. (1987) Nature 327:70).

Introduced: As used herein, the term "introduced," when referring to translocation of an exogenous nucleic acid into a cell, refers to the incorporation of the nucleic acid into the cell using any methodology available in the art. This term encompasses nucleic acid introduction methods including, for example and without limitation, transfection; transformation; and transduction.

Transgene: As used herein, the term "transgene" refers to an exogenous nucleic acid coding sequence of interest. For example, a transgene may encode an industrially or pharmaceutically useful compound, or an expression product that contributes to a desirable agricultural trait (e.g., herbicide resistance or pest resistance). In a further example, a transgene may be an antisense nucleic acid, wherein expression of the antisense nucleic acid inhibits expression of a target nucleic acid sequence. A transgene may comprise regulatory sequences operably linked to the transgene (e.g., a promoter). In some embodiments, a nucleic acid molecule of interest to be introduced by site-specific targeting at a FAD2 locus is a transgene. However, in other embodiments, a nucleic acid molecule of interest may be a PTU, an ELP, an ETIP, or an endogenous nucleic acid sequence (e.g., wherein additional, exogenous genomic copies of the endogenous nucleic acid sequence are desired).

Elements can also include DNA that encodes for a structural RNA, such as shRNA. Such RNA can modify exogenous or endogenous genes including, but not limited to affecting postings or conferring herbicide resistance.

Recombinant: As used herein, the term "recombinant" refers to a material (e.g., nucleic acid, gene, polynucleotide, and/or polypeptide) that has been altered by human intervention. For example, the arrangement of the parts or elements of a recombinant molecule may not be a native arrangement, and/or the primary sequence of the recombinant molecule may have been changed from its native sequence, e.g., to optimize its expression and/or activity. A material may be altered to produce a recombinant material within or removed from its natural environment or state. As one example, an open reading frame of a nucleic acid is recombinant if the nucleotide sequence of the open reading frame has been removed from it natural context and cloned into an artificial nucleic acid molecule (e.g., a vector). Protocols and reagents to produce recombinant molecules (e.g., recombinant nucleic acids) are common in the art, and their use is routine. The term "recombinant" may also refer herein to a cell or organism that comprises recombinant material (e.g., a plant and/or plant cell that comprises a recombinant nucleic acid). In some examples, a recombinant organism is a transgenic organism.

Vector: As used herein, the term "vector" refers to a polynucleotide or other molecule that is capable of transferring at least one nucleic acid segment(s) into a cell. A vector may optionally comprise components/elements that mediate vector maintenance and/or enable its intended use (e.g., sequences necessary for replication, genes imparting drug or antibiotic resistance, a multiple cloning site, and/or operably linked promoter/enhancer elements that enable the expression of a cloned gene). Vectors may be derived, for example, from plasmids, bacteriophages, or plant or animal viruses. A "cloning vector," "shuttle vector," or "subcloning vector" generally comprises operably linked elements to facilitate cloning or subcloning steps (e.g., a multiple cloning site containing multiple restriction endonuclease sites).

Expression Vector: The term "expression vector," as used herein, refers to a vector comprising operably linked polynucleotide sequences that may facilitate expression of a coding sequence in a particular host organism. For example, a bacterial expression vector may facilitate expression of a coding sequence in a bacterium. Likewise, a plant expression vector may facilitate expression of a coding sequence in a plant cell. Polynucleotide sequences that facilitate expression in prokaryotes may include, for example and without limitation, a promoter; an operator; and a ribosome binding site. Eukaryotic expression vectors (e.g., a plant expression vector) may comprise, for example, promoters; enhancers; termination signals; and polyadenylation signals (and other sequences) that are generally different from those used in prokaryotic expression vectors.

Sequence identity: The term "sequence identity" or "identity," as used herein in the context of two nucleic acid or polypeptide sequences, refers to the residues in the two sequences that are the same when aligned for maximum correspondence over a specified comparison window. A value of sequence identity may be determined by comparing two optimally aligned sequences (e.g., nucleic acid sequences and amino acid sequences) over a comparison window, wherein the portion of the sequence in the comparison window may comprise additions or deletions (i.e., gaps) as compared to the reference sequence (which does not comprise additions or deletions) for optimal alignment of the two sequences. The sequence identity is calculated as a percentage by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in Altschul et al. (1990) J. Mol. Biol. 215:403-10.

The National Center for Biotechnology Information (NCBI) Basic Local Alignment Search Tool (BLAST™; Altschul et al. (1990)) may be used to align sequences, and it is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with greater similarity to the reference sequences will show increasing percentage identity when assessed by this method.

As used herein, the term "substantially identical" may refer to nucleotide sequences that are more than 80% identical. For example, a substantially identical nucleotide sequence may be at least 85%, at least 86%; at least 87%; at least 88%; at least 89%; at least 90%; at least 91%; at least 92%; at least 93%; at least 94%; at least 95%; at least 96%; at least 97%; at least 98%; at least 99%; or at least 99.5% identical to the reference sequence.

Locus: As used herein, the term "locus" refers to a position on a genome that corresponds to a measurable characteristic (e.g., a trait). In some embodiments, a locus of particular interest is the genomic position of a FAD2 gene, where disruption of the gene reduces or eliminates expression of the mRNA transcribed from the wild-type gene. A locus may be defined by a probe that hybridizes to a unique nucleotide sequence contained within the locus either during Southern hybridization or PCR.

Marker: As used herein, a "marker" refers to a gene or nucleotide sequence that can be used to identify plants that are likely to have a particular allele and/or exhibit a particular trait or phenotype. A marker may be described as a variation at a given genomic locus. A genetic marker may be a short DNA sequence, such as a sequence surrounding a single base-pair change (single nucleotide polymorphism, or "SNP"), or a long sequence, for example, a minisatellite/simple sequence repeat ("SSR"). A "marker allele" refers to the version of the marker that is present in a particular plant. The term marker as used herein may refer to a cloned segment of plant chromosomal DNA (e.g., a segment comprising a FAD2 locus, or a modified and/or disrupted FAD2 locus), and may also or alternatively refer to a DNA molecule that is complementary to a cloned segment of plant chromosomal DNA. As is recognized by those of ordinary skill in the art, the process of obtaining additional, contiguous nucleotide sequence for inclusion in a marker may be repeated nearly indefinitely (limited only by the length of the chromosome), thereby identifying additional markers along the chromosome. Any and all of the above-described varieties of markers may be used in some embodiments of the present invention.

In some embodiments, the presence of a transgene or marker (which are characterized by a "target" sequence) in a germplasm may be detected through the use of a nucleic acid probe; e.g., an oligonucleotide. A probe may be a DNA molecule or an RNA molecule. An oligonucleotide probe may be prepared synthetically or by cloning. Suitable cloning vectors are well-known to those of skill in the art. RNA probes can be synthesized by means known in the art, for example, using a DNA molecule template.

An oligonucleotide probe may be labeled or unlabeled. A wide variety of techniques exist for labeling nucleic acid molecules, including, for example and without limitation, radiolabeling by nick translation; random priming; and tailing with terminal deoxytransferase, where the nucleotides employed are labeled, for example, with radioactive $^{32}P$. Other labels which may be used include, for example and without limitation, fluorophores; enzymes; enzyme substrates; enzyme cofactors; and enzyme inhibitors. Alternatively, the use of a label that provides a detectable signal, by itself or in conjunction with other reactive agents, may be replaced by ligands to which receptors bind, where the receptors are labeled (for example, by the above-indicated labels) to provide detectable signals, either by themselves, or in conjunction with other reagents. See, e.g., Leary et al. (1983) Proc. Natl. Acad. Sci. USA 80:4045-9.

A probe may be an exact copy of a transgene or marker to be detected. A probe may also be a nucleic acid molecule comprising, or consisting of, a nucleotide sequence that is substantially identical to a cloned segment of chromosomal DNA comprising the transgene or marker to be detected. A probe may further comprise additional nucleic acid sequences, for example, promoters; transcription signals; and/or vector sequences.

A probe may contain all or a portion of the target nucleotide sequence and additional, contiguous nucleotide sequence from the genome. This is referred to herein as a "contiguous probe." The additional, contiguous nucleotide sequence is referred to as "upstream" or "downstream" of the original target, depending on whether the contiguous nucleotide sequence from the chromosome is on the 5' or the 3' side of the original marker, as conventionally understood. A probe may also contain a nucleotide sequence that is not contiguous to that of the original target; this probe is referred to herein as a "non-contiguous probe." The sequence of the non-contiguous probe may be located sufficiently close to the sequence of the original target on the chromosome so that the non-contiguous probe is linked to the original marker or transgene.

In some embodiments, a probe is a nucleic acid molecule that is "specifically hybridizable" or "specifically complementary" to an exact copy of the target to be detected. "Specifically hybridizable" and "specifically complementary" are terms that indicate a sufficient degree of complementarity, such that stable and specific binding occurs between the nucleic acid molecule and the target. A nucleic acid molecule need not be 100% complementary to its target sequence to be specifically hybridizable. A nucleic acid molecule is specifically hybridizable when there is a sufficient degree of complementarity to avoid non-specific binding of the nucleic acid to non-target sequences under conditions where specific binding is desired, for example, under stringent hybridization conditions.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual,* $2^{nd}$ ed., vol. 1-3, Cold Spring Harbor Laboratory Press, Cold Spring Harbor, N.Y., 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology—Hybridization with Nucleic Acid Probes*, Part I, Chapter 2, Elsevier, NY, 1993; and Ausubel et al., Eds., *Current Protocols in Molecular Biology*, Chapter 2, Greene Publishing and Wiley-Interscience, NY, 1995.

As used herein, "stringent conditions" encompass conditions under which hybridization will only occur if there is less than 25% mismatch between the hybridization molecule and the DNA target. "Stringent conditions" include further particular levels of stringency. Thus, as used herein, "moderate stringency" conditions are those under which molecules with more than 25% sequence mismatch will not hybridize; conditions of "medium stringency" are those under which molecules with more than 15% mismatch will not hybridize; and conditions of "high stringency" are those under which sequences with more than 10% mismatch will not hybridize. Conditions of "very high stringency" are those under which sequences with more than 6% mismatch will not hybridize.

In particular embodiments, stringent conditions are hybridization at 65° C. in 6× saline-sodium citrate (SSC) buffer, 5×Denhardt's solution, 0.5% SDS, and 100 μg sheared salmon testes DNA, followed by 15-30 minute sequential washes at 65° C. in 2×SSC buffer and 0.5% SDS, followed by 1×SSC buffer and 0.5% SDS, and finally 0.2×SSC buffer and 0.5% SDS.

Linkage (dis)equilibrium: As used herein, the term "linkage equilibrium" refers to the situation where a marker and a second nucleic acid (e.g., transgene, PTU, and second marker) independently segregate; i.e., the marker and the second nucleic acid sort randomly among progeny. Nucleic acids that show linkage equilibrium are considered unlinked (whether or not they lie on the same chromosome). As used herein, the term "linkage disequilibrium" refers to the situation where a marker and a second nucleic acid segregate in a non-random manner; i.e., the nucleic acids have a recombination frequency of less than 50% (and thus by definition, are separated by less than 50 cM on the same linkage group). In some examples, nucleic acids that show linkage disequilibrium are considered linked.

Linked, tightly linked, and extremely tightly linked: As used herein, linkage between a marker and a second nucleic acid (e.g., transgene, PTU, and second marker) may refer to the phenomenon in which nucleic acids on a chromosome show a measurable probability of being passed on together to individuals in the next generation. Thus, linkage of one marker to a second nucleic acid may be measured and/or expressed as a recombination frequency. The closer two nucleic acids are to each other, the closer to "1" this probability becomes. Thus, the term "linked" may refer to one or more genes or markers that are passed together with a second nucleic acid with a probability greater than 0.5 (which is expected from independent assortment where markers/genes are located on different chromosomes). When the presence of a gene (e.g., a transgene) contributes to a phenotype in an individual, markers that are linked to the gene may be said to be linked to the phenotype. Thus, the term "linked" may refer to a relationship between a marker and a gene, or between a marker and a phenotype.

A relative genetic distance (determined by crossing over frequencies and measured in centimorgans (cM)) is generally proportional to the physical distance (measured in base pairs) that two linked markers or genes are separated from each other on a chromosome. One centimorgan is defined as the distance between two genetic markers that show a 1% recombination frequency (i.e., a crossing-over event occurs between the two markers once in every 100 cell divisions). In general, the closer one marker is to another marker or gene (whether the distance between them is measured in terms of genetic distance or physical distance,) the more tightly they are linked. Because chromosomal distance is approximately proportional to the frequency of recombination events between traits, there is an approximate physical distance that correlates with recombination frequency. This correlation is generally known or readily determinable across the major crop plants (Helentjaris and Burr (eds.) (1989) *Development and Application of Molecular Markers to Problems in Plant Genetics*. Cold Spring Harbor Laboratory, Cold Spring Harbor, N.Y.; Gresshoff (ed.) (1994) *Plant Genome Analysis*. CRC Press, Boca Raton, Fla.; Lander et al. (1987) Genomics 1:174-81; Tanksley et al. (1988) "Molecular mapping of plant chromosomes," In *Chromosome Structure and Function*. Gustafson and Appels (eds.) Plenum Press, NY, pp. 157-73) and many other organisms. For example, 1 cM corresponds to about 2.5-3.0 kb in yeast, about 140 kb in *Arabidopsis*, about 400 kb in sunflower, and about 350 kb in *Eucalyptus.*

The term "linked" may refer herein to one or more nucleic acids that show a recombination frequency of less than 50% (i.e., less than 50 cM). For example, "linked" nucleic acids may recombine with a frequency of about 45% or less, about 40% or less, about 35% or less, about 30% or less, about 25% or less, about 20% or less, about 15% or less, and about 10% or less. The physical distances between such nucleic acids on the same chromosome (nucleic acids on different chromosomes are expected to be in linkage equilibrium) that correspond to the foregoing recombination frequencies depend on the host genome, and may be easily calculated as set forth, supra.

As used herein, the term "tightly-linked" may refer to one or more nucleic acids that show a recombination frequency of about 20% or less (i.e., about 20 cM or less). For example, "tightly linked" nucleic acids may recombine with a frequency of 22% or less, about 18% or less, about 16% or less, about 14% or less, about 12% or less, about 10% or less, about 8% or less, about 6% or less, about 4% or less, and about 2% or less.

As used herein, the term "extremely tightly-linked" may refer to one or more nucleic acids that show a recombination frequency of about 10% or less (i.e., about 10 cM or less). For example, "extremely tightly linked" nucleic acids may recombine with a frequency of 11% or less, about 9% or less, about 8% or less, about 7% or less, about 6% or less, about 5% or less, about 4% or less, about 3% or less, about 2% or less, and about 1% or less.

The closer a particular nucleic acid is to a gene that encodes a polypeptide that contributes to a particular phenotype (whether measured in terms of genetic or physical distance), the more tightly-linked is the particular nucleic acid to the phenotype. In view of the foregoing, it will be appreciated that nucleic acids linked to a particular gene or phenotype include those nucleic acids that are tightly linked, and those nucleic acids that are extremely tightly linked, to the gene or phenotype. In some embodiments, the closer a particular nucleic acid is to a FAD2 locus (e.g., a modified or disrupted FAD2 locus), whether measured in terms of genetic or physical distance, the more tightly-linked is the particular nucleic acid to any trait/phenotype conferred by an exogenous nucleic acid integrated at the FAD2 locus (or to a wild-type FAD2 phenotype in the case of an unmodified locus). Thus, genetic markers that are linked, tightly linked, and/or extremely tightly linked to a FAD2 locus comprising an integrated exogenous nucleic acid may be useful in an MAS program to identify organisms (e.g., plants and plant varieties) comprising the integrated nucleic acid, to identify organisms comprising a phenotype conferred by the integrated nucleic acid, and to breed such an integrated nucleic acid and/or a phenotype conferred by the integrated nucleic acid into other compatible organisms.

Marker-assisted breeding: As used herein, the term "marker-assisted breeding" may refer to an approach to breeding plants directly for one or more trait(s) (e.g., a polygenic trait). In current practice, plant breeders attempt to identify easily detectable traits, such as flower color, seed coat appearance, or isozyme variants that are linked to an agronomically desired trait. The plant breeders then follow the agronomic trait in the segregating, breeding populations by following the segregation of the easily detectable trait. However, there are very few of these linkage relationships between traits of interest and easily detectable traits available for use in plant breeding. In some embodiments of the invention, marker-assisted breeding comprises identifying one or more genetic markers (e.g., SNP, isozyme, and/or SSR markers) that are linked to a FAD2 locus wherein an exogenous nucleic acid contributing to a trait of interest has been integrated, and following the trait of interest in a segregating, breeding population by following the segregation of the one or more genetic markers. In some examples, the segregation of the one or more genetic markers may be determined utilizing a probe for the one or more genetic markers by assaying a genetic sample from a progeny plant for the presence of the one or more genetic markers. Marker-assisted breeding provides a time- and cost-efficient process for improvement of plant varieties.

Trait or phenotype: The terms "trait" and "phenotype" are used interchangeably herein. For the purposes of the present disclosure, traits of particular interest include agronomically important traits, as may be expressed, for example, in a crop plant, and the production of transgene expression products from a targeted integration event. The term "molecular phenotype" may refer to a phenotype that is detectable at the level of a population of (one or more) molecules. In some examples, the molecular phenotype may only be detectable at the molecular level. The detectable molecules of the phenotype may be nucleic acids (e.g., genomic DNA or RNA); proteins; and/or metabolites. For example, a molecular phenotype may be an expression profile for one or more gene products (e.g., at a specific stage of plant development, or in response to an environmental condition or stress).

Quantitative Trait Locus: Traits that are continuously varying due to genetic (additive, dominant, and epistatic) and environmental influences are commonly referred to as "quantitative traits." Quantitative traits may be distinguished from "qualitative," or "discrete," traits on the basis of two factors; environmental influences on gene expression that produce a continuous distribution of phenotypes, and the complex segregation pattern produced by multigenic inheritance. The identification of one or more regions of the genome linked to the expression of a quantitative trait defines such regions as Quantitative Trait Loci ("QTL").

Plant: As used herein, the term "plant" may refer to a whole plant, a cell or tissue culture derived from a plant, and/or any part of any of the foregoing. Thus, the term "plant" encompasses, for example and without limitation, whole plants; plant components and/or organs (e.g., leaves, stems, and roots); plant tissue; seed; and a plant cell. A plant cell may be, for example and without limitation, a cell in and/or of a plant, a cell isolated from a plant, and a cell obtained through culturing of a cell isolated from a plant.

A "transgenic plant" is a plant comprising within at least one of its cells an exogenous polynucleotide. The term "transgenic" is used herein to refer to any cell, cell line, callus, tissue, plant part, or plant, the genotype of which has been altered by the presence of a exogenous nucleic acid. Thus, this term encompasses transgenic organisms and cells that have been initially altered to comprise the exogenous polynucleotide, and those organisms and cells created by crosses or asexual propagation of the initial transgenic organism or cell. The term "transgenic," as used herein, does not encompass genome (chromosomal or extra-chromosomal) alternations introduced by conventional plant breeding methods (e.g., crosses of only non-transgenic organisms) or by naturally-occurring events (e.g., random cross-fertilization, non-recombinant viral infection, non-recombinant bacterial transformation, non-recombinant transposition, and spontaneous mutation).

A plant "line," "variety," or "strain" is a group of individual plants having the same parentage. Plants of a line generally are inbred to some degree, and are generally homozygous and homogeneous at most genetic loci (e.g., a FAD2 locus). A "subline" may refer to an inbred subset of descendents from a common progenitor that are genetically distinct from other similarly inbred subsets descended from the same progenitor. In some embodiments, a "subline" may be produced by inbreeding seed from an individual transgenic plant selected at the $F_3$ to $F_5$ generation until the residual segregating loci are homozygous across most or all loci.

A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication No. 20110301073.

A "selected" zinc finger protein or TALE is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197, WO 02/099084 and U.S. Publication No. 20110301073.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and – cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 20070218528, 2008/0131962 and 2011/0201055, incorporated herein by reference in their entireties.

Means for generating a double strand DNA break: As used herein, the term "means for generating a double strand DNA break" is intended to invoke the special claiming provisions authorized by Congress in 35 U.S.C. § 112, sixth paragraph. Specifically, a "means for generating a double strand DNA break" refers to a molecular structure that is capable of cleaving both strands of a double-stranded DNA molecule. Such structures include polypeptide domains comprised within many known nuclease proteins, for example, the FokI nuclease domain, the catalytic domain is selected from the group consisting of proteins Mmel, Colicin-E7 (CEA7_ECOLX), Colicin-E9, APFL, EndA, Endo I (END1_EC0LI), Human Endo G (NUCG_HUMAN), Bovine Endo G (NUCG_BOVIN), R.HinPll, 1-Basl, 1-Bmol, 1-Hmul, 1-Tevl, 1-Tevll, 1-Tevlll, 1-Twol, R.Mspl, R.Mval, NucA, NucM, Vvn, Vvn_CLS, Staphylococcal nuclease (NUC_STAAU), Staphylococcal nuclease (NUC_STAHY), Micrococcal nuclease (NUC_SHIFL), Endonuclease yncB, Endodeoxyribonuclease I (ENRN_BPT7), Metnase, Nb.BsrDI, BsrDI A, Nt.BspD61 (R.BspD61 large subunit), ss.BspD61 (R.BspD61 small subunit), R.PIel, Mlyl, Alwl, Mval2691, Bsrl, Bsml, Nb.BtsCI, Nt.BtsCI, R1.Btsl, R2.Btsl, BbvCI subunit 1, BbvCI subunit 2, BpulOI alpha subunit, BpulOI beta subunit, Bmrl, Bfil, 1-Crel, hExol (EX01JHUMAN), Yeast Exol (EX01_YEAST), *E. coli* Exol, Human TREX2, Mouse TREX1, Human TREX1, Bovine TREX1, Rat TREX1, Human DNA2, Yeast DNA2 (DNA2 YEAST).

Means for repairing a double strand DNA break: As used herein, the term "means for repairing a double strand DNA break" is also intended to invoke the special claiming provisions authorized by Congress in 35 U.S.C. § 112, sixth paragraph. Specifically, a "means for repairing a double strand DNA break" refers to a molecular structure that is capable of facilitating/catalyzing the joining of the ends of double-stranded DNA molecules, for example, by joining ends generated by cleaving a single double-stranded DNA molecule, or by joining one end generated by cleaving a single double-stranded DNA molecule with the end of an exogenous double-stranded DNA molecule. Such structures include polypeptide domains comprised within many known ligase proteins, for example, Cre recombinase. In some examples, the same molecular structure may serve as both a means for generating a double strand DNA break and a means for repairing a double strand DNA break, where the same structure facilitates both the cleavage and repair of double-stranded DNA molecules (e.g., Hin recombinase).

The induction of the site specific double stranded breaks in the genome induces the host plant cell DNA repair pathway which resolves the double stranded break through homology-directed repair (HDR) or non-homologous end joining (NHEJ) repair. In plants, the scientific literature reports that precise gene or donor DNA integration into native genomic or at pre-engineered locations have involved incoming donor DNA construct(s) that comprise varying amounts of sequence homologous to the sequences flanking the targeted double stranded break. The integration of such donors into the specific target locus presumably has relied on the HDR pathway. Exclusively relying on the HDR approach for gene targeting in plants can have limitations due to reports that the HDR repair pathway is not the dominate DNA repair pathway when compared to NHEJ. The published plant scientific literature utilizing target specific DNA breaks (ZFN, TALeNs, or Engineered Meganucleases, etc.) the NHEJ pathway has been reported as the method to introduce specific point mutations (insertions, or deletions) into the geneome. Here we report that site specific double stranded breaks (induced by ZFN, TALeNs, etc.) in the presents of various donor DNA design with homology regions of 0 to <10 bp can be specifically inserted at targeted break via the NHEJ repair pathway in plants. A variety of different DNA donor designs with zero homology to small 1-10 bp of ranging from linear to circular, single stranded to double stranded can be targeted to specific locations using the NHEJ pathway. NHEJ based donor DNA plant genome targeting can be based on "sticky end capture", where the targeted double stranded break in the genome generated by Fok1 (or other Type II endonuclease domains) and the corresponding sticky ends are on the NHEJ donor DNA designs. The sticky ends donor DNA can be delivered directly to the cell as linear donor DNA with predefined overhangs. An alternative approach is to produce the donor DNA sticky ends in vivo by co-delivering the host target ZFN and a circular DNA donor molecule that contains at least one ZFN recognition site that is identical to the target recognition site. Expression of at least one ZFN cuts the host genomic DNA (native or pre-engineered) and the circular donor DNA to produce sticky ends that are resolved using the hosts NHEJ repair pathway.

It is possible to have one or more ZFN cuts sites on the donor molecule (a single ZFN cut site to linearize the entire donor molecule, 2 of the same ZFN sites to release a smaller donor DNA fragment or 2 different ZFN sites to release a fragment from the donor and a corresponding fragment from the host genomic DNA (DNA replacement).

Thus, the donor polynucleotide can be DNA or RNA, single-stranded and/or double-stranded and can be introduced into a cell in linear or circular form. See, e.g., U.S. Patent Publication Nos. 20100047805 and 20110207221. In certain, embodiments of the present invention may also include linear exogenous (donor) nucleic acid(s), compositions comprising these nucleic acids and methods of making and using these linear donor molecules. In certain embodiments, the linear donor molecule stably persists in the cell into which it is introduced. In other embodiments, the linear donor molecule is modified to resist exonucleolytic cleavage, for example by placing one or more phosphorothioate phosphodiester bonds between one or more base pairs on the ends of the donor molecule. The linear exogenous nucleic acid may also include single stranded specific DNA.

III. FAD2 Performance Loci

The loci designated FAD2 (fatty acid desaturase 2) are included in QTLs involved in the inheritance of the complex multigenic trait of fatty acid content in plants. FAD2 encodes the enzyme responsible for the desaturation of oleic acid (18:1) to linoleic acid (C18:2). Tanhuanpaa et al. (1998) Mol. Breed. 4:543-50; Schierholt et al. (2001) Crop Sci. 41:1444-9.

Within the plant oil biosynthetic pathway the fatty acid desaturases (FADs) play a key role in plant lipid biosynthesis and their activity significantly influences the fatty acid composition. FADs are abundant in plants, and expression analysis suggested that FAD mRNAs are produced in over-abundance. Furthermore, FAD genes are expressed in various, tissues, and cell types, as well as subcellular compartments including the plastid and endoplasmic reticulum.

The fatty acid composition of plants, and the performance of oils produced therefrom in many applications, is determined by the relative concentrations of the major fatty acid constituents; oleic, linoleic, and linolenic (C18:3). The concentrations of these fatty acids are predominantly regulated by the function of the enzymes FAD2 and FAD3. Oleic acid is converted to linoleic acid and linolenic acid in plants according to the scheme:

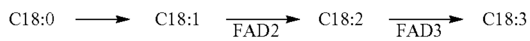

FAD2 genes have been identified in major plant and algal species including but not limited to maize, soybean, cotton, *Arabidopsis*, wheat, forage grasses, rice, sunflower and *Brassica*, and modification of FAD2 expression leads to altered fatty acid profiles in such organisms. Furthermore, plants comprising modified FAD2 genes have been commercialized, and disruption of a FAD2 gene has been shown to be able to improve the nutritional and functional properties of oil produced by a host plant without an agronomic penalty to the host plant. For example, canola and sunflower varieties that have been commercialized under the Nexera® brand (Dow AgroSciences, LLC) are characterized by a higher oleic acid, lower linoleic aced, and lower linolenic acid (and lower saturated fatty acid) composition, when compared to wild-type canola and sunflower profiles.

The dominant canola species grown in Europe, North America, and Australia is *Brassica napus*, a polyploid *Brassica* species considered to have arisen from the hybridization of *B. oleracea* (having a diploid C genome) and *B. rapa* (having a diploid A genome). Cytogenetic investigation revealed the AA and CC genomes show a degree of relatedness as being partially homologous to one another. Both the A and C genomes contain a high percentage of homeologous or paralogous genes. Thus, it is thought that the AA and CC genomes are derived from a common ancestor genome. Prakash and Hinata (1980) Opera Botanica 55:1-57. Although the genomes of both progenitor species are technically classified as diploids, these genomes contain a high percentage of regions that are duplicative of one another. Song et al. (1991) Theor. Appl. Genet. 82:296-304. A detailed organelle and nuclear RFLP analysis revealed that the AA genome of *B. rapa* contributed ten chromosomes to *B. napus*, while *B. oleracea* contributed nine chromosomes from its CC genome as the maternal donor. Song et al. (1992) Genome 35:992-1001. Through the number of genome duplications in both ancestral genomes, as well as the high percentage of similarity between the A, B and C genomes, there have arisen several copies of FAD2 and FAD3 genes. As a practical matter, this fact makes breeding canola with modified and/or disrupted copies of these genes in order to produce a particular fatty acid profile particularly challenging.

The known functional gene copies of FAD2 in canola are located on linkage group N4 of the A genome. Scheffler et al. (1997) TAG 94(5):583-91; Schierholt et al. (2000) TAG 101(5-6):897-901. More recently, a high oleic trait in canola has been associated with a modified and disrupted FAD2 gene that is located on the A genome. U.S. Patent Application Publication No. US 2006/0248611 A1; Hu et al. (2006) "Identification and Mapping of FAD2 and FAD3 Mutations and Development of Allele-specific Markers for High Oleic and Low Linolenic Acid Contents in Canola (*Brassica napus* L.)," Plant & Animal Genomes XIV Conference, Jan. 14-18, 2006, San Diego, Calif. An inactivating FAD2 allele contributes to the control of oleic acid content by reducing the desaturation of oleic acid to linoleic acid. This high oleic acid and fad2 trait was identified in a *B. napus* variety (DMS 100) that has a characteristic oleic acid content of about 77%. See, U.S. application Ser. No. 10/545,100. Additionally, FAD2 genes were recently located on the A5 chromosome and were alleged to be responsible for high C18:1 content. See, Yang et al., "*Brassica napus* genome" Theor Appl Genet (2012 125:715-729. Further, genetic markers have been developed to assist the introgression of the FAD2 and high oleic acid trait into canola.

FAD2 loci may be modified and/or disrupted in a plant without detrimentally affecting the value of the plant, and for many purposes, with an actual increase in its value, including alteration of FAD2 expression, alteration of oil content/ratios and/or integration and expression of desired transgenes. Furthermore, according to the ubiquitous nature of FAD loci in plants, FAD2 loci may be modified and/or disrupted without detriment for at least some purposes in many species, including, for example and without limitation: canola; soybean; maize; wheat; forage grasses; *brassica* sp.; rice, tomatoes, barley; oats; sorghum; cotton; and sunflower, as well as fungi and algae. Embodiments of the invention include FAD2 loci, and the use thereof as performance loci for integration of exogenous nucleic acids. In examples, a FAD2 locus exhibits at least one of several features that have been found to be desirable within the context of its use as a performance locus, including, for example and without limitation: that there is an approximately consistent level of expression during the life cycle of the host organism; and surprisingly, that integration of donor DNA at a FAD2 locus does not induce a quality or fitness penalty on the host.

In some embodiments of the present invention, at least one FAD2 locus (e.g., a FAD2A, FAD2A', FAD2C and/or FAD2C' locus) is used as a target site for the site-specific integration of an exogenous nucleic acid (e.g., a nucleic acid comprising a nucleotide sequence encoding a polypeptide of interest). In particular embodiments, integration of the exogenous nucleic acid results in a modified locus. For example, integration of the exogenous nucleic acid may modify the locus so as to produce a disrupted (i.e., inactivated) FAD2 gene.

In some embodiments, a FAD2 locus may comprise a nucleotide sequence that is specifically hybridizable to the complement of a nucleotide sequence selected from the group consisting of SEQ ID NOs: 22-26, SEQ ID NOs: 28-33 and SEQ ID NOs: 35-38. For example, a FAD2 locus may comprise a nucleotide sequence selected from the group consisting of SEQ ID NOs: 22-26, SEQ ID NOs: 28-33 and SEQ ID NOs: 35-38. In some embodiments, a FAD2 locus may comprise a nucleotide sequence that is substantially identical to a nucleotide sequence selected from the group consisting of SEQ ID NOs: 22-26, SEQ ID NOs: 28-33 and SEQ ID NOs: 35-38. For example, in some embodiments, a FAD2 locus is a FAD2 homologue (e.g., an ortholog or a paralog) that comprises a nucleotide sequence that is at least about 85% identical to a nucleotide sequence selected from the group consisting of SEQ ID NOs: 22-26, SEQ ID NOs: 28-33 and SEQ ID NOs: 35-38. A FAD2 homologue may comprise a nucleotide sequence that is, for example and without limitation: at least 80%; at least 85%; at least about 90%; at least about 91%; at least about 92%; at least about 93%; at least about 94%; at least about 95%; at least about 96%; at least about 97%; at least about 98%; at least about 99%; at least about 99.5%; 99.6%, 99.7%, 99.8% and/or at least about 99.9% identical to a nucleotide sequence selected from the group consisting of SEQ ID NOs: 22-26, SEQ ID NOs: 28-33 and SEQ ID NOs: 35-38. Such a FAD2 homologue may be readily identified and isolated from any complete or partial genome readily available to those of skill in the art for a variety of organisms.

IV. Targeted Integration of a Nucleic Acid at a FAD2 Locus

Site-specific integration of an exogenous nucleic acid at a FAD2 locus may be accomplished by any technique known to those of skill in the art. In some embodiments, integration of an exogenous nucleic acid at a FAD2 locus comprises contacting a cell (e.g., an isolated cell or a cell in a tissue or organism) with a nucleic acid molecule comprising the exogenous nucleic acid. In examples, such a nucleic acid molecule may comprise nucleotide sequences flanking the exogenous nucleic acid that facilitate homologous recombination between the nucleic acid molecule and at least one FAD2 locus. In particular examples, the nucleotide sequences flanking the exogenous nucleic acid that facilitate homologous recombination may be complementary to endogenous nucleotides of the FAD2 locus. In particular examples, the nucleotide sequences flanking the exogenous nucleic acid that facilitate homologous recombination may be complementary to previously integrated exogenous nucleotides. In some embodiments, a plurality of exogenous nucleic acids may be integrated at one FAD2 locus, such as in gene stacking.

Integration of a nucleic acid at a FAD2 locus may be facilitated (e.g., catalyzed) in some embodiments by endogenous cellular machinery of a host cell, such as, for example and without limitation, endogenous DNA and endogenous recombinase enzymes. In some embodiments, integration of a nucleic acid at a FAD2 locus may be facilitated by one or more factors (e.g., polypeptides) that are provided to a host cell. For example, nuclease(s), recombinase(s), and/or ligase polypeptides may be provided (either independently or as part of a chimeric polypeptide) by contacting the polypeptides with the host cell, or by expressing the polypeptides within the host cell. Accordingly, in some examples, a nucleic acid comprising a nucleotide sequence encoding at least one nuclease, recombinase, and/or ligase polypeptide may be introduced into the host cell, either concurrently or sequentially with a nucleic acid to be integrated site-specifically at a FAD2 locus, wherein the at least one nuclease, recombinase, and/or ligase polypeptide is expressed from the nucleotide sequence in the host cell.

A. DNA-Binding Polypeptides

In some embodiments, site-specific integration may be accomplished by utilizing factors that are capable of recognizing and binding to particular nucleotide sequences, for example, in the genome of a host organism. For instance, many proteins comprise polypeptide domains that are capable of recognizing and binding to DNA in a site-specific manner. A DNA sequence that is recognized by a DNA-binding polypeptide may be referred to as a "target" sequence. Polypeptide domains that are capable of recognizing and binding to DNA in a site-specific manner generally fold correctly and function independently to bind DNA in a site-specific manner, even when expressed in a polypeptide other than the protein from which the domain was originally isolated. Similarly, target sequences for recognition and binding by DNA-binding polypeptides are generally able to be recognized and bound by such polypeptides, even when present in large DNA structures (e.g., a chromosome), particularly when the site where the target sequence is located is one known to be accessible to soluble cellular proteins (e.g., a gene).

While DNA-binding polypeptides identified from proteins that exist in nature typically bind to a discrete nucleotide sequence or motif (e.g., a consensus recognition sequence), methods exist and are known in the art for modifying many such DNA-binding polypeptides to recognize a different nucleotide sequence or motif. DNA-binding polypeptides include, for example and without limitation: zinc finger DNA-binding domains; leucine zippers; UPA DNA-binding domains; GAL4; TAL; LexA; a Tet repressor; LacR; and a steroid hormone receptor.

In some examples, a DNA-binding polypeptide is a zinc finger. Individual zinc finger motifs can be designed to target and bind specifically to any of a large range of DNA sites. Canonical $Cys_2His_2$ (as well as non-canonical $Cys_3His$) zinc finger polypeptides bind DNA by inserting an α-helix into the major groove of the target DNA double helix. Recognition of DNA by a zinc finger is modular; each finger contacts primarily three consecutive base pairs in the target, and a few key residues in the polypeptide mediate recognition. By including multiple zinc finger DNA-binding domains in a targeting endonuclease, the DNA-binding specificity of the targeting endonuclease may be further increased (and hence the specificity of any gene regulatory effects conferred thereby may also be increased). See, e.g., Urnov et al. (2005) Nature 435:646-51. Thus, one or more zinc finger DNA-binding polypeptides may be engineered and utilized such that a targeting endonuclease introduced into a host cell interacts with a DNA sequence that is unique within the genome of the host cell.

Preferably, the zinc finger protein is non-naturally occurring in that it is engineered to bind to a target site of choice. See, for example, See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In some examples, a DNA-binding polypeptide is a DNA-binding domain from GAL4. GAL4 is a modular transactivator in *Saccharomyces cerevisiae*, but it also operates as a transactivator in many other organisms. See, e.g., Sadowski et al. (1988) Nature 335:563-4. In this regulatory system, the expression of genes encoding enzymes of the galactose metabolic pathway in *S. cerevisiae* is stringently regulated by the available carbon source. Johnston (1987) Microbiol. Rev. 51:458-76. Transcriptional control of these metabolic enzymes is mediated by the interaction between the positive regulatory protein, GAL4, and a 17 bp symmetrical DNA sequence to which GAL4 specifically binds (the UAS).

Native GAL4 includes 881 amino acid residues, with a molecular weight of 99 kDa. GAL4 comprises functionally autonomous domains, the combined activities of which account for activity of GAL4 in vivo. Ma and Ptashne (1987) Cell 48:847-53); Brent and Ptashne (1985) Cell 43(3 Pt 2):729-36. The N-terminal 65 amino acids of GAL4 comprise the GAL4 DNA-binding domain. Keegan et al. (1986) Science 231:699-704; Johnston (1987) Nature 328: 353-5. Sequence-specific binding requires the presence of a divalent cation coordinated by 6 Cys residues present in the DNA binding domain. The coordinated cation-containing domain interacts with and recognizes a conserved CCG triplet at each end of the 17 bp UAS via direct contacts with the major groove of the DNA helix. Marmorstein et al. (1992) Nature 356:408-14. The DNA-binding function of the protein positions C-terminal transcriptional activating domains in the vicinity of the promoter, such that the activating domains can direct transcription.

Additional DNA-binding polypeptides that may be utilized in certain embodiments include, for example and without limitation, a binding sequence from a AVRBS3-inducible gene; a consensus binding sequence from a AVRBS3-inducible gene or synthetic binding sequence engineered therefrom (e.g., UPA DNA-binding domain); TAL; LexA (see, e.g., Brent & Ptashne (1985), supra); LacR (see, e.g., Labow et al. (1990) Mol. Cell. Biol. 10:3343-56; Baim et al. (1991) Proc. Natl. Acad. Sci. USA 88(12):5072-6); a steroid hormone receptor (Ellliston et al. (1990) J. Biol. Chem. 265:11517-121); the Tet repressor (U.S. Pat. No. 6,271,341) and a mutated Tet repressor that binds to a tet operator sequence in the presence, but not the absence, of tetracycline (Tc); the DNA-binding domain of NF-κB; and components of the regulatory system described in Wang et al. (1994) Proc. Natl. Acad. Sci. USA 91(17):8180-4, which utilizes a fusion of GAL4, a hormone receptor, and VP 16.

In certain embodiments, the DNA-binding domain of one or more of the nucleases used in the methods and compositions described herein comprises a naturally occurring or engineered (non-naturally occurring) TAL effector DNA binding domain. See, e.g., U.S. Patent Publication No. 20110301073, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like (TAL) effectors which mimic plant transcriptional activators and manipulate the plant transcriptome (see Kay et al (2007) Science 318:648-651). These proteins contain a DNA binding domain and a transcriptional activation domain. One of the most well characterized TAL-effectors is AvrBs3 from *Xanthomonas* campestgris pv. *Vesicatoria* (see Bonas et al (1989) Mol Gen Genet. 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) J Plant Physiol 163(3): 256-272). In addition, in the phytopathogenic bacteria Ralstonia solanacearum two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) Appl and Envir Micro 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Pat. Nos. 8,420,782 and 8,440,431 and U.S. Patent Publication No. 20110301073.

In other embodiments, the nuclease comprises a CRISPR/Cas system. The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

In particular embodiments, a DNA-binding polypeptide specifically recognizes and binds to a target nucleotide sequence comprised within a genomic nucleic acid of a host organism. Any number of discrete instances of the target nucleotide sequence may be found in the host genome in some examples. The target nucleotide sequence may be rare within the genome of the organism (e.g., fewer than about 10, about 9, about 8, about 7, about 6, about 5, about 4, about 3, about 2, or about 1 copy(ies) of the target sequence may exist in the genome). For example, the target nucleotide sequence may be located at a unique site within the genome of the organism. Target nucleotide sequences may be, for example and without limitation, randomly dispersed throughout the genome with respect to one another; located in different linkage groups in the genome; located in the same linkage group; located on different chromosomes; located on the same chromosome; located in the genome at sites that are expressed under similar conditions in the organism (e.g., under the control of the same, or substantially functionally identical, regulatory factors); and located closely to one another in the genome (e.g., target sequences may be comprised within nucleic acids integrated as concatemers at genomic loci).

B. Targeting Endonucleases

In particular embodiments, a DNA-binding polypeptide that specifically recognizes and binds to a target nucleotide sequence may be comprised within a chimeric polypeptide, so as to confer specific binding to the target sequence upon the chimeric polypeptide. In examples, such a chimeric polypeptide may comprise, for example and without limitation, nuclease, recombinase, and/or ligase polypeptides, as these polypeptides are described above. Chimeric polypeptides comprising a DNA-binding polypeptide and a nuclease, recombinase, and/or ligase polypeptide may also comprise other functional polypeptide motifs and/or domains, such as for example and without limitation: a spacer sequence positioned between the functional polypeptides in the chimeric protein; a leader peptide; a peptide that targets the fusion protein to an organelle (e.g., the nucleus); polypeptides that are cleaved by a cellular enzyme; peptide tags (e.g., Myc, His, etc.); and other amino acid sequences that do not interfere with the function of the chimeric polypeptide.

Functional polypeptides (e.g., DNA-binding polypeptides and nuclease polypeptides) in a chimeric polypeptide may be operatively linked. In some embodiments, functional polypeptides of a chimeric polypeptide may be operatively linked by their expression from a single polynucleotide encoding at least the functional polypeptides ligated to each other in-frame, so as to create a chimeric gene encoding a chimeric protein. In alternative embodiments, the functional polypeptides of a chimeric polypeptide may be operatively linked by other means, such as by cross-linkage of independently expressed polypeptides.

In some embodiments, a DNA-binding polypeptide that specifically recognizes and binds to a target nucleotide sequence may be comprised within a natural isolated protein (or mutant thereof), wherein the natural isolated protein or mutant thereof also comprises a nuclease polypeptide (and may also comprise a recombinase and/or ligase polypeptide). Examples of such isolated proteins include TALENs, recombinases (e.g., Cre, Hin, Tre, and FLP recombinase), RNA-guided CRISPR-Cas9, and meganucleases.

As used herein, the term "targeting endonuclease" refers to natural or engineered isolated proteins and mutants thereof that comprise a DNA-binding polypeptide and a nuclease polypeptide, as well as to chimeric polypeptides comprising a DNA-binding polypeptide and a nuclease. Any targeting endonuclease comprising a DNA-binding polypeptide that specifically recognizes and binds to a target nucleotide sequence comprised within a FAD2 locus (e.g., either because the target sequence is comprised within the native sequence at the locus, or because the target sequence has been introduced into the locus, for example, by recombination) may be utilized in certain embodiments.

Some examples of chimeric polypeptides that may be useful in particular embodiments of the invention include, without limitation, combinations of the following polypeptides: zinc finger DNA-binding polypeptides; a FokI nuclease polypeptide; TALE domains; leucine zippers; transcription factor DNA-binding motifs; and DNA recognition and/or cleavage domains isolated from, for example and without limitation, a TALEN, a recombinase (e.g., Cre, Hin, RecA, Tre, and FLP recombinases), RNA-guided CRISPR-Cas9, a meganuclease; and others known to those in the art. Particular examples include a chimeric protein comprising a site-specific DNA binding polypeptide and a nuclease polypeptide. Chimeric polypeptides may be engineered by methods known to those of skill in the art to alter the recognition sequence of a DNA-binding polypeptide comprised within the chimeric polypeptide, so as to target the chimeric polypeptide to a particular nucleotide sequence of interest.

In certain embodiments, the chimeric polypeptide comprises a DNA-binding domain (e.g., zinc finger, TAL-effector domain, etc.) and a nuclease (cleavage) domain. The cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases, Cold Spring Harbor Laboratory Press,* 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding, for example, such that one or more exogenous sequences (donors/trangsenes) are integrated at or near the binding (target) sites. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a DNA binding domain and two Fok I cleavage half-domains can also be used.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in U.S. Patent Publication No. 20070134796, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:1538K" and by mutating positions 486 (Q→E) and 499 (I→L) in another cleavage half-domain to produce an engineered cleavage half-domain designated "Q486E:1499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes.

In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I)

residue at position 538 with a Lys (K) residue, and the wild-type His (H) residue at position 537 with a Lys (K) residue or a Arg (R) residue (also referred to as "KIK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See US Patent Publication No. 20110201055). Engineered cleavage half-domains described herein can be prepared using any suitable method, for example, by site-directed mutagenesis of wild-type cleavage half-domains (Fok I) as described in U.S. Patent Publication Nos. 20050064474; 20080131962; and 20110201055.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

C. Zinc Finger Nucleases

In specific embodiments, a chimeric polypeptide is a custom-designed zinc finger nuclease (ZFN) that may be designed to deliver a targeted site-specific double-strand DNA break into which an exogenous nucleic acid, or donor DNA, may be integrated (See co-owned US Patent publication 20100257638, incorporated by reference herein). ZFNs are chimeric polypeptides containing a non-specific cleavage domain from a restriction endonuclease (for example, FokI) and a zinc finger DNA-binding domain polypeptide. See, e.g., Huang et al. (1996) J. Protein Chem. 15:481-9; Kim et al. (1997a) Proc. Natl. Acad. Sci. USA 94:3616-20; Kim et al. (1996) Proc. Natl. Acad. Sci. USA 93:1156-60; Kim et al. (1994) Proc Natl. Acad. Sci. USA 91:883-7; Kim et al. (1997b) Proc. Natl. Acad. Sci. USA 94:12875-9; Kim et al. (1997c) Gene 203:43-9; Kim et al. (1998) Biol. Chem. 379:489-95; Nahon and Raveh (1998) Nucleic Acids Res. 26:1233-9; Smith et al. (1999) Nucleic Acids Res. 27:674-81. In some embodiments, the ZFNs comprise non-canonical zinc finger DNA binding domains (see co-owned US Patent publication 20080182332, incorporated by reference herein). The FokI restriction endonuclease must dimerize via the nuclease domain in order to cleave DNA and introduce a double-strand break. Consequently, ZFNs containing a nuclease domain from such an endonuclease also require dimerization of the nuclease domain in order to cleave target DNA. Mani et al. (2005) Biochem. Biophys. Res. Commun. 334:1191-7; Smith et al. (2000) Nucleic Acids Res. 28:3361-9. Dimerization of the ZFN can be facilitated by two adjacent, oppositely oriented DNA-binding sites. Id.

The flexibility and specificity of the ZFN system provides a level of control previously unachievable by known recombinase-mediated gene editing strategies. As one example, ZFNs can be easily engineered, for example, to recognize specific nucleic acid sequences. Wu et al. (2007) Cell. Mol. Life. Sci. 64:2933-44 (See, US Patent Publications 20090205083, 20110189775, 20110167521 and 20100199389, incorporated by reference in their entireties herein). Randomization of the codons for zinc finger recognition residues allows the selection of new fingers that have high affinity for arbitrarily chosen DNA sequences. Furthermore, zinc fingers are natural DNA-binding molecules, and engineered zinc fingers have been shown to act on their designed targets in living cells. Thus, nucleases based on zinc fingers are targetable to specific but arbitrary recognition sites.

In particular examples, a method for the site-specific integration of an exogenous nucleic acid into at least one FAD2 performance locus of a host comprises introducing into a cell of the host a ZFN, wherein the ZFN recognizes and binds to a target nucleotide sequence, wherein the target nucleotide sequence is comprised within at least one FAD2 locus of the host. In certain examples, the target nucleotide sequence is not comprised within the genome of the host at any other position than the at least one FAD2 locus. For example, a DNA-binding polypeptide of the ZFN may be engineered to recognize and bind to a target nucleotide sequence identified within the at least one FAD2 locus (e.g., by sequencing the FAD2 locus). A method for the site-specific integration of an exogenous nucleic acid into at least one FAD2 performance locus of a host that comprises introducing into a cell of the host a ZFN may also comprise introducing into the cell an exogenous nucleic acid, wherein recombination of the exogenous nucleic acid into a nucleic acid of the host comprising the at least one FAD2 locus is facilitated by site-specific recognition and binding of the ZFN to the target sequence (and subsequent cleavage of the nucleic acid comprising the FAD2 locus).

V. Exogenous nucleic acids for integration at a FAD2 locus

Embodiments of the invention may include one or more nucleic acids selected from the group consisting of: an exogenous nucleic acid for site-specific integration in at least one FAD2 locus, for example and without limitation, a PTU, ELP, ETIP or an ORF; a nucleic acid comprising a nucleotide sequence encoding a targeting endonuclease; and a vector comprising at least one of either or both of the foregoing. Thus, particular nucleic acids for use in some embodiments include nucleotide sequences encoding a polypeptide, structural nucleotide sequences, and/or DNA-binding polypeptide recognition and binding sites.

A. Exogenous nucleic acid molecules for site-specific integration

As noted above, integration of an exogenous sequence (also called a "donor sequence" or "donor" or "transgene") is provided, for example for expression of a polypeptide, correction of a mutant gene or for increased expression of a wild-type gene. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted integration of sequences not normally present in a region of interest, said sequences can be present in a donor nucleic acid molecule and flanked by regions of homology to sequence in the region of interest.

The donor polynucleotide can be DNA or RNA, single-stranded or double-stranded and can be introduced into a cell in linear or circular form. See, e.g., U.S. Patent Publication Nos. 20100047805, 20110281361, 20110207221 and U.S. application Ser. No. 13/889,162. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) Proc. Natl. Acad. Sci. USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The donor is generally integrated so that its expression is driven by the endogenous promoter at the integration site, namely the promoter that drives expression of the endogenous gene into which the donor is integrated (e.g., FAD2). However, it will be apparent that the donor may comprise a promoter and/or enhancer, for example a constitutive promoter or an inducible or tissue specific promoter.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

Exogenous nucleic acids that may be integrated in a site-specific manner into at least one FAD2 locus, so as to modify the FAD2 locus, in embodiments include, for example and without limitation, nucleic acids comprising a nucleotide sequence encoding a polypeptide of interest; nucleic acids comprising an agronomic gene; nucleic acids comprising a nucleotide sequence encoding an RNAi molecule; or nucleic acids that disrupt the FAD2 gene.

In some embodiments, an exogenous nucleic acid is integrated at a FAD2 locus, so as to modify the FAD2 locus, wherein the nucleic acid comprises an agronomic gene or nucleotide sequence encoding a polypeptide of interest, such that the agronomic gene or nucleotide sequence is expressed in the host from the FAD2 locus. In some examples, the polypeptide of interest (e.g., a foreign protein) is expressed from a nucleotide sequence encoding the polypeptide of interest in commercial quantities. In such examples, the polypeptide of interest may be extracted from the host cell, tissue, or biomass. In some embodiments, the host is a plant, and plant material provided for commercial production of a polypeptide of interest may be a plant, plant part, plant tissue, or plant cell. In some examples, the plant part may be plant seed. Protein extraction from a plant biomass may be accomplished by known methods which are discussed, for example, in Heney and On (1981) Anal. Biochem. 114:92-6.

Likewise, agronomic genes may be expressed in transformed plant cells, plants, and/or their progeny. For example, a plant may be genetically engineered via methods of particular embodiments to express various phenotypes of agronomic interest from at least one FAD2 locus.

In some embodiments, nucleic acids comprising an agronomic gene or nucleotide sequence encoding a polypeptide of interest may include, for example and without limitation: a gene that confers resistance to a pests or disease (See, e.g., Jones et al. (1994) Science 266:789 (cloning of the tomato Cf-9 gene for resistance to *Cladosporium fulvum*); Martin et al. (1993) Science 262:1432; Mindrinos et al. (1994) Cell 78:1089 (RSP2 gene for resistance to *Pseudomonas syringae*); PCT International Patent Publication No. WO 96/30517 (resistance to soybean cyst nematode); PCT International Patent Publication No. WO 93/19181); a gene that encodes a *Bacillus thuringiensis* protein, a derivative thereof, or a synthetic polypeptide modeled thereon (See, e.g., Geiser et al. (1986) Gene 48:109 (cloning and nucleotide sequence of a Bt δ-endotoxin gene; moreover, DNA molecules encoding δ-endotoxin genes can be purchased from American Type Culture Collection (Manassas, Va.), for example, under ATCC Accession Nos. 40098; 67136; 31995; and 31998)); a gene that encodes a lectin (See, e.g., Van Damme et al. (1994) Plant Molec. Biol. 24:25 (nucleotide sequences of several *Clivia miniata* mannose-binding lectin genes)); a gene that encodes a vitamin-binding protein, e.g., avidin (See PCT International Patent Publication No. US93/06487 (use of avidin and avidin homologues as larvicides against insect pests)); a gene that encodes an enzyme inhibitor, e.g., a protease, proteinase inhibitor, or amylase inhibitor (See, e.g., Abe et al. (1987) J. Biol. Chem. 262:16793 (nucleotide sequence of rice cysteine proteinase inhibitor); Huub et al. (1993) Plant Molec. Biol. 21:985 (nucleotide sequence of cDNA encoding tobacco proteinase inhibitor I); Sumitani et al. (1993) Biosci. Biotech. Biochem. 57:1243 (nucleotide sequence of *Streptomyces nitrosporeus* alpha-amylase inhibitor) and U.S. Pat. No. 5,494,813); a gene encoding an insect-specific hormone or pheromone, e.g., an ecdysteroid or juvenile hormone, a variant thereof, a mimetic based thereon, or an antagonist or agonist thereof (See, e.g., Hammock et al. (1990) Nature 344:458 (baculovirus expression of cloned juvenile hormone esterase, an inactivator of juvenile hormone)); a gene encoding an insect-specific peptide or neuropeptide that, upon expression, disrupts the physiology of the affected pest (See, e.g., Regan (1994) J. Biol. Chem. 269:9 (expression cloning yields DNA coding for insect diuretic hormone receptor); Pratt et al. (1989) Biochem. Biophys. Res. Comm. 163:1243 (an allostatin in *Diploptera puntata*); and U.S. Pat. No. 5,266,317 (genes encoding insect-specific, paralytic neurotoxins)); a gene encoding an insect-specific venom produced in nature by a snake, a wasp, or other organism (See, e.g., Pang et al. (1992) Gene 116:165 (heterologous expression in plants of a gene coding for a scorpion insectotoxic peptide)); a gene encoding an enzyme responsible for a hyperaccumulation of a monoterpene, a sesquiterpene, a steroid, hydroxamic acid, a phenylpropanoid derivative or other molecule with insecticidal activity; a gene encoding an enzyme involved in the modification, including the post-translational modification, of a biologically active molecule, e.g., a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, or a glucanase, whether natural or synthetic (See, e.g., PCT International Patent Publication No. WO 93/02197 (nucleotide sequence of a callase gene); moreover, DNA molecules containing chitinase-encoding sequences can be obtained, for example, from the ATCC, under Accession Nos. 39637 and 67152; Kramer et al. (1993) Insect Biochem. Molec. Biol. 23:691 (nucleotide sequence of a cDNA encoding tobacco hornworm chitinase); and Kawalleck et al. (1993) Plant Molec. Biol. 21:673 (nucleotide sequence of the parsley ubi4-2 polyubiquitin gene)); a gene encoding a molecule that stimulates signal transduction (See, e.g., Botella et al. (1994) Plant Molec. Biol. 24:757 (nucleotide sequences for mung bean calmodulin cDNA clones); and Griess et al. (1994) Plant Physiol. 104:1467 (nucleotide sequence of a maize calmodulin cDNA clone)); a gene that encodes a hydrophobic moment peptide (See, e.g., PCT International Patent Publication No. WO 95/16776 (peptide derivatives of Tachyplesin which inhibit fungal plant pathogens); and PCT International Patent Publication No. WO 95/18855 (synthetic antimicrobial peptides that confer disease resistance)); a gene that encodes a membrane permease, a channel former, or a channel blocker (See, e.g., Jaynes et al. (1993) Plant Sci 89:43 (heterologous expression of a cecropin-β lytic peptide analog to render transgenic tobacco plants resistant to *Pseudomonas solanacearum*)); a gene that encodes a viral-invasive protein or complex toxin derived therefrom (See, e.g., Beachy et al. (1990) Ann. rev. Phytopathol. 28:451); a gene that encodes an insect-specific antibody or immunotoxin derived therefrom (See, e.g., Taylor et al., Abstract #497, Seventh Intl Symposium on Molecular Plant-Microbe Interactions (Edinburgh, Scotland) (1994) (enzymatic inactivation in transgenic tobacco via production of single-chain antibody fragments)); a gene encoding a virus-specific antibody (See, e.g., Tavladoraki et al. (1993) Nature 366:469 (transgenic plants expressing recombinant antibody genes are protected from virus attack)); a gene encoding a developmental-arrestive protein produced in nature by a pathogen or a parasite (See, e.g., Lamb et al. (1992) Bio/Technology 10:1436 (fungal endo α-1,4-D-polygalacturonases facilitate fungal colonization and plant nutrient release by solubilizing plant cell wall homo-α-1,4-D-galacturonase); Toubart et al. (1992) Plant J. 2:367 (cloning and characterization of a gene which encodes a bean endopolygalacturonase-inhibiting protein)); a gene encoding a developmental-arrestive protein produced in nature by a plant (See, e.g., Logemann et al. (1992) Bio/Technology 10:305 (transgenic plants expressing the barley ribosome-inactivating gene have an increased resistance to fungal disease)).

In some embodiments, nucleic acids comprising an agronomic gene or nucleotide sequence encoding a polypeptide of interest may also and/or alternatively include, for example and without limitation: genes that confer resistance to an herbicide, such as an herbicide that inhibits the growing point or meristem, for example, an imidazolinone or a sulfonylurea (exemplary genes in this category encode mutant ALS and AHAS enzymes, as described, for example, by Lee et al. (1988) EMBO J. 7:1241, and Mild et al. (1990) Theor. Appl. Genet. 80:449, respectively); glyphosate resistance as conferred by, e.g., mutant 5-enolpyruvylshikimate-3-phosphate synthase (EPSPs) genes (via the introduction of recombinant nucleic acids and/or various forms of in vivo mutagenesis of native EPSPs genes (including but not limited to CP4, DMMG, and DGT-28); aroA genes and glyphosate acetyl transferase (GAT) genes, respectively); other phosphono compounds, such as glufosinate phosphinothricin acetyl transferase (PAT) genes from *Streptomyces* species, including *Streptomyces hygroscopicus* and *Streptomyces viridichromogenes*); and pyridinoxy or phenoxy proprionic acids and cyclohexones (ACCase inhibitor-encoding genes). See, e.g., U.S. Pat. Nos. 4,940,835 and 6,248,876 (nucleotide sequences of forms of EPSPs which can confer glyphosate resistance to a plant). A DNA molecule encoding a mutant aroA gene can be obtained under ATCC accession number 39256. See also U.S. Pat. No. 4,769,061 (nucleotide sequence of a mutant aroA gene). European patent application No. 0 333 033 and U.S. Pat. No. 4,975,374 disclose nucleotide sequences of glutamine synthetase genes, which may confer resistance to herbicides such as L-phosphinothricin. Nucleotide sequences of exemplary PAT genes are provided in European application No. 0 242 246, and DeGreef et al. (1989) Bio/Technology 7:61 (production of transgenic plants that express chimeric bar genes coding for PAT activity). Exemplary of genes conferring resistance to phenoxy proprionic acids and cyclohexones, such as sethoxydim and haloxyfop, include the Accl-S1, Accl-S2 and Accl-S3 genes described by Marshall et al. (1992) Theor. Appl. Genet. 83:435. GAT genes capable of conferring glyphosate resistance are described, for example, in WO 2005012515. Genes conferring resistance to 2,4-D, phenoxyproprionic acid and pyridyloxy auxin herbicides are described, for example, in WO 2005107437 and WO 2007053482.

Nucleic acids comprising an agronomic gene or nucleotide sequence encoding a polypeptide of interest may also include, for example and without limitation: a gene conferring resistance to an herbicide that inhibits photosynthesis, such as a triazine (psbA and gs+ genes) or a benzonitrile (nitrilase gene). See, e.g., Przibila et al. (1991) Plant Cell 3:169 (transformation of *Chlamydomonas* with plasmids encoding mutant psbA genes). Nucleotide sequences for nitrilase genes are disclosed in U.S. Pat. No. 4,810,648, and DNA molecules containing these genes are available under ATCC Accession Nos. 53435; 67441; and 67442. See also Hayes et al. (1992) Biochem. J. 285:173 (cloning and expression of DNA coding for a glutathione S-transferase).

In some embodiments, nucleic acids comprising an agronomic gene or nucleotide sequence encoding a polypeptide of interest may also and/or alternatively include, genes that confer or contribute to a value-added trait, for example and without limitation: modified fatty acid metabolism, e.g., by transforming a plant with an antisense gene of stearyl-ACP desaturase to increase stearic acid content of the plant (See, e.g., Knultzon et al. (1992) Proc. Natl. Acad. Sci. U.S.A. 89:2624); decreased phytate content, e.g., introduction of a phytase-encoding gene may enhance breakdown of phytate, adding more free phosphate to the transformed plant (See, e.g., Van Hartingsveldt et al. (1993) Gene 127:87 (nucleotide sequence of an *Aspergillus niger* phytase gene); a gene may be introduced to reduce phytate content-in maize, for example, this may be accomplished by cloning and then reintroducing DNA associated with the single allele which may be responsible for maize mutants characterized by low levels of phytic acid (See Raboy et al. (1990) Maydica 35:383)); and modified carbohydrate composition effected, e.g., by transforming plants with a gene encoding an enzyme that alters the branching pattern of starch (See, e.g., Shiroza et al. (1988) J. Bacteol. 170:810 (nucleotide sequence of *Streptococcus* mutant fructosyltransferase gene); Steinmetz et al. (1985) Mol. Gen. Genet. 20:220 (levansucrase gene); Pen et al. (1992) Bio/Technology 10:292 (α-amylase); Elliot et al. (1993) Plant Molec. Biol. 21:515 (nucleotide sequences of tomato invertase genes); Sogaard et al. (1993) J. Biol. Chem. 268:22480 (barley α-amylase gene); and Fisher et al. (1993) Plant Physiol. 102:1045 (maize endosperm starch branching enzyme II)).

In some embodiments, an exogenous nucleic acid is integrated at a FAD2 locus, so as to modify the FAD2 locus, wherein the nucleic acid comprises a PTU or ELP, such that, for example, the subsequent site-specific integration of a second exogenous nucleic acid at the site of the PTU or ELP is facilitated. See, also, U.S. application Ser. No. 13/889,162.

Targeting endonuclease-mediated integration of a nucleic acid molecule of interest into a plant genome via targeted integration requires delivery of targeting endonucleases or targeting endonuclease-encoding nucleic acid molecules, followed by expression of a functional targeting endonuclease protein in the host. An exogenous nucleic acid is preferably also be present in the host cell at the same time as the targeting endonuclease is delivered or expressed therein, such that functional targeting endonuclease protein induces double-stranded breaks at the target site(s) in the at least one FAD2 locus, which are then repaired, for example via homology-driven integration of the exogenous nucleic acid into the locus. One skilled in the art may envision that expression of a functional targeting endonuclease protein may be achieved by several methods, including, but not limited to, transgenesis of a targeting endonuclease-encoding construct, and transient expression of a targeting endonuclease-encoding construct. In both these cases, expression of a functional targeting endonuclease protein and delivery of an exogenous nucleic acid in the host cell may be simultaneously achieved in order to drive targeted integration at a FAD2 locus.

A particular advantage obtained in embodiments utilizing ZFNs as targeting endonucleases, is that the requirement for dimerization of cleavage domains of chimeric zinc finger nucleases imparts a high level of sequence, and hence cleavage, specificity. Since each set of three fingers binds nine consecutive base pairs, two chimeric nucleases effectively demand an 18 bp target if each zinc finger domain has perfect specificity. Any given sequence of this length is predicted to be unique within a single genome (assuming approximately $10^9$ bp). Bibikova et al. (2001) Mol. Cell. Biol. 21(1):289-97; Wu et al. (2007), supra. Furthermore, additional fingers can provide enhanced specificity, Beerli et al. (1998) Proc. Natl. Acad. Sci. USA 95:14628-33; Kim and Pabo (1998) Proc. Natl. Acad. Sci. USA 95:2812-7; Liu et al. (1997) Proc. Natl. Acad. Sci. USA 94:5525-30, so the number of zinc fingers in each DNA-binding domain may be increased to provide even further specificity. For example, specificity may be further increased by using a pair of 4-, 5-, 6- or more finger ZFNs that recognize a 24 bp sequence. Urnov et al. (2005) Nature 435:646-51. Thus, ZFNs may be used such that a recognition sequence is introduced into the host plant genome is unique within the genome.

B. Nucleic Acid Molecules Comprising a Nucleotide Sequence Encoding a Targeting Endonuclease In some embodiments, a nucleotide sequence encoding a targeting endonuclease may be engineered by manipulation (e.g., ligation) of native nucleotide sequences encoding polypeptides comprised within the targeting endonuclease. For example, the nucleotide sequence of a gene encoding a protein comprising a DNA-binding polypeptide may be inspected to identify the nucleotide sequence of the gene that corresponds to the DNA-binding polypeptide, and that nucleotide sequence may be used as an element of a nucleotide sequence encoding a targeting endonuclease comprising the DNA-binding polypeptide. Alternatively, the amino acid sequence of a targeting endonuclease may be used to deduce a nucleotide sequence encoding the targeting endonuclease, for example, according to the degeneracy of the genetic code.

In exemplary nucleic acid molecules comprising a nucleotide sequence encoding a targeting endonuclease, the last codon of a first polynucleotide sequence encoding a nuclease polypeptide, and the first codon of a second polynucleotide sequence encoding a DNA-binding polypeptide, may be separated by any number of nucleotide triplets, e.g., without coding for an intron or a "STOP." Likewise, the last codon of a nucleotide sequence encoding a first polynucleotide sequence encoding a DNA-binding polypeptide, and the first codon of a second polynucleotide sequence encoding a nuclease polypeptide, may be separated by any number of nucleotide triplets. In these and further embodiments, the last codon of the last (i.e., most 3' in the nucleic acid sequence) of a first polynucleotide sequence encoding a nuclease polypeptide, and a second polynucleotide sequence encoding a DNA-binding polypeptide, may be fused in phase-register with the first codon of a further polynucleotide coding sequence directly contiguous thereto, or separated therefrom by no more than a short peptide sequence, such as that encoded by a synthetic nucleotide linker (e.g., a nucleotide linker that may have been used to achieve the fusion). Examples of such further polynucleotide sequences include, for example and without limitation, tags, targeting peptides, and enzymatic cleavage sites. Likewise, the first codon of the most 5' (in the nucleic acid sequence) of the first and second polynucleotide sequences may be fused in phase-register with the last codon of a further polynucleotide coding sequence directly contiguous thereto, or separated therefrom by no more than a short peptide sequence.

A sequence separating polynucleotide sequences encoding functional polypeptides in a targeting endonuclease (e.g., a DNA-binding polypeptide and a nuclease polypeptide) may, for example, include any sequence, such that the amino acid sequence encoded is not likely to significantly alter the translation of the targeting endonuclease. Due to the autonomous nature of known nuclease polypeptides and known DNA-binding polypeptides, intervening sequences will not in examples interfere with the respective functions of these structures.

C. Vectors and Expression Constructs

In some embodiments, at least one nucleic acid molecule(s) comprising at least one exogenous polynucleotide sequence encoding a polypeptide of interest, and/or a targeting endonuclease, may be introduced into a cell, tissue, or organism for expression therein. For example, a nucleic acid molecule comprising a polynucleotide sequence encoding a targeting endonuclease that specifically recognizes a nucleotide sequence comprised within at least one FAD2 locus may be introduced into a cell for expression of the targeting endonuclease, and a nucleic acid molecule comprising a polynucleotide sequence encoding a polypeptide of interest may be introduced into the cell, such that the polynucleotide sequence encoding the polypeptide of interest is integrated into the at least one FAD2 locus, e.g., by homologous recombination following introduction of a double strand break at the locus by the expressed targeting endonuclease, and the polypeptide of interest is expressed from the integrated polynucleotide sequence.

In some embodiments, a nucleic acid molecule such as one of the foregoing may, for example, be a vector system including, for example and without limitation, a linear plasmid, or a closed circular plasmid. In particular examples, the vector may be an expression vector. Nucleic acid sequences according to particular embodiments may, for example, be integrated into a vector, such that the nucleic acid sequence is operably linked to one or more regulatory sequences. Many vectors are available for this purpose, and selection of the particular vector may depend, for example, on the size of the nucleic acid to be inserted into the vector, the particular host cell to be transformed with the vector, and/or the amount of any encoded polypeptide that is desired to be expressed. A vector typically contains various components, the identity of which depend on a function of the vector (e.g., amplification of DNA or expression of DNA), and the particular host cell(s) with which the vector is compatible.

In some embodiments, a regulatory sequence operably linked to one or more coding sequence(s) may be a promoter sequence that functions in a host cell, such as a bacterial cell, algal cell, fungal cell, or plant cell, wherein the nucleic acid molecule is to be amplified or expressed. Some embodiments may include a plant transformation vector that comprises a nucleotide sequence comprising at least one regulatory sequence operably linked to one or more nucleotide sequence(s) encoding a polypeptide of interest or a targeting endonuclease, wherein the one or more nucleotide sequence(s) may be expressed, under the control of the regulatory sequence(s), in a plant cell, tissue, or organism to produce the polypeptide of interest or the targeting endonuclease.

Promoters suitable for use in nucleic acid molecules according to some embodiments include those that are inducible, tissue-specific, viral, synthetic, or constitutive, all of which are well known in the art. Non-limiting examples of promoters that may be useful in embodiments of the invention are provided by: U.S. Pat. No. 6,437,217 (maize RS81 promoter); U.S. Pat. No. 5,641,876 (rice actin promoter); U.S. Pat. No. 6,426,446 (maize RS324 promoter); U.S. Pat. No. 6,429,362 (maize PR-1 promoter); U.S. Pat. No. 6,232,526 (maize A3 promoter); U.S. Pat. No. 6,177,611 (constitutive maize promoters); U.S. Pat. Nos. 5,322,938, 5,352,605, 5,359,142, and 5,530,196 (35S promoter); U.S. Pat. No. 6,433,252 (maize L3 oleosin promoter); U.S. Pat. No. 6,429,357 (rice actin 2 promoter, and rice actin 2 intron); U.S. Pat. No. 6,294,714 (light-inducible promoters); U.S. Pat. No. 6,140,078 (salt-inducible promoters); U.S. Pat. No. 6,252,138 (pathogen-inducible promoters); U.S. Pat. No. 6,175,060 (phosphorous deficiency-inducible promoters); U.S. Pat. No. 6,388,170 (bidirectional promoters); U.S. Pat. No. 6,635,806 (gamma-coixin promoter); U.S. Pat. No. 5,447,858 (soybean heat shock promoter); and U.S. patent application Ser. No. 09/757,089 (maize chloroplast aldolase promoter).

Additional exemplary promoters include the nopaline synthase (NOS) promoter (Ebert et al. (1987) Proc. Natl. Acad. Sci. USA 84(16):5745-9); the octopine synthase (OCS) promoter (which is carried on tumor-inducing plasmids of *Agrobacterium tumefaciens*); the caulimovirus promoters such as the cauliflower mosaic virus (CaMV) 19S promoter (Lawton et al. (1987) Plant Mol. Biol. 9:315-24); the CaMV 35S promoter (Odell et al. (1985) Nature 313: 810-2; the figwort mosaic virus 35S-promoter (Walker et al. (1987) Proc. Natl. Acad. Sci. USA 84(19):6624-8); the sucrose synthase promoter (Yang and Russell (1990) Proc. Natl. Acad. Sci. USA 87:4144-8); the R gene complex promoter (Chandler et al. (1989) Plant Cell 1:1175-83); the chlorophyll a/b binding protein gene promoter; CaMV35S (U.S. Pat. Nos. 5,322,938, 5,352,605, 5,359,142, and 5,530, 196); FMV35S (U.S. Pat. Nos. 6,051,753, and 5,378,619); a PC1SV promoter (U.S. Pat. No. 5,850,019); the SCP1 promoter (U.S. Pat. No. 6,677,503); and AGRtu.nos promoters (GenBank Accession No. V00087; Depicker et al. (1982) J. Mol. Appl. Genet. 1:561-73; Bevan et al. (1983) Nature 304:184-7).

In particular embodiments, nucleic acid molecules may comprise a tissue-specific promoter. A tissue-specific promoter is a nucleotide sequence that directs a higher level of transcription of an operably linked nucleotide sequence in the tissue for which the promoter is specific, relative to the other tissues of the organism. Examples of tissue-specific promoters include, without limitation: tapetum-specific promoters; anther-specific promoters; pollen-specific promoters (See, e.g., U.S. Pat. No. 7,141,424, and International PCT Publication No. WO 99/042587); ovule-specific promoters; (See, e.g., U.S. Patent Application No. 2001/047525 A1); fruit-specific promoters (See, e.g., U.S. Pat. Nos. 4,943,674, and 5,753,475); and seed-specific promoters (See, e.g., U.S. Pat. Nos. 5,420,034, and 5,608,152). In some embodiments, a developmental stage-specific promoter (e.g., a promoter active at a later stage in development) may be used.

Additional regulatory sequences that may in some embodiments be operably linked to a nucleic acid molecule include 5' UTRs located between a promoter sequence and a coding sequence that function as a translation leader sequence. The translation leader sequence is present in the fully-processed mRNA, and it may affect processing of the primary transcript, and/or RNA stability. Examples of translation leader sequences include maize and petunia heat shock protein leaders (U.S. Pat. No. 5,362,865), plant virus coat protein leaders, plant rubisco leaders, and others. See, e.g., Turner and Foster (1995) Molecular Biotech. 3(3):225-36. Non-limiting examples of 5' UTRs are provided by: GmHsp (U.S. Pat. No. 5,659,122); PhDnaK (U.S. Pat. No. 5,362,865); AtAntl; TEV (Carrington and Freed (1990) J. Virol. 64:1590-7); and AGRtunos (GenBank Accession No. V00087; and Bevan et al. (1983), supra).

Additional regulatory sequences that may in some embodiments be operably linked to a nucleic acid molecule also include 3' non-translated sequences, 3' transcription termination regions, or poly-adenylation regions. These are genetic elements located downstream of a nucleotide sequence, and include polynucleotides that provide polyadenylation signal, and/or other regulatory signals capable of affecting transcription or mRNA processing. The polyadenylation signal functions in plants to cause the addition of polyadenylate nucleotides to the 3' end of the mRNA precursor. The polyadenylation sequence can be derived from a variety of plant genes, or from T-DNA genes. A non-limiting example of a 3' transcription termination region is the nopaline synthase 3' region (nos 3'; Fraley et al. (1983) Proc. Natl. Acad. Sci. USA 80:4803-7). An example of the use of different 3' nontranslated regions is provided in Ingelbrecht et al. (1989) Plant Cell 1:671-80. Non-limiting examples of polyadenylation signals include one from a *Pisum sativum* RbcS2 gene (Ps.RbcS2-E9; Coruzzi et al. (1984) EMBO J. 3:1671-9) and AGRtu.nos (GenBank Accession No. E01312).

Additional information regarding regulatory sequences that may be useful in particular embodiments is described, for example, in Goeddel (1990) "Gene Expression Technology," Methods Enzymol. 185, Academic Press, San Diego, Calif.

A recombinant nucleic acid molecule or vector may comprise a selectable marker that confers a selectable phenotype on a transformed cell, such as a plant cell. Selectable markers may also be used to select for cells or organisms that comprise a nucleic acid molecule comprising the selectable marker. A marker may encode biocide resistance, antibiotic resistance (e.g., kanamycin, Geneticin (G418), bleomycin, and hygromycin), or herbicide resistance (e.g., glyphosate). Examples of selectable markers include, but are not limited to: a neo gene that confers kanamycin resistance and can be selected for using, e.g., kanamycin and G418; a bar gene that confers bialaphos resistance; a mutant EPSP synthase gene that confers glyphosate resistance; a nitrilase gene that confers resistance to bromoxynil; a mutant acetolactate synthase gene (ALS) that confers imidazolinone or sulfonylurea resistance; and a methotrexate-resistant DHFR gene. Multiple selectable markers are available that confer resistance to chemical agents including, for example and without limitation, ampicillin; bleomycin; chloramphenicol; gentamycin; hygromycin; kanamycin; lincomycin; methotrexate; phosphinothricin; puromycin; spectinomycin; rifampicin; streptomycin; and tetracycline. Examples of such selectable markers are illustrated in, e.g., U.S. Pat. Nos. 5,550,318; 5,633,435; 5,780,708 and 6,118,047.

A nucleic acid molecule or vector may also or alternatively include a screenable marker. Screenable markers may be used to monitor expression. Exemplary screenable markers include a β-glucuronidase or uidA gene (GUS) which encodes an enzyme for which various chromogenic substrates are known (Jefferson et al. (1987) Plant Mol. Biol. Rep. 5:387-405); an R-locus gene, which encodes a product that regulates the production of anthocyanin pigments (red color) in plant tissues (Dellaporta et al. (1988) "Molecular cloning of the maize R-nj allele by transposon tagging with Ac." *In 18th Stadler Genetics Symposium*, P. Gustafson and R. Appels, eds., Plenum, N.Y. (pp. 263-82); a β-lactamase gene (Sutcliffe et al. (1978) Proc. Natl. Acad. Sci. USA 75:3737-41); a gene which encodes an enzyme for which various chromogenic substrates are known (e.g., PADAC, a chromogenic cephalosporin); a luciferase gene (Ow et al. (1986) Science 234:856-9); a xylE gene that encodes a catechol dioxygenase that converts chromogenic catechols (Zukowski et al. (1983) Gene 46(2-3):247-55); an amylase gene (Ikatu et al. (1990) Bio/Technol. 8:241-2); a tyrosinase gene which encodes an enzyme capable of oxidizing tyrosine to DOPA and dopaquinone, which in turn condenses to melanin (Katz et al. (1983) J. Gen. Microbiol. 129:2703-14); and an α-galactosidase.

All of the nucleotide sequences that encode, for example, a particular polypeptide of interest or a particular targeting endonuclease, will be immediately recognizable by those of skill in the art. The degeneracy of the genetic code provides a finite number of coding sequences for a particular amino acid sequence. The selection of a particular sequence to encode a polypeptide according to embodiments of the invention is within the discretion of the practitioner. Different coding sequences may be desirable in different applications.

In some embodiments, it may be desirable to modify the nucleotides of a nucleic acid, for example, to enhance expression of a polynucleotide sequence comprised within the nucleic acid in a particular host. The genetic code is redundant with 64 possible codons, but most organisms preferentially use a subset of these codons. The codons that are utilized most often in a species are called optimal codons, and those not utilized very often are classified as rare or low-usage codons. Zhang et al. (1991) Gene 105: 61-72. Codons may be substituted to reflect the preferred codon usage of a particular host in a process sometimes referred to as "codon optimization." Optimized coding sequences containing codons preferred by a particular prokaryotic or eukaryotic host may be prepared, for example, to increase the rate of translation or to produce recombinant RNA transcripts having desirable properties (e.g., a longer half-life, as compared with transcripts produced from a non-optimized sequence).

Nucleic acids may be introduced into a host cell in embodiments of the invention by any method known to those of skill in the art, including, for example and without limitation: by transformation of protoplasts (See, e.g., U.S. Pat. No. 5,508,184); by desiccation/inhibition-mediated DNA uptake (See, e.g., Potrykus et al. (1985) Mol. Gen. Genet. 199:183-8); by electroporation (See, e.g., U.S. Pat. No. 5,384,253); by agitation with silicon carbide fibers (See, e.g., U.S. Pat. Nos. 5,302,523 and 5,464,765); by *Agrobacterium*-mediated transformation (See, e.g., U.S. Pat. Nos. 5,563,055, 5,591,616, 5,693,512, 5,824,877, 5,981,840, and 6,384,301); and by acceleration of DNA-coated particles (See, e.g., U.S. Pat. Nos. 5,015,580, 5,550,318, 5,538,880, 6,160,208, 6,399,861, and 6,403,865). Through the application of techniques such as these, the cells of virtually any species may be stably transformed. In some embodiments, transforming DNA is integrated into the genome of the host cell. In the case of multicellular species, transgenic cells may be regenerated into a transgenic organism. Any of these techniques may be used to produce a transgenic plant, for example, comprising one or more nucleic acid sequences of the invention in the genome of the transgenic plant.

The most widely-utilized method for introducing an expression vector into plants is based on the natural transformation system of *Agrobacterium*. *A. tumefaciens* and *A. rhizogenes* are plant pathogenic soil bacteria that genetically transform plant cells. The $T_i$ and $R_i$ plasmids of *A. tumefaciens* and *A. rhizogenes*, respectively, carry genes responsible for genetic transformation of the plant. The $T_i$ (tumor-inducing)-plasmids contain a large segment, known as T-DNA, which is transferred to transformed plants. Another segment of the $T_i$ plasmid, the vir region, is responsible for T-DNA transfer. The T-DNA region is bordered by left-hand and right-hand borders that are each composed of terminal repeated nucleotide sequences. In some modified binary vectors, the tumor-inducing genes have been deleted, and the functions of the vir region are utilized to transfer foreign DNA bordered by the T-DNA border sequences. The T-region may also contain, for example, a selectable marker for efficient recovery of transgenic plants and cells, and a multiple cloning site for inserting sequences for transfer such as a nucleic acid encoding a fusion protein of the invention.

Thus, in some embodiments, a plant transformation vector is derived from a $T_i$ plasmid of *A. tumefaciens* (See, e.g., U.S. Pat. Nos. 4,536,475, 4,693,977, 4,886,937, and 5,501, 967; and European Patent EP 0 122 791) or a $R_i$ plasmid of *A. rhizogenes*. Additional plant transformation vectors include, for example and without limitation, those described by Herrera-Estrella et al. (1983) Nature 303:209-13; Bevan et al. (1983), supra; Klee et al. (1985) Bio/Technol. 3:637-42; and in European Patent EP 0 120 516, and those derived from any of the foregoing. Other bacteria, such as *Sinorhizobium, Rhizobium*, and *Mesorhizobium*, that naturally interact with plants can be modified to mediate gene transfer to a number of diverse plants. These plant-associated symbiotic bacteria can be made competent for gene transfer by acquisition of both a disarmed $T_i$ plasmid and a suitable binary vector.

After providing exogenous DNA to recipient cells, transformed cells are generally identified for further culturing and plant regeneration. In order to improve the ability to identify transformed cells, one may desire to employ a selectable or screenable marker gene, as previously set forth, with the vector used to generate the transformant. In the case where a selectable marker is used, transformed cells are identified within the potentially transformed cell population by exposing the cells to a selective agent or agents. In the case where a screenable marker is used, cells may be screened for the desired marker gene trait.

Cells that survive the exposure to the selective agent, or cells that have been scored positive in a screening assay, may be cultured in media that supports regeneration of plants. In some embodiments, any suitable plant tissue culture media (e.g., MS and N6 media) may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

To confirm the presence of a nucleic acid molecule of interest (for example, a nucleotide sequence encoding a polypeptide comprising at least one fusion protein of the invention) in a regenerating plant, a variety of assays may be performed. Such assays include, for example: molecular biological assays, such as Southern and Northern blotting, PCR, and nucleic acid sequencing; biochemical assays, such as detecting the presence of a protein product, e.g., by immunological means (ELISA and/or Western blots) or by enzymatic function; plant part assays, such as leaf or root assays; and analysis of the phenotype of the whole regenerated plant.

Integration events may be analyzed, for example, by PCR amplification using, e.g., oligonucleotide primers that are specific for a nucleotide sequence of interest. PCR genotyping is understood to include, but not be limited to, polymerase-chain reaction (PCR) amplification of genomic DNA derived from isolated host plant tissue predicted to contain a nucleic acid molecule of interest integrated into the genome, followed by standard cloning and sequence analysis of PCR amplification products. Methods of PCR genotyping have been well described (see, e.g., Rios, G. et al. (2002) Plant J. 32:243-53), and may be applied to genomic DNA derived from any plant species or tissue type, including cell cultures.

A transgenic plant formed using *Agrobacterium*-dependent transformation methods typically contains a single to multiple copies of recombinant DNA. The single recombinant DNA sequence is referred to as a "transgenic event" or "integration event." Such transgenic plants are heterozygous for the inserted DNA sequence. In some embodiments, a transgenic plant homozygous with respect to a transgene may be obtained by sexually mating (selfing) an independent segregant transgenic plant that contains a single exogenous gene sequence to itself, for example, an $F_0$ plant, to produce $F_1$ seed. One fourth of the $F_1$ seed produced will be homozygous with respect to the transgene. Germinating $F_1$ seed results in plants that can be tested for heterozygosity, typically using a SNP assay or a thermal amplification assay that allows for the distinction between heterozygotes and homozygotes (i.e., a zygosity assay).

In addition to direct transformation of a plant or plant cell with a nucleic acid molecule in some embodiments, transgenic plants may be prepared in particular embodiments by crossing a first plant having at least one transgenic event with a second plant lacking such an event. For example, a nucleic acid comprising at least one modified FAD2 locus, wherein an exogenous nucleic acid has been integrated in a site-specific manner, may be introduced into a first plant line that is amenable to transformation, to produce a transgenic plant, which transgenic plant may be crossed with a second plant line to introgress the at least one modified FAD2 locus (and therefore the exogenous nucleic acid) into the second plant line.

To confirm the presence of a nucleic acid molecule of interest in regenerating plants, a variety of assays may be performed. Such assays include, for example: molecular biological assays, such as Southern and Northern blotting and PCR; biochemical assays, such as detecting the presence of a protein product, e.g., by immunological means (ELISA and/or Western blots) or by enzymatic function; plant part assays, such as leaf or root assays; and analysis of the phenotype of the whole regenerated plant.

Targeted integration events may be screened, for example, by PCR amplification using, e.g., oligonucleotide primers specific for nucleic acid molecules of interest. PCR genotyping is understood to include, but not be limited to, polymerase-chain reaction (PCR) amplification of genomic DNA derived from isolated host plant callus tissue predicted to contain a nucleic acid molecule of interest integrated into the genome, followed by standard cloning and sequence analysis of PCR amplification products. Methods of PCR genotyping have been well described (for example, Rios, G. et al. (2002) Plant J. 32:243-53) and may be applied to genomic DNA derived from any plant species or tissue type, including cell cultures. Combinations of oligonucleotide primers that bind to both target sequence and introduced sequence may be used sequentially or multiplexed in PCR amplification reactions. Oligonucleotide primers designed to anneal to the target site, introduced nucleic acid sequences, and/or combinations of the two are feasible. Thus, PCR genotyping strategies may include (but are not limited to) amplification of specific sequences in the plant genome, amplification of multiple specific sequences in the plant genome, amplification of non-specific sequences in the plant genome, or combinations thereof. One skilled in the art may devise additional combinations of primers and amplification reactions to interrogate the genome. For example, a set of forward and reverse oligonucleotide primers may be designed to anneal to nucleic acid sequence(s) specific for the target outside the boundaries of the introduced nucleic acid sequence.

Forward and reverse oligonucleotide primers may be designed to anneal specifically to an introduced nucleic acid molecule of interest, for example, at a sequence corresponding to a coding region within the nucleic acid molecule of interest, or other parts of the nucleic acid molecule of interest. These primers may be used in conjunction with the primers described above. Oligonucleotide primers may be synthesized according to a desired sequence, and are commercially available (e.g., from Integrated DNA Technologies, Inc., Coralville, Iowa). Amplification may be followed by cloning and sequencing, or by direct sequence analysis of amplification products. One skilled in the art might envision alternative methods for analysis of amplification products generated during PCR genotyping. In one embodiment, oligonucleotide primers specific for the gene target are employed in PCR amplifications.

VI. Transgenic Plants and Plant Materials Comprising a Nucleic Acid Integrated at a FAD2 Performance Locus In some embodiments, a transgenic plant is provided, wherein the plant comprises a plant cell comprising at least one modified (e.g., disrupted and/or targeted integration of an exogenous sequence) FAD2 locus. In particular embodiments, such a plant may be produced by transformation of a plant tissue or plant cell, and regeneration of a whole plant. In further embodiments, such a plant may be obtained through introduction of an exogenous nucleic acid at the at least one FAD2 locus in a site-specific manner, or through introgression of the modified FAD2 locus into a germplasm. Plant materials comprising such a plant cell are also provided. Such a plant material may be obtained from a plant comprising the plant cell.

A transgenic plant or plant material comprising a plant cell comprising at least one modified FAD2 locus may in some embodiments exhibit one or more of the following characteristics: expression of a targeting endonuclease in a cell of the plant; expression of a polypeptide of interest in a cell of the plant (or in a plastid therein); expression of a targeting endonuclease in the nucleus of a cell of the plant; localization of a targeting endonuclease in a cell of the plant; integration at a FAD2 locus in the genome of a cell of the plant; integration of a nucleotide sequence encoding a polypeptide of interest or an agronomic gene at a FAD2 locus in the genome of a cell of the plant; and/or the presence of an RNA transcript corresponding to a coding sequence integrated at a FAD2 locus in the genome of a cell of the plant. Such a plant may additionally have one or more desirable traits, including, for example and without limitation, those resulting from the expression of an endogenous or transgenic nucleotide sequence, the expression of which is regulated by a polypeptide of interest or an agronomic gene integrated at a FAD2 locus in the genome of a cell of the plant; resistance to insects, other pests, and disease-causing agents; tolerances to herbicides; enhanced stability, yield, or shelf-life; environmental tolerances; pharmaceutical production; industrial product production; and nutritional enhancements.

A transgenic plant according to the invention may be any plant capable of being transformed with a nucleic acid that is subsequently integrated in at least one FAD2 locus according to methods described herein. Accordingly, the plant may be a dicot or monocot. Non-limiting examples of dicotyledonous plants usable in the present methods include *Arabidopsis*, alfalfa, beans, broccoli, cabbage, canola, carrot, cauliflower, celery, Chinese cabbage, cotton, cucumber, eggplant, lettuce, melon, pea, pepper, peanut, potato, pumpkin, radish, rapeseed, spinach, soybean, squash, sugarbeet, sunflower, tobacco, tomato, and watermelon. Non-limiting examples of monocotyledonous plants usable in the present methods include corn, barley, onion, rice, sorghum, wheat, rye, millet, sugarcane, oat, triticale, switchgrass, and turfgrass. Transgenic plants according to the invention may be used or cultivated in any manner.

Some embodiments also provide commodity products produced from transgenic plants of the invention. Commodity products include, for example and without limitation: food products, meals, oils, or crushed or whole grains or seeds of a plant comprising one or more nucleotide sequences integrated in at least one FAD2 locus. The detection of one or more such nucleotide sequences in one or more commodity or commodity products is de facto evidence that the commodity or commodity product was at least in part produced from a transgenic plant produced according to an embodiment of the invention. In some embodiments, a transgenic plant or seed comprising a plant cell comprising at least one modified FAD2 locus may comprise at least one other transgenic event in its genome, including without limitation: a transgenic event from which is transcribed an RNAi molecule; a gene encoding an insecticidal protein (e.g., a *Bacillus thuringiensis* insecticidal protein); an herbicide tolerance gene (e.g., a gene providing tolerance to glyphosate); and a gene contributing to a desirable phenotype in the transgenic plant (e.g., increased yield, altered fatty acid metabolism, or restoration of cytoplasmic male sterility).

A transgenic plant comprising a plant cell comprising at least one modified FAD2 locus may have one or more desirable traits. Such traits can include, for example: resistance to insects, other pests, and disease-causing agents; tolerances to herbicides; enhanced stability, yield, or shelf-life; environmental tolerances; pharmaceutical production; industrial product production; and nutritional enhancements. The desirable traits may be conferred by one or more nucleic acid molecules integrated by targeted recombination at the FAD2 locus that are expressed in the plant exhibiting the desirable traits. Thus, in some embodiments, the desired trait can be due to the presence of a transgene(s) in the plant, which is introduced into the genome of the plant at the site of at least one modified FAD2 locus. In an additional embodiment, the desirable trait can be obtained through conventional breeding, which trait may be conferred by one or more nucleic acid molecules integrated by targeted recombination at the at least one modified FAD2 locus.

Transgenic plants according to the invention may be used or cultivated in any manner, wherein presence of at least one modified FAD2 locus is desirable. Accordingly, a plant may be engineered to, inter alia, have one or more desired traits, by being transformed with nucleic acid molecules that are subsequently integrated in a site-specific manner in at least one FAD2 locus according to the invention, and cropped and cultivated by any method known to those of skill in the art.

VII. Marker-Assisted Breeding of Transgenic Plants Comprising a Nucleic Acid Integrated at a FAD2 Performance Locus Molecular markers that are linked (e.g., tightly-linked) to fad2 in *Brasicca* spp. are provided. For example, DNA segments containing sequences involved in the HO trait (fad2) are identified. These segments are located around and between markers that are linked (e.g., tightly-linked) to the mutant alleles in a genomic linkage group. Thus, nucleic acid molecules comprising a mutant FAD2 gene having an inactivating mutation are also provided. The segments identified, and the markers thereof, are included in the present subject matter, in part, by their position in linkage groups in the *B. napus* genome. For example, FAD2 and molecular markers linked thereto may be located in linkage groups N5 and N1.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention. The following examples are provided to illustrate certain particular features and/or embodiments. The examples should not be construed to limit the disclosure to the particular features or embodiments exemplified.

EXAMPLES

Example 1: Identification of FAD2 Target Sequences from a Bacterial Artificial Chromosome Library BAC Library Construction A Bacterial Artificial Chromosome (BAC) library was sourced from a commercial vendor (Amplicon Express, Pullman, Wash.). The BAC library included 110,592 BAC clones containing high molecular weight genomic DNA (gDNA) fragments isolated from *Brassica napus* L. var. *DH*10275. The gDNA was digested with either the BamHI or HindIII restriction enzyme. Isolated gDNA fragments of about 135 Kbp were ligated into the pCC1BAC vector (Epicentre, Madison, Wis.) and transformed into *Escherichia coli* str. DH10B (Invitrogen). The BAC library was made up of an even number of BAC clones that were constructed using the two different restriction enzymes. As such, the Hind III constructed BAC library was contained in 144 individual 384-well plates. Likewise, the BamHI constructed BAC library was contained in 144 individual 384-well plates. A total of 110,592 BAC clones were isolated and arrayed into 288 individual 384-well plates. Each of the 288 individual 384 well plates were provided by the vendor as a single DNA extraction for rapid PCR based screening. The resulting BAC library covers approximately 15 Gbp of gDNA, which corresponds to a 12-fold genome coverage of *Brassica napus* L. var. *DH*10275genome (estimate of the *Brassica napus* L. genome is ca. 1.132 Gbp as described in Johnston et al. (2005) Annals of Botany 95:229-235).

Sequence Analysis of FAD2 Coding Sequences Isolated from the BAC Library

The constructed BAC library was used to isolate FAD2 gene coding sequences. Sequencing experiments were conducted to identify the specific gene sequences of four FAD2 gene paralogs from *Brassica napus* L. var. *DH*10275.

The FAD2 gene sequence was initially identified within the model species *Arabidopsis thaliana*. The gene sequence is listed in Genbank as Locus Tag: At3g12120. Comparative genomic relationships between the model plant species *Arabidopsis thaliana* and the diploid *Brassica rapa*, one of the progenitors of the tetraploid *Brassica napus*, have been previously described. (Schranz et al. (2006) Trends in Plant Science 11(11):535-542). With specific relation to the FAD2 gene the comparative analysis predicted that 3-4 copies of the gene may occur within the diploid *Brassica* genome. Additional genetic mapping studies were completed by Scheffler et al. (1997) Theoretical and Applied Genetics 94; 583-591. The results of these genetic mapping studies indicated that four copies of the FAD2 gene were present in *Brassica napus*.

Sequencing analysis of the BAC library which was constructed from *B. napus* L. var. *DH*12075 resulted in the isolation of four BAC sequences (SEQ ID NO:1, SEQ ID NO:2, SEQ ID NO:3, and SEQ ID NO:4) from which the coding sequences for the FAD2A (SEQ ID NO:5), FAD2-1 (SEQ ID NO:6), FAD2-2 (SEQ ID NO:7), and FAD2-3(SEQ ID NO:8) genes were determined. The FAD2A, FAD2-1, FAD2-2, and FAD2-3 gene sequences were identified and genetically mapped. Sequence analysis of the four FAD2 genes was conducted using a sequence alignment program and a neighbor-joining tree using percentage of identity. The sequence alignment was made via the AlignX® program from the Vector NTI Advance 11.0 computer program (Life Technologies, Carlsbad, Calif.) and is shown in FIG. 1. AlignX® uses a modified Clustal W algorithm to generate multiple sequence alignments of either protein or nucleic acid sequences for similarity comparisons and for annotation.

The neighbour joining tree was created with Jalview v2.3® software and is shown in FIG. 2. (Waterhouse et al. (2009) Bioinformatics 25 (9) 1189-1191). As shown in FIG. 2, the analysis of the isolated sequences indicated that the FAD2A and FAD2-3 sequences shared high levels of sequence similarity and that, likewise, FAD2-1 and FAD2-2 shared high levels of sequence similarity. The four sequences can be categorized in two clades, wherein FAD2A and FAD2-3 comprise a first clade, and FAD2-1 and FAD2-2 comprise a second clade.

Next, the newly isolated FAD2 sequences from *Brassica napus* were used to BLAST genomic libraries isolated from a *Brassica rapa* genomic BAC library and *Brassica oleracea* shotgun genomic sequence reads. Both, *Brassica rapa* and *Brassica oleracea* are diploid progenitors of *Brassica napus* which is an amphidiploid species (AC genome, n=19). *Brassica napus* derived from a recent hybridization event between *Brassica rapa* (A sub-genome, n=10) and *Brassica oleracea* (C sub-genome, n=9). The diploid progenitor sequences were compared to the four different FAD2 coding sequences isolated from *Brassica napus* using a BLASTn analysis. This sequence analysis identified specific, annotated gene sequences from *Brassica rapa* and *Brassica oleracea* which shared the highest sequence similarity to the newly discovered *Brassica napus* FAD2 sequences. Table 1 lists the newly identified FAD2 coding sequence and the corresponding progenitor reference sequence accession number and source organism.

TABLE 1

FAD2 sequences from *Brassica napus* and the corresponding progenitor organism and related FAD sequence accession number.

| Isolated gene sequence | Progenitor organism and sequence accession number | |
|---|---|---|
| FAD2A | *B. rapa* | Genbank Accession No: KBrB063G23 (A05) |
| FAD2-3 | *B. oleracea* | Genbank Accession No: GSS23580801 |
| FAD2-1 | *B. rapa* | Genbank Accession No: KBrB130I19 |
| FAD2-2 | *B. oleracea* | Genbank Accession No: GSS 17735412 |

The FAD2 genes exist in the *Brassica napus* genome as two copies of each gene per sub-genome. One copy of each gene is located on the A sub-genome, and likewise one copy of each gene is located on the C sub-genome. New naming conventions are described to indicate which sub-genome that each gene is located on. The high levels of sequence similarity between the four different FAD2 coding sequences isolated from the *Brassica napus* BAC genomic DNA library and the progenitor sequence data suggest that FAD2-3 is a duplicate of the FAD2 sequence from the C sub-genome and could be relabeled as FAD2C; FAD2-1 is a duplicate of the FAD2 sequence from the A sub-genome and could therefore be labeled as FAD2A'; and finally, FAD2-2 is a second copy that was duplicated from the FAD2 sequence of the C sub-genome and could be labeled as FAD2C'.

PCR Based Screening

A cohort of PCR primers were design to screen the aforementioned BAC library. The primers were designed as either universal primers, which would amplify all members of the gene family, or as gene specific primers for targeted allele amplification. The PCR primers were designed to be 20 bp long (+/−1 bp) and contain a G/C content of 50%

(+/−8%). Table 2 lists the primers which were designed and synthesized. The clones of the BAC library were pooled and screened via the Polymerase Chain Reaction (PCR).

TABLE? 2

PCR primer sequences designed for BAC library screening for FAD2 gene identification.

| Primer Name | SEQ ID NO: | Sequence |
|---|---|---|
| D_UnivF2_F1 | SEQ ID NO: 9 | ATGGGTGCAGGTGGAAGAATG |
| D_UnivF2_F2 | SEQ ID NO: 10 | AGCGTCTCCAGATATACATC |
| D_UnivF2_R1 | SEQ ID NO: 11 | ATGTATATCTGGAGACGCTC |
| D_UnivF2_R2 | SEQ ID NO: 12 | TAGATACACTCCTTCGCCTC |
| D_SpecificF2_F3 | SEQ ID NO: 13 | TCTTTCTCCTACCTCATCTG |
| D_SpecificF2_R3 | SEQ ID NO: 14 | TTCGTAGCTTCCATCGCGTG |
| D_UnivF2_F4 | SEQ ID NO: 15 | GACGCCACCATTCCAACAC |
| D_UnivF2_R4 | SEQ ID NO: 16 | ACTTGCCGTACCACTTGATG |

Two different sets of conditions were used for the polymerase chain reactions (PCR). The first series of PCR reactions contained: 1×PCR buffer (containing dNTPs); 1.5 mM $MgCl_2$; 200 μM of 0.25 U Immolase® DNA polymerase (Bioline, London, UK); 250 nM of each primer; and, about 5-10 ng template DNA. A second series of PCR reactions were developed for the amplification of genomic DNA and contained: 5-10 ng of genomic DNA, 1×PCR buffer, 2 mM dNTPs, 0.4 μM forward and reverse primer, and 0.25 U Immolase® DNA polymerase (Bioline, London, UK). Amplifications were pooled into a final volume of 13 μL and amplified using an MJ PTC200® thermocycler (BioRad, Hercules, Calif.) or an ABI 9700 Gene Amp System® (Life Technologies, Carlsbad, Calif.). PCR based screening of specific plates was conducted using a 4 dimension screening approach based on the screening system described by Bryan et al (Scottish Crops Research Institute annual report: 2001-2002) with the above described PCR conditions. Following PCR based screening of pooled BAC libraries; the amplified PCR product was sequenced using a direct Sanger sequencing method. The amplified products were purified with ethanol, sodium acetate and EDTA following the BigDye® v3.1 protocol (Applied Biosystems) and electrophoresis was performed on an ABI3730xl® automated capillary electrophoresis platform.

Following PCR based screening and conformational Sanger sequencing, a collection of plates were identified that contained the various different FAD2 gene family members. A total of four unique FAD2 paralogous gene sequences were identified (Table 2). A total of two plates per each FAD2 paralogous gene sequence were chosen to undergo plate screening to identify the specific well and clone within the plate that contained the FAD2 gene (Table 3). The specific wells were identified for both of the plates and an individual clone was selected for each of the FAD2 gene family members.

TABLE 3

Identification of the BAC clone plates that provided positive reaction with the detailed PCR primer combinations, along with two plate identities that were taken forward for clone identification within the plate

| Gene Name | Primer Sets | Positive Plate Pools | Chosen Plates | Well Id |
|---|---|---|---|---|
| FAD2A | F4 + R1, F1 + R1, F1 + R4, F3 + R3 | 8, 27, 30, 83, 109, 147, 180, 199, 209, 251, 288 | Plate 199<br>Plate 27 | L23<br>D20 |
| FAD2-1 | F1 + R4, F4 + R1, F1 + R1, F2 + R2 | 12, 89, 123, 148, 269 | Plate 123<br>Plate 148 | N17<br>B15 |
| FAD2-2 | F4 + R1, F1 + R1, F1 + R4, F2 + R2 | 24, 44, 46, 47, 80, 91, 104, 110, 119, 121, 124, 248 | Plate 44<br>Plate 121 | H03<br>A17 |
| FAD2-3 | F1 + R4, F4 + R1, F1 + R1, F3 + R3 | 8, 62, 113, 205, 276 | Plate 62<br>Plate 205 | I16<br>K11 |

The single BAC clone, for each identified FAD gene family member, was further analysed via sequencing. The DNA was isolated for the BAC clone and was prepared for sequencing using a Large Construct Kit® (Qiagen, Valencia, Calif.) following the manufacturer's instructions. The extracted BAC DNA was prepared for sequencing using GS-FLX Titanium Technology® (Roche, Indianapolis, Ind.) following manufacturer's instructions. Sequencing reactions were performed using a physically sectored GS-FLX TI Pico-titer Plate® with the BACs pooled in pairs for optimal data output. The BACs were combined in pairs where the FAD2 gene was paired with a FAD3 gene. All generated sequence data was assembled by Newbler v2.0.01.14® (454 Life Sciences, Branford, Conn.). The assembled contigs were manually assessed for the presence of the corresponding FAD gene using Sequencher v3.7® (GeneCodes, Ann Arbor, Mich.).

After the full genomic sequence of all four FAD2 genes had been identified and fully characterized, zinc finger nucleases were designed to bind to the sequences for each specific gene family member.

Example 2: Design of Zinc Finger Binding Domains Specific to FAD2 Genes

Novel zinc finger proteins directed against DNA sequences encoding various functional sequences of the FAD2 gene locus were designed essentially as previously described. See, e.g., Urnov et al. (2005) Nature 435:646-651. Exemplary target sequence and recognition helices are shown in Table 4 (recognition helix regions designs) and Table 5 (target sites). In Table 5, nucleotides in the target site that are contacted by the ZFP recognition helices are indicated in uppercase letters; non-contacted nucleotides indicated in lowercase.

Zinc Finger Nuclease (ZFN) target sites were designed to bind five target sites of FAD2A. The FAD2A zinc finger designs were incorporated into zinc finger expression vectors encoding a protein having at least one finger with a CCHC structure. See, U.S. Patent Publication No. 2008/0182332. In particular, the last finger in each protein had a CCHC backbone for the recognition helix. The non-canonical zinc finger-encoding sequences were fused to the nuclease domain of the type IIS restriction enzyme FokI (amino acids 384-579 of the sequence of Wah et al., (1998) Proc. Natl. Acad. Sci. USA 95:10564-10569) via a four amino acid ZC linker and an opaque-2 nuclear localization signal derived from *Zea mays* to form FAD2A zinc-finger nucleases (ZFNs). Expression of the fusion proteins was driven by a relatively strong constitutive promoter such as a promoter derived from the Cassava Vein Mosaic Virus (CsVMV) promoter and flanked by the *Agrobacterium tumefaciens* ORF23 3'UnTranslated Region (AtuORF23 3'UTR v1). The self-hydrolyzing 2A encoding nucleotide sequence from Thosea asigna virus (Szymczak et al., 2004) was added between the two Zinc Finger Nuclease fusion proteins that were cloned into the construct. Exemplary vectors or plasmids are described in Table 5, below.

The optimal FAD2 zinc finger nucleases were verified for cleavage activity using a budding yeast based system previously shown to identify active nucleases. See, e.g., U.S. Patent Publication No. 20090111119; Doyon et al. (2008) *Nat. Biotechnol.* 26:702-708; Geurts et al. (2009) *Science* 325:433. Zinc fingers for the various functional domains were selected for in-vivo use. Of the numerous ZFNs that were designed, produced and tested to bind to the putative FAD genomic polynucleotide target sites, eleven ZFNs were identified as having in vivo activity at high levels, and selected for further experimentation. These ZFNs were characterized as being capable of efficiently binding and cleaving the unique FAD2 genomic polynucleotide target sites in planta.

TABLE 4

FAD2 Zinc Finger Designs

| ZFP | F1 | F2 | F3 | F4 | F5 | F6 |
|---|---|---|---|---|---|---|
| 24800 | RSDNLST (SEQ ID NO: 94) | HSHARIK SEQ ID NO: 95 | HRSSLRR SEQ ID NO: 96 | RSDHLSE SEQ ID NO: 97 | QNANRIT SEQ ID NO: 98 | N/A |
| 24801 | DRSNLSR SEQ ID NO: 99 | HRSSLRR SEQ ID NO: 96 | TSGNLTR SEQ ID NO: 101 | MSHHLRD SEQ ID NO: 102 | DQSNLRA SEQ ID NO: 103 | N/A |
| 24794 | QSGNLAR SEQ ID NO: 104 | RSDNLSR SEQ ID NO: 105 | DNNARIN SEQ ID NO: 106 | DRSNLSR SEQ ID NO: 99 | RSDHLTQ SEQ ID NO: 108 | N/A |
| 24795 | RSDNLRE SEQ ID NO: 109 | QSGALAR SEQ ID NO: 110 | QSGNLAR SEQ ID NO: 104 | RSDVLSE SEQ ID NO: 112 | SPSSRRT SEQ ID NO: 113 | N/A |
| 24810 | RSDSLSR SEQ ID NO: 114 | RKDARIT SEQ ID NO: 115 | RSDHLSA SEQ ID NO: 116 | WSSSLYY SEQ ID NO: 117 | NSRNLRN SEQ ID NO: 118 | N/A |
| 24811 | DQSTLRN SEQ ID NO: 119 | DRSNLSR SEQ ID NO: 99 | DRSNLWR SEQ ID NO: 121 | DRSALSR SEQ ID NO: 122 | RSDALAR SEQ ID NO: 123 | N/A |
| 24814 | RSDALSR SEQ ID NO: 124 | DRSDLSR SEQ ID NO: 125 | RSDHLTQ SEQ ID NO: 108 | QSGALAR SEQ ID NO: 110 | QSGNLAR SEQ ID NO: 104 | N/A |
| 24815 | DRSNLSR SEQ ID NO: 99 | DSSARNT SEQ ID NO: 130 | DRSSRKR SEQ ID NO: 131 | QSGDLTR SEQ ID NO: 132 | LAHHLVQ SEQ ID NO: 133 | N/A |
| 24818 | RSDNLST SEQ ID NO: 94 | HSHARIK SEQ ID NO: 95 | TSGHLSR SEQ ID NO: 136 | RSDNLSV SEQ ID NO: 137 | IRSTLRD SEQ ID NO: 138 | N/A |
| 24819 | TSGHLSR SEQ ID NO: 136 | DRSNLSR SEQ ID NO: 99 | HRSSLRR SEQ ID NO: 96 | TSGNLTR SEQ ID NO: 101 | MSHHLRD SEQ ID NO: 102 | N/A |
| 24796 | RSDALSR SEQ ID NO: 124 | DRSDLSR SEQ ID NO: 125 | RSDHLTQ SEQ ID NO: 108 | QSGALAR SEQ ID NO: 110 | QSGNLAR SEQ ID NO: 104 | N/A |
| 24797 | RSAVLSE SEQ ID NO: 149 | TNSNRIT SEQ ID NO: 150 | LKQHLNE SEQ ID NO: 151 | QSGALAR SEQ ID NO: 110 | QSGNLAR SEQ ID NO: 104 | N/A |
| 24836 | DRSNLSR SEQ ID NO: 99 | QSGDLTR SEQ ID NO: 132 | QSGALAR SEQ ID NO: 110 | DRSNLSR SEQ ID NO: 99 | QRTHLTQ SEQ ID NO: 158 | N/A |
| 24837 | RSDNLSN SEQ ID NO: 159 | TNSNRIK SEQ ID NO: 160 | QSSDLSR SEQ ID NO: 161 | QSSDLRR SEQ ID NO: 162 | DRSNRIK SEQ ID NO: 163 | N/A |
| 24844 | RSANLAR SEQ ID NO: 164 | RSDNLTT SEQ ID NO: 165 | QSGELIN SEQ ID NO: 166 | RSADLSR SEQ ID NO: 167 | RSDNLSE SEQ ID NO: 168 | DRSHLAR SEQ ID NO: 169 |

TABLE 4-continued

| FAD2 Zinc Finger Designs | | | | | | |
|---|---|---|---|---|---|---|
| ZFP | F1 | F2 | F3 | F4 | F5 | F6 |
| 24845 | DRSHLAR SEQ ID NO: 169 | RSDNLSE SEQ ID NO: 168 | SKQYLIK SEQ ID NO: 172 | ERGTLAR SEQ ID NO: 173 | RSDHLTT SEQ ID NO: 174 | N/A |
| 24820 | QSGALAR SEQ ID NO: 110 | QSGNLAR SEQ ID NO: 104 | DRSHLAR SEQ ID NO: 169 | DRSDLSR SEQ ID NO: 125 | RSDNLTR SEQ ID NO: 179 | N/A |
| 24821 | DRSHLAR SEQ ID NO: 169 | RSDNLSE SEQ ID NO: 168 | SKQYLIK SEQ ID NO: 172 | ERGTLAR SEQ ID NO: 173 | RSDHLTT SEQ ID NO: 174 | N/A |
| 24828 | DRSDLSR SEQ ID NO: 125 | RSDNLTR SEQ ID NO: 179 | QRTHLTQ SEQ ID NO: 158 | RSDNLSE SEQ ID NO: 168 | ASKTRKN SEQ ID NO: 189 | N/A |
| 24829 | RSDTLSE SEQ ID NO: 190 | QSHNRTK SEQ ID NO: 191 | QSDHLTQ SEQ ID NO: 192 | RSSDLSR SEQ ID NO: 193 | QSSDLSR SEQ ID NO: 161 | RSDHLTQ SEQ ID NO: 108 |
| 24832 | RSDSLSR SEQ ID NO: 114 | RKDARIT SEQ ID NO: 115 | DRSHLSR SEQ ID NO: 198 | QSGNLAR SEQ ID NO: 104 | QSSDLSR SEQ ID NO: 161 | DRSALAR SEQ ID NO: 201 |
| 24833 | RSDDLSK SEQ ID NO: 202 | RSDTRKT SEQ ID NO: 203 | DRSNLSR SEQ ID NO: 99 | DRSNLWR SEQ ID NO: 121 | RSDSLSR SEQ ID NO: 114 | NNDHRKT SEQ ID NO: 207 |

TABLE 5

| Target Sites of FAD2 Zinc Fingers | | | |
|---|---|---|---|
| ZFP | Plasmid No. | Target Site (5' to 3') | ZFP target/binding site present in SEQ ID Nos. |
| 24800 | pDAB104001 | ccCAAAGGGTTGTTGAGgtacttgccgt | SEQ ID NO: 17 |
| 24801 | pDAB104001 | cgCACCGTGATGTTAACggttcagttca | SEQ ID NO: 18 |
| 24794 | pDAB104002 | taAGGGACGAGGAGGAAggagtggaaga | SEQ ID NO: 19 |
| 24795 | pDAB104002 | ttCTCCTGGAAGTACAGtcatcgacgcc | SEQ ID NO: 20 |
| 24810 | pDAB104003 | gtCGCTGAAGGcGTGGTGgccgcactcg | SEQ ID NO: 21 |
| 24811 | pDAB104003 | caGTGGCTgGACGACACCgtcggcctca | SEQ ID NO: 22 |
| 24814 | pDAB104004 | gaGAAGTAAGGGACGAGgaggaaggagt | SEQ ID NO: 23 |
| 24815 | pDAB104004 | gaAGTACAGTCATCGACgccaccattcc | SEQ ID NO: 24 |
| 24818 | pDAB104005 | tcCCAAAGGGTtGTTGAGgtacttgccg | SEQ ID NO: 25 |
| 24819 | pDAB104005 | acCGTGATGTTAACGGTtcagttcactc | SEQ ID NO: 26 |
| 24796 | pDAB104006 | gaGAAGTAAGGGACGAGgaggaaggagt | SEQ ID NO: 23 |
| 24797 | pDAB104006 | tgGAAGTAcAGTCATCGAcgccaccatt | SEQ ID NO: 28 |
| 24836 | pDAB104007 | gtAGAGACcGTAGCAGACggcgaggatg | SEQ ID NO: 29 |
| 24837 | pDAB104007 | gcTACGCTGCTgTCCAAGgagttgcctc | SEQ ID NO: 30 |
| 24844 | pDAB104008 | gaGGCCAGGCGAAGTAGGAGagagggtg | SEQ ID NO: 31 |
| 24845 | pDAB104008 | acTGGGCCTGCCAGGGCtgcgtcctaac | SEQ ID NO: 32 |
| 24820 | pDAB104009 | gaGAGGCCaGGCGAAGTAggagagaggg | SEQ ID NO: 33 |
| 24821 | pDAB104009 | acTGGGCCTGCCAGGGCtgcgtcctaac | SEQ ID NO: 32 |

TABLE 5-continued

| Target Sites of FAD2 Zinc Fingers | | | |
|---|---|---|---|
| ZFP | Plasmid No. | Target Site (5' to 3') | ZFP target/binding site present in SEQ ID Nos. |
| 24828 | pDAB104010 | agGCCCAGtAGAGAGGCCaggcgaagta | SEQ ID NO: 35 |
| 24829 | pDAB104010 | ccAGGGCTGCGTCCTAACCGgcgtctgg | SEQ ID NO: 36 |
| 24832 | pDAB104011 | taGTCGCTGAAGGCGTGGTGgccgcact | SEQ ID NO: 37 |
| 24833 | pDAB104011 | agTGGCTGGACGACaCCGTCGgcctcat | SEQ ID NO: 38 |

Example 3: Evaluation of Zinc Finger Nuclease Cleavage of FAD2 Genes

Construct Assembly

Plasmid vectors containing ZFN expression constructs of the exemplary zinc finger nucleases, which were identified using the yeast assay, as described in Example 2, were designed and completed using skills and techniques commonly known in the art. Each zinc finger-encoding sequence was fused to a sequence encoding an opaque-2 nuclear localization signal (Maddaloni et al. (1989) *Nuc. Acids Res.* 17(18):7532), that was positioned upstream of the zinc finger nuclease.

Next, the opaque-2 nuclear localization signal::zinc finger nuclease fusion sequence was paired with the complementary opaque-2 nuclear localization signal::zinc finger nuclease fusion sequence. As such, each construct included a single open reading frame comprised of two opaque-2 nuclear localization signal::zinc finger nuclease fusion sequences separated by the 2A sequence from Thosea asigna virus (Mattion et al. (1996) *J. Virol.* 70:8124-8127). Expression of the fusion proteins was driven by a relatively strong constitutive promoter such as a promoter derived from the Cassava Vein Mosaic Virus (CsVMV) promoter and flanked by the *Agrobacterium tumefaciens* ORF23 3'UnTranslated Region (AtuORF23 3'UTR).

The vectors were assembled using the IN-FUSION™ Advantage Technology (Clontech, Mountain View, Calif.). Restriction endonucleases were obtained from New England BioLabs (NEB; Ipswich, Mass.) and T4 DNA Ligase (Invitrogen) was used for DNA ligation. Plasmid preparations were performed using NUCLEOSPIN® Plasmid Kit (Macherey-Nagel Inc., Bethlehem, Pa.) or the Plasmid Midi Kit (Qiagen) following the instructions of the suppliers. DNA fragments were isolated using QIAquick Gel Extraction Kit™ (Qiagen) after agarose Tris-acetate gel electrophoresis. Colonies of all assembled plasmids were initially screened by restriction digestion of miniprep DNA. Plasmid DNA of selected clones was sequenced by a commercial sequencing vendor (Eurofins MWG Operon, Huntsville, Ala.). Sequence data were assembled and analyzed using the SEQUENCHER™ software (Gene Codes Corp., Ann Arbor, Mich.). Before delivery to *B. napus* protoplasts, Plasmid DNA was prepared from cultures of *E. coli* using the Pure Yield Plasmid Maxiprep System® (Promega Corporation, Madison, Wis.) or Plasmid Maxi Kit® (Qiagen, Valencia, Calif.) following the instructions of the suppliers.

The resulting eleven plasmid constructs; pDAB104008 (containing the ZFN24845 and ZFN24844 construct), pDAB104009 (containing the ZFN24820 and ZFN24821 construct), pDAB104010 (containing the ZFN24828 and ZFN24829 construct) (FIG. 3), pDAB104003 (containing the ZFN24810 and ZFN24811 construct), pDAB104011 (containing the ZFN24832 and ZFN24833 construct), pDAB104002 (containing the ZFN24794 and ZFN24795 construct), pDAB104006 (containing the ZFN24796 and ZFN24797 construct), pDAB104004 (containing the ZFN24814 and ZFN24815 construct), pDAB104001 (containing the ZFN24800 and ZFN24801 construct), pDAB104005 (containing the ZFN24818 and ZFN24819 construct), and pDAB104007 (containing the ZFN24836 and ZFN24837 construct) were confirmed via restriction enzyme digestion and via DNA sequencing. Table 6 lists the different constructs and the specific FAD2A sequence which each ZFN was designed to cleave and bind.

TABLE 6 lists the Zinc Finger protein binding motif and the corresponding construct number. Each Zinc Finger was designed to bind and cleave the FAD2A which is described in the table

| ZFN Design | Construct No. | Locus ID. | Target Cut Site in FAD2A Sequence |
|---|---|---|---|
| 24844-2A-24845 | pDAB104008 | FAD2_ZFN_Locus1_F2A | 263-265 |
| 24820-2A-24821 | pDAB104009 | FAD2_ZFN_Locus1_F2B | 265 |
| 24828-2A-24829 | pDAB104010 | FAD2_ZFN_Locus1_F2C | 275 |
| 24810-2A-24811 | pDAB104003 | FAD2_ZFN_Locus2_F1D | 343-345 |
| 24832-2A-24833 | pDAB104011 | FAD2_ZFN_Locus2_F1E | 345-346 |
| 24794-2A-24795 | pDAB104002 | FAD2_ZFN_Locus3_F2F | 402 |
| 24796-2A-24797 | pDAB104006 | FAD2_ZFN_Locus3_F2G | 408 |
| 24814-2A-24815 | pDAB104004 | FAD2_ZFN_Locus3_F2H | 408-410 |
| 24800-2A-24801 | pDAB104001 | FAD2_ZFN_Locus4_F1J | 531 |

TABLE 6-continued lists the Zinc Finger protein binding motif and the corresponding construct number. Each Zinc Finger was designed to bind and cleave the FAD2A which is described in the table

| ZFN Design | Construct No. | Locus ID. | Target Cut Site in FAD2A Sequence |
|---|---|---|---|
| 24818-2A-24819 | pDAB104005 | FAD2_ZFN_Locus4_F1K | 532-534 |
| 24836-2A-24837 | pDAB104007 | FAD2_ZFN_Locus5_F1L | 724 |

Preparation of DNA for Transfection

Plasmid DNA of the above described vectors was sterilized by precipitation and washing in 100% (v/v) ethanol and dried in a laminar flow hood. The DNA pellet was suspended in 30 μA of sterile double-distilled water at a final concentration of 0.7 μg/μl for transfection into protoplast cells as described below. The preparation of the plasmid DNA was undertaken to result in supercoiled plasmid DNA for transient transfection and linearized plasmid DNA for stable transfection. The addition of carrier DNA (e.g. fish-sperm DNA) to the transforming plasmid was not required for the transient transfection of protoplast cells. For transient studies about 30 μg of plasmid DNA per $10^6$ protoplasts was used per transformation.

Transfection

Transfection of *Brassica napus* L. var. *DH*10275 was completed as described in Spangenberg et al., (1986) Plant Physiology 66: 1-8, the media formulations are described in Spangenberg G. and Protrykus I. (1995) Polyethylene Glycol-Mediated Direct Gene Transfer in Tobacco Protoplasts. In: *Gene Transfer to Plants*. (Protrykus I. and Spangenberg G. Eds.) Springer-Verlag, Berlin. *Brassica napus* seeds were surface sterilized in 70% ethanol. The seeds were immersed in 12 mL of the 70% ethanol solution and mixed by gently rocking the cocktail for 10 minutes. The 70% ethanol solution was removed by decanting the solution and exchanged with a seed sterilization solution consisting of 1% w/v calcium hypochlorite and 0.1% v/v Tween-20. The seeds were immersed in the seed sterilization solution and mixed by gently rocking the cocktail for 25 minutes. The seed sterilization solution was decanted and the sterilized seeds were rinsed three times in 50 mL of sterile water. Finally, the seeds were transferred to a sterile 80 mm Whatman filter paper Disc® (Fisher-Scientific, St. Louis, Mo.) that had been laid within a Petri dish and the seeds were lightly saturated with sterile water. The Petri dish was sealed with Parafilm® (Fisher-Scientific, St. Louis, Mo.) and the plates were incubated at 25° C. under complete darkness for one to two days. After signs of seedling emergence were observed from the seeds, the seedlings were transferred to Petri dish containing solidified GEM medium to encourage further seed germination. The seedlings were incubated on the GEM medium at 25° C. for four to five days.

A volume of liquid PS medium (about 10 mL) was decanted into a sterile Petri dish. Using sterile forceps and a scalpel, an aerial portion of the four to five day old seedling in the 4-leaf stage of growth and development, was removed and discarded. Hypocotyl segments in lengths of 20-40 mm were determined to produce the highest population of small, cytoplasmic-rich protoplasts. The hypocotyl segments were aseptically excised and transferred to liquid PS medium. The excised hypocotyl segments were grouped together and cut transversely into 5-10 mm segments. Next, the hypocotyl segments were transferred to fresh PS medium and incubated at room temperature for 1 hour. The plasmolysed hypocotyls were transferred to a Petri dish containing enzyme solution. Care was taken to immerse all of the hypocotyl segments into the solution. The Petri dishes were sealed with Parafilm® and incubated overnight for sixteen to eighteen hours at 20-22° C. with gentle rocking.

Protoplast cells were released from the hypocotyl segments. The overnight hypocotyl digests were gently agitated to release protoplasts into the enzyme solution. The Petri dish was angled slightly to aid the transfer of the digesting suspension of enzyme solution and plant debris. Using a 10 mL pipette the digesting suspension was transferred to a sterilized protoplast filtration (a filter of 100 micron mesh) unit to further separate the protoplasts from the plant debris. The filtration unit was tapped gently to release the excess liquid that had been caught in the sieve. The protoplast suspension, about 8 to 9 mL, was gently mixed and distributed into 14 mL sterile plastic round-bottomed centrifuge tubes. Each suspension was overlaid with 1.5 mL of W5 solution. The W5 solution was carefully dispensed over the protoplast suspension at an angle and dispensed drop-by-drop with minimal agitation. The addition of the W5 solution to the protoplast suspension resulted in the production of a protoplast rich interface. This interface was collected using a pipette. Next, the collected protoplasts were transferred into a new 14 mL centrifuge tube, and gently mixed. The yield or obtained protoplasts were determined using a haemocytometer to determine the number of protoplasts per milliliter. The method was repeated, wherein leaf tissue was digested to produce mesophyll protoplasts.

Next, W5 solution was added to a volume of 10 mL and the protoplasts were pelleted at 70 g, before removing the W5 solution. The remaining protoplast suspension was resuspended by gentle shaking. Each tube containing the protoplast suspension was filled with 5 mL of W5 solution and incubated at room temperature from one to four hours. The protoplast suspensions were pelleted at 70 g, and all of the W5 solution was removed. Next, 300 μL of transformation buffer was added to each of the pelleted protoplast suspensions which contained the isolated protoplasts. To each of the tubes, 10 μg of plasmid DNA was added to the protoplast suspensions. The plasmid DNA included the zinc finger nuclease constructs described above (e.g., pDAB104010). Next, 300 μL of pre-warmed PEG 4000 solution was added to the protoplast suspension and the tubes were gently tapped. The protoplast suspensions and transformation mixture was allowed to incubate at room temperature for fifteen minutes without any agitation. An additional 10 mL of W5 solution was added to each tube in sequential aliquots of 1 mL, 1 mL, 1 mL, 2 mL, 2 mL, and 3 mL with gentle inversion of the tubes between each addition of W5 solution. The protoplasts were pelleted by spinning in a centrifuge at 70 g. All of the W5 solution was removed leaving a pure protoplast suspension.

Next, 0.5 mL of K3 medium was added to the pelleted protoplast cells and the cells were resuspended. The resuspended protoplast cells were placed in the center of a Petri dish and 5 mL of K3 and 0.6 mL Sea Plaque™ agarose (Cambrex, East Rutherford, N.J.) in a 1:1 concentration. The Petri dishes were shaken in a single gentle swirling motion and left to incubate for 20-30 minutes at room temperature. The Petri dishes were sealed with Parafilm® and the protoplasts were cultured for twenty-four hours in complete darkness. After the incubation in darkness, the Petri dishes were cultured for six days in dim light (5 μMol $m^{-2}$ $s^{-1}$ of Osram L36 W/21 Lumilux white tubes). After the culture step, a sterile spatula was used to divide the agarose containing the protoplasts into quadrants. The separated quadrants were placed into a 250 mL plastic culture vessel containing 20 mL of A medium and incubated on a rotary shaker at 80 rpm and 1.25 cm throw at 24° C. in continuous dim light for 14 days and then analyzed to determine the level of activity of each Zinc Finger Nuclease construct.

Genomic DNA Isolation from Canola Protoplasts

Transfected protoplasts were supplied in individual 1.5 or 2.0 mL microfuge tubes. The cells were pelleted at the base of the tube in a buffer solution. DNA extraction was carried out by snap freezing the cells in liquid nitrogen followed by freeze drying the cells, for about 48 hours in a Labconco Freezone 4.5® (Labconco, Kansas City, Mo.) at −40° C. and about $133\times10^{-3}$ mBar pressure. The lyophilized cells were subjected to DNA extraction using the DNeasy® (QIAGEN, Carlsbad, Calif.) plant kit following manufactures instructions, with the exception that tissue disruption was not required and the protoplast cells were added directly to the lysis buffer.

Testing of FAD2A ZFN's for Genomic DNA Sequence Cleavage in Canola Protoplasts

The design of the ZFN target sites in the FAD2A gene locus were clustered, so that multiple pairs of ZFN were designed to overlapping target sites. The clustering of ZFN target sites enabled PCR primers to be designed that would amplify the surrounding genomic sequence from all FAD2A gene family members within a 100 bp window as to encompass all of the overlapping ZFN target sites. As such, the Illumina short read sequence technology could be used to assess the integrity of the target ZFN site of the transfected protoplasts. In addition, the PCR primers designs are needed to include specific nucleotide bases that would attribute sequence reads to the specific gene member of the FAD2A family. Therefore, all of the PCR primers would be required to bind 5-10 nucleotides away from any ZFN target cut site as non-homologous end joining (NHEJ) activity is known to cause small deletions that could remove a priming site, inhibit amplification and therefore distort the assessment of NHEJ activity.

Primers were designed to bind to all of the ZFN target loci for the FAD2A gene families (Table 7) and were empirically tested for amplification of all gene family members through Sanger based sequencing of PCR amplification products. In several instances primers could not be developed that would distinguish all gene family members (Table 8), however in all instances the target gene sequences of FAD2A, could be distinguished. Following PCR primer design custom DNA barcode sequences were incorporated into the PCR primers that were used to distinguish the different ZFN target loci and identify specific sequence reads to a transfection and ZFN (Tables 7 and 8).

TABLE 7

Primer sequences designed for FAD2 ZFN activity assessment of activity. Primers include custom barcodes, along with both requisite Illumina adaptor sequences for construction of Illumina library for sequencing-by-synthesis analysis. Purchased primer was the sum of all three columns presented.

| Locus ID | SEQ ID NO: | Illumina Adaptor Primer Sequence Barcode Locus Primer |
|---|---|---|
| FAD2_ZFN_Locus 1_F2A | SEQ ID NO: 39 | ACACTCTTTCCCTACACGACGCTCTTCCGATCTACGTA*CCCTCTCYCYTACYTCGCC* |
| FAD2_ZFN_Locus 1_F2B | SEQ ID NO: 40 | ACACTCTTTCCCTACACGACGCTCTTCCGATCTCGTAC*CCCTCTCYCYTACYTCGCC* |
| FAD2_ZFN_Locus 1_F2C | SEQ ID NO: 41 | ACACTCTTTCCCTACACGACGCTCTTCCGATCTGTACG*CCCTCTCYCYTACYTCGCC* |
| FAD2_ZFN_Locus 2_F1D | SEQ ID NO: 42 | ACACTCTTTCCCTACACGACGCTCTTCCGATCTTACGT*GTCATAGCCCACGAGTGCGGC* |
| FAD2_ZFN_Locus 2_F1E | SEQ ID NO: 43 | ACACTCTTTCCCTACACGACGCTCTTCCGATCTCTGAC*GTCATAGCCCACGAGTGCGGC* |
| FAD2_ZFN_Locus 3_F2F | SEQ ID NO: 44 | ACACTCTTTCCCTACACGACGCTCTTCCGATCTTGACT*GTCGGCCTCATCTTCCACTCC* |
| FAD2_ZFN_Locus 3_F2G | SEQ ID NO: 45 | ACACTCTTTCCCTACACGACGCTCTTCCGATCTGACTG*GTCGGCCTCATCTTCCACTCC* |

TABLE 7-continued

Primer sequences designed for FAD2 ZFN activity assessment of activity. Primers include custom barcodes, along with both requisite Illumina adaptor sequences for construction of Illumina library for sequencing-by-synthesis analysis. Purchased primer was the sum of all three columns presented.

| Locus ID | SEQ ID NO: | Illumina Adaptor Primer Sequence Barcode Locus Primer |
|---|---|---|
| FAD2_ZFN_Locus 3_F2H | SEQ ID NO: 46 | ACACTCTTTCCCTACACGACGCTCTTCCGATCTACTGA*GTCGGCCTCATC TTCCACTCC* |
| FAD2_ZFN_Locus 4_F1J | SEQ ID NO: 47 | ACACTCTTTCCCTACACGACGCTCTTCCGATCTGCTAG*CAGACATCAAGT GGTACGGC* |
| FAD2_ZFN_Locus 4_F1K | SEQ ID NO: 48 | ACACTCTTTCCCTACACGACGCTCTTCCGATCTCTAGC*CAGACATCAAGT GGTACGGC* |
| FAD2_ZFN_Locus 5_F1L | SEQ ID NO: 49 | ACACTCTTTCCCTACACGACGCTCTTCCGATCTTAGCT*ATCTCCGACGCT GGCATCCTC* |
| FAD2_ZFN_Locus 1_R1A | SEQ ID NO: 50 | CGGTCTCGGCATTCCTGCTGAACCGCTCTTCCGATCTACGTA*CTGGTAGT CGCTGAAGGCGT* |
| FAD2_ZFN_Locus 1_R1B | SEQ ID NO: 51 | CGGTCTCGGCATTCCTGCTGAACCGCTCTTCCGATCTCGTAC*CTGGTAGT CGCTGAAGGCGT* |
| FAD2_ZFN_Locus 1_R1C | SEQ ID NO: 52 | CGGTCTCGGCATTCCTGCTGAACCGCTCTTCCGATCTGTACG*CTGGTAGT CGCTGAAGGCGT* |
| FAD2_ZFN_Locus 2_R1D | SEQ ID NO: 53 | CGGTCTCGGCATTCCTGCTGAACCGCTCTTCCGATCTTACGT*GGACGAGG AGGAAGGAGTGGA* |
| FAD2_ZFN_Locus 2_R1E | SEQ ID NO: 54 | CGGTCTCGGCATTCCTGCTGAACCGCTCTTCCGATCTCTGAC*GGACGAGG AGGAAGGAGTGGA* |
| FAD2_ZFN_Locus 3_R1F | SEQ ID NO: 55 | CGGTCTCGGCATTCCTGCTGAACCGCTCTTCCGATCTTGACT*AGTGTTGG AATGGTGGCGTCG* |
| FAD2_ZFN_Locus 3_R1G | SEQ ID NO: 56 | CGGTCTCGGCATTCCTGCTGAACCGCTCTTCCGATCTGACTG*AGTGTTGG AATGGTGGCGTCG* |
| FAD2_ZFN_Locus 3_R1H | SEQ ID NO: 57 | CGGTCTCGGCATTCCTGCTGAACCGCTCTTCCGATCTACTGA*AGTGTTGG AATGGTGGCGTCG* |
| FAD2_ZFN_Locus 4_R1J | SEQ ID NO: 58 | CGGTCTCGGCATTCCTGCTGAACCGCTCTTCCGATCTGCTAG*CCCGAGAC GTTGAAGGCTAAG* |
| FAD2_ZFN_Locus 4_R1K | SEQ ID NO: 59 | CGGTCTCGGCATTCCTGCTGAACCGCTCTTCCGATCTCTAGC*CCCGAGAC GTTGAAGGCTAAG* |
| FAD2_ZFN_Locus 5_R1L | SEQ ID NO: 60 | CGGTCTCGGCATTCCTGCTGAACCGCTCTTCCGATCTTAGCT*GAAGGATG CGTGTGCTGCAAG* |

Amplification performance of the designed PCR primers on the FAD2 gene families are shown in Table 8. An "X" indicates gene copy detection specificity, a "+" indicates that at the specific locus in question the sequence reads designed by the two primers were unable to be distinguished.

TABLE 8

Results of cleavage at the FAD2A and FAD2C locus

| ZFN Locus | FAD Gene Copy | | | |
|---|---|---|---|---|
| | FAD2A | FAD2C | FAD2A' | FAD2C' |
| Locus 1 | X | X | X | X |
| Locus 2 | X | X | X | X |
| Locus 3 | + | + | X | X |
| Locus 4 | X | X | X | X |
| Locus 5 | X | X | X | X |

Following DNA extraction of canola protoplasts transfected with the ZFN(s), PCR amplification of the target ZFN loci was performed to generate the requisite loci specific DNA molecules in the correct format for Illumina based sequencing by synthesis technology. Each assay was optimised to work on 25 ng starting DNA (about 12,500 cell equivalents of the *Brassica napus* genome). Multiple reactions were performed, per sample to provide the coverage required to assess NHEJ efficiency and specificity at the appropriate level, about sixteen PCR reactions equivalent to 200,000 copies of the *Brassica napus* genome taken from individual protoplasts. PCR amplification master-mixes were made for all samples to be tested with the same assay and one reaction, performed in triplicate, was assayed using a quantitative PCR method that was used to determine the optimal number of cycles to perform on the target tissue, to ensure that PCR amplification had not become reagent limited and was still in an exponential amplification stage. The experimentation with the necessary negative control reactions, was performed in 96 well format using a MX3000P Thermocycler® (Stratagene, LaJolla, Calif.). From the output gathered from the quantitative PCR platform, the relative increase in fluorescence was plotted from cycle-to-cycle and the cycle number was determined per assay that would deliver sufficient amplification, while not allowing the reaction to become reagent limited, in an attempt to reduce over cycling and the amplification of common transcripts or molecules. The unused master mix, remained on ice until the quantitative PCR analysis was concluded and the cycle number determined and was then aliquoted into the desired number of reaction tubes (about 16 per ZFN assay) and the PCR reaction was performed.

Following amplification, samples for a single ZFN locus were pooled together and 200 μL of pooled product per ZFN was cleaned using the MinElute PCR purification Kit® (Qiagen) following manufacturer's instructions. To enable the sample to be sequenced using the Illumina short read technology additional paired end primers were required to be attached by amplification onto the generated fragments. This was achieved by PCR amplification using primers that would be, in part complementary to the sequence added in the first round of amplification, but also contain the paired end sequence required. The optimal number of PCR cycles to perform, that would add the paired end sequences without over amplifying common fragments to the template was again determined using a sample pass through a quantitative PCR cycle analysis, as described previously.

Following PCR amplification, the generated product was cleaned using a MinElute Column® (Qiagen) following manufacturer's instructions and was resolved on a 2.5% agarose gel. DNA fragments visualised using Syber® Safe (Life Technologies, Carlsbad, Calif.) as bands of the correct size were gel extracted to remove any residual PCR generated primer-dimer or other spurious fragments, the DNA was extracted from the gel slice using a MinElute gel extraction Kit® (Qiagen) following manufacturer's instructions. After completion of the gel extraction an additional clean up of the DNA was performed using AMPure magnetic Beads® (Beckman-Coulter, Brea, Calif.) with a DNA to bead ratio of 1:1.7. The DNA was then assessed for concentration using a quantitative PCR based library quantification kit for Illumina sequencing (KAPA) with a 1/40,000 and a 1/80,000 dilution and with the reaction being performed in triplicate. Based on the quantitative PCR results the DNA was diluted to a standard concentration of 2 nM and all libraries were combined for DNA sequencing. The samples were prepared for sequencing using a cBot cluster generation Kit® (Illumina, San Diego, Calif.) and were sequenced on an Illumina GA2x® with 100 bp paired-end sequencing reads following manufacturer's instructions.

Method of Data Analysis for Detection of Non-Homologous End Joining at Target Zinc Finger Sites Following completion of the sequencing reaction and primary data calling performed using the Illumina bioinformatic pipeline for base calling, full analysis was performed to identify deleted bases at the target ZFN site in each instance. A custom PERL script was designed to extract and sort barcodes from DNA sequences computationally following a list of input sequences. The barcode had to match the reference sequence at a Phred score of greater than 30 to be accepted, to reduce misattributing sequence reads. After the sequence reads had been binned into the different barcode groups that had been used, a quality filter was passed across all sequences. The quality filter was a second custom developed PERL script. Sequence reads were excluded if there were more than three bases called as "N", or if the median Phred score was less than 20, or if there were 3 consecutive bases with a Phred score of less than 20, or if the sequence read was shorter than 40 bp in length. The remaining sequences were merged where both of the paired sequence reads were available using the NextGENe® (SoftGenetics, State College, Pa.) package. The remaining merged sequence reads were then reduced to a collection of unique sequence reads using a third custom PERL script with a count of the number of redundant sequences that had been identified recorded on the end of the remaining sequence identifier. The unique sequence reads were then aligned to the FAD2 reference sequence using the NextGENe® software that created a gapped FASTA aligned file.

Using the gapped FASTA file a conversion of the gapped base position number to the input reference was performed using a fourth custom PERL script. This enabled bases that discriminate the different gene family members (either homoeologous or paralogous sequence variation between the different gene family members) to be identified in the assembled data. Once the conversion of base numbering had been performed it was possible to generate haplotype reports for each unique sequence reads and assign the reads to specific gene family members. Once the reads had been grouped by gene a 10 bp window was identified and assessed that surrounded the ZFN target site. The number of sequences with deletions was recorded per gene along with the number of missing bases.

Figure 4:
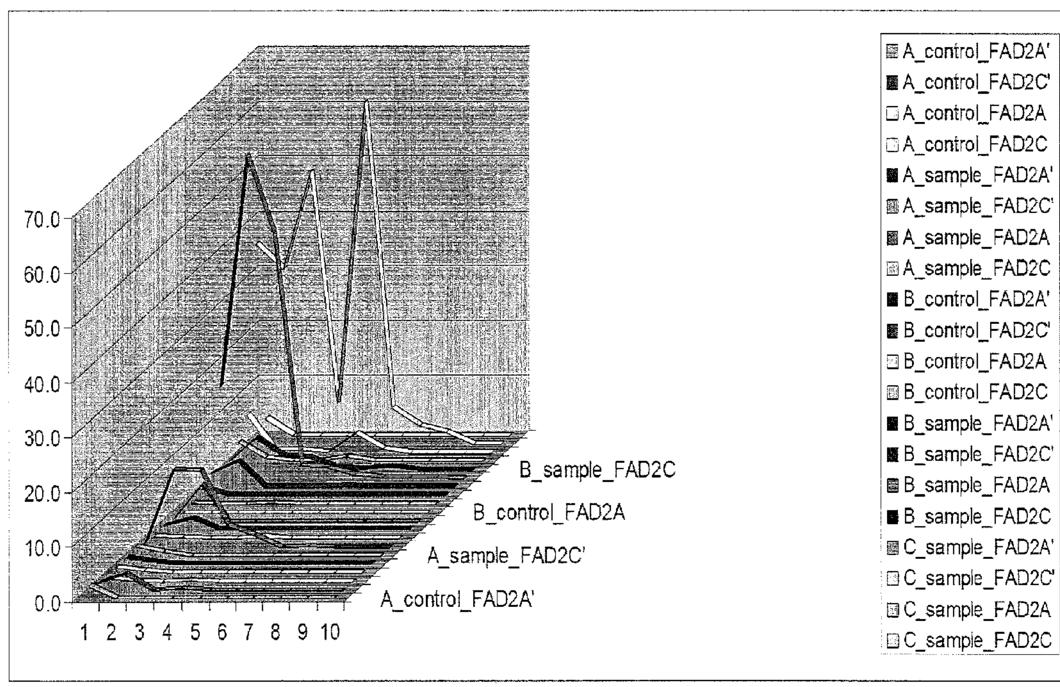
FIG. 4 is an example multiple line graph showing number of sequence reads per 10,000 sequence reads with deletions at the target ZFN site. The X axis on the graph denotes number of bases deleted, the Y axis denotes number of sequence reads and the Z axis denotes colour-coded sample identity as described to the right of the graph. Specific example shown is for locus 1 of the FAD2 gene family that contains 3 target ZFN sites, A, B and C with the four gene family members and two control transfections assessed as control samples A and B. The lines listed from top to bottom (A-control_FADA' at the top of the legend to C_sample_FAD2C at the bottom of the legend) are shown on the graph from closest to the labeled X-axis (A_control_FADA') to farthest from the labeled X-axis (C_sample_FAD2C).
Figure 5A:
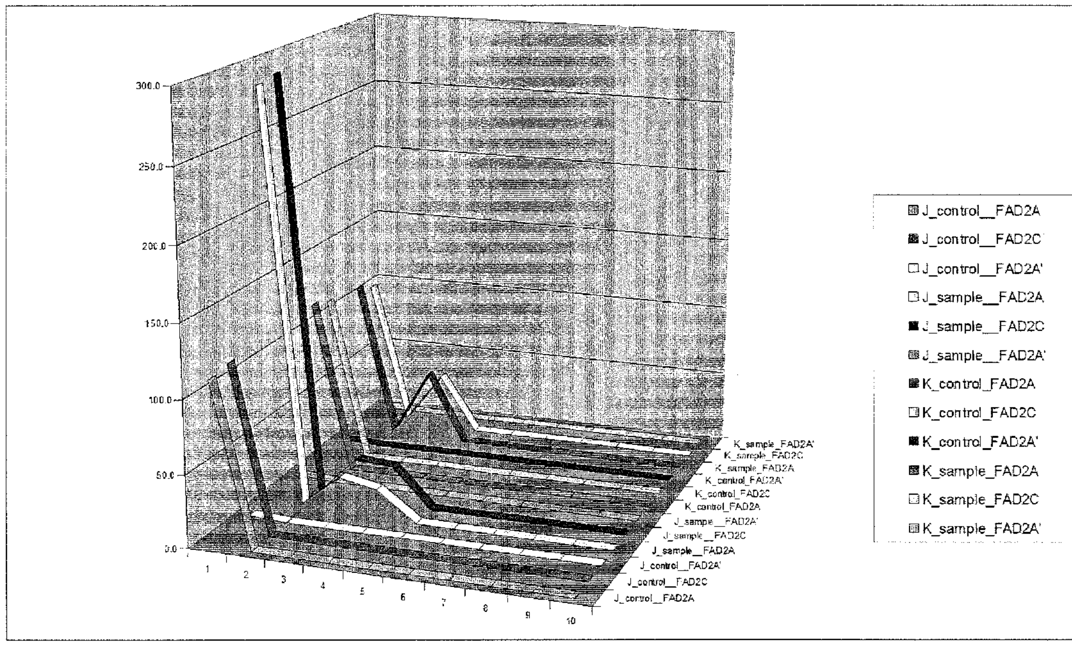
FIG. 5A is a graph depicting data from ZFN targeting locus 4 of the FAD2 gene family. The locus contains two ZFN sites and two requisite control transfections.
Figure 5B:
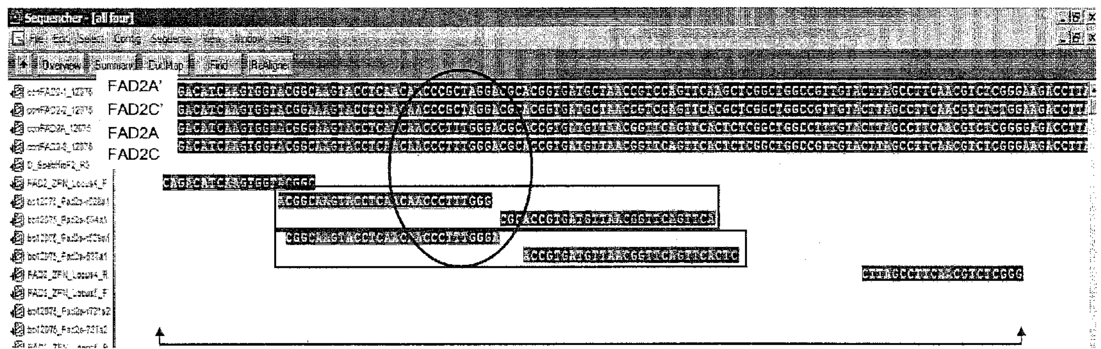
FIG. 5B shows specific sequence context (SEQ ID NOs:471-480, respectively, in order of appearance) surrounding the ZFN target site, identifying FAD2A and C containing tri-nucleotide repeats of C, T and G, leading to the observed increase in single base deletions through sequencing of the FAD2A and C loci.

The data was then graphically displayed as a multiple line graph, with the number of sequences with 1 through 10 bases deleted at the target ZFN site per 10,000 sequence reads (FIG. 4). This analysis was performed for all ZFN transfections along with control transfections. In several instances, repeats in the native DNA sequence lead to an increase in sequencing error in the target ZFN site, such an error can be commonly seen as an increase in the prevalence of single base deletions that were reported in all samples, both transfected with ZFN or controls (FIG. 5).

From these results highest level of ZFN activity at a FAD2 target site, as determined by the greater activity of NHEJ, was identified at locus E. The ZFNs which were encoded on plasmid pDAB104010 (i.e., ZFN24828 and 24829) were selected for in planta targeting of an Engineered Transgene Integration Platform (ETIP) given its characteristics of significant genomic DNA cleavage activity and minimal non-target activity.

Example 4: DNA Constructs for Engineered Transgene Integration Platform (ETIP) Canola Plant Lines The plasmid vector constructs described below were built using methods and techniques commonly known by one with skill in the art. The application of specific reagents and techniques described within this paragraph are readily known by those with skill in the art, and could be readily interchanged with other reagents and techniques to achieve the desired purpose of building plasmid vector constructs. The restriction endonucleases were obtained from New England BioLabs (NEB; Ipswich, Mass.). Ligations were completed with T4 DNA Ligase (Invitrogen, Carlsbad, Calif.). Gateway reactions were performed using GATEWAY® LR CLONASE® enzyme mix (Invitrogen) for assembling one entry vector into a single destination vector. IN-FUSION™ reactions were performed using IN-FUSION™ Advantage Technology (Clontech, Mountain View, Calif.) for assembling one entry vector into a single destination vector Plasmid preparations were performed using NUCLEOSPIN Plasmid Kit (Macherey-Nagel Inc., Bethlehem, Pa.) or the Plasmid Midi Kit® (Qiagen) following the instructions of the suppliers. DNA fragments were isolated using QIAquick Gel Extraction Kit™ (Qiagen) after agarose Tris-acetate gel electrophoresis. Colonies of all assembled plasmids were initially screened by restriction digestion of miniprep DNA. Plasmid DNA of selected clones was sequenced by a commercial sequencing vendor (Eurofins MWG Operon, Huntsville, Ala.). Sequence data were assembled and analyzed using the SEQUENCHER™ software (Gene Codes Corp., Ann Arbor, Mich.).

Figure 6:
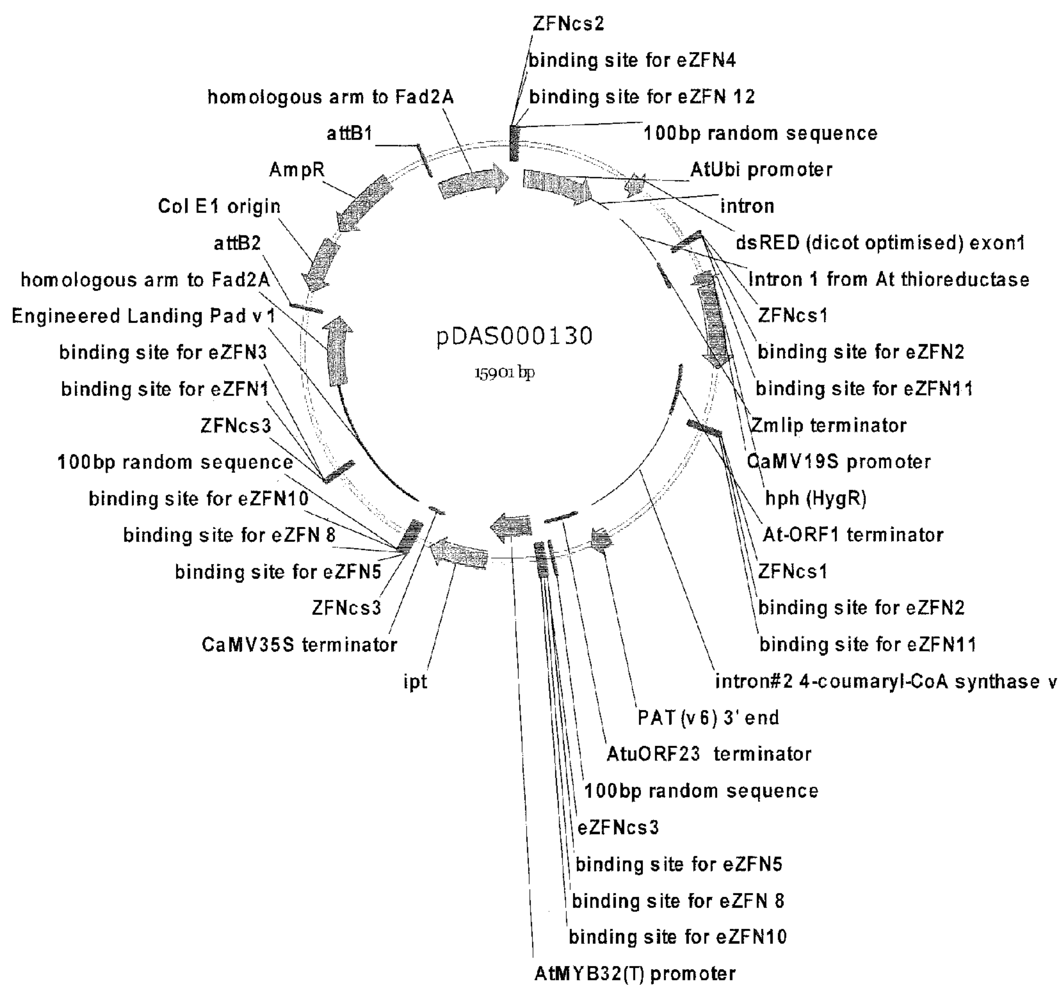
FIG. 6 shows a plasmid map of pDAS000130.

Direct-Delivery Vectors for Precision Integration of ETIP in the FAD2A Locus of Canola Standard cloning methods were used in the construction of the ETIP-containing vectors pDAS000130 (FIG. 6, T-strand insert as SEQ ID NO:61), for specific integration into the FAD2A gene of *B. napus*. This construct has been designed to be delivered into canola protoplasts with the Zinc Finger Nuclease construct pDAB104010. The Zinc Finger Nuclease Construct will cleave the FAD2A locus and then the pDAS000130 construct will integrate within the canola genome via a homology directed or non homologous end joining repair mechanism. The ETIP includes four expression cassettes (two incomplete) separated by additional ZFN recognition sequences and an Engineered Landing Pad (ELP) containing another ZFN recognition sequences. The additional ZFN recognition sequences are unique and have been designed to be targeted for the introduction of polynucleotide sequences within the ETIP and ELP transgene insertions. Similarly, the ZFN recognition sequences can be utilized for excision of polynucleotide sequences. The first gene expression cassette was an incomplete dsRED expression cassette and contained the promoter, 5' untranslated region and intron from the *Arabidopsis thaliana* Polyubiquitin 10 (AtUbi promoter) gene (Callis, et al., (1990) *J. Biol. Chem.*, 265: 12486-12493) followed by 210 bp of a dsRed gene from the reef coral *Discosoma* sp. (Clontech, Mountain View, Calif.) codon-optimised for expression in dicot plants (ds RED (dicot optimized)exon 1) followed by an intron from the *Arabidopsis thaliana* thioreductase-like gene (Intron 1 from At thioreductase: Accession No: NC_00374) and the 3' untranslated region comprising the transcriptional terminator and polyadenylation site of the *Zea mays* Viviparous-1 (Vp1) gene (Zmlip terminator: Paek et al., (1998) Molecules and Cells, 8(3): 336-342). The second expression cassette contained the 19S promoter including 5' UTR from cauliflower mosaic virus (CaMV 19S: Cook and Penon (1990) *Plant Molecular Biology* 14(3): 391-405) followed by the hph gene from *E. coli*, codon-optimised for expression in dicots (hph(HygR): Kaster et al., (1983) Nucleic Acids Research 11(19): 6895-6911) and the 3'UTR comprising the transcriptional terminator and polyadenylation site of open reading frame 1 of *A. tumefaciens* pTi15955 (At-ORF1 terminator: Barker et al., (1983) Plant Molecular Biology 2(6): 335-50). The third expression cassette was an incomplete PAT expression cassette and contained the first intron from *Arabidopsis* 4-coumaryl-CoA synthase (intron#2 4-coumaryl-CoA synthase v: Accession No: At3g21320/NC003074) followed by the last 256 bp of a synthetic, plant-optimized version of phosphinothricin acetyl transferase gene, isolated from *Streptomyces viridochromogenes*, which encodes a protein that confers resistance to inhibitors of glutamine synthetase comprising phosphinothricin, glufosinate, and bialaphos (PAT(v6) 3' end: Wohlleben et al., (1988) Gene 70(1): 25-37). This cassette was terminated with the 3'UTR comprising the transcriptional terminator and polyadenylation sites of open reading frame 23 of *A. tumefaciens* pTi15955 (AtuORF23 terminator: Barker et al., (1983) Plant Molecular Biology 2(6): 335-50). The fourth Expression Cassette was the ipt gene cassette and contained a 588 bp truncated version of the promoter and 5' UTR from the *Arabidopsis* DNA-binding protein MYB32 gene (U26933) (AtMYB32(T) promoter: Li et al., (1999) Plant Physiology 121: 313) followed by the isopentyl transferase (ipt) gene from *A. tumefaciens* and the 35s terminator comprising the transcriptional terminator and polyadenylation sites from cauliflower mosaic virus (CaMV 35S terminator: Chenault et al., (1993) Plant Physiology 101 (4): 1395-1396). For delivery to FAD2A, each end of the ETIP sequence was flanked by 1 kb of FAD2A genomic sequence from either side of the location of the double-stranded break induced by delivery of the ZFN encoded in pDAB104010 to the FAD2A gene of *B. napus*.

The ETIP sequence was synthesized by a commercial gene synthesis vendor (GeneArt, Life Technologies). The 1 kb segments of FAD2A genome sequence were amplified from genomic DNA purified from leaf tissue of *B. napus* DH12075 using a Qiagen DNeasy plant mini Kit® (Qiagen, Hilden) following instructions supplied by the manufacturer. The 1 kb FAD2A sequences were ligated into the ETIP vector using T4 ligase (NEB, Ipswich, Mass.). Colonies of all assembled plasmids were initially screened by restriction digestion of miniprep DNA. Restriction endonucleases were obtained from New England BioLabs (NEB, Ipswich, Mass.) and Promega (Promega Corporation, Wis.). Plasmid preparations were performed using the QIAprep Spin Miniprep Kit® (Qiagen) or the Pure Yield Plasmid Maxiprep System® (Promega Corporation, Wis.) following the instructions of the suppliers. Plasmid DNA of selected clones was sequenced using ABI Sanger Sequencing and Big Dye Terminator v3.1 cycle sequencing Protocol® (Applied Biosystems, Life Technologies). Sequence data were assembled and analyzed using the SEQUENCHER™ software (Gene Codes Corp., Ann Arbor, Mich.).

Control Vectors

Figure 7:
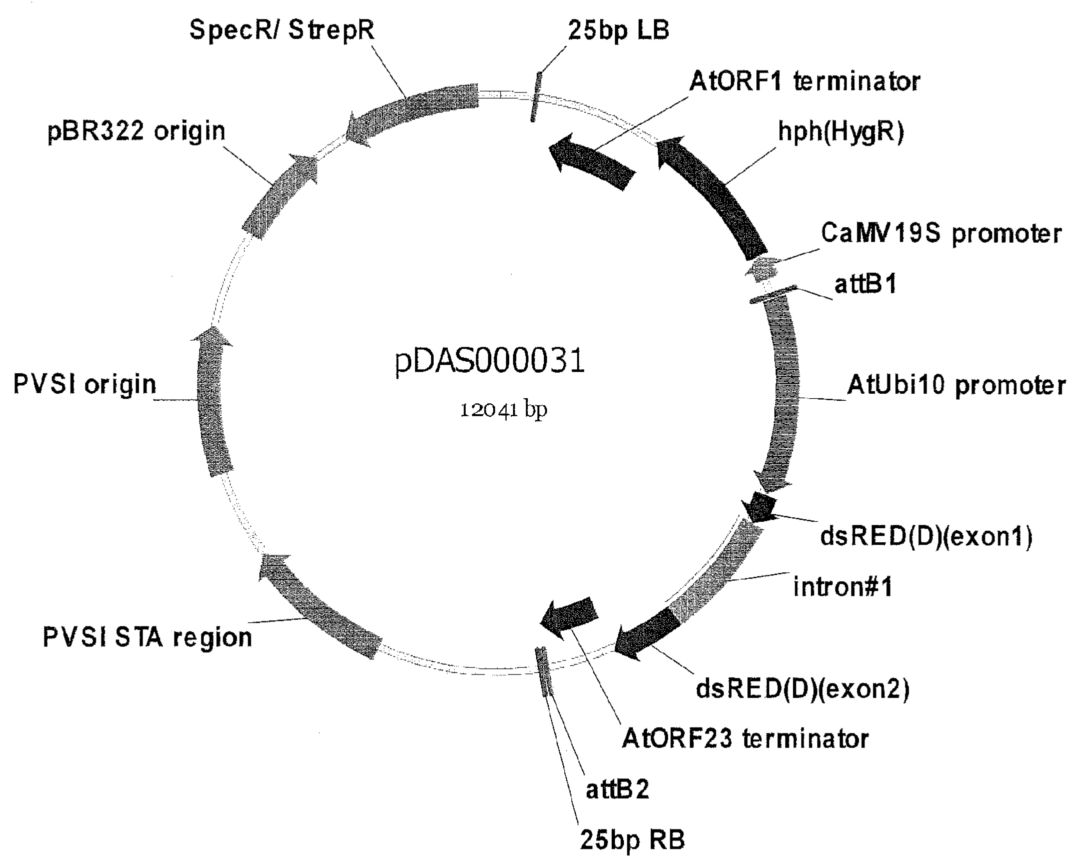
FIG. 7 shows a plasmid map of pDAS000031.

A control vector was used to develop a Fluorescence Activated Cell Sorting (FACS) cell based sorting method. Standard cloning methods were used in the construction of a control vector, pDAS000031 (FIG. 7: T-strand insert as SEQ ID NO:62) including two gene expression cassettes. The first gene expression cassette contained the Cauliflower mosaic virus 19s promoter (CaMV 19S promoter; Shillito, et al., (1985) *Bio/Technology* 3; 1099-1103)::hygromycin resistance gene (hph(HygR); U.S. Pat. No. 4,727,028)::and the *Agrobacterium tumefaciens* Open Reading Frame 1 3'UnTranslated Region (AtORF1 terminator; Huang et al., (1990) *J. Bacteriol.* 1990 172:1814-1822). The second gene expression cassette contained the *Arabidopsis thaliana* Ubiquitin 10 promoter (AtUbi10 promoter; Callis, et al., (1990) *J. Biol. Chem.,* 265: 12486-12493)::dsRED (dsRED (D); U.S. Pat. No. 6,852,849) and an intron from *Arabidopsis* (intron #1; GenBank: AB025639.1)::*Agrobacterium tumefaciens* Open Reading Frame 23 3'UnTranslated Region (AtORF23 terminator; U.S. Pat. No. 5,428,147) as an in-frame fusion with a trans orientation (e.g., head to head orientation). The plasmid vector was assembled using the IN-FUSION™ Advantage Technology (Clontech, Mountain View, Calif.).

Example 5: Generation of ETIP Canola Plant Lines

Transformation of *Brassica Napus*

The FAD2A site specific integration deploys the use of the ETIP construct (pDAS000130), accompanying Zinc Finger Nuclease (pDAB104010), and the DS-Red control construct (pDAS000031) described in Example 4. The binary vectors were transformed into *Agrobacterium tumefaciens* strain GV3101: PM90. Transformation of *Brassica napus* protoplast cells was completed using the transfection protocol described in Example 3 with some modification.

The modifications to the protocol included the use of sodium alginate instead of Sea Plaque™ agarose. The transfection experiments in which both the Zinc Finger Nuclease construct, pDAB104010, and the ETIP construct, pDAS000130, were co-delivered into *Brassica napus* protoplast cells were completed at DNA concentrations comprising a 5:1 and a 12:1 molar ratio, wherein pDAS000130 had a concentration of 27.8 μg of plasmid DNA and pDAB104010 had a concentration of 2.2 μg of plasmid DNA. The control plasmid constructs were transformed at concentrations of 30 μg of plasmid DNA.

Additional modifications to the protocol included the propagation of whole plants from the transformed protoplast cells in medium containing 1.5 mg/mL of hygromycin. The propagation of whole plants required that the A medium was replaced every two weeks and the growth of the protoplast-derived colonies was monitored. After the protoplast-derived colonies had grown to approximately 2-3 mm in diameter, the colonies were transferred into individual wells of a 12-well Costar® plate (Fisher Scientific, St. Louis, Mo.) containing solidified MS morpho medium. The plates were incubated for one to two weeks at 24° C. under continuous dim light until the calli had proliferated to a size of 8-10 mm in diameter.

After the protoplast cells had reached a diameter of 1-2 cm, the protoplast cells were transferred to individual 250 mL culture vessels containing MS morpho medium. The vessels were incubated at 24° C. under 16 h light (20 μMol $m^{-2}$ $s^{-1}$ of Osram L36 W/21 Lumilux white tubes) and 8 h dark conditions. Within one to two weeks, multiple shoots were visible. The shoots were transferred into 250 mL culture vessels containing MS medium after they reached a length of 3-4 cm. The 250 mL culture vessels were incubated at 24° C. under 16 h light (20 μMol $m^{-2}$ $s^{-1}$ of Osram L36 W/21 Lumilux white tubes) and 8 h dark conditions. The shoots were maintained in the culture vessels until they developed into plantlets at which time they were transferred to a greenhouse to grow to maturity.

Example 6: Molecular Confirmation of Integration of T-DNAS Containing ETIPS in Canola Genomic DNA was extracted from leaf tissue of all putative transgenic plants using a DNeasy Plant Mini Kit™ (Qiagen) following the manufacturer's instructions, with the exception that tissue was eluted in 80 μl of AE buffer. Thirty milligrams of young leaf tissue from regenerated plants was snap frozen in liquid nitrogen before being ground to a powder.

Molecular characterization of the FAD2A locus was performed using three independent assays. Assays were designed and optimized using the following controls; characterized transgenic events comprising a single randomly integrated transgene, characterized transgenic event with five randomly integrated transgenes, wildtype canola c.v. DH12075 plants and non-template control reactions. The results from the three following molecular analyses are considered together in order to provide evidence for integration of the ETIP at FAD2A via HDR.

Identifying Transgene Integration by Real-Time Polymerase Chain Reaction

Figure 8:
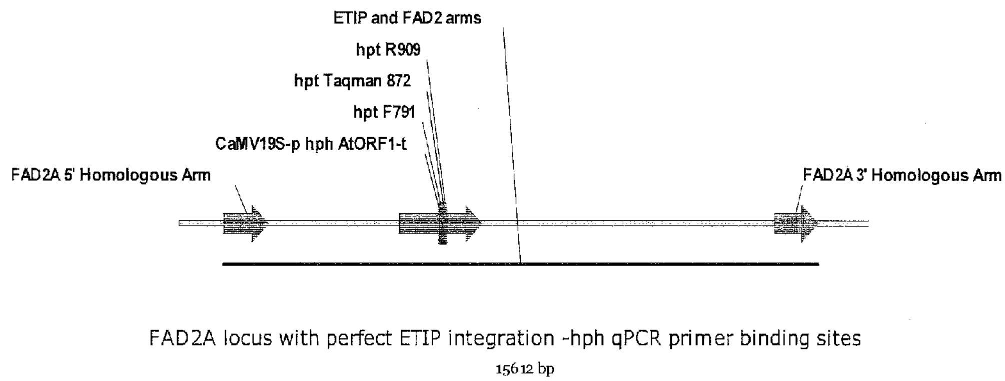
FIG. 8 is a schematic showing binding sites of transgene target primers and probe for transgene copy number estimation assay.

Four replicates of each plant were analyzed using primers specific to the hph (also described as hpt) target gene (SEQ ID NO:63, hpt F791 5' CTTACATGCTTAGGATCGGACTTG 3; SEQ ID NO:64, hpt R909 5' AGTTCCAGCACCAGATCTAACG 3'; SEQ ID NO:65, hpt Taqman 872 5' CCCTGAGCCCAAGCAGCATCATCG 3' FAM) (FIG. 8) and reference gene encoding High Mobility Group protein I/Y (HMG I/Y) (SEQ ID NO:66, F 5' CGGAGAGGGCGTGGAAGG 3; SEQ ID NO:67, R 5' TTCGATTTGCTACAGCGTCAAC 3; SEQ ID NO:68, Probe 5' AGGCACCATCGCAGGCTTCGCT 3' HEX). The reactions were amplified using the following conditions: 95° C. for 10 minutes followed by 40 cycles of 95° C. for 30 seconds, 60° C. for 1 minute, with amplification data being captured at the end of each annealing step. Copy number was calculated using the ΔCq method, where ΔCq=Cq(target gene)−Cq(reference gene). Livak, K. J. and T. D. Schmittgen, *Analysis of relative gene expression data using real-time quantitative PCR and the* 2 (*-Delta Delta C*(*T*)) *Method*. Methods, 2001. 25(4): p. 402-8. Plants with amplification of hph and HMG I/Y and a copy number of 0.5 or more were considered transgenic, while plants with a copy number of ≥0.5 and ≤1.2 were scored as putatively single copy. Amplification was performed on a BioRad CFX96 Touch™ Real-Time PCR Detection System with FastStart Universal Probe Master (ROX), (Roche, Basel, Switzerland).

Detection of Disrupted FAD2a ZFN Site

Figure 9:
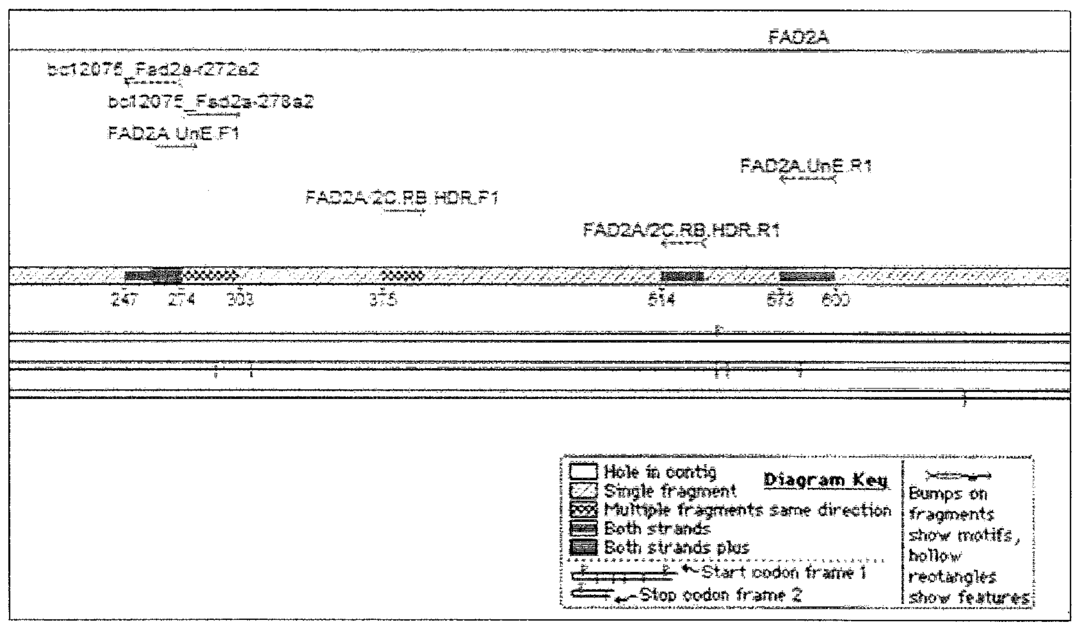
FIG. 9 shows a Sequencher file showing FAD2A ZFN DNA recognition domain (bc12075_Fad2a-r272a2 and bc12075_Fad2a-278a2), and binding sites of ZFN specific primers (FAD2A.UnE.F1 and FAD2A.UnE.R1) and endogenous primers (FAD2A/2C.RB.UnE.F1 and FAD2A/2C.RB.UnE.R1).
Figure 10:
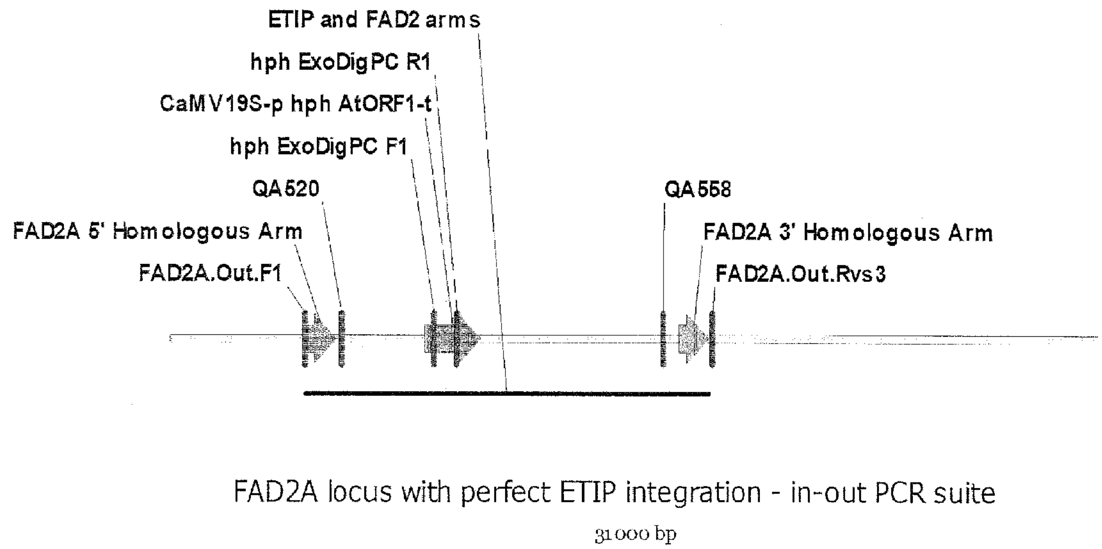
FIG. 10 shows a schematic showing binding sites of endogenous and transgene target primers used in the detection of transgene integration at FAD2A via perfect HDR.

Each plant was analysed for presence or absence of amplification of endogenous target in the disrupted locus test, which is a dominant assay. The assay is a SYBR® Green I qPCR assay and in singleplex, but with each reaction run simultaneously on the same PCR plate, targets an endogenous locus (FAD2A/2C.RB.UnE.F1, SEQ ID NO:69, 5' CTTCCACTCCTTCCTCCTCGT*C 3' and FAD2A/2C.RB.UnE.R1, 5' SEQ ID NO:70, GCGTCCCAAAGGGTTGTTGA*G 3') and the ZFN locus (locus at which the ZFN pDAB104010 binds and cuts the genome) (FAD2A.UnE.F1, SEQ ID NO:71, 5'TCTCTACTGGGCCTGCCAGGG*C 3' and FAD2A.UnE.R1, SEQ ID NO:72, 5' CCCCGAGACGTTGAAGGCTAAGTACAA*A 3') (FIG. 9). Both primer pairs were amplified using the following conditions: 98° C. for 30 seconds followed by 35 cycles of (98° C. for 10 seconds, 65° C. for 20 seconds, 72° C. for 90 seconds) then followed by 95° C. for 10 seconds then a melt analysis from 50° C. to 95° C. with 0.5° C. increments for 0.05 seconds and a plate read at each increment. The reaction conditions are listed in Table 9.

TABLE 9

Single reaction reagent components and concentrations for PCR amplification

| Reaction Components | Volume (μl) |
|---|---|
| 10 mM dNTP | 0.40 |
| 5X Phusion HF Buffer | 4.00 |
| Phusion Hot Start II High-Fidelity DNA Polymerase (2 U/μl) (Thermo Scientific) | 0.25 |
| Forward Primer 10 μM | 0.40 |
| Reverse Primer 10 μM | 0.40 |
| 1:10000 dilution of SYBR Green I dye (Invitrogen) | 1.00 |
| Molecular Biology Grade $H_2O$ | 11.55 |
| Genomic DNA template (~20 ng/μl) | 2.00 |
| Total Volume | 20.00 |

Plants that had amplification of the endogenous target but no amplification of the ZFN target, were scored as positive for the disrupted locus test and were considered to have a disrupted ZFN locus. This assay was considered to be positive when the ZFN binding site on both alleles at the FAD2A locus have been disrupted.

PCR Detection of Transgene Integration at FAD2A Via Homology Directed Repair

Figure 3:
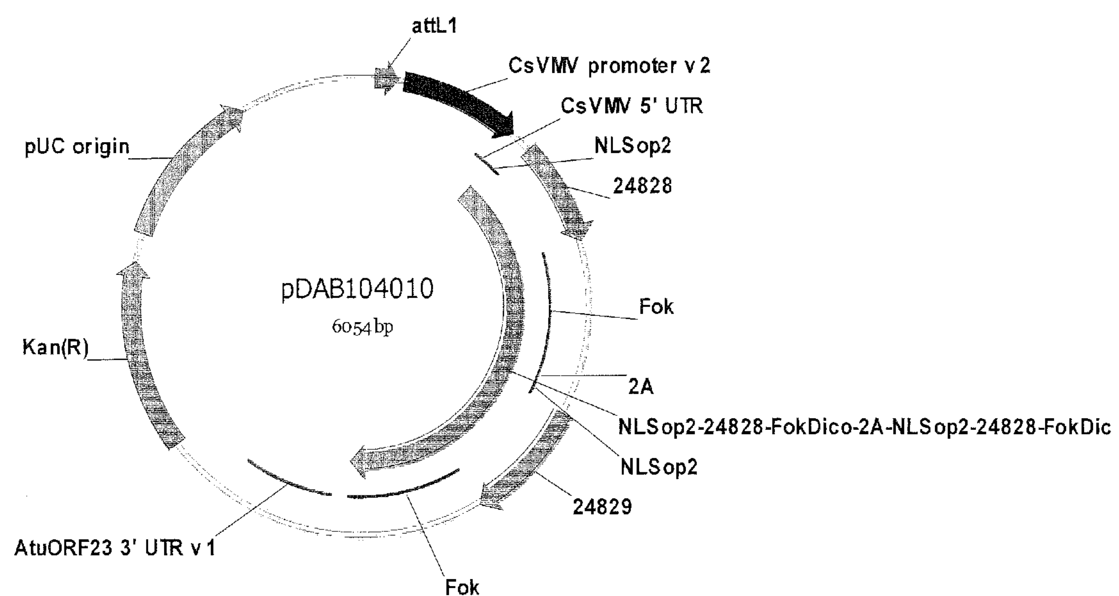
FIG. 3 shows a plasmid map of pDAB104010 which that is a representative Zinc Finger Nuclease expression cassette. The lay-out of this construct was similar for the other ZFN expression cassettes, wherein the Zinc Finger domains, 24828 and 24829, were exchanged with alternative Zinc Finger domains that are described above.

Each putative plant transformant was analysed using endpoint with PCR primers designed to amplify the transgene target hph (hph_ExoDigPC_F1, SEQ ID NO:73, 5' TTGCGCTGACGGATTCTACAAGGA 3' and hph_ExoDigPC_R1, SEQ ID NO:74, 5'TCCATCAGTCCAAACAGCAGCAGA 3'), the FAD2A endogenous locus (FAD2A.Out.F1, SEQ ID NO:75, 5' CATAGCAGTCTCACGTCCTGGT*C 3' and FAD2A.Out.Rvs3, SEQ ID NO:76, 5' GGAAGCTAAGCCATTACACTGTTCA*G 3'), the region spanning the 5' end of any transgene integrated into the FAD2A locus via HDR, upstream of the transgene into the FAD2 A locus (FAD2A.Out.F1, SEQ ID NO:77, 5' CATAGCAGTCTCACGTCCTGGT*C 3' and QA520, SEQ ID NO:78, 5' CCTGATCCGTTGACCTGCAG 3') and the region spanning the 3' end of any transgene integrated into the FAD2A locus via HDR, downstream of the transgene into the FAD2 A locus (QA558, SEQ ID NO:79, 5' GTGTGAGGTGGCTAGGCATC 3' and FAD2A.Out.Rvs3, SEQ ID NO:80, 5' GGAAGCTAAGCCATTACACTGTTCA*G 3') (FIG. 3). All primer pairs were amplified using the following conditions 98° C. for 30 seconds followed by 35 cycles of (98° C. for 10 seconds, 65° C. for 20 seconds, 72° C. for 90 seconds). Reaction reagent conditions are as described in Table 10.

TABLE 10

Single reaction reagent components and concentrations for PCR amplification

| Reaction Components | Volume (μl) |
|---|---|
| 5x Phusion HF Buffer | 6.00 |
| 10 mM dNTPs | 0.60 |
| Forward Primer 10 μM | 0.60 |
| Reverse Primer 10 μM | 0.60 |
| Phusion Hot Start II High-Fidelity DNA Polymerase (2 U/μl) (Thermo Scientific) | 0.25 |
| Molecular Biology Grade $H_2O$ | 19.95 |
| Genomic DNA template (~20 ng/μl) | 2.00 |
| Total Volume | 30.0 |

Amplification of the 5' transgene-genome flanking target and/or amplification of the 3' transgene-genome flanking target indicated a putative insertion event. It must be noted that due to the approximately 1,000 bp FAD2A homology arms in the pDAS000130 cassette (comprising polynucleotide sequences with 100% sequence identity to the FAD2A regions immediately upstream and downstream of the ZFN cut site), the PCR reactions were subject to false positive PCR product amplification due to PCR chimerism arising from amplification of off-target ETIP integration events. Amplification of the hph target confirmed transgene integration had occurred. Amplification of the FAD2A target suggests that the FAD2A locus is intact or contains only a partial insertion. Due to the size of the ETIP (11,462 bp for the ETIP cassettes or 13,472 bp including the FAD2A homologous arms and the ETIP cassettes) it is expected that the FAD2A primers would not amplify a product when an intact ETIP is integrated into the FAD2A locus.

Southern Detection of FAD2A Editing

Figure 11:
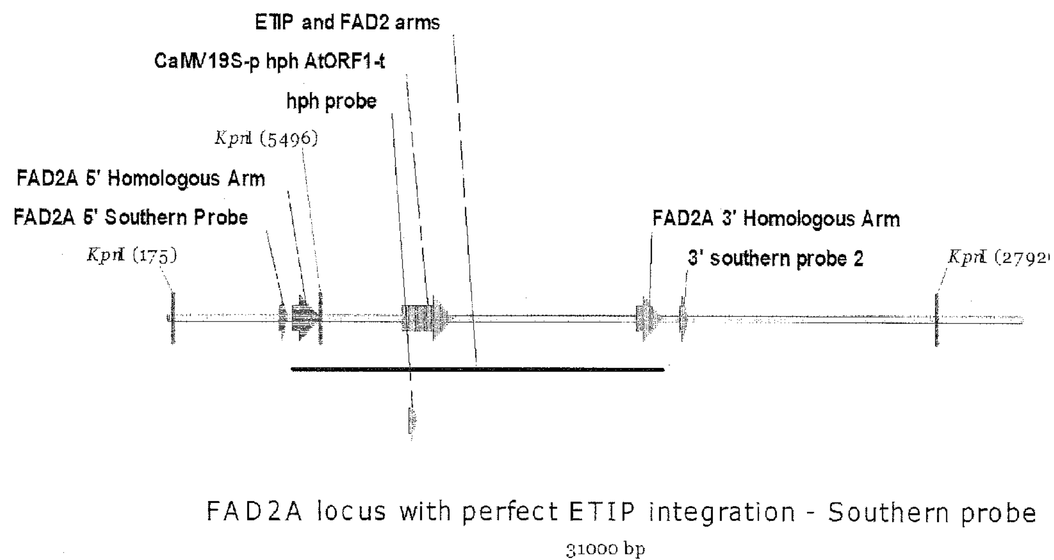
FIG. 11 is a schematic showing where Kpn1 restriction endonuclease sites would occur in a perfectly edited FAD2A locus, and where FAD2a 5', hph and FAD2A 3' Southern probes bind.

Plants that had amplification of either a 5' genome-transgene flanking target product and/or amplification of a 3' transgene-genome flanking target, or no amplification of the ZFN locus target, or both, were subject to Southern analysis for detection of transgene integration at the FAD2A locus. Genomic DNA was purified from 5 g of leaf tissue using a modified CTAB method (Maguire, T. L., G. G. Collins, and M. Sedgley *A modified CTAB DNA extraction procedure for plants belonging to the family proteaceae*. Plant Molecular Biology Reporter, 1994. 12(2): p. 106-109). Next, 12 μg of genomic DNA was digested with Kpn1-HF (New England BioLabs) and digestion fragments were separated by electrophoresis on a 0.8% agarose gel before transfer to membrane using a standard Southern blotting protocol. Primers to FAD2A 5' target region (F, SEQ ID NO:81, 5' AGAGAGGAGACAGAGAGAGAGT 3' and R, SEQ ID NO:82, 5' AGACAGCATCAAGATTTCACACA 3'), FAD2A 3' target region (F, SEQ ID NO:83, 5' CAACGGCGAGCGTAATCTTAG 3' and R, SEQ ID NO:84, 5' GTTCCCTGGAATTGCTGATAGG 3') and hph (F, SEQ ID NO:85, 5' TGTTGGTGGAAGAGGATACG 3' and R, SEQ ID NO:86, 5' ATCAGCAGCAGCGATAGC 3') were used to generate probes to detect the presence of the ETIP within the FAD2A locus using the DIG Easy Hyb System® (Roche, South San Francisco, Calif.) following the manufacturer's instructions (FIG. 11). Hybridization was performed at 42° C. for FAD2A 5' region, 45° C. for FAD2A 3' region and 42° C. for detection of hph.

Figure 12:
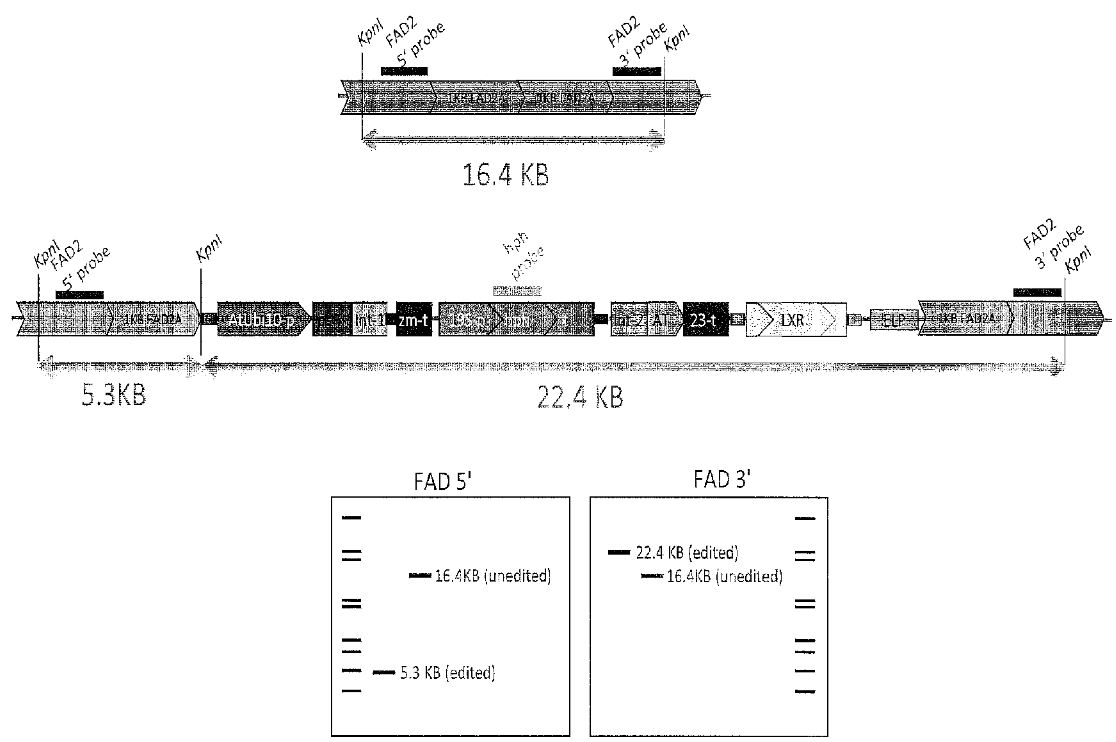
FIG. 12 shows the location and size of Kpn1 fragments, FAD2A 5', hph, FAD2A 3' probes and expected outcomes of Southern analysis for plants that have integration of ETIP at FAD2A locus via HDR.

Membrane-bound genomic DNA was probed in a specific order; firstly FAD2A 5' sequences were probed, then the FAD2A 3' sequences were probe, and finally the hph sequences were probed (FIG. 12). The rational for this is as follows. The first probe (FAD2A 5') is the diagnostic probe, and if the ETIP has integrated into FAD2A via perfect HDR, a 5,321 bp fragment will be visible on the membrane. The resulting band size is easily differentiated during electroporation and will sit close to the 5,148 bp fragments in the DIG labeled Roche DNA Molecular Weight Marker III® (Roche, Indianapolis, Ind.). The second probe of the membrane is with the FAD2A 3' probe and an edited plant will have a 22,433 bp fragment whereas an unedited plant will have a 16,468 bp fragment. The same 22,433 bp fragment identified with the FAD2A 3' probe should also be bound by and identified with the hph probe. These fragments are difficult to differentiate on a gel as they are extremely large and it may be difficult to determine any difference between a fragment occurring above or below the largest, 21,226 bp fragment in the DIG labeled Roche DNA Molecular Weight Marker III®. As such, these probes provide evidence that may strengthen the identification of ETIP integration into FAD2A via homology directed repair (HDR), by visualization of a 5 kb fragment using the FAD2A 5' probe. The restriction enzyme, KpnI was the only suitable restriction endonuclease for use in this assay, as KpnI sites occurred in a single locus of the cut the ETIP cassette in a single locus, and was present in two sites of the FAD2A ZFN locus. One site was located upstream and the second site located downstream of the FAD2A homology arms. In addition, KpnI is not methylation sensitive, and is available as a recombinant enzyme with increased fidelity (New England Biolabs).

Results of Molecular and Southern Analysis

Figure 13:
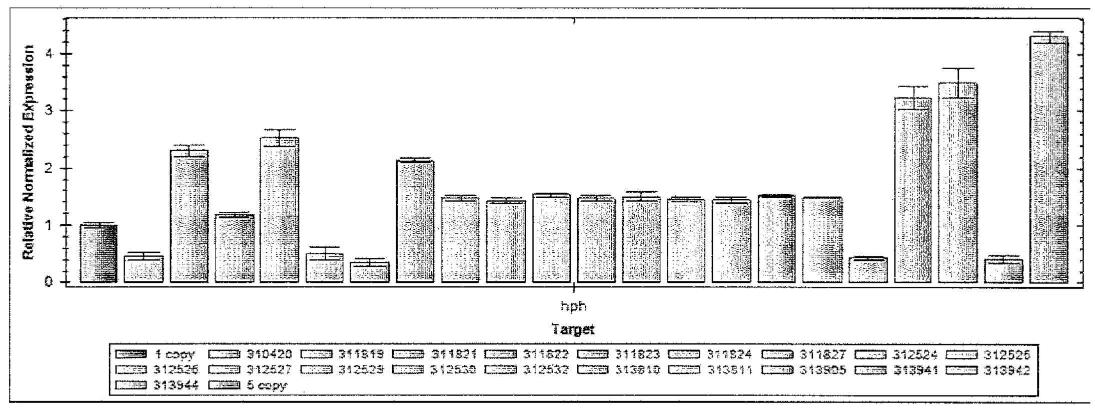
FIG. 13 shows representative data output from copy number estimation qPCR. The left hand column represents data obtained from a known $T_0$ transgenic plant with a single random transgene insert and is used as the calibrator sample to which all other samples are 'normalized' against. The right hand column is a known $T_0$ transgenic plant with 5 transgene integrations. The insert copy numbers for both plants was determined using Southern analysis. The remaining columns provide copy number estimates for the putative transgenic plants. The columns are labeled as; 1 copy control, 310420, 311819, 311821, 311822, 311823, 311824, 311827, 312524, 312525, 312526, 312527, 312529, 312530, 312532, 313810, 313811, 313905, 313941, 313942, 313944, and 5 copy control. The columns can be used to determine the estimated copy number for each transgenic plant. When using the software to estimate copy numbers, wildtype plants, non-transformed control plants, and plasmid only controls do not result in a copy number as they do not possess a Cq for both the hph and HMG EY target.

Following transfection, culturing, and selection the transgenic plants were transferred to soil. From this process, 139 plants survived and had tissue sampled for gDNA extraction and analysis. All 139 plants were analyzed for copy number estimation. Of these 139 plants, 56 were positive for the ETIP and 11 of the 56 positive plants had a putative single copy integration (FIG. 13) (Table 11). Of the 56 plants that were positive for ETIP integration, amplification of the FAD2A 5'-genome-transgene flanking sequence occurred in 7 plants. Amplification of the FAD2A 3'-transgene-genome flanking sequence did not occur in any of the 56 plants that were positive for ETIP integration. Additionally, of the 56 plants that were positive for transgene integration, 11 plants were positive for the disrupted locus qPCR test. Fourteen plants that were positive for amplification of the FAD2A 5' genome-transgene flanking sequence and/or positive for the disrupted locus qPCR test were subject to Southern analysis, with the 3 probes described above. Of the 14 plants advanced for Southern analysis, all of the plants showed partial integration within the FAD2A locus, but none of these plants showed evidence of a complete full-length integration of the ETIP at the FAD2A locus via HDR when probed with the FAD2A 5' probe, FAD2A 3' and hph probes. No bands that appeared to be i) larger than WT and ii) identical to bands observed for those samples when probed with FAD2A 3' probe (Table 11).

TABLE 11

| Overview of outcomes from analysis of ETIP integration. | |
|---|---|
| No. of plants surviving in soil | 139 |
| No. of plants sampled | 139 |
| No. of plants for which qPCR copy number analysis was completed | 139 |
| No. of plants positive for ETIP integration | 56 |
| No. of plants comprising a putative single copy insert | 11 |
| No. of ETIP/FAD2 in-out 5' reactions | 7 (from 56) |
| No. of ETIP/FAD2 in-out 3' reactions | 0 (from 56) |
| No. of locus disrupted qPCR tests | 9 (from 56) |
| ETIP on-target (Southern) | 0 (from 14) |

Results of ETIP Transgenic Canola Transformed with pDAS000130 and pDAB104010.

The transgenic *Brassica napus* events which are produced via transformation of pDAS000130 and pDAB104010 result in the integration of a single copy, full length T-strand insertion of the ETIP polynucleotide sequence from pDAS000130 within the FAD2A locus. Three to four events are fully characterized and confirmed to contain the integrated ETIP. The confirmation is completed using an in-out PCR amplification method, and further validated via Southern blot. The selected $T_0$ events are grown to the $T_1$ stage of development. The $T_1$ plants are re-screened to determine the zygosity of the integrated T-strand. Screened events are categorized as homozygous, hemizygous, or null.

The homozygous events are used to produce protoplasts via the previously described method. The protoplasts are subsequently co-transformed with at least one zinc finger nuclease that is designed to target a binding site which is incorporated within the ETIP sequence and a donor plasmid which shares homology with specific regions of the ETIP wherein the donor is integrated within the ETIP via an HDR mechanism. Likewise, the protoplasts are subsequently co-transformed with at least one zinc finger nuclease that is designed to target a binding site which is incorporated within the ETIP sequence and a donor plasmid which does not share homology with specific regions of the ETIP, wherein the donor is integrated within the ETIP via an non-homologous end joining mechanism. The ZFN(s) cleave(s) the ETIP locus and the donor plasmid is integrated within the genome of *Brassica napus* cells via homology directed repair or non-homologous end joining.

As a result of the integration of the donor plasmid, the partial DS-red transgene is repaired to a full length DS-red transgene. The expression of the now fully operational DS-red transgene is used to sort protoplast cells with a FACS method. Putative transgenic plants are sorted using the FACS method described in Example 7 and the isolated protoplasts are regenerated into mature plants. The integration of the donor plasmid is confirmed within the ETIP-targeted plants using molecular confirmation methods. As such, the ETIP locus serves as a site-specific locus for gene targeted integration of a donor polynucleotide sequence.

Example 7: FACs Based Sorting of Protoplast Cells

*Brassica napus* protoplasts that were transfected with the DS-Red control construct, pDAS000031, were sorted via FACS-mediated cell sorting using a BD Biosciences Influx-Cell Sorter™ (San Jose, Calif.). The protoplast cells were isolated and transfected as described in Example 3. After the cells had been transfected with pDAS000031, the cells were sorted using the FACS sorter with the conditions described in Table 12.

TABLE 12

Conditions used for sorting protoplast cells transfected with pDAS000031.

| Parameters | |
|---|---|
| Drop frequency | 6.1 KHz |
| Nozzle diameter | 200 μm |
| Sheath pressure | 4 psi |
| Recovery media | W5 media |
| Culture conditions | Bead type culture using sea-plaque agarose and sodium alginate |
| Sort criteria | Sorting based on chlorophyll autofluorescence, reporter gene expression (Ds-Red) |
| Sort recovery (%) | 50-75 |
| Viability post sorting (%) | >95 |

The protoplasts which expressed the DS-red transgene were sorted and isolated. The FACS isolated protoplasts were counted using the sorter. About $1\times10^5$ to $1.8\times10^5$ of cells were placed in a well of a 24-well micro titer plate on the first day after the FACS isolation. The cells were transferred to a bead culture for 5 to 20 days. Similar conditions were tested, wherein about $1\times10^4$ of cells were placed in a well of a 2 or 4-well micro titer plate on the second day after the FACS isolation. The various conditions that were tested resulted in the recovery of cells at a viability or 95-98% of the total isolated protoplast cells. The FACS sorted protoplast cells were transferred to a bead culture for 3-20 days. The FACS sorted protoplast cells were regenerated into plants on media which contained 1.5 mg/mL of hygromycin using the above described protocol. The putative transgenic plants were confirmed to contain an intact T-strand insert from pDAS000031 via molecular conformation protocols.

The FACS sorting method is directly applicable to screen any fluorescent transgene sequence and is used to isolate a proportion of *Brassica napus* protoplast cells that are targeted with a fluorescent transgene via homology mediated repair within a specific site in the ETIP region within a genomic locus.

Example 8: Targeted Integration and Disruption of *Brassica napus* Omega-3 Fatty Acid Desaturase (FAD2) Via Homology Directed Repair Selection of Zinc Finger Binding Domains Specific to FAD2A The transcribed regions for homoeologous FAD2 genes were identified and characterized, zinc finger nucleases that were designed to bind and cleave these sites for NHEJ-mediated targeting of a donor sequence. Zinc finger proteins (ZFPs) directed against DNA sequences from homeologues of FAD2 sequences were designed and tested as described above. From the ZFNs showing on-target activity, one zinc finger proteins were selected that cut the FAD2 target at high efficiency: ZFP 24828-2A-24829 recognizes SEQ ID NO:35 5'-agGCCCAGtAGAGAGGCCaggcgaagta-3' and SEQ ID NO:36 5'-ccAGGGCTGCGTCCTAACCGgcgtctgg-3'. This ZFN was shown to specifically bind and cleave the FAD2A genomic locus.

Design and Construction of "Donor" Vectors for HDR-Directed DNA Repair

Figure 14:
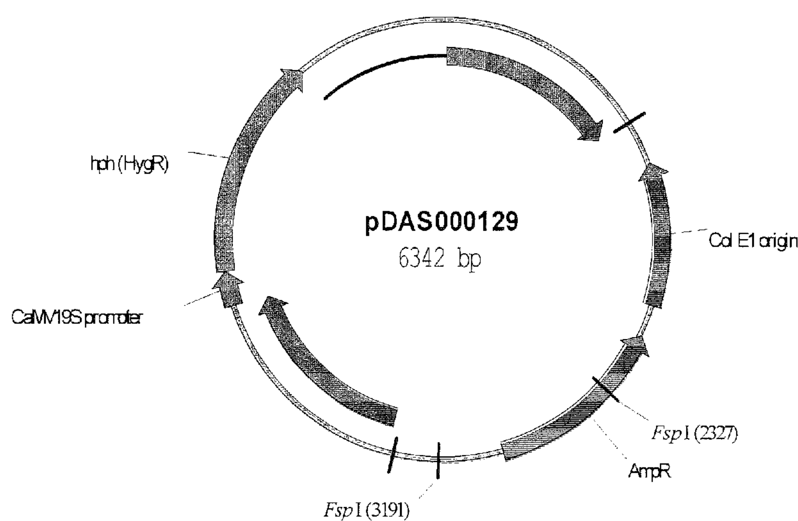
FIG. 14 shows a plasmid map of pDAS000129.

For integration of a donor sequence via HDR, a single vector was constructed. The vector encoded a hygromycin (hph or hpt) resistance gene expression cassette. The hygromycin resistance gene expression cassette included the 19S promoter including a 5' UTR from cauliflower mosaic virus (CaMV) (Cook and Penon Plant Molecular Biology 1990 14(3), 391-405) followed by the hygromycin phosphotransferase (hph) gene (Kaster et al Nucleic Acids Research 1983 11 (19), 6895-6911). The hph gene was codon-optimised for expression in dicotyledonous plants and was flanked by a 3'UTR comprising the transcriptional terminator and polyadenylation site of Open Reading Frame 1 (ORF1) of *A. tumefaciens* pTi15955 (Barker et al, Plant Molecular Biology 1983, 2(6), 335-50). The cassettes were synthesized by a commercial gene synthesis vendor (GeneArt, Life Technologies, Regensberg, Germany). Flanking FAD2A sequences were added upstream and downstream of the gene expression cassette. The hygromycin resistance cassette was cloned into specific restriction enzyme sites of each vector resulting in a "donor" vectors: pDAS000129 (hygromycin-resistant gene-splicing donor: SEQ ID NO:87 FIG. 14).

Colonies of the assembled plasmids were initially screened by restriction endonuclease digestion of DNA purified from overnight cultures of *E. coli*. Restriction endonucleases were obtained from NEW ENGLAND BIOLABS™ (NEB, Ipswich, Mass.) and PROMEGA™ (Promega Corporation, Wis.). Plasmid preparations were performed using the QIAPREP SPIN MINIPREP KIT™ (Qiagen, Hilden, Germany) or the PURE YIELD PLASMID MAXIPREP SYSTEM™ (Promega Corporation, Wis.) following the instructions of the suppliers. After the restriction fragments were confirmed by agarose gel electrophoresis of resulting fragments, plasmid DNA of selected clones were sequenced using ABI Sanger Sequencing and BIG DYE TERMINATOR V3.1™ cycle sequencing protocol (Applied Biosystems, Life Technologies). Sequence data were assembled and analyzed using the SEQUENCHER™ software (Gene Codes, Ann Arbor, Mich.).

Transformation of *Brassica napus*

PEG-Mediated Protoplast Transfection and Regeneration of ETIP Targeted to FAD2A and FAD2A ZFN (Precision Events)

Mesophyll derived protoplasts were isolated from three weeks old sterile shoot cultures of *Brassica napus* (DH10275). The corresponding seeds were germinated. The seeds were surface-sterilized using 70% ethanol for 1 minute by gentle shaking followed by 3-4 rinses in sterile double-distilled water and subsequently sterilized using 20% bleach and 10 μl of Tween 20™; the seeds were treated with the bleach on a shaker (table top rotary shaker approximately 100 RPM) for 15 minutes followed by 3-4 rinses in sterile double-distilled water, seeds were carefully transferred to a sterile filter paper to remove the excess moisture and plated on seed germination medium (½ strength MS/B5 Vitamins+1% sucrose+0.8% Agar; pH 5.8 and 50-60 ml of the media was poured per Petri dish (15×100 mm) that was placed with a slight angle using a support); approximately 50 seeds were placed in each plate. The plates were incubated upright at 22° C. in 16 h/d light (20 μmol $m^{-2}$ $s^{-1}$) for 6 days. Hypocotyl segments of 0.5 cm size were dissected from the six day old seedlings and cultured on shoot induction medium (MS/B5 Vitamins+3% sucrose+500 mg/L MES+BAP (13 μm)+Zeatin (5 μm)+Silver Nitrate (5 mg/L)+0.8% Agar (pH 5.8) and poured in 100×20 mm sterile Petri dish) approximately 20 explants were placed on each plate. Shoot meristems that appeared after 3-4 weeks were transferred to shoot elongation medium (MS/B5 Vitamins+2% sucrose+500 mg/L MES+BAP (2 μm)+GA-3 (0.1 μm)+0.8% Agar (pH 5.8) and poured in 250 ml culture vessels) and the cultures were maintained in this medium for 4 weeks with one round of sub-culturing in between. Shoots of 2-3 cm height were then transferred to root initiation media (½ strength MS/B5 Vitamins+1% sucrose+500 mg/L MES+IBA (2.5 μm)+0.6% Agar (pH 5.8) and poured in 700 ml culture vessels) for root development. Rooted shoots were sub-cultured in fresh root initiation media at 3-4 weeks intervals as stem cuttings for two-three rounds before use. The cultures were maintained throughout at 22° C. in 16 h/d light (30 $\mu mol\ m^{-2}\ s^{-1}$).

Protoplast Isolation and Purification

In vitro grown DH12075 *Brassica napus* plants were used as the explant source for isolating mesophyll protoplasts. The 3rd to 4$^{th}$ upper fully expanded leaves from 3 to 4 weeks old plantlets were cut into small strips (0.5 to 1 mm) with a sharp scalpel for protoplast isolation. Enzymatic digestion was carried out by treating 250-500 mg of leaf material with 25 ml of digestion buffer (1.2% (w/v) Cellulase "Onozuka" R10® and 0.2% (w/v) Macerozyme® R10 dissolved in K4 media (Spangenberg et al. 1998)). The Petri dish containing the leaf material and digestion buffer was sealed with Parafilm™ and incubated at room temperature for 12 to 15 h in darkness. After overnight incubation the digests were filtered through a BD® cell strainer (mesh size 70 μm). Protoplasts suspension (5-6 ml) were collected in a 14 ml round bottomed tube that was over layered with 1 ml of washing solution W5 buffer (154 mM NaCl, 125 mM $CaCl_2$, 5 mM KCl and 5 mM glucose; pH 5.8 Mcnczel et al. 1981) and centrifuged at 400 RPM for 10 min. After centrifugation, protoplasts that floated in the interphase were withdrawn and washed by centrifugation using 10 ml of W5 buffer at 400 RPM for 10 min. After the final wash, isolated protoplasts were resuspended at a density of $1\times10^6$ protoplasts per mL of W5 buffer and incubated for 1 hour before transfections.

Assessment of Protoplasts Yield and Viability

Protoplasts yield was assessed using a haemocytometer following Sambrook and Russel, 2006 and the viability was tested using Evans blue stain (400 mg/L dissolved in 0.5 M of Mannitol) following Huang et al. 1996 with few modifications.

PEG 4000 Mediated Stable DNA Delivery

Plasmid DNA of the ETIP-containing vector pDAS000129 and the ZFN vector (pDAB104010) targeting the FAD2 A locus was isolated from cultures of *E. coli* using the Pure Yield Plasmid Maxiprep System™ (Promega Corporation, Wis.) or Plasmid Maxi Kit™ (Qiagen, Hilden) following the instructions of the suppliers. The plasmid DNA was dissolved at a density of 0.7 μg per μL of sterile double-distilled water. A total of thirty micrograms (30 μg) of the plasmid DNA (5:1 molar of pDAS000129 and pDAB104010) was applied to one million protoplasts (viability≥95) suspended in 100 μA of transformation buffer (15 mM $MgCl_2$, 0.1% (w/v) morpholinoethanesulphonic acid (MES) and 0.5 M mannitol; pH 5.8) followed by 150 μl of PEG solution (40% (w/v) PEG 4000 in 0.4 M Mannitol and 0.1 M Ca $(NO_3)_2$ (pH 6-7) Spangenberg and Potrykus (1995). Control transformations included a total of thirty micrograms (30 μg) of plasmid DNA of either pDAS000129 or pDAB104010. After 10-15 minutes of incubation at room temperature, 5 ml of W5 buffer was added in a drop wise manner and the protoplasts were gently mixed and another 5 ml of W5 buffer was added as slow stream to the protoplasts suspension. Protoplasts were mixed gently and centrifuged at 400 RPM for 10 min and the W5 supernatant was removed carefully leaving behind the protoplasts in the form of a pellet. Transfected protoplasts were then incubated in 1 ml of W5 buffer at room temperature until they were embedded in bead type cultures. Protoplasts samples co-transfected with the construct pDAS000129 and pDAB104010 exhibited a cell viability ranging between 60-80% immediately after transfection. The transfected protoplasts were embedded following either sea plaque agarose or sodium alginate method.

Culturing of Mesophyll Derived Protoplasts to Recover Viable Microcalli

Before embedding the transfected protoplasts were centrifuged at 400 RPM for 10 min and the W5 buffer was carefully removed. The protoplasts were then resuspended in 0.5 ml of K3 media (Spangenberg et al. 1998). Exactly 0.5 ml of the transfected protoplast suspension (ca. $5\times10^5$ protoplasts) was placed in a 6 cm Petri dish and to this 4.5 ml of pre-warmed (melted in a microwave oven and incubated in a water bath at 40-45° C.) 1:1 mix of K3:H medium (Spangenberg et al. 1998) containing 0.6% Sea Plaque™ agarose was added. The agarose and the protoplasts suspension was mixed gently and allowed to set. After solidification (after 20-30 min.), seal the dishes were sealed with Parafilm® and the protoplasts were cultured for 24 h in darkness at 24° C., followed by 6 days in continuous dim light (5-10 $\mu mol\ m^{-2}\ s^{-1}$), where first and multiple cell divisions occur. After 6 days the protoplasts embedded in agarose was cut into four quadrants and placed in 100 ml of A medium (Spangenberg et al. 1998) in a 700 ml culture vessel. The liquid A medium, was supplemented with 1.5 mg/l hygromycin. The cultures were incubated on a rotary shaker with 80-100 RPM at 24° C. in continuous dim light. Resistant colonies appear after 5-6 weeks and 3-4 weeks post protoplast plating in the case of sea-plaque agarose and sodium alginate method respectively. Microcalli of size between 2-3 mm diameter were transferred onto B1 medium (MS/MS Vitamins+3.5% Sucrose+500 mg/L MES+BAP (5 μm)+NAA (5 μm)+2,4-D (5 μm)+1.5 mg/L Hygromycin+0.7% Agarose Type I (pH 6.0) and poured in 100×20 mm sterile Petri dish) by gently breaking the agarose beads. The microcalli thus obtained was resuspended in sufficient quantity of liquid A (50 ml of liquid A was used for one ml of the settled cell volume (SCV: This was measured after transferring all the released microcalli to a sterile 50 or 15 ml falcon tube and allowed to settle down for 5 min)). After mixing the microcalli uniformly, 0.5 ml of the microcalli suspended in the liquid A media was transferred to B1 plates and using 1-2 ml of additional liquid A media the microcalli was distributed uniformly in the B1 media and the excess liquid A media was carefully removed from each plate. The plates were sealed using a micropore tape which enhanced the embryo maturation.

Sodium-Alginate Method

Before embedding the transfected protoplasts were centrifuged at 400 RPM for 10 min and the W5 buffer was carefully removed. The protoplasts were then resuspended in 1.0 ml of 0.5 M Mannitol and incubated in ice. To this equal volume of 1.0% sodium alginate was added and mixed gently. The protoplasts suspension was incubated in ice until it was embedded. Bead forming solution (0.4 M Mannitol+50 mM $CaCl_2$ (pH 5.8)) was transferred to a sterile six well plate (3-4 ml per well) using a serological pipette. Exactly 1.0 ml of the protoplasts suspension was added in a drop wise manner using a 1 ml pipette into the bead forming solution and each transfected sample (ca. $5\times10^5$ protoplasts) was embedded per well. The protoplasts suspension was incubated for 1-2 hours at room temperature to form sodium alginate beads. After the incubation period the bead forming solution was carefully removed and replaced with 4-5 ml of 1:2 mixture of K3+H:A media (Spangenberg et al. 1998) supplemented with 1.5 mg/L of Hygromycin. The protoplasts were cultured for 3-4 weeks in darkness at 22° C. in a shaker (50 RPM). After 3-4 weeks the resistant microcalli (0.5-1.0 mm) were released by treating with depolymerisation buffer (0.3 M Mannitol+20 mM Sodium Citrate (pH 5.8)). After removing the liquid media 3-4 ml of depolymerisation buffer (was added to each well containing the bead-type cultures and incubated at room temperature for 2 hours. Using a sterile forceps the beads were gently mixed and to enhance the efficient release of the microcalli. Using a sterile 1.0 ml pipette gently mix gelling agent released in the depolymerisation buffer was removed. The microcalli was washed twice using 5 ml of liquid A media and the microcalli was resuspended in sufficient quantity of liquid A (50 ml of liquid A was used for one ml of the settled cell volume (SCV: This was measured after transferring all the released microcalli to a sterile 50 or 15 ml falcon tube and allowed to settle down for 5 min)). After mixing the microcalli uniformly, 0.5 ml of the microcalli suspended in the liquid A media was transferred to B1 media (MS/MS Vitamins+3.5% Sucrose+500 mg/L MES+BAP (5 μm)+NAA (5 μm)+2,4-D (5 μm)+1.5 mg/L Hygromycin+0.7% Agarose Type I (pH 6.0) and poured in 100×20 mm sterile Petri dish) and using 1-2 ml of additional liquid A media the microcalli was distributed uniformly in the B1 media and the excess liquid A media was carefully removed from each plate. The plates were sealed using a micropore tape which enhanced the embryo maturation. The cultures were maintained at 22° C. in 16 h/d light (30 μmol $m^{-2}$ $s^{-1}$).

Isolation of Genomic DNA from Mesophyll Protoplasts

Transfected protoplasts were transferred from the 3 cm PETRI™ dish to a 2 mL microfuge tube. The cells were pelleted by centrifugation at 70 g and the supernatant was removed. To maximize the recovery of transfected protoplasts, the PETRI™ dish was rinsed three times with 1 mL of wash buffer. Each rinse was performed by swirling the wash buffer in the PETRI™ dish for 1 minute, followed by transfer of the liquid to the same 2 mL microfuge tube. At the end of each rinse, the cells were pelleted by centrifugation at 70 g and the supernatant was removed. The pelleted protoplasts were snap frozen in liquid nitrogen before freeze drying for 24 h in a LABCONCO FREEZONE 4.5® (Labconco, Kansas City, Mo.) at −40° C. and 133×$10^{-3}$ mBar pressure. The lyophilized cells were subjected to DNA extraction using the DNEASY® PLANT DNA EXTRACTION MINI KIT (Qiagen) following the manufacturer's instructions, with the exception that tissue disruption was not required and the protoplast cells were added directly to the lysis buffer.

Isolation of Genomic DNA from Callus Tissue

Individual calli was snap frozen in liquid nitrogen before freeze drying for 24 h in a LABCONCO FREEZONE 4.5® (Labconco, Kansas City, Mo.) at −40° C. and 133×$10^{-3}$ mBar pressure. The lyophilized calli was subjected to DNA extraction using the DNEASY® PLANT DNA EXTRACTION MAXI kit (Qiagen, Hilden, Germany) following the manufacturer's instructions.

Detection of Gene Addition to FAD2A by Homology Directed Repair in Proliferated Callus Genomic DNA was extracted from protoplast pools (one million protoplast per pool) to which donor DNA encoding a functional HGH reporter cassette (pDAS000129), ZFN DNA (pDAB104010) or a mixture of donor and ZFN DNA had been delivered twenty-four hours earlier. Quantities of DNA delivered for transformation are described above. PCR products were cloned into plasmid vectors. The genomic editing occurs independently in each cell giving rise to a variety of different insertion events, by cloning into a plasmid vector, each genomic edit can be sequenced without ambiguity. Several clones were sequenced on an ABI3730XL® automated capillary electrophoresis platform. Analysis of gene sequences was done using SEQUENCHER SOFTWARE V5.0™ (GeneCodes, Ann Arbor, Mich.).

Evidence of gene addition to the FAD2A locus by homologous directed repair was provided by amplification of both the 5' and 3' FAD2A cassette and junctions from genomic DNA extracted from protoplasts using the primers described in Table 13. No amplification was observed from protoplasts to which ZFN plasmid or donor plasmid alone had been delivered. All junction sequences were indicative of insertion of the hgh cassette at the Fad2A locus via an HDR-mediated repair pathway. Deletions of varying lengths from either or both the genome and the cassette were observed as well as the addition of sequences derived from the vector backbones (either from the donor or ZFN) being inserted between the genome and the cassette (FIG. 15).

TABLE 13

List of constructs used for donor integration within the FAD2A locus

| Treatments | Constructs | Hph Assay | In-out PCR (LB) | In-out PCR (RB) |
|---|---|---|---|---|
| ZFN | pDAB104010 (No Hyg) | NO | NO | NO |
| ZFN | pDAB104010 (1.5 mg/L Hyg) | NO | NO | NO |
| DNR | pDAS000129 (No Hyg) | YES | NO | NO |
| DNR | pDAS000129 (1.5 mg/L Hyg) | YES | NO | NO |
| DNR + ZFN2c | pDAS000129 + pDAB104010 (No Hyg) | YES | NO | NO |
| DNR + ZFN2c | pDAS000129 + pDAB104010 (1.5 mg/L Hyg) | YES | YES | YES |
| DsRed Ctrl | pDAS00097 (2 mg/L PPT) | NO | NO | NO |
| negative control | untrasfected DH12075 | NO | NO | NO |
| negative control | water | NO | v | NO |

Example 9: Targeted Integration and Disruption of *Brassica napus* Omega-3 Fatty Acid Desaturase (Fad2) Via Non Homologous End Joining Selection of Zinc Finger Binding Domains Specific to FAD2A The transcribed regions for homoeologous FAD2 genes were identified and characterized, zinc finger nucleases that were designed to bind and cleave these sites for NHEJ-mediated targeting of a donor sequence. Zinc finger proteins (ZFPs) directed against DNA sequences from homeologues of FAD2 sequences were designed and tested as described above. From the ZFNs showing on-target activity, one zinc finger proteins were selected that cut the FAD2A target at high efficiency: ZFP 24828-2A-24829 recognizes SEQ ID NO:35 5'-agGCCCAGtAGAGAGGCCaggcgaagta-3' and SEQ ID NO:36 5'-ccAGGGCTGCGTCCTAACCG-gcgtctgg-3'. This ZFN was shown to specifically bind and cleave the FAD2A genomic locus. The plasmid construct, pDAB104010 that is previously described above was constructed and is used for transformation experiments.

Figure 16:
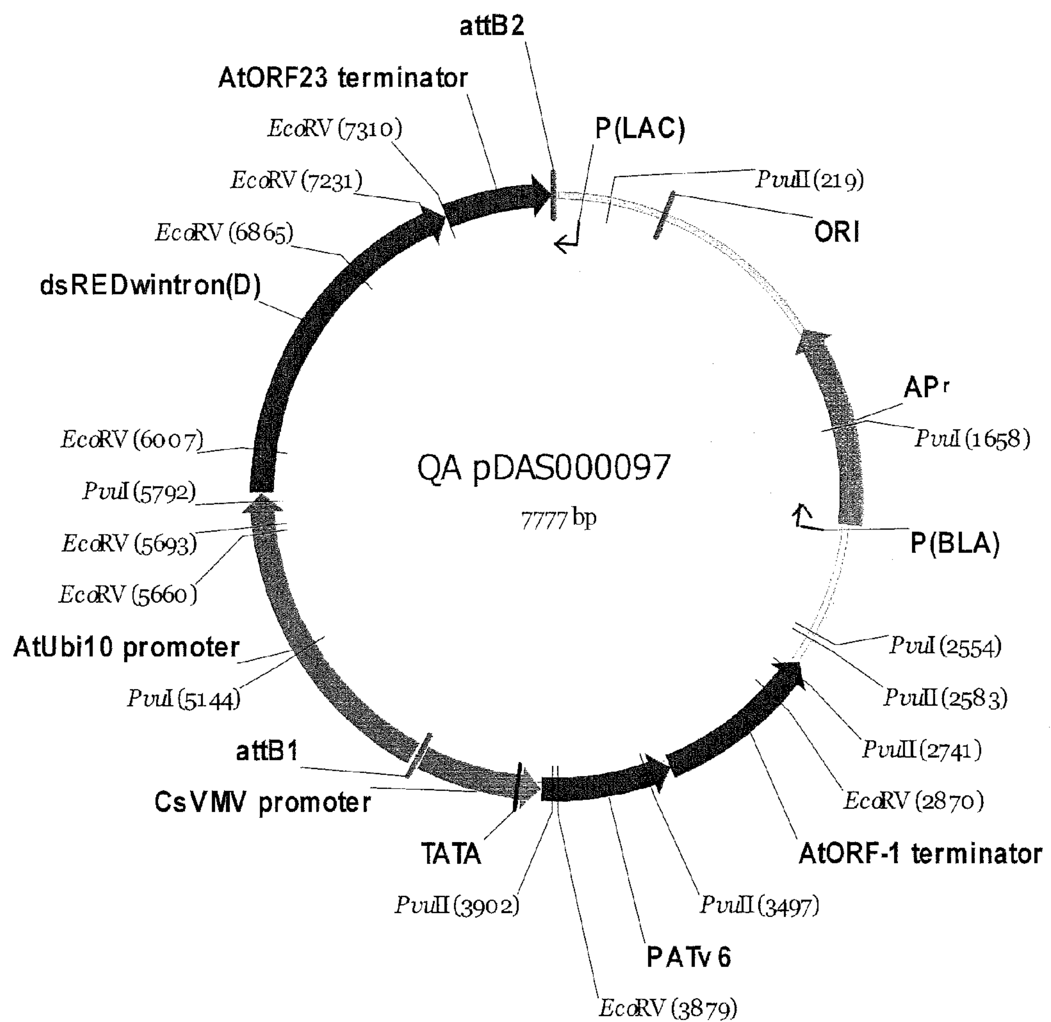
FIG. 16 shows plasmid map pDAS000097.

Design and Construction of Expression Vectors Encoding Zinc Finger Nucleases and Donor Vectors Specific to FAD2A For integration of a donor sequence via NHEJ, a single donor vector was constructed. The vector encoded a dsRED reporter gene expression cassette. The dsRED reporter gene expression cassette included the *Arabidopsis thalinana* Ubiquitin 10 promoter (Callis, et al., 1990, *J. Biol. Chem.*, 265:12486-12493) followed by the dsRED gene (Dietrich et al. (2002) Biotechniques 2(2):286-293). The dsRED gene was codon-optimised for expression in dicotyledonous plants and was flanked by a 3'UTR comprising the transcriptional terminator and polyadenylation site of Open Reading Frame 23 (ORF23) of *A. tumefaciens* pTi15955 (Barker et al, Plant Molecular Biology 1983, 2(6), 335-50). The selectable marker cassette included the CsVMV promoter fused to the pat transgene. The pat transgene was terminated with Open Reading Frame 1 (ORF1) of *A. tumefaciens* pTi15955 (Barker et al, Plant Molecular Biology 1983, 2(6), 335-50). The dsRED resistance cassette was cloned into specific restriction enzyme sites of each vector resulting in "donor" vector: pDAS000097 (SEQ ID NO:88, FIG. 16). The pDAS00097 donor is designed to be delivered as linear DNA or circular DNA into the plant cell and integrated within the FAD2A locus upon cleavage of the FAD2A genomic locus by the ZFN pDAB104010. The linear DNA mediated integration is the result of integrating a linearized pDAS000097 plasmid into the plant cell during transformation. The plasmid can be linearized by cleavage at a unique restriction enzyme site. The circular DNA mediated integration is the result of integrating a circularized pDAS000097 plasmid into the plant cell during the transformation. pDAS000097 is modified to contain a zinc finger binding site that can be cleaved by the ZFP 24828-2A-24829 zinc finger nuclease. The circular plasmid, pDAS000097, is cleaved in the plant cell by the pDAB104010 encoded zinc finger nuclease, and the dsRED gene cassette is integrated into the FAD2A genomic locus.

Colonies of the assembled plasmids were initially screened by restriction endonuclease digestion of DNA purified from overnight cultures of *E. coli*. Restriction endonucleases were obtained from NEW ENGLAND BIOLABS™ (NEB, Ipswich, Mass.) and PROMEGA™ (Promega Corporation, Wis.). Plasmid preparations were performed using the QIAPREP SPIN MINIPREP KIT™ (Qiagen, Hilden, Germany) or the PURE YIELD PLASMID MAXIPREP SYSTEM™ (Promega Corporation, Wis.) following the instructions of the suppliers. After the restriction fragments were confirmed by agarose gel electrophoresis of resulting fragments, plasmid DNA of selected clones were sequenced using ABI Sanger Sequencing and BIG DYE TERMINATOR V3.1™ cycle sequencing protocol (Applied Biosystems, Life Technologies). Sequence data were assembled and analyzed using the SEQUENCHER™ software (Gene Codes, Ann Arbor, Mich.).

Transformation of *Brassica napus*

Mesophyll derived protoplasts are isolated and prepared from *Brassica napus* (DH10275) plants as described above. The protoplasts are transformed with purified plasmid DNA. Aliquots of donor and ZFN plasmid DNA are prepared in three molar ratios: 1:1 (30 μg of each plasmid), 5:1 (donor plasmid to ZFN plasmid to a total of 30 μg of plasmid DNA) and 10:1 (donor plasmid to ZFN plasmid to a total of 30 μg of plasmid DNA). Additionally, donor-only and ZFN-only aliquots (30 μg) are prepared as controls. The amounts of DNA delivered to the *B. napus* protoplasts via a PEG4000 mediated transformation are summarized in Table 14. The transformed protoplast cells are cultured as previously described, wherein the selection medium is glufosinate selection medium, and putative transformants are assayed via qPCR analysis for transgene insertions.

TABLE 14

Quantities of ZFN and donor DNA delivered to protoplasts

| | Molar Ratio of plasmid DNA | Total quantity of DNA (μg) delivered to 1 million protoplasts |
|---|---|---|
| Splicing | Donor plasmid only | 30 |
| | ZFN plasmid only (pDAB104010) | 30 |
| | 1:1 Donor:ZFN | 60 |
| | 5:1 Donor:ZFN | 30 |
| | 10:1 Donor:ZFN | 30 |
| Editing | Donor plasmid only | 30 |
| | 1:1: ZFN plasmids (pDAB104010) | 30 |
| | 1:1:1 Donor:ZFN:ZFN | 90 |
| | 5:1:1 Donor:ZFN:ZFN | 30 |
| | 10:1:1 Donor:ZFN:ZFN | 30 |

Detection of Gene Addition to FAD2A by Non-Homologous End Joining in Protoplasts Genomic DNA is extracted from protoplast pools (one million protoplast per pool) to which donor DNA encoding a functional dsRFP reporter cassette (pDAS000097), ZFN DNA (pDAB104010) or a mixture of donor and ZFN DNA are delivered twenty-four hours earlier. Quantities of DNA delivered for transformation are described above. PCR products are cloned into plasmid vectors. The genomic editing occurs independently in each cell giving rise to a variety of different insertion events, by cloning into a plasmid vector, each genomic edit can be sequenced without ambiguity. Several clones are sequenced on an ABI3730XL® automated capillary electrophoresis platform. Analysis of gene sequences is done using SEQUENCHER SOFTWARE V5.0™ (GeneCodes, Ann Arbor, Mich.).

Evidence of gene addition to the FAD2A locus by editing or splicing is provided by amplification of both the 5' and 3' FAD2A-cassette junctions from genomic DNA extracted from protoplasts. No amplification is observed from protoplasts to which ZFN plasmid or donor plasmid alone had been delivered. All junction sequences are indicative of insertion of the dsRED cassette at the FAD2A locus via an NHEJ-mediated repair pathway. Deletions of varying lengths from either or both the genome and the cassette are observed as well as the addition of sequences derived from the vector backbones (either from the donor or ZFN) being inserted between the genome and the cassette.

Detection of Gene Addition to FAD2A by Non-Homologous End Joining in Callus Tissue Regenerated from Protoplasts Further evidence of splicing and editing of the FAD2A locus was obtained from callus tissue regenerated from protoplasts on selection to which donor DNA encoding a dsRED cassette (pDAS000097), ZFN DNA only (pDAB104010) or donor and ZFN DNA are delivered. DNA is extracted from approximately 80 calli for each ratio.

Integration of the dsRED cassette into the *B. napus* genome is confirmed by TAQMAN™ qPCR using primer and probes specific to the donor insert and the genomic flanking sequences. Relative quantification is calculated according to the $2^{-\Delta\Delta Ct}$ method (Livak and Schmittgen, 2001), which provided an estimation of the number of copies of dsRED cassette inserted into the genome. Evidence of NHEJ-mediated splicing and editing of FAD2A is obtained by conducting PCR assays with one primer specific to FAD2A and a second primer specific to either the promoter or terminator of the dsRED cassette. PCR products are gel-purified using QIAQUICK MINIELUTE PCR PURIFICATION KIT™ (Qiagen) and sequenced using a direct Sanger sequencing method. The sequencing products are purified with ethanol, sodium acetate and EDTA following the BIGDYE® v3.1 protocol (Applied Biosystems) and sequenced and analysed as above.

The numbers of calli containing the donor cassette in each experiment are determined. Evidence of donor gene addition to the FAD2A locus by editing and/or splicing is provided by PCR amplification across the ZFN cut sites and both the 5' and 3' FAD2A-dsRED cassette junctions. PCR amplification of the genomic DNA isolated from callus tissue recovered from control protoplasts which are transformed with only the dsRED plasmid (pDAS000097) or only the ZFN plasmid (pDAB104010) do not result in the production of PCR amplification products.

The PCR amplicons produced from the amplification of the 5' and 3' FAD2A-dsRED cassette junctions are purified from the agarose gel and sequenced to confirm specificity of the integration within the FAD2A genomic locus. The results of the sequencing analysis of the PCR products indicate that each isolated callus which is generated from an individually transformed protoplast only produce a single PCR amplification product and do not contain cells of mixed genotypes.

Detection of Gene Addition to FAD2A by Non-Homologous End Joining in Plants

DNA is extracted from plants that are regenerated from protoplasts and transferred to potting medium. The majority of plants recovered are estimated to contain only 1-2 copies of the dsRED cassette encoded in the donor DNA. Plants are analyzed with the same suite of assays described for callus tissue as well as with assays to determine if the cassette had inserted in the FAD2A locus.

The frequency of on-target splicing, where the dsRED cassette is inserted into FAD2A locus is determined using the PCR assays described above. The amplicon bands obtained are sequenced to determine the flanking sequences. Additionally, plants are screened for off-target insertions to determine the frequency of integration of dsRED at sites other than FAD2A.

Figure 17:
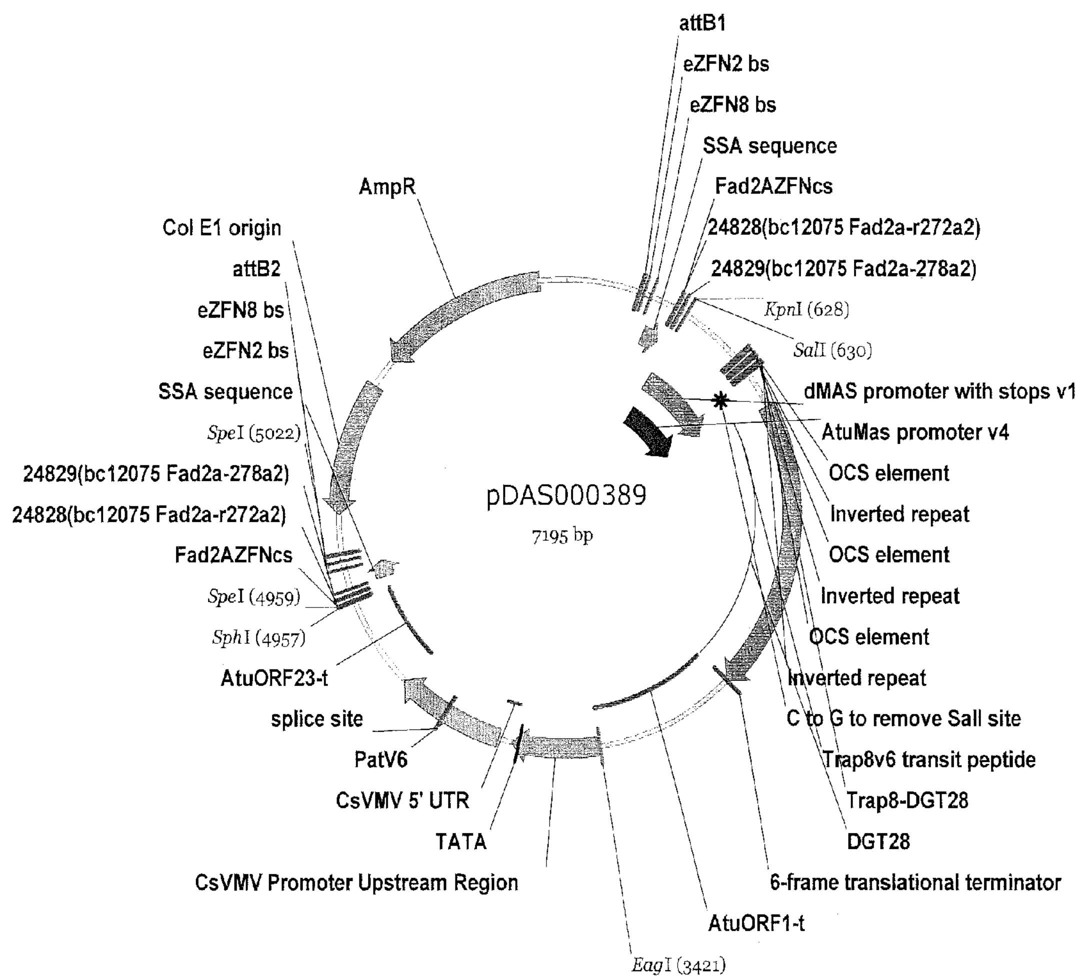
FIG. 17 shows a plasmid map of pDAS000389.
Figure 18:
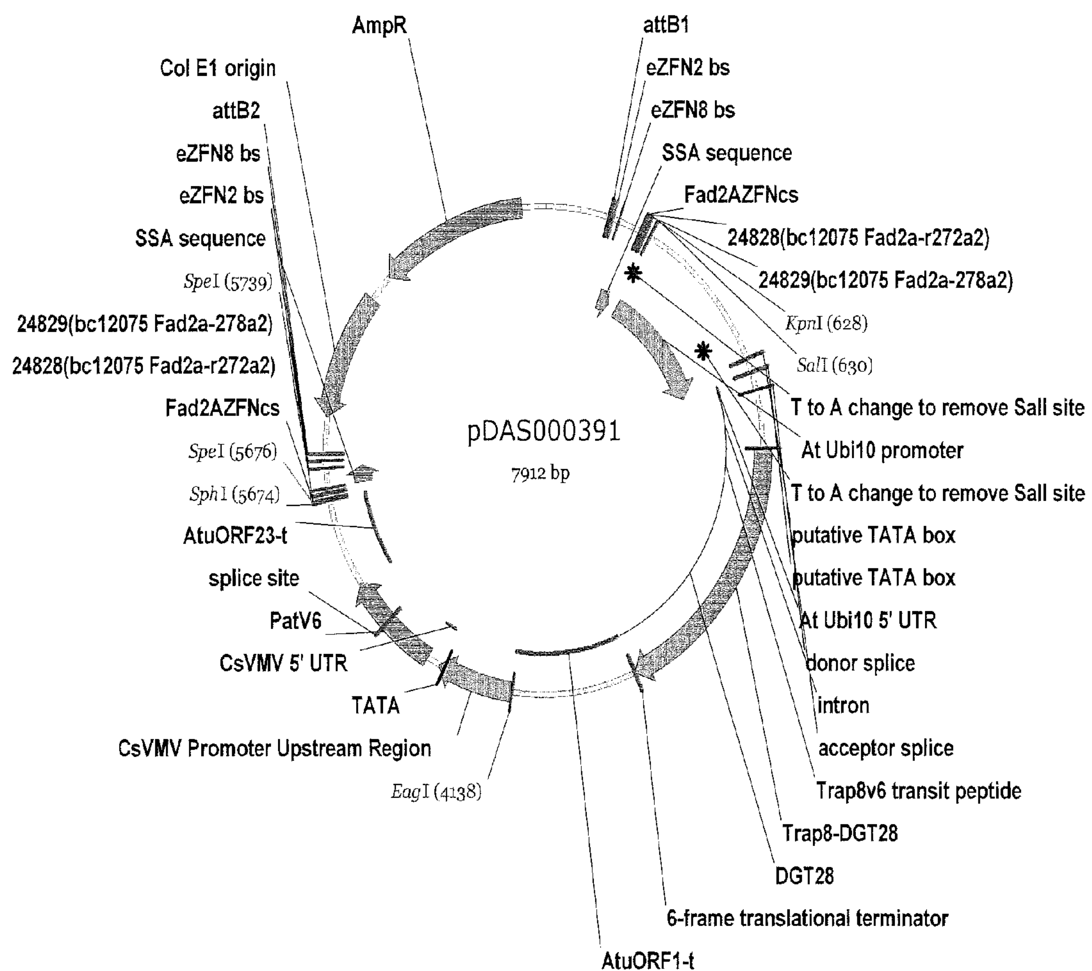
FIG. 18 shows a plasmid map of pDAS000391.
Figure 19:
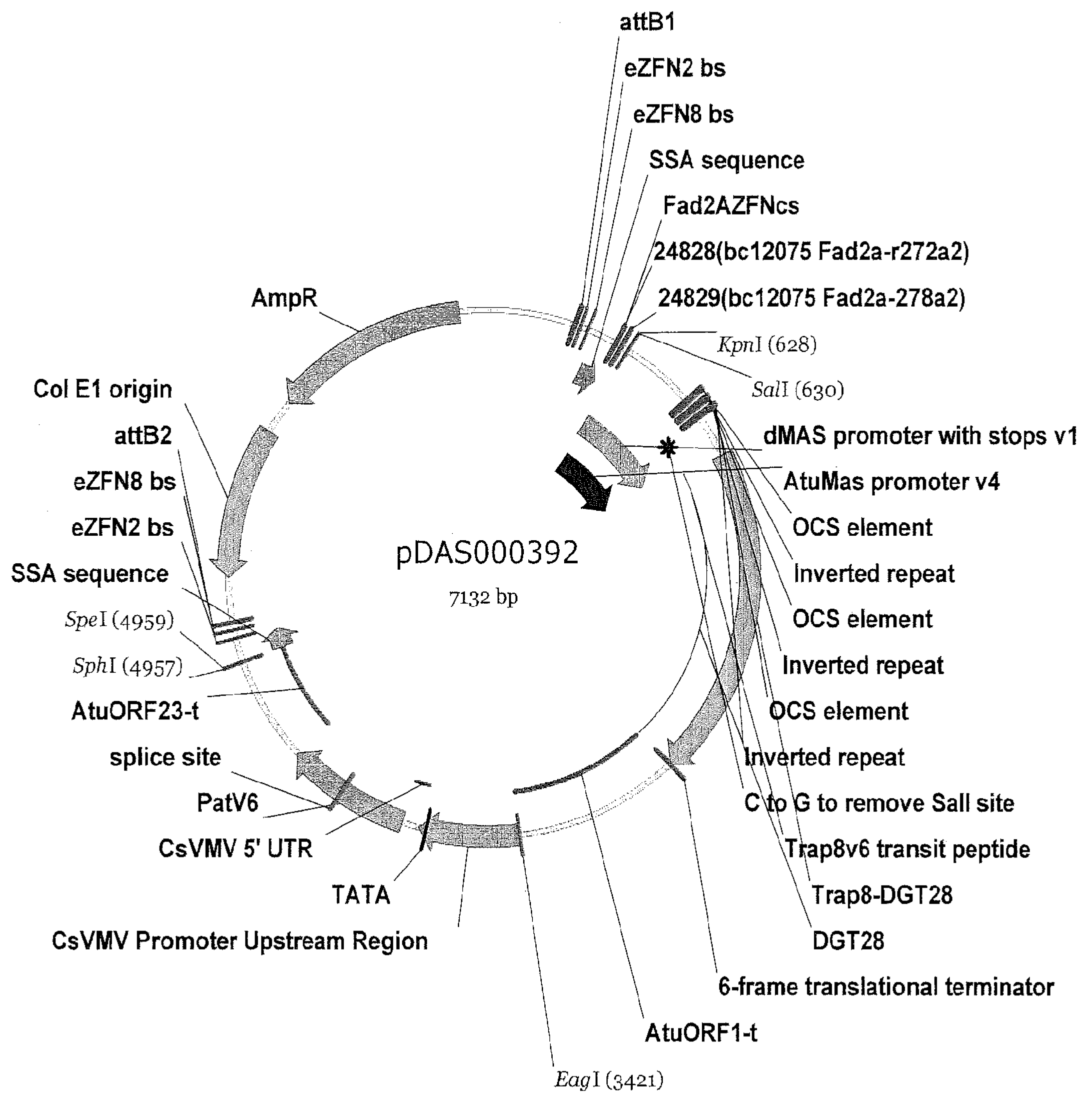
FIG. 19 shows a plasmid map of pDAS000392.
Figure 20:
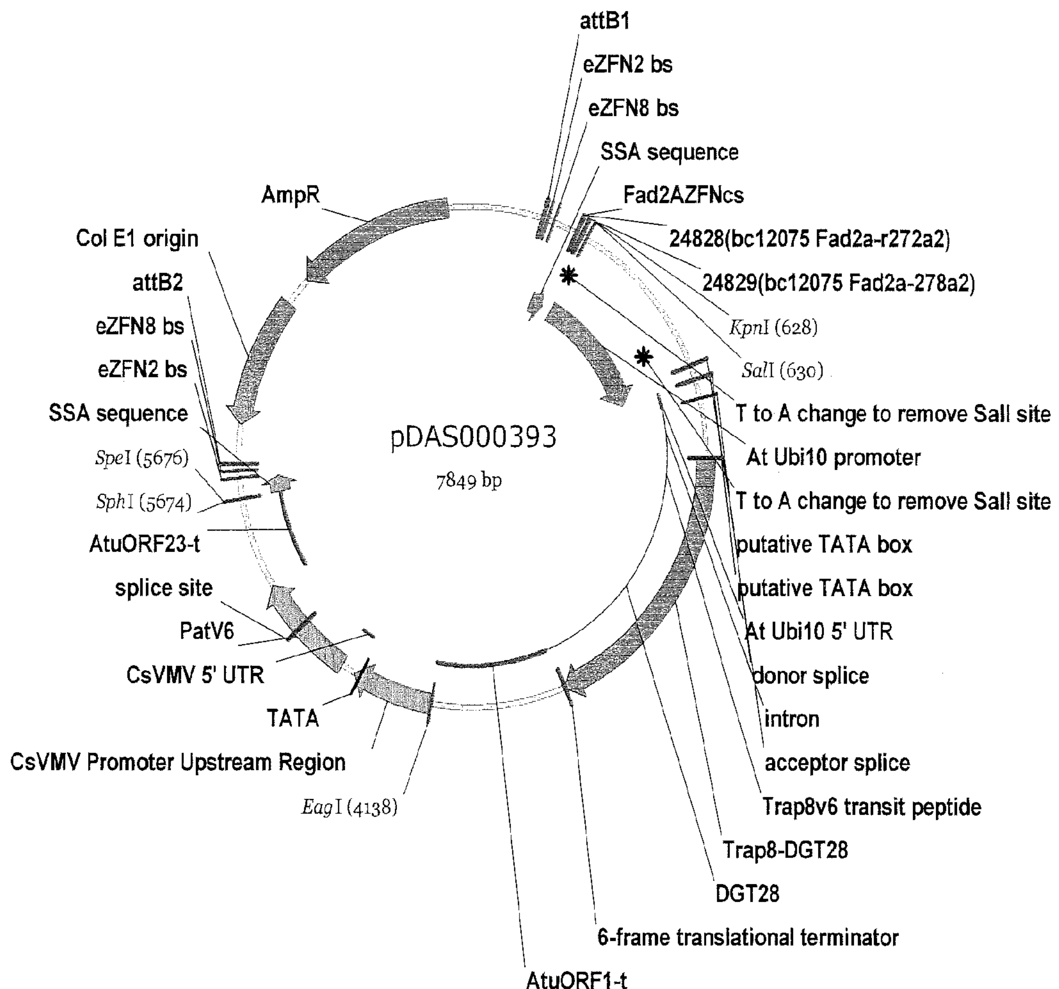
FIG. 20 shows a plasmid map of pDAS000393.
Figure 21:
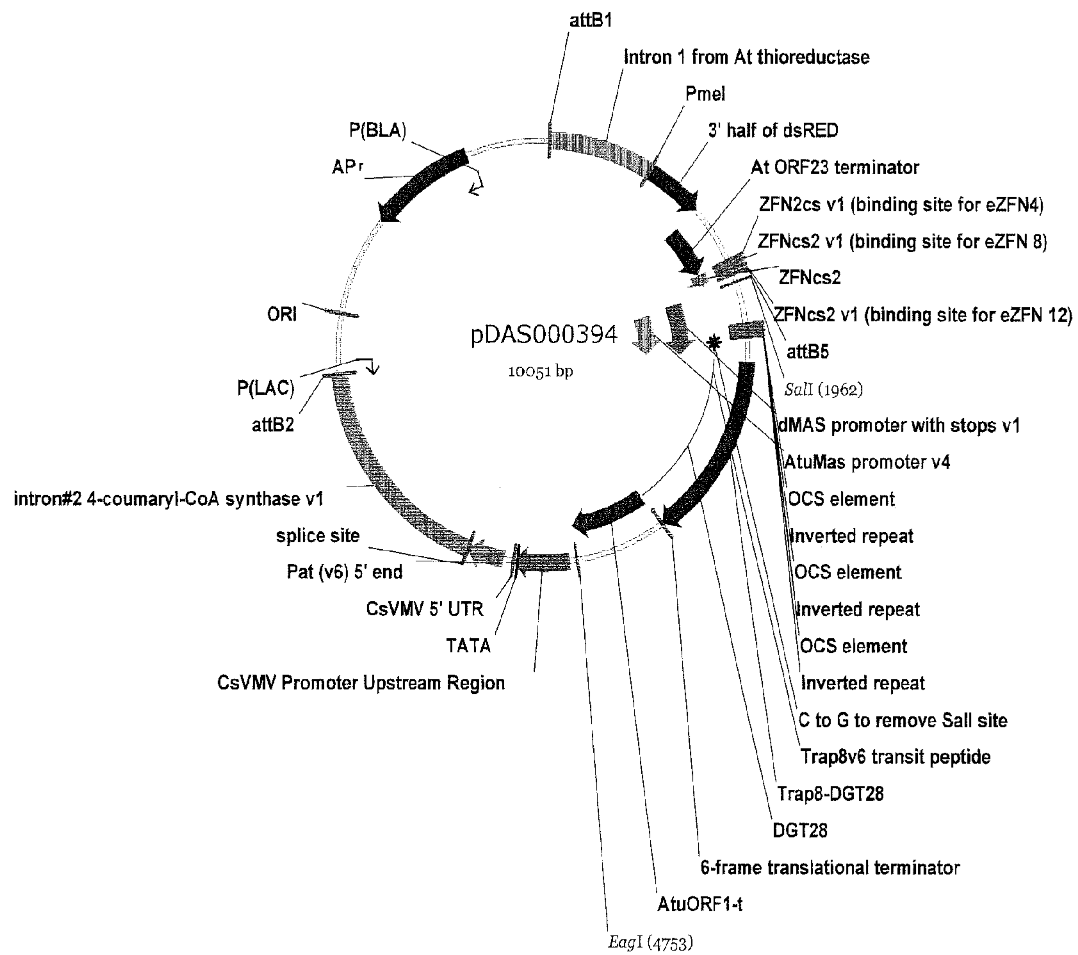
FIG. 21 shows a plasmid map of pDAS000394.
Figure 22:
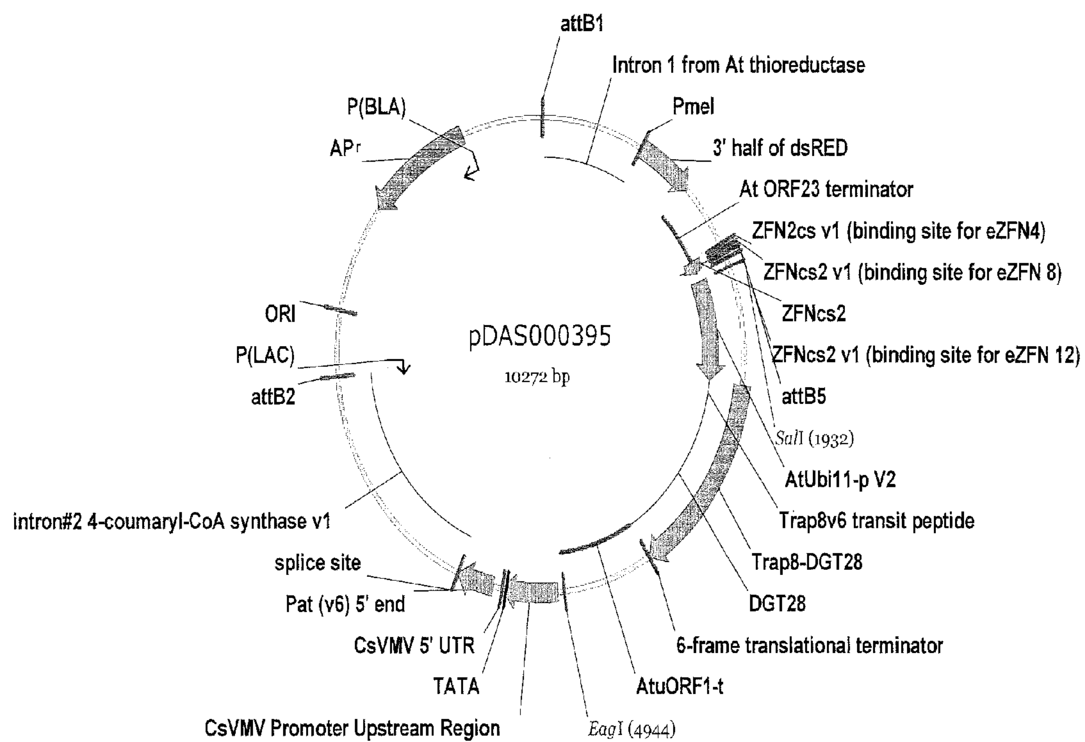
FIG. 22 shows a plasmid map of pDAS000395.
Figure 23:
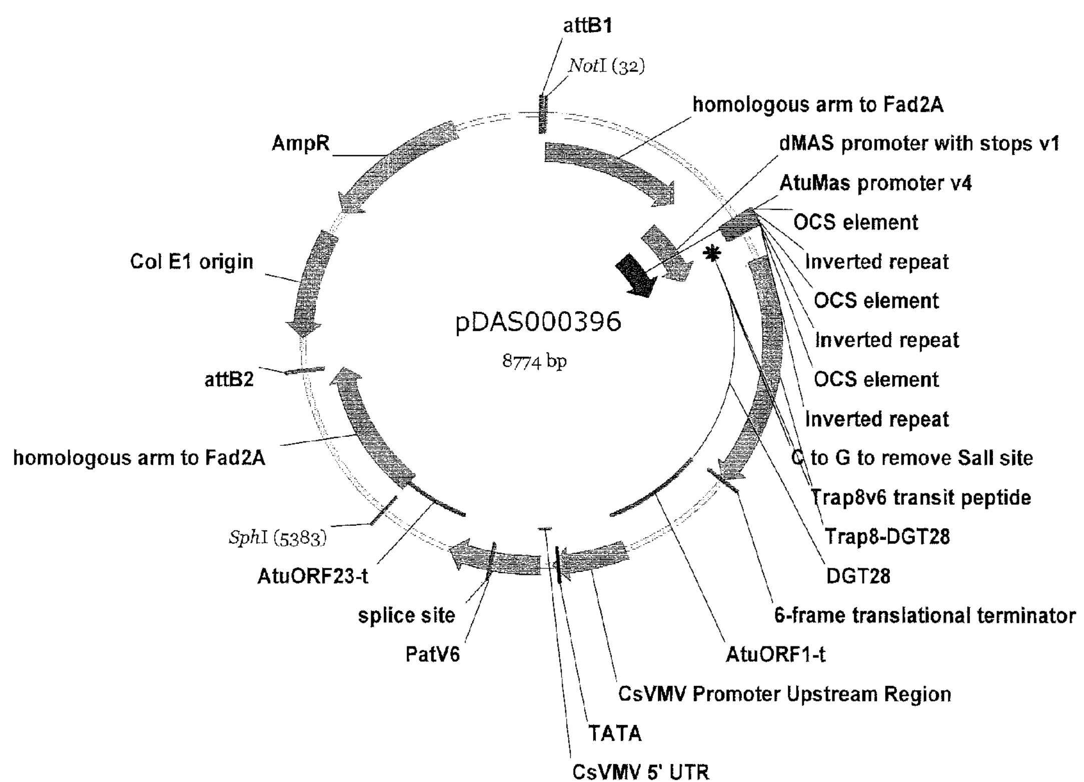
FIG. 23 shows a plasmid map of pDAS000396.
Figure 24:
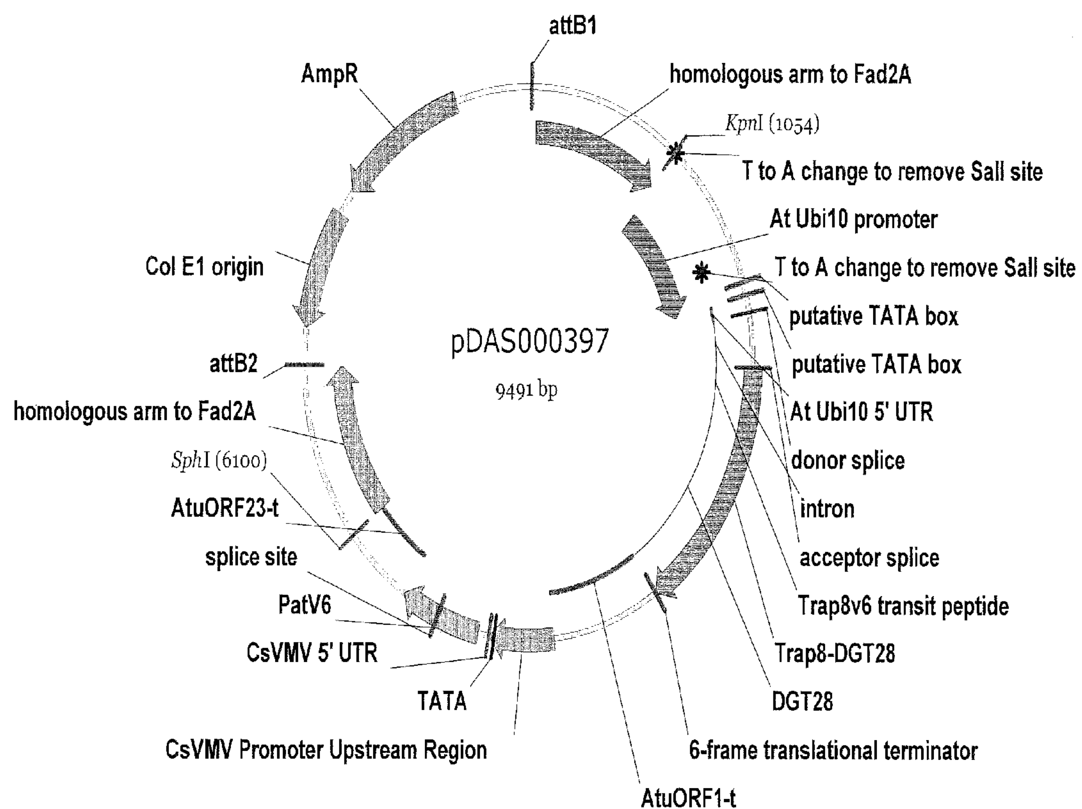
FIG. 24 shows a plasmid map of pDAS000397.

Example 10: Targeted Integration of *Brassica napus* Omega-3 Fatty Acid Desaturase (FAD2) with an Agronomically Important Gene Constructs containing the DGT-28 transgene (International Patent Application No. WO/2013/116700, herein incorporated by reference) that confers resistance to the herbicide glyphosate are designed and built for integration within the FAD2A genomic loci of *Brassica napus*. Exemplary donor constructs include pDAS000389 (FIG. 17, SEQ ID NO:89) for NHEJ integration within FAD2A locus, pDAS000391 (FIG. 18, SEQ ID NO:90) for NHEJ integration within FAD2A locus, pDAS000392 (FIG. 19, SEQ ID NO:91) for NHEJ integration within FAD2A locus, pDAS000393 (FIG. 20, SEQ ID NO:92) for NHEJ integration within FAD2A locus, pDAS000394 (FIG. 21, SEQ ID NO:93) for HDR integration within the ETIP site of the FAD2A locus, pDAS000395 (FIG. 22, SEQ ID NO:208) for HDR integration within the ETIP site of the FAD2A locus, pDAS000396 (FIG. 23, SEQ ID NO:209) for HDR integration within FAD2A locus, and pDAS000397 (FIG. 24, SEQ ID NO:210) for HDR integration within FAD2A locus. The constructs and associated zinc finger nuclease constructs (e.g., pDAB104010) are transformed into *Brassica napus* cells as previously described above. Transformants are identified and confirmed via molecular confirmation assays as previously described. The FAD2A chromosomal integrants, comprising an integrated dgt-28 transgene are isolated. The integration of the dgt-28 transgene within the FAD2A locus is exemplified via NHEJ mediated integration and HDR mediated integration. The integration within the FAD2A locus can be directed into the FAD2A endogenous sequence or into the previouslt described ETIP (pDAS000130) that is stably integrated within the FAD2A locus. The integration within the FAD2A locus via an NHEJ mediated mechanism can be made using linearized donor or circular donor DNA designs. Transformed DGT-28 *Brassica napus* events are obtained and tested for robust expression of the DGT-28 and the subsequent resistance to the herbicide glyphosate.

While certain exemplary embodiments have been described herein, those of ordinary skill in the art will recognize and appreciate that many additions, deletions, and modifications to the exemplary embodiments may be made without departing from the scope of the following claims. In addition, features from one embodiment may be combined with features of another embodiment.

What may be claimed is:

1. A transgenic cell comprising a non-naturally occurring exogenous nucleotide sequence integrated within any of SEQ ID Nos:17-26, 28-33 or 35-38 into an endogenous FAD2A, FAD2A', FAD2C and/or FAD2C' gene, wherein the non-naturally occurring exogenous nucleotide sequence comprises non-coding sequences comprising a plurality of unique nuclease target sites and two or more expression cassettes separated by the non-coding sequences.

2. The transgenic cell of claim 1, further comprising a donor molecule comprising a sequence flanked by regions of homology to the integrated exogenous nucleotide sequence.

3. The transgenic cell of claim 1, wherein the exogenous nucleotide sequence is integrated into some but not all copies of the FAD2A, FAD2A', FAD2C and/or FAD2C' gene.

4. A transgenic plant or seed, comprising the transgenic cell of claim 1.

5. The transgenic cell of claim 1, wherein presence of the exogenous nucleotide sequence in the FAD2A, FAD2A', FAD2C and/or FAD2C' gene does not negatively influence the agronomic or quality properties of the plant.

* * * * *

SEQUENCE LISTING

```
<160> NUMBER OF SEQ ID NOS: 480

<210> SEQ ID NO 1
<211> LENGTH: 47493
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

ttcccaaaca acacaataag ttattgtcaa taactaatct tatgtccaaa gaatataaaa      60

cattaggtcc agtcttttta ataacttttt atttatattt tttaaattat ttgatttaaa     120
```

```
tccactcaaa taatttatac gaagttgaaa ataactataa ctatttttgc gggtttagat    180
actacagaaa agcatttaac ttgaaattaa ttaaattaaa attttatttt gtttgtattt    240
tcagaaataa aaaatcgaat tccttttaac ttaataaata ttagattgtt ctttgtaaat    300
tatttttatt aattcataag aacatattat tatatatgct atattatgct tggtttaagt    360
taaaattaaa tagttttata gaaataaaat gttagaatca ataaattaac atcaaataag    420
ttttataatt aaaattttat caaataagca tatattaaaa atttaatcca acaaattaaa    480
gatgttttct taaaacctcg taatgataca ggttgaagta attaaaaaaa aattaagtaa    540
tattttagat aattttcctc tttaataaaa taatttatta tgtatgttta aatacactaa    600
aataaaaatg ttaaaacatt acttatataa taatgttaaa atatattgat attataaatt    660
agattttttt ttaaagatat tttcgcacat ttaatcgtgg gttatagtct agtatatttt    720
aaaacctaac tattaaatgc tgaattttat gaagttataa cataaagtga ttaatgaaca    780
aacgtcttat caattaatta tgcttccgca aagcatcatg ttcattgccc tataaaatca    840
tctctcgttc actgatacca atcaaacatc aaccaatatc aaaaactaaa gcaaatatgg    900
caaagtctct ttacattgca atgtttgtat ctatagtaat gttcttcatg gcaaattcaa    960
tttcttccaa ggaaattggt caatattcac aagaggcacc aggagatgta aagatatctc   1020
ccacatcgga ttttgatatt tacgtcgaat ctcccgatga atctctattt gaagaagtcg   1080
attcacccgc aatggaatat gagatgaagt ctggacatca ttacacacac aaacaacttg   1140
gttttcttga ggcttgcttt caaaatctaa actcattaga ctgtggagat aatattttca   1200
agaacatgtt agatgaggca gcacaagtat tatcaaatga atgttgtcat gatctattaa   1260
agattagcaa agattgttac ctaggaatga ctcaaagcat tttatcgagt tatgagtata   1320
gatttattgc gtctaaggct attcccaaaa gtaaacagac atggaatgat tgtgttctta   1380
gagttgggaa cctgattggt agcccaatcg cttttgagga actacactaa ttgatgttcc   1440
ggtgtgctga tgttttatat atgtgatttt gtaactcagg cgttatgaga cttaccatta   1500
tataaataaa gctaaagatc ttttacagat cttatattag tatacgagac tcattagagt   1560
aacatgaaag ctgaatcaac tatcaacatt ggtggtattt gtctttaggt ttctttaatg   1620
gatatagatg tttggggaca acgctagcag ctcttagtaa ttccgcatat ttatggacta   1680
tgagctcttc gctctaaatt acacaatccg acccaccatt tcagatatca atactcgcaa   1740
acccagtaga gttacagtct ctattgtact tctccttgca ttccttcagc ctgattctct   1800
tatccacaat ggttatactt gtctctgaca acgatcatgt tcctcaagag caaaaaacca   1860
tctaggtctc cgcagctcag tggcgagcct ctcacacaac cattgaacac atctaccaaa   1920
gcaaatgacg tggcattctt gggaatgaaa cctttgatac agttacatgt cagtatcgtg   1980
ctaatgttat agtaaacatt ttattatcat atttttaata ctaatgaggc atgatttgat   2040
tttaatttgc atattttatc tcttaatcct ggattatata tagttttcag cagacaagaa   2100
aatgttattt ccacattcta tgacttgttt ttagactttc atcaattcat tacaacatat   2160
tattgttatt agtcgataac tttgacttaa ccacgtgaat tttatcccaa aaaaaactta   2220
accacctaaa atctaatttt ttttataaag aaattagttt ttgatccgcg ttttgcagat   2280
ttatttttca tttttatatg tttatatctt tgagaatgcc atgaaattga ccgtgtgttt   2340
ctattgtgtt tagtttttgg tctttctaat ttttgagatt attttttctt taaacgatgc   2400
ccgggttatt attaatttta tttgataaat taaacattga aatataatta gaattcgaag   2460
```

```
tatactttta ggttttatca gttttaaaga tggtcatttg atttgaaatt tgtataaaaa   2520
ttccaacttt tattttggaa tttttaaaag aaatatatgt ttactgatgt gtggtatatt   2580
ttaataagat aaatatatta atataatatg gcatagtatt atgtagataa ttaaaattta   2640
tatttacaat tatgtaatat aaaactatag atattattga aaactataat atttgttgta   2700
atatgaatta gtttaaatta tgtacaacta tctgtgcaaa attacgtagt ttgtaaatgt   2760
gtatatgtga taaaactata ataatacata ctatatttta actaatattg gtttatatat   2820
ctaatatatt taattgtgta tttcatatta atcaaaaata taaaagattt aaattagaca   2880
gaaaccgttc aaaaataaat atagtttttc atttgacccg caatttcaaa atgcgagatg   2940
ttttataaat aattaacata atctttaatt ttggaaatga tatatgtttt tgaattattt   3000
tacgtttttt atattaccat taacatttat tttaaatttt aaatgagaaa tgattttgta   3060
attgtaacta aaatttatat aaatgtaact tatgaaaatt aaaaaaaatg taaccaggat   3120
aattaccaaa aatagcattt tgaatatacc acttttcact tctactttat tcaactttgc   3180
cattaaactt ttaattggca aatgactatt atatccctaa ttaattgaac ctaaactatt   3240
caattagata ggttatatat tcttcctcca tgtgagatcc ggcgagctcc ggcaaaggac   3300
gatgattgga gattattggg gatactgtga acaagaacga ggaacatatc tggaaatatg   3360
taaatgggaa gagatttcta cacagattag attaatgaac atgatatcag attcattgac   3420
atcttgtact gattccaatt ttgtctcgtg cttgttattc ctggctttta atgttttggt   3480
gttgatgtat ctgatagagc aagtggaaag aggagctgga acaagcggaa agaccgagaa   3540
aataaaagta accaataaac atggacacgt taaggaagaa actgactcca atgattcaga   3600
gttttggatg cttaagtcaa gttttggttc agagtcagag taggagagtg atgaagaaaa   3660
ctgcaaaggt acctcttttt ggtgtttttt gttggttcta ctttcatctt tctatcgaaa   3720
cttaaactag atttgtgtct gatcttggta caggttctca ttgtgatgcc agataatatg   3780
aggagctctc agaaaggtaa aggtaaatgt atacatttac tcttatttct gtgtatttct   3840
tacaaaattg cggattggtt ttgatgttca cctctagttg ttttgtctct tctacagagc   3900
aaagaggatg tcaatagaga ttggaccaag tatgatcatt acggcagcgc cactatgatc   3960
atgaggcagt ctttggaaga gcagatgagt tctgttacgg agaagagtgc taagtatgct   4020
cagattgctg ctgaggaagt gcccaagagt ctttactgcc ttggtgttcg tctcactact   4080
gagtgatttc agaactcgag ttttagggga agctcgcgga gagaatctat gttgtggctt   4140
ctaagctcac cgataacagt ctttaccatg tctatgtgtt ttctaataac attgttgcta   4200
cttcggttgt ggttaactcc actgctctca aatccaaggc ccctgagaaa ttcgtccttc   4260
atcttgtcac taatgcgatg aagtcatggt ttgctatgaa tatgaacttc ttaattgatt   4320
ccggcttggt tgattcagta tgtggaaatt gcaggtgacg agtgtgcaat cttcgctgtt   4380
tttagaagca gcatttgcgt caaatgatat gcagcatttg gctgcaatgt taagggtctt   4440
gtcggaattg attccaggat tcaaagaaac taccgagtat tacacattct aaggtcttct   4500
taatgagacc agttccccag ttgctgtctg agatttaaca tctcttacct tatttatgtt   4560
caataactta gataataaga aatttcgttg ataatatttc aatttatgta tgtttcattc   4620
aaagaaaaca atgattagtt ttctcaaatc agtcttctta tttgtttgag ttaagatctt   4680
ccaaacttat gttttttttgt aattcaggag taacaaaatg aatatagtct aaatctggat   4740
ctaattttga aattttttta actggatttt ctttcaaatt aaatccttat ttactcttta   4800
agaatttttt taaaagttta ggtttgacat ctctaaccta tacgttgcga acttggacaa   4860
```

```
aaccaaaaca agattaagca ttgttttcag aatatttaat ttttaatttt gttgggtttg   4920
atttggatct ttccagtgta catatgttta aacaccatcc tcttcaaaac ggttgtttaa   4980
gtgttcattt ttgggtaggt ccaagacgtg actgggacaa ttcaaagcgc tagttatctc   5040
cgtaacacat catatttccc cttacattaa gataaagtat actcgtgaat ctcaattgga   5100
tgcaataaat aaaaacaaaa tcccttccca tcaaggcatc aaactgccaa agtcaattct   5160
agaaaaatat taaaaactat tcttttttta ttttatttta gagacttctc ttccttttta   5220
ttctgtagga agaaaaaaca aaaaaagaag aagaagagga gaatcgtctc tttctttctc   5280
ttagaccatc tacaatgcta cgctaaaatt tactctatat ttcactctaa aatagagtaa   5340
ctctattata gagtgaaata tagagtaaat tttagtgttg cattggagat gcccttaact   5400
gtatccgtga aggcaaaaag atacgtataa acaaatacat ttacacataa atatgtatat   5460
gtatgtattt atactcttct agctctctct ctctcacctg tacctttaat atggtgtttc   5520
tgtttacgag aaaccaaacc cacaccaatt gaaaacgcga cttgttgtta ttcaatcgca   5580
atcaacgagt aatctgctac ctcgtctcct ctctgagatc tctcttcctc ccattagatt   5640
cgcctgagga ggtactcatt cttattcctt ttttctctgt ctttttatgg aatttttctaa  5700
aaatgctgta aggtttcaga catatccggt aataactgga ctctgaacta atgacttgtt   5760
caagtgttcc agctcttatt acatagtacc gatttggatt gtgttttttt ttttgtttga   5820
ccttcttgca attgtgatgc tctgatttgt tttcacgttc gtagcttatg ctttaatttt   5880
tttttgtcat ttatcttctt ttccccctaa ttttttttg tttaattgca aaccttttttg   5940
tgtgtgcttc ggcatgaact taggggccct actactggcg taagtttagg cttctttttt   6000
ggtgcttttt tagctttact gcttgttggt ggaattcact tttcttttta agttaatttc   6060
agagacatcc ttattgtaac tgctcacttt tcagtgttgt tagtttaagg aatgatgaaa   6120
gaaagaaagc tttctataac tgcttgattt agcttcagtt gttagtaata tgggttagaa   6180
ctgttagcct tgagtagata tcactgtctt tattttttgg tttattgttg atttattttt   6240
gtggtcttgt tttgattcag tgttctcgag gttttgactt cgacttgtga tgatggcatc   6300
atctaaacaa ggatcaaagt cgagaaaaac agggtttagc aatttcaagg gtgctgattc   6360
tactgcttcc tcaacaacct cttcttcaaa gctttatcaa gagacatcta tcgatgatgg   6420
acatagctct cctgcttctt catctgctca aagcaagcag cacttcttct caccggactc   6480
cgcaccgcaa agtgctcagc gttctaaaga gaacgtcaca gtgacagttc gctttcgtcc   6540
actcaggttc acagtgatgt gctttttttat tagggcttgc aaatattagg ttgcctgttt  6600
gttctgtgaa tttgaaataa cttttccgtg acagtccaag ggaaatccgc caaggggagg   6660
aggttgcttg gtatgcagat ggcgaaacaa tcgtacggaa tgagtataat ccgacgatag   6720
cttatgcata tggttagtct taatagtttc attaatgtca cagtggttcc ataatcatct   6780
taaatattgt atgtcggcat atcactcgag aataacaaac taaggatgat agtgttgttc   6840
ttatgtggta taatcttcct tttttgatgt ctgggtctct atgtctgtta acgattggtt   6900
ctctttatga cagatcgtgt ctttggacct acaaccacaa cacgcaatgt ctacgatgtt   6960
gctgcacacc atgttgttaa tggggctatg gaggggatta acggtatgaa gtgaccatat   7020
ttaatggcag tctattttgt atttagaact caatttatga tatcaactct tttatcgaaa   7080
agcatacttt cttccaaact ctatcaacaa ggctgactgt tcctaattta tgatgaattc   7140
gtcagaacca attttgactt tcgatgtact taccagttga tttgtatata actttgaatg   7200
```

```
ttaatccatc tacagggacc atttttgcat atggagtgac aagcagtgga aagactcaca   7260
ctatgcatgt aagatacctt catctggata gcttttggct tgttttgtac gatgtagttc   7320
aatttgtcat aaagatatag tgctttgtca gagaatcatg tatttctttt aatttcaact   7380
ccacaagctt aactaacaca tgtaagaatc tttctgcaat agttatagat aaacaacctt   7440
gcgatagata agttttctac cctaatactg ttaggtttct gtgcacccta ctgttgaaac   7500
catatctgat agatttcgat tgggtttttt tttgggttca aatgtcaggg tgaccagaga   7560
tctcctggta ttataccatt agcagtgaaa gatgctttca gcattatcca agaggtactt   7620
cttaggatat tgattttgtc agattccgtg gcctaagtac tagcaacctc acatatctat   7680
tttcttacag acaccaagcc gagaatttct cctgcgtatt tcctacatgg aaatttataa   7740
tgaggtgcta ttatttatcc actttctttc tctgctccat tacctatatt cagcttcaag   7800
agtagtggag tgatagaata ctctgccttt aaaatcttcc tttgagatta attcccttaa   7860
gatccaccgt atttcaggtt gtcaatgatt tattgaatcc agcaggacat aatttgagga   7920
tcagagaaga taaacaggta tgtgtttcag cttcagatca tcttttgatt acacgggctg   7980
ctgctctcac ttacttgtaa tattttcttt tattacattg ctcgtctaaa atcccaaaat   8040
gtttacatca tattcttaaa ttagtaggaa cccatgtcta ggcttgtttg gtacctgaaa   8100
actatactgg ttccattttt ttcttgtgaa atttgatctc tctgagaact ctgctgttac   8160
aatgatgata tgtgggtcac attgctttca agcagacttg tagatgatcg ctatgagttc   8220
ttttcttcca tgtgttttaa ttgaacgcat ccttttaatt tattctaggg aacctttgtc   8280
gaagggatta aagaagaagt tgttttatca cctgctcatg cgctttctct tatagcagct   8340
ggagaaggta tgtggtgctt ccacttttcc ctttagctaa agaaataggt ttactataca   8400
tcctcataac gccagcaaag actgttgcag tcattgtaca tttgttaaag atattgtcat   8460
caggaaagtg gttctcctct acctgcttgg ggctgtacaa aacgttaaaa attgtgtttg   8520
tttttcttt tatttaatat gagagagtag ttctctctct ctcatgattc cagtatacat   8580
atatcatcct taaaatttgt catgatctag taaatttaca tttaattcaa ttcacattga   8640
ttggagtttt gtccttatga cagagcaacg ccatgttgga tccacgaact ataatctgct   8700
cagcagccgg agccatacaa tatttacgtt ggtatgtaaa tactctcttt gaaatattgg   8760
tagctatatc ctttttcttt ctccgcacgt atatacactt gtattgtgga tggatgcacg   8820
caaaaccaac gttcttttct attactataa ttggttaaaa ggtaaaaatg atagtttttt   8880
gtcttataat cacgatagta tttgaaaata gaataccgaa attctatttc ttattcagaa   8940
taagttgtgg accacgttct tcttttcacg tgttttcttc cgttcaagga atttctgttt   9000
gtcttttatt ctaattctag ttgtttagtc gtgtcaagtg ttccaccggt tatggtacta   9060
ctttcttttc attgtaactc atatagctgt accgtttcta aaagatgata aactcatttg   9120
gatgcagaca atagagagta gtcccttagg caacaagatt aaaggtgaag ctgttcacct   9180
ctctcagctg gtaagcttct cctgtgccag tgatattatg tatggttatg atcaacactt   9240
tcttcaacac taagagcaac tgacattaac tacccataat ctcttccgca cccgcagaac   9300
ctcgttgatc tggcaggttc cgagagttca aaggttgaaa ccagtggttt aagacgcaag   9360
gaaggatcat acataaataa aagtttgctg acattaggca ctgtgagttt tttcttacca   9420
cagttttctc ttagtcaaca ataagttttg gagtcagtta aatcgaagga cttcattttc   9480
ttttaaatcc ggtcaatctg tgcttgtcca aacctaaagt taaatagttg tctattcttg   9540
tttatattct ggtcctgttt gaacattctc ctgttggctc aattcaggta attctgttgt   9600
```

```
gatattgtag gtgatatcaa agctcacgga tgtgaaggct tcgcatgtac catacagaga   9660
ctctaagtta accaggatcc ttcagtcctc attgagtggc catgaccgag tatctgtaag   9720
ttattagatc ttttctccat cctcttgcta ctataaatat aaaatccaca acatgatcat   9780
cagcagagtg atgtacttta ctgattagtt gtcccttctg gatatggtag ctcatttgta   9840
cagtgactcc tgcatcaagc agctcggaag aaacacacaa cacattgaaa tttgctcatc   9900
gtgcaaaaca tattgagatt caagccgaac aaaacaaggt ttgcctcata tcttcttcta   9960
tcagacctta ttttattgta ctaaagttct tgcttggttt ctaaatctat attactgcag  10020
atacttgatg agaaatcatt aatcaagaag taccaacacg agattcggca gctgaaggag  10080
gagttggaac agattaaaca ggacattgta ccaattcctc agctgaatga tattggcaca  10140
gatgatatcg ttctcctgaa acagaaggta tgagttatat gctcgattag acaagtggaa  10200
ggatgttttg tgtctttaca ttgagagaat ctgtagtaac cttgtctttt tttttgtttc  10260
tggctatata acgtgatgat attagctaga agatggtcaa gtgaaactgc aatccagact  10320
cgaagaagag gaagaagcta aagcagctct attgagtcga atccaacggt tgacgaaatt  10380
aattttggtg tcgactaaaa cttcacaaac atctcgatta cctcatcgct ttgagcctcg  10440
gaggagacat tcatttgggg aagaagaggt agaatcactg attatagcct tgatattata  10500
aattgtttcc atggtcgttt ctgagaatat tttgctggag caagtacaca aaattgctag  10560
ttttgtttgg ctaatcttgg ttgataatat gcgtgtgcag cttgcttacc taccatacaa  10620
gaggcgggac atgatggacg atgagcacct tgatctgtat gtctctgcgg agggaaataa  10680
tgagattaga gatattgcgt ttagagaaga aaagaagacc aggaagcatg gattgttaaa  10740
ctggttaaag cctaaggtat gcaaacgatt gaattttctt attagcactg tggtttattc  10800
tggttcgttt cagaactgca cctagcaact ataggtttgt actattgcgc actatagatt  10860
tatagagttc tcatgttctt caaagaacaa tgatataagt aaagagtgct aatcatatga  10920
ccttgtgtgc ttatttgatt atttggtgcc tctcttgtcc cctttttttgt aacaatctta  10980
tttttctcct atcagaaaag agataacagt tcaagtgcca gcgaccagtc gagtgtggta  11040
aaatccaaca gcacaccatc gactcctcaa ggaggaggaa ataatctgca tgcagagtca  11100
agattttcag aaggatcgcc tttgatggaa caattctcag agcctaagga agacagagaa  11160
gctctagagg acacttccca tgaaatggag acgccagagg tacgaagaga cattttcaca  11220
tatgttatgg ttccaaagta actacatctt tatcttttcc acttcctgcc ctgttcccag  11280
actagcaata aagtgatcga tgagttggat cttctgaggg aacagaaaaa gattttatct  11340
gaggaggcgg cgttgcaatc aagttcatta aaacggctat tagatgaagc tgcaaagtct  11400
cctgaaaatg aagagattaa agtaatataa ccacttggtt catgatttgt atctagcttc  11460
cgtttaaatc taccaaacat tcactttcct ggttatctgt gttacttagg aggagatcaa  11520
agtcctcaat gatgacatca aggctaagaa tgacgagatt gcaacgttgg agaaacaaat  11580
cttggacttt gttatcacat cacatgaggc gttggacaaa tccgacatcg tgcaggtaag  11640
ttcattgtta agtattatgc agtgactttt tttttctgtg gttcatttct caagctattt  11700
ctctataaat atcttcaggc acttgctgag ctgagagatc aagttaatga gaagtctttt  11760
gaactcgagg taaagaattg tttctgctac agcacctaga gatgtcttgc tactgcgtgg  11820
atgataatta tttctcttag ctccagtata atatctactc atgcctgcat aaagttgctt  11880
ctctgcaaat aatgatgaaa gctaattgca tctataacgt ttttttttct ttctcattct  11940
```

```
tgatcttgtt tacaggttaa agctgcagat aataacatca ttcaggaaca actcaatcaa  12000
aaggttgaga gatttttttct tttatcgatt tgtcttaagt ttataatctg taaataattt  12060
aataaccaac gaagtatttt gctgcagaca tgtgaatgtg aagcgtttca agaagaagtt  12120
gcaaacctaa agcaggaact ctctaatgcc ctggaactag cacaggttct caaacttttt  12180
atatgaaaaa agcaacacct aatagctaaa tgattctcaa actaaagtca cttgcctttc  12240
tgacatgaca ggaaaccaag atcgaagagc tgaaacagaa agctaaggag ctaagtgaat  12300
cgaaggagca attagaacat cgtaacagga aactcgcaga agagagttca tatgcaaaag  12360
gtcttgcatc agcagctgca gttgagctca aggcattatc tgaagaagtc gcaaaactca  12420
tgaatcacaa cgaacgacta gcatctgagc tagcaacact caagagctca gtcccacagc  12480
acggtaataa gccaggaaca acaacaacaa ccaatgcaag gaacaatggg agaagagaga  12540
gtcttgcaaa gagacaacaa gagcaagaga gctcgtcgat cgagctgaag agagaactga  12600
ggatgagcaa agagcgggaa cgatcatacg aagctgcact tgttgataga gaccaaagag  12660
aagccgagct tgtgaggata gtagaagaat cgaagcagag agaagcgtat ttggagaacg  12720
agcttgctag tatgtgggtt cttgtttcta agctgagaag gtctcaagaa ggtggttctg  12780
agatctctga ttctgtatcg gagacgctac agaccgatcg atcgttttga gacgtgaagt  12840
agtaggatat gtttgtgcag tgattccaag agtttgtgtt tgtgtaagta tgataaaaca  12900
taaagtaatg atttatttga aaatcatcag attgtttaaa attcaagaaa aaaaaacact  12960
gtttaaatta agaggtaaga gaagtgaaaa gtgggtaaaa gaagaaaata atgatagttc  13020
tggggagctt agagcatgat gattatcccg gtctcttata actcatgatt ttaatatatt  13080
tttttacac tttttggtta aaaaacatct cttatatatt ttatttaaaa aatgttctta  13140
gttttttaat taaaaactaa gaaacgatta gctaaaaaac tcagttaaga aaccagggtt  13200
aatcatggtc ttagtaaagt tcttaaaatt ttcactttca cccaatacct ttccactaat  13260
ccacatttgc cccaattgat ttccttcttt gtgtatacaa cccaaattaa taattgttaa  13320
caaaacagta aaacactata caaacaccaa gaagtgtact caatcagatg tctgaaaaca  13380
agaagtgcaa ctgaagagtc ttggattgaa gttagagagg cttaagagtg ttcttaggag  13440
cacttatcca cggagtgtct ccaatggcaa atctccacaa ggcattgaca tgttgaggca  13500
atgcgtaatc tattccaacg cgaggaccaa ctagtacttt ctccacatct tctcctccat  13560
ccagaacctc caatcctcct gtttttcata catcatttat tacaacaaag cttaaactct  13620
cttaaagaat cagaaaaaac cagaaactcc attaactgat tttggtttat ttgtctgact  13680
aacccggaga atagaggga tgatgagacc actctgttga aagtccaagc gcctgcccga  13740
cctgcaagag gcacatatga acagatttca tgcattgtgg atttgcaagg tgcattctgt  13800
ttgatgcaga tcagactaac ctttcctggt ccatttagaa gaacaggttt gtcggttttc  13860
tggccacgac gctcctgtat ggtctccagc cctgcaatac catcacaccc ttttaagcca  13920
acgtaagatc tatgtaatca ttcttaacgc aaaaacagta tcaataaagc aattatttaa  13980
gtagaaacat gcatcgataa gagagagtgt aatgaacagt ctcacagaac tgatgtggag  14040
agattattac cggtaacagg agaacaagat cgtatcaaaa cagcagctcc aactccatcc  14100
ttatcagcaa caatattgag catcatatga agaccgtaac aaagataaac atatgcatgt  14160
cctcctggtc caaactaata aacaaaaaaa acacacattt tagagaatgt tatcatgtgt  14220
atttaactaa atgataacaa agcagaatga agaaactcac aataggtgcg gtccgtgggg  14280
tattcccgaa ccgtccatgg caagctgagt catttggtct ataagcttcc acctgccaaa  14340
```

```
ggaggaacaa tgttagagag tattaacttc gttaatccaa aatcaaaaat tttttaccaa  14400
caattatagt cagaatatca aaaatcccaa gaaaacaaca aaaaaaacta aattctttta  14460
atgaggaaac aagaacaaaa ctttgtatct gacctctgtg atccgtagga caacattgtc  14520
tctcctcagg aacttcccga gcaaacgtgg cgctagatca agcgcgtcta tttgaaagaa  14580
ctcaggaggc attatcttca tctcgggggt ggagcgggtc agtgggtact cgggtctgac  14640
ccgaaccgcc cgagccttgg aacagtgctt cttctctcgt gctgcacgta gagccactgg  14700
agttgtaacc ttgggtagtt ccgattcctg atcaactcgt ttggaacgac gaggcggcgt  14760
tttcattgac ggacagaacc aaaagatttt tgactttttc gaatgtgttc gactctttga  14820
cttttcttcg ttttgttatt tggcgggtga ctgttacgct gtccgaaggt taagccttaa  14880
acataaactt tccttattat gaccgtcata tcaatttttt cctccgtttt tcaatatttg  14940
gcgttttaaa aaaaaatttg agaaaaattg attttttttt gtttatccga tttaaattat  15000
atggttacta ataatccggt taaaacttaa aagtaaaact atagtttata gataattaag  15060
tttgtaattc tcaatttgaa gagaaataaa ataatttatg gagagctagc ctgaaattat  15120
aatcggtgga gatattttga ctttatatga tagtggggaa ataaaacaca aaataaataa  15180
tgttttcaaa taaacattta ttaattttat attaattcct attctgtaat tttgaattat  15240
ttttgaaatt attaatgaat aaatgattaa gaatattttt ttaaaagaaa aattagatat  15300
accactctaa aataatactt cctccatttc agaataaatg atgttttata aagtttttgt  15360
tgtttcataa tagattgatg atgttttgat atatttatgt tatttttaat tttattgaaa  15420
aattgtgtaa ctaattagat attagagtaa tttatgtagt tggttgaatg atttttaaat  15480
tatattctta aaactaactt ttagttataa aagtaaaatt tttaaaacat catgtgaaat  15540
agatggagta ggatttaaca taatttgtac gttctagaca cttccaaagc gtttcaaaag  15600
ttaattagtt tttctttttc tggcataagt attattttat atttttccat ttttcagtag  15660
gaaaaaaata aataaaaaaa aaacattttc tagaggcttc gtttacatat atctaggttt  15720
acctcctctg cttcttccca cacatctcat cgaattcgac tagctcccca ctcaatcact  15780
cctcgttagt tcaatctcga atccctaatc cactcaccat ggcgaagttc ggcgaaggcg  15840
acaagcgatg gatcgtcgaa gaccgccccg acggcaccaa cgtccacaac tggcactggg  15900
ccgaaaccaa ctgcctcgag tggtcccgca gcttcttcac caaccaattc tccaacgccg  15960
tcatcctctc cggcgaaggc aacctcttca tcaaaatcaa gaaactggag aagctcgaag  16020
gcgaggcgta cgtgaacgtg cgcaagggga agatcatccc cggctacgag ctcagcgtct  16080
ctctctcctg ggaaggcgag gcgaaggatt cggaagggaa gacgatctcg aaggcggagg  16140
gggccgtgga tatgccgtat atctccgatg agaatgcgga tgaggatccg gaggttaggg  16200
tttcggttaa ggacgagggg gcggttggga aggcgttgaa ggaggcgatg gtgaagaagg  16260
ggaagggggt tgttttggag aaggttaggg tttttgtgga ggctatggcg aaaggagggc  16320
cttgtaggga tgaattggag aataagaagg tggctcctaa gtgggtggcg gcggcggcag  16380
cggctgtgga gaagactagt gttttgcctg ctgtggtggt gaaggagaag aagaaggtga  16440
agacgaagga ggggttcaag acgattagta tgactgagaa gttcagttgt agagctaagg  16500
acttgtatga gatcttgatg gatgagaata ggtggaaggg attcacgcag agcaatgcta  16560
agattagtaa agatgtgaat gggcctatta gtgtttttga tgggtcggtt actggggtga  16620
atgtggagct ggaggaaggg aagttgattg tgcagaagtg gaggtttggg agttggtctg  16680
```

```
atggtcttga ttctacggtt agtttagttg ttatttttct ttgtgacctt tggtttctat  16740
gtcattgtgg ctgatgtatt gtgctttgac attttcaggt gaagataact tttgaggaac  16800
ctgaaccagg agtcaccatt gtcaatctta ctcacaccga cgtccctgaa gaagacaggt  16860
tagtgtcact gcttgaaatc tttcttataa tagtatggta gtatgcaatg aatatttatg  16920
gtgtttggag tgcttgatag cttggtctta tatataactt tcatattgat gtactatctt  16980
gagggaattg taaccacctt tagcctgttt tgttctcaat gacagacact aattctgacc  17040
ttagtatctg tgctaatcct tgcgactgtt tagcttgctg tatgtagttg ttggactcat  17100
ccagtctttg ttctagtgaa tgaactcttt tggaatttgg gttttgcttt atttgttaat  17160
atatgataga acatttctat ctctaaatcg ctcaatggcc tacacgtctt taaatcttct  17220
acctatgcta cctttccact aactagcttt aggttatgct gatagagcgc ttctttgttc  17280
cttgtgaaca cctgttggct tattcctgaa agtatttgtt tgtccacatt ctcttactcg  17340
tcctgttgtg aagtgatttt gtccgttact ggatgtgact tatttttctc tgacgtttct  17400
actggctgat gcaggtatgg gaatgcgact gtggtggaaa acacggagag aggatggaga  17460
gacctgatct tccataggat ccgtgctgtt ttcgggtttg gaatgtgatt tgtgattttg  17520
attatcaagt aatcaaaatc agcattgctt catccataag ttcgattatg atttcaattc  17580
acaaggagac ataaagacga tgcagaaatt tggtttttac ttgtagttta tgcattttcc  17640
atgaactctt tggtcttttg ttaacactat ttggattaat ggcacacaac aaactattca  17700
catgagaata agttgtttta agtgttttat tctaaaagtg gtgtccatag tcaaccacgg  17760
catcaagatt gcctaaggaa cattgtctaa agactgatga aaactaggaa caagaagctt  17820
tggtttggaa ctataagctt tttgctaatc gcaatgccta accaacaagt tacacatcaa  17880
ccggtaatta accagttacc agaacctgct ttgaccaaaa tattacacat cacagcaagc  17940
tctttggatc gtttatctaa aagggttttg gtttagcctg gaaccacgtg gatgaaatat  18000
ttattaacca caacatcaac agaaacgttt ttactagctt tgtcaggtat agacgtgggc  18060
acaaacaaga cctacttgaa atcagcacct acaaaataaa accaaaaaac atcttactct  18120
taatgtatgg cggtctttaa gacaacaaaa atttcttcta ccacttttaa tcatcaagaa  18180
gagacttgaa atgttacaga ttaaggtatc aagctcagac tcttaaaatg tcatattgtc  18240
agtgcatatg atttgaacta gattgtaata tttaacatta agaatttagt tatggtatac  18300
agagtataac ggtttgtgga tctgtcattg tgttatcatt aagctttgta aagatagtca  18360
ttgttttggt tttgttaaaa tgatgttagg tagaaaatag taataatttc aaatcagcat  18420
ttagtataat tatgaaactt cacaaaatcg tgtggaaaac tattaaagac gagttttaaa  18480
tatggttgac cggatagtta attttcttac atcagatcca agattagtat tccgaagatt  18540
gttgcggtta ctggtatcaa tttcctggaa gatttaaaat atcatcatgt cacgtacttc  18600
attactagta accttcgttg tttaaagcgg aaatgtcgca actcgtttgc ttcattttgt  18660
tttctttttg gatccttcaa atgatccgca acacttccgt tggagttgat gccatagaga  18720
gtgcgtcgag ttatttaacg tataataaat attcttgcgt ccttgtacac atcatacgtt  18780
aattaagcca tcaagatgta gcattactgg cgttgtttca gtaaaaaaaa ttattggtaa  18840
aatattaaat tttaattacg cagaaacaac aaagaagaca ggaaaaaaaa ctacaaccag  18900
agactatgtt acaacgaatt caaagagaaa aagaactgag aagaaaagca cacatcttcg  18960
tcattcaaaa attaaaccgt ttattgacaa agaaattaat cgtgactaat aagctccttt  19020
gtcggcccca tgtaacccat cttttacgtg taatctgatg cttgcttcca cggttccacc  19080
```

```
ccgacttaac tgccacatat acactttggt cattcaaact taccaaacac aaagcgaatt  19140
cgtttttgtt tcatgctttt aagaatcaca atctcaacat tccaaatata tataaaacac  19200
aatctcaaca ttccaagcat ggggtggcat tctcgtagtt atctccatga caaggggcac  19260
tttacaatag aaaacactcg ggatactttt ttatcgacga ttcctaagca aaatattacc  19320
gaacagacac ctctctgtct gtctctttta tatgtcttct caaaaacgaa aaagtctctt  19380
ctccgtcaac atttcacttt ccctctttcc ctcttgttaa tctctctctc tctctctaca  19440
ctcaaagaaa acacagagac tcttcacgcg ccaaaaaaaa aaactcacca ccttcctctc  19500
tcccttacca tgacttcaga ctctgtcaag catacttcta tccacggcgg aacaaccatc  19560
tccgccgcat ccttcgaatt aaaaagcttt atctccgccg cgaaaccaag aaaagcctcg  19620
acttttgtat acgccttcgt cataagcttc gttgccttca ctgttctctt agtcttcaca  19680
ccttctccca tcaccgtctc tcattccatt ccttcataca tcctccctaa tgtcactgcc  19740
tccttgactt caccgtccag tttcaccgga aacaccccat tgccggaaaa tctcactccg  19800
gcgccggaaa atctcgctcc ggctactaaa aacgcaacct ttgagtctcc catcgctaat  19860
ggagcaaatt cacttgcttc tcagccccgg accgaccatg cattggacaa catgttgtct  19920
ccggacaaca agactaatga tactgctcca agttccgaca aacttggatc cgcggaagca  19980
cctctgtccg aaaatctaac cgtcaattcc tctgctttaa agaagagaaa acagaggagg  20040
aagtcgtgga tgagacgaga gataaagtct ttaaagaact gcgagtttta cgagggagag  20100
tgggtgaaag acgattcgta tccgctttac aaacccggtt cgtgtaatct catcgatgaa  20160
cagtttactt gtatctccaa cgggagacct gacgctgagt ttcagaaact caagtggaag  20220
ccaaagcaat gcactttacc acggtaaagg ataaaacttt gctttttaat tttgacttta  20280
aaatctattt ctttgtctta tatggttggt tgatgttttt tttttttga aaaattataa  20340
aaggttgaat ggaggcaaat tgctggagat gattagagga agaagacttg cgtttgttgg  20400
agattcactg aacaggaaca tgtgggagtc tttggtttgt attctcaaag gatcagtgaa  20460
agatgagagt caagtctttg aagctcatgg acggcatcag ttccgttggg aggctgagta  20520
ctctttcgtc ttcaaagtag gtttctttta gtaatctaaa tcagtttcat tagttgttgt  20580
ctctcgggac ttgatttgta tgtggttgat aggattataa ctgcactgtg gagttctttg  20640
catcaccttt cttggttcaa gaatgggaac ttacggacaa gaacgggact aagaaggaga  20700
ctttgaggtt agatgtggtc gggaagtcgt ctgagcagta caagggagct gatattcttg  20760
tgttcaatac aggacattgg tggactcatg acaaaacttc caaagggtaa tagagttctg  20820
tcagctactt tgatccttga tttgagggat ctgtctcatt tgttatgttt ggatgctttc  20880
attagggagg attactatca agaaggaagc aatgtacacc cgaaactcga cgtggatgaa  20940
gcttttaaga aagcattaac aacttggggt cgatgggttg ataagaatgt gaatccaaag  21000
aagtctcttg tcttcttccg tggatactca ccttcacatt tcaggtatat acagatctca  21060
ttttgtttca taatataggt agttgtaggc ttgtagctaa aagcacaaag attaagaacg  21120
ttattatttt ttttaaagta tcatctaatt ttatagttta gatatatctt aaaccaatca  21180
taaactagtc tatataattt gactggtcac actatatcca ataattcaat aaatataaaa  21240
gttaagtaga aatgtaaaaa ctacataatc ttgaaaagaa aaaaaatatt cactaaaact  21300
acttataata tgtgaaatag agggagtata aaaagagtgt ttctaaaagt tggtttggtt  21360
tggttgcagt ggagggcaat ggaatgcagg aggggcatgt gatgatgaaa cagaaccgat  21420
```

```
caagaacgag acttacctaa cgccttaccc ttctaaaatg ttaatacttg aaacagttct  21480
aaagggaatg aaaacgccgg tcacgtatct caacatcacg aggctaacag attacaggaa  21540
ggacgctcac ccatctgttt ataggaaaca taaactatct gcaaaagaaa ggaaatcacc  21600
attgttgtac caagactgta gtcactggtg cctcccaggt gtgcctgatt cttggaacga  21660
gattctctat gctgagatgc ttgtaaagct ccaccagctt cgtggcaata gaaggcggaa  21720
acctaaaagt ttataggagt tagaatcctt ttcttaagat gatgaataca gatcttttag  21780
gaaacactta gaatcaattt tcacttttca gatttgtgcc actgaaggtg tagagaaagt  21840
aagagatggg agtcacatta gtgtttcatg atgtacgtac gtaagagatg agttaatcac  21900
cttatgttgc tgcatttgta gtcaactaca actagtgact catttttttg tgaaaataaa  21960
agattgagcc aacatttgta taaattccaa tgcatacccc tttacttata ataatgatca  22020
atcgattggt caaacgaata catttagaat taagaaccct gcaacgactt tggatttaaa  22080
ttgacacaga tcttttgctt caaagtaaca gtttgagcta agaacataaa gaatgcacca  22140
gtcctttaat tacagtatta tgataaaact cactagagcc atctagatac aatctgaatg  22200
ataatgtcac aggtggaaag aaagcatgaa catactcagt cgtccttcat gagactcctc  22260
cggtcctctt ggtgtgcaac caaaaccacc accatccacg tctttcgtat ctcacaatgt  22320
tatcagcagc cttatccaag tcctcctcct tcgcgtcagt tccctctctc tttctttctt  22380
tctttctttc tttctttctt tcttgagatt gcaagtttga aattaagctc ttatagattg  22440
tttattttga tgttgttatg tcggtctctg tgtaaatgtt tagttatttt tttcgattct  22500
ttctcagaaa agtgtctcga ccttaagtat tttcttgtta gagacttaga gctgctactc  22560
tttgattctc gtaagattta gtttcctcag ttattgcttt aagcaagcga gagactactc  22620
tcttgactgt tttggccttc tgatttgttg aatccatggc aatatttgtg gtttttgtct  22680
cctgctctct ctctctctct ctatgtggat gggctttgtt tcatgttact attattagct  22740
ccaccttcga gattattatt cttttttttt ttttttttga atgaatgtta aattttattc  22800
aatccaaaaa aacccttgtt acatttacaa tgtttcctac tccaattgtt ttataacatt  22860
atcaccccta tttgaattta tctactcaag aaactggtct tgtggagaac cagtgttgta  22920
aaccctcctg ccatctatca tcccctgctc tttgaataga cagaaatcta ttcctcactc  22980
ctctatcaat cagccttatc atcgtagtag tcggctgggg agcttcacca tgccttctac  23040
cattcctctc caaccacagc ccatgtatag tagcttggaa cacatacttc aatgtgaatg  23100
tcttgatagt attctggttt gtagatatca gagctactat ttctgaccag tcacaagtaa  23160
actcatttcc catcaagcct ctcaccaagt ttccccaaac ttctgccgaa tatccacaat  23220
caaagaataa atggtttctg gtttccaatg gatcaccgca gagagagcat gctgtattta  23280
cacttcctcc ccatccttgc attctctctc ccgttgataa tctgttcttg attgtaaccc  23340
acgcaagaaa agcaaactta ggtgtcgcaa aagtgaacca gattccttta ctccactcac  23400
agcttactcc tctagttcgc aattgactcc atgtttgctt agtagaaaac ttccgcttga  23460
atttgtcttc cttatacctc cataatccaa catcatcttc ccttgatgcc atcattttac  23520
atttatctat ctcatcctca atcaagttca aaacagggat tctatgtctt ctccttcgat  23580
gagtgctcat tacttcctct acagtagcgt ctttatggat ccccatatcc atgtatcctc  23640
tttcaccagc tctttctacc agacaaccca aatctgacca agcttcatgc caaaacgaag  23700
tttgcttccc actcttcacc ctcaccttat agaaaccttt tgccttgtct caaagagatt  23760
attatctctt ccatatggtt cagtactgtt tagtttgact tgctttgtcc gttgatattg  23820
```

```
ttagctagct aggttagagg actaatttat aacccccaca tctttaactg ttttctctac  23880
aaactgttat ataggcctgg ccataatatc cgtaacccga aatccgaacc gaacccgaac  23940
cgaaaaacac gatccgtatc cggtccgaaa tgtaaaaaat atctgaatga gtcttgtaag  24000
gtggcacaaa acatatccga acccgaagtg ttattaaccg aacccgaacg gataacccga  24060
aaaactgaaa aaaccgaaaa ttccgaaaaa tatccaaaaa aaccgatctg aatgtccaaa  24120
ataatataca atataattat ataaaacatg aatatatact tcaaatattc aatttcatat  24180
ttattttgat atgttatcta acaataagta tttaaaattt aaataactac cttaaatact  24240
tgattatata taaataaata tatattttta tatttacctt taaattttag attttatttc  24300
gggtatatcc gaaccgatcc gatataaccc gaatccgaat gatatatgat tactttatgg  24360
gttgtgatac aaaaccgacc cgaacccgat gtgttatatc agaacccgac cgtacttgca  24420
aatttactag aatggaacct aagaagtatt ataagagaga accaaaatcc gaaaaacccg  24480
atccgaacgc caacgggtac ccgaacgccc aggcctactg ttatatatca ataatttccg  24540
ctttcaaatt tttgtttgat gcagatgaat ttgaaatttc tttgccttac gactccaaaa  24600
cggtgactgg atttgttgga ttaatcaaca atcaatgtgg tgaaaacgca tatgcgagtg  24660
ctctcattca aatgatgttt cacattccat gcttttgaaa agctatctta gaaattccag  24720
agactatccc tgtcaagagt ctcttccact gtcttgagag cagcaagact actgtttcat  24780
tagagagccc agacataacc agtaataccc tgaaaaaggg tttattttga aacagtgaat  24840
gacaagatga aagtaagtta ttttttgcat aaccttatag ttcacactgt agatgctttg  24900
atgtaaatta ttttgtaatt acaaggctca cattggaaga tttgtaattc tcggtttgag  24960
tgaaatatgt gtattttctg caactaatga ctactccaaa actaatactt tgtgtccaac  25020
ttgtgcacaa tgtaatggta attagtcgtt gaaaactaac atatgtgatt taacaataaa  25080
ttcatatatt aacaattcaa aattaattta aagctttcgg atcccaaact atgctgtcaa  25140
taatcatgtc caagtcatca atccatttgc gtaaggttaa tgagatatca agaaaaatca  25200
aattcgtaaa ttttttttaaa atatggttgt tacttctcac acactagagc atcgtccaca  25260
aattccttag aaaaatttag tgttctgatc gtaatttgag tctcattgca atcaggaaca  25320
agctgaaatc tacttatttt ttattgatgc tacctcatgt acttcatttt gtttggcagg  25380
tgaaccagat gtatgagtgt atccttatga aatagatctc gagaagtttc ttctaaccac  25440
tgatgctgat gggacaaatc atttcactta caaattgaaa aggtaaactg tgtgttttgt  25500
ttgatgtggt tgagaaatag tagacacgca ccagattcat tctcaagaca cagcttcatc  25560
ttcagaaaca gcttccctag aaagtctaat gtggtcatcg agagtattca ccattagttc  25620
tcagatgatt gatccatcat cacaaactca atcaaaactc tcttctttgt ttctggcatg  25680
ttgatataaa ccaaaacaag agactgaaaa ggaaaaaatt caaatgccag ctatagtgaa  25740
catagacaag agcatgagga agttgaatga tatagctttg tagcatattt tctgccatca  25800
gaatgtaccg gacatgcttg cctgccatca tatcatcagc attttaattt agacccaact  25860
tgcttcacac cagactctct tccacatgat ttttatatat atcttctaac caaaaaatag  25920
gacagaacaa attaaaaaaa aagtttcatc gggctgttct tgttaaatgc aatgaaaaca  25980
acaaaatcta acagttcccc attgtcactc tttaaggtga cttgtttagc ctttactcac  26040
ctgaaggaaa aaaacaacta ctataacggt gatgaagcaa gttggataaa caaaaaaaag  26100
attggaaaag ggcaaaactt atagtgaaca ttgcacccaa aaaaaaaaag ttatagtgaa  26160
```

```
catagacact aaaatgaagt atctagcttt cttacctttt ctaccgttag aatgtacggg  26220
acagcttgtc agctacgagc ttgtctgcca aactttacaa tgtatcgttc tattggttac  26280
ataacatata aaaatgaata gacagagaga catagaaccg agcatatgaa gatgagagaa  26340
acgaactaac ctaaattaaa ccagaatgtt aataaatata atccaggaaa aacccgaact  26400
aaactaaatt gaaccggtag agaactcaaa aaccagaaac cccgagttta tggaaactta  26460
accggatgaa tcgaatccgg ttcggtataa taaaacccag aagaagaaga taaacctttt  26520
cgcagtttgc ttctttctct gctcaaacac gaacaatggc gagtctactt gactcactca  26580
caaccagaaa cttcttctct aaacccataa tctctaggat ctcctctcct tcatcttcct  26640
ttgcttcttc ttcttcttcg aatatctcac ccttttctcc tccctccgtt ctctcttact  26700
ctcacaaaag gtcgcattct cgcttccctt accctgtcgc agcaactctc gatggtccct  26760
ccgttgaaga agacgagcta gagttcgagg aatccgaaga agacagctac cctgatgagt  26820
cggatgaaga agatgacctc tccatagata tctcaattct tgagaaagaa gcgagagata  26880
tcgttagaga ctacgctact actctgtctc gcgagctcaa actcggtaaa agattgtgtc  26940
tttctttttg cattatgctc cattgactgt tgaataatga tcgtagcttg atgttttaca  27000
gaggatgatg tagttgaagg gaaggagtca cgtagaaagg ggaagaggca agccaaaaat  27060
gttagtcttt tttcagtaaa gtctagtcct ttgagcttga gatcttcttt aagtagataa  27120
agttttgatt ttttttgttt ggttactgac atttactcta aaaaaaaaag aaccagacgc  27180
agataccaga gcatcttctc caaagagttg ctatcgttgg aaggcccaat gtgggcaaat  27240
cagcattgtt caaccgtctt gttggggtaa aagagtttga ctgttttctc cttacccatt  27300
caagttttag agagttgtta acttgtcctt aatataattg caggagaata aagcaatagt  27360
ggtggatgag cctggagtta ctagggatag actgtacggt agatcctact ggggcgacca  27420
agagtttgtg gtggtggaca ctggtggtgt tatgactgtt tctaagtcgc cagctggtgt  27480
tatggaagag cttaacgttt cgaccaccat tggcatggaa ggtataccat taagctccag  27540
ggaggcagct gttgcgagaa tgccttccat gattgagaag caagctacag cggctgttga  27600
agagtcagat gttattgttt tcgttgttga tggccaggtt cggttcttat cttcaatctt  27660
ctctacgttt atgtctttgg cttattaatt attttggctg tcatgcaatg ttgttgatgg  27720
gtggtaatga ttttttggta ctcgatcaat acgcagacag ggcctacagg tgctgatgtg  27780
gagattgcag actggttgcg gaagtattac tcacataaga atatcatcct cgcggtgaac  27840
aaatgtgaat cgccacgtaa aggactcatg caggcttcag agttttggtc tcttgggtaa  27900
tttcactttc atcctaccct cagaatcatg tttgtgcaca ttcatagttt tcattgatat  27960
ttcagttgcc tacaaaaata aaactcatgg ataaacgtca tttggtactt ttttatcaga  28020
tgatttgaat atttgttgct ttgttgtgtt cacatttaac aaaaaatttg ttctaatttt  28080
acggatttag tattgttatt ttgatgagtt tgtagacctg acgatacttg taagcatcat  28140
aaaatacttt cctccgttgc tatacatttc tttgtcaatt ttggagatta tttggcattg  28200
agcttaacaa gcatgtcatg atggaacttc caggttttca cccatcccta tttccgcatt  28260
gtcgggaact ggaacaggag agctacttga tcttgtttgt tctggactaa acaaactcga  28320
ggtttgtatg taacctttta gtatgttcaa ctggcatcag tttaccaatt atatatcaaa  28380
accaatgatt tttttttct agatcatgga gaccatggaa gaggaggaag aagaaaacta  28440
catacctgcc attgcaatta taggcaggcc aaatgttggg aaaagtagca ttttgaatgc  28500
acttgtccga gaggatagaa caattgttag ccctgttagt ggcactaccc gtgatgctat  28560
```

```
cgatgctgag tttaccggac cagatggaga ggttagttca attttttctc gtgtttgttg  28620
agctgcttag ttttcttgcg gcttctatga tacagtgcct gctgtttcgc tatatgctaa  28680
ttggcatcta tttgatgcgc tttccatgtt aactcctacc atttttctc aatttggttt  28740
ggctactatc atcaatgact agcattgtcc aagttgaata ttgctgaact ctgaatatga  28800
gcagtgttca aaggtgcatt ggatccgtat aacactgaaa atgatttatg aactgtgttg  28860
cagaagttta ggctaataga tacggctggg atcaggaaaa aggcagctgt ggcgtcatca  28920
gggagcacta cagaggccat gtcagtgaac cgtgcattcc gagcaattcg tcgttctgat  28980
gtggttgctc ttgtcattga agccatggca tgcataacag agcaggtatc tcactagttc  29040
taaacaatgt gggaaacgaa ctcatctttc tctccttcct taatggtttc ttatttggaa  29100
acacaggaca tgaagatcgc agaaagaata gaaagagaag ggaaaggatg tctggtagta  29160
gtaaacaaat gggatacaat accaaacaaa aaccaacaga ctgcagcaca ctacgaggat  29220
gatgttaggg agaagctccg ttccctcaaa tgggcaccca ttgtttattc tactgctata  29280
actggccata gcgttgacaa gtacgtctcc ttccaaagtt ttataaacta attcaacctt  29340
tacattttta actttattct gttggagaaa aatgtagtat tgtggttgct gctgcgacgg  29400
ttcaaaagga gagatcaaga agacttagta ctgctacatt gaaccaagtg attagagaag  29460
ctgttgcgtt taaatcccct ccaagaaccc gaggaggcaa acgaggccgc gtttattatt  29520
gcactcaggt gaataacgat aagatctccc aatgtttttt tttattagca gtgaaggcaa  29580
atctttggag actaattgat gtgattaatg caggcagcaa taaggccacc gacatttgtg  29640
ttctttgtaa acgatgcaaa gctgttttcg gatacgtaca ggagatatat ggagaagcag  29700
ctacgcactg atgcaggctt tgctgggact cctattcggc ttctttggcg cagccgtaag  29760
agatctgaca aaaatggagg aggtacgtgt tttgctagcg taaacttgtg attcattttg  29820
aaaaatatga caatgttttg tatgtataac tttaaatgaa atttgcaggt ggaggtacaa  29880
tgagaatgtc aagtctttca cgtgagagaa atcttgcaac aaaaaggtca taatgttaag  29940
tcatctactc atctttgtta aattttgtgt attttttgag aaataatgta ttgaaattcg  30000
atattatata aattcatagt ttgttcaaaa aaaaaaataa attcatagtc tctgactctc  30060
cattgatctt ccatgtatgt tccattttgt ttctttctga gaatcaaaac aagatattac  30120
taatcttctt gacagtttat agaaaacaga actacaacgt ttctttatgt ttatgttttc  30180
ttaatctcaa gctgataaaa aaaagataaa cagaccaaag cacaggcgat gagtctctta  30240
gtaaagctgc tctttctttt catgccacca tctccacctg taatagaaca aagaaacacg  30300
aaactatctt tgtcaaaaac attagaaata ttcatttttg tcagaagaaa aaagtgaaat  30360
gagatgatat atgataatga tataagtcta cgtagtatac gtaccagtaa tagtcccaac  30420
gaggacggac tttcgtcatg cggttatcat cagaaggatg ataaggatga gcggcgtggc  30480
gagtgttgtg gaaggcgcag caaccagctg catagacagc gatgaggagg acaaggacca  30540
gaatattaac gaccgacaac tttttccagt caagacggat ctcctcaaga acaccagctt  30600
tgcaagcatc acactcgtag cataacgttt caataccatt gttccatcta tagcaatctt  30660
ctcctcctac tattactccg gtaacgtacg tgcacgccgt cggtggctta caacatcccg  30720
actataaatc aaacacacac atacaaagtt gatgaagatg ctagcttaca ccatagggca  30780
atgaatatga gaaaatatta atgaggatca tggcagtctt ttagcatgtg taaatggaaa  30840
gattgaaaat ggtttgattt tttttttaat gtataaattg gagtaaaatt taaaatttaa  30900
```

```
aatatattta taaattaata cttataattt caaaaaaata acatatataa atggagttat  30960
taatacttat aaaaaaaatc tacagttaat aattttattg aacatggttc taggcactga  31020
aaatggtacc tgaacagaag tcatgtctct ttggaagtaa tcaagtgtag tccaagattc  31080
aatctgagca caagtcttgg aactcaagat acagcttctt atagagatcc aatactgagg  31140
atctctaact ctctctctca accatggatg ataatcaccg agcctatact ctttataaac  31200
cctccctggt acttccacac cgcctccttg gctcgtcacc accaggccaa acagagttag  31260
acccataaga gtcgcgatga ggaagatcat gaccactagg taaacccaaa gagcccatgc  31320
cacgttgaaa caggctccta tgaatccggc gagagatact aagagtatga tgaaacctat  31380
aacgagtaga ggagtctgga ggaagttttc gcaagttgtg ctgcttcttg ccttccatag  31440
agcggctcct atgattggta ttgaagctag taagctgagg aggtttaaga ctccaatcac  31500
tgtgttgctg aatctgtaca tagtagtagt gttatcaaga agaaaccaga gacttagcag  31560
tgccttctct tatatctcgc tcttttgtaa taagcagatt ctcttcttgc aatgtgaact  31620
tcatcagctt tatcttacaa tcttctttgt tttttagtta ttatattggt taactctacc  31680
ttttttttgc ttttgattct ctcttatcaa ttgggaattt tttaagcgaa aaagtttaga  31740
gttaatggtt tgatgattca tgctcatatt ctctggtcgt ctcttgattt gaatcatcca  31800
aacaataaca ttagaaatag tatttttttc aaataaaagt gtctttttgg acaattggtt  31860
cttgtttatt attctatttt atacgtttaa ctaacaataa agcagaccaa aagtagtgcc  31920
ttaattaaaa tatgatatac catattatta gatacatttt tctagcttag agtccaaaaa  31980
atgcaatcat ggattatata gtggatcata tcatatgtgg gtattgtata ctttgaaatt  32040
gttgactcgt tacgggaaat aattgagata ctttttatat atactagatc ctttctccgc  32100
gctacgcgcg gataatatat ttaaatttgt tacatttatc atttttattt gtatgtaaat  32160
ttttctatat taaattatat ataactaatt tttaaatttg agttttttta tatttttagt  32220
ttgaagtaaa tatttctatt atatgtaaca caattaacta ataaaatatg aagaatcaag  32280
tctgagattt taaagttatg taaaaaatat ataattatgt atagaacaca aattatctta  32340
gtttaaaaga tcggaatctc atctcgaata aatttacgaa aaaaaaagta ctccaataac  32400
ctacttaaaa tataaaaact ccttttaaaa aaaaagcgta cttaataata tttttttaca  32460
tgtaatagtt gaaaactaac aattgaatat cgatctagaa tattatttta atatatctaa  32520
tgtaaaatat taattgtaat aaacaaattt tgaattttgt aatattacat gaattagaag  32580
tctttaaaat ctaaaatcta ttttattaac atactatatt ttttattcat ttattatttt  32640
gacgttacaa aatattgctt tagttttatt tgtatattat ttttttaata atttagtttc  32700
tttttaagta attttaaaat tatcaagaat gtaatatatt taaaattatt tatttaaata  32760
tatccaaata taatgtctca tttttatgtg tgtttgcgtt gagcatattt aatttgtaat  32820
ttgtatattt aataacacct tattgcgtgt cgttctatgg ttttaataaa tgtgttgtca  32880
tctcattttt attactacta acatgatttt ttagtgatca atgataatgt attttaaacg  32940
ttatgtatta tattttattg tatatttttt aactcttcgt gctggcactt tttttagaat  33000
cattttaatt agataatagg ttttaagatg taaataaaac tgtgtatgtt gtaaatttag  33060
acttcttagt gtagctgagc actatcaatt atggaaatta tattatgatt ttattttaca  33120
aaatcttttt ttctgtgtat ttttttgtt ttattttgta tttttaaaat tttattgcat  33180
tattctttaa ctgcagagaa ttgatatttc taatttttgt ttcatatacc ttaaaagtct  33240
tcggttgatt tttgtttgtt ttctttctcc aattataatg tatagttcga ccgtttcttc  33300
```

```
ttttttttg gatcaaacta ctaatatcat cagatagaaa agcttaaact ctaagaattg  33360
agtgaatatt tgtgttagag aaaactgatt taaccaataa tatagtgaga tattataata  33420
ttagaaggta tggaaactct tctatgttgt cctacgctgg acataattaa gttgttgtca  33480
attgatttta tatttgtgat aactggaaat gcatctttat gtcttcctta catcatcctt  33540
aattggtttg cggttcgact atttctaata tactgagagt aacataaaat tagatgttga  33600
ttatctcctc ccaattagga atgcacagaa tgagagaaat tcaagatgag accagtttac  33660
aattttgtcc tcatatctat atagagttag tttatagatt actctatttg tttcaaaatg  33720
taatcaattt ttattaaaat atgtaatatt taaaaattat tactttagaa atctgtcatt  33780
taatatataa atttaatcaa ttacacagta atttacataa tttaattggc tacacaatat  33840
ccaataaata taaagttaca ttgaaatata aaaataattt atatagtgaa acaaaaaata  33900
cttttaaacc attattatat tataaaacaa agagaatatt taaattatat tgaacattag  33960
aatagtaaaa atcagaaaag ctgaaatctc aacgtcgatc atttacgttg gctatgttat  34020
taactttgaa gataacgtga atgatcaaga acaaaaaagt taattttagc ttcagtcatt  34080
tttttataat cattttacca aaaagaaaaa aataacagga agatgactaa taaaaaaaga  34140
tacaaacaga gtactgtaaa aaggtgttga tcataatagc aaacattata gtctcaaaaa  34200
ttgtcaactt tatattaaat attagtcaaa aataataaaa tatataatat taataaattt  34260
tattttaaat ataatttaac ttttaaaaat tttatcatta cacatggtgc agaaaagcac  34320
ctagtattat ttgaatttca aaaactatct gatgcactaa ctttttgtga caaatcaaat  34380
ttaaggaact gggcaagaga ttgagaagag ggatgtggag aggtacaaag agtcttcact  34440
tgatgagtta taatggagca ttgaagtgcc attgttgtag tcgtaagagt tacaccggtg  34500
aagttgggta gacgaacaga tttggagtcg ctggagacgt ctgaggcaag taggctaaag  34560
aaaaggaagc tataagttat acaatgggct ggctattttg atggttttag atggttcgag  34620
acccatcatc taaacattcg cgatgacgtg gcagtttgat tggtagagaa tattttatcc  34680
tatgtggcat tcctaagaag cttcaaaatt agtagctttt atatagtagg atcttgtgtt  34740
ttaatttagt taaatccaaa aatttatttt caagttccat taataatgtt catgtgcatg  34800
tagtcaatta gtaaactaag ttacaatttt gtatgcttac taattgacaa tatgtttacc  34860
aattttgtgt aacgtttagt aaactacgtt aaatttacaa tgacccatga agcgaacgag  34920
ggtaagcaaa gaataataga catggacgga tgaatttgct ttttaagatg cttgtgctgt  34980
cccatcccca taactttcag aatattaggt tttgtaggtt gatgagcaca atatgatctt  35040
tgattcctcc acttcgcttt tttgtgtaag caagaagaac aaaaaaatct tgtttcagct  35100
gacaatttta cgtaccaccg ttttgatttt acattttgca gatgattttt tgacaggaaa  35160
aagggttttt ttttaaaaca acatttgagc caaaagacac acaaacttga aaggctaaaa  35220
gagtttacaa agattgtggt ccttgtgtgt gtggttcaaa agacaaacgg gaaaaggaaa  35280
ataaaatgct aaataagagt ataacaagaa aatcgcaagc ttgaaacaaa gtgttatctt  35340
cctatagaac cataatctct actagtatac atccaaaatc ctcagtattt gaagacatag  35400
aagcagatgc tgctcagttg tactcagttt gcaaggtcaa gtcttgtaca cccaagtcat  35460
ggtatacatc atacacatat tgcagtaaag gcctttcatc tatcccgctc ttcacctaaa  35520
cacaaatacc cgaaataacc aactcaacat cagtgccgtt cttattgagt actcatgttt  35580
taaccgataa gaaaacagga aggaagctag tacctggatt ctgagtgagc caacagtgtg  35640
```

```
accaggcaca acctcccaaa aacgagcctg taaaacctct atgacatcct ctcgagaagt  35700

aatctgtaaa taaagagagt tgaagagaaa cccagcttga tcgatctata tgtacacgtt  35760

caggaaacac tttatggaac agagcgaacc tgacgcaagc atttacttaa tgcggaagaa  35820

ggaatgtttg gaggtgccat ctgaagcaag acaccaccgg tggctttgaa gagtggcata  35880

acaagcataa acactgtaac agataccaat cccaaacata ggacctcagc attttcaacc  35940

ctgaaaaatc caaagaccgg aggagaaaaa tggaaaatgt aagaggtcag gtactaagac  36000

atttttattc attttgttcc ttttaaagga agcgagcatt acccgagaga gaggagccag  36060

gatgccagta tcagacctgc actgaaaaga cagaagcaaa gaatatgtca tgtgggatgt  36120

atataagttt catgcaaaga gaaacatttt tccagctagc tctccgcggc tctgcttgag  36180

ataaagaaag ccaaagagaa tatcacacct gcggatggaa tctgatatga catgcaagca  36240

aacggagtgg tagttcatat cttctgcttt tctgtacact gcatcatttt acgaatttaa  36300

gaaacacatt caagaaaaat gcaatatgta cgaagggaac aattcttggc cagatcagtt  36360

gctttcatgc tgtctctctg ttttcactaa tcctcctact tattctatct taattggaaa  36420

cccttgcttc tttgtggctt tacattgaca ggggtggcca gtttttacaa tgaaatatag  36480

caaagccgcc aaacaaggct ataccatata aagcaccagt atcggtatta gttaattcaa  36540

gtctaaccag aacttaagca taataataaa acagagaata cataccaata ttcatacgag  36600

cataattccg gaagaaccaa acaccaagta ggttcaccag cagatttgtt accgctgata  36660

caataagata atgcctgcat gaagtcgatt tcagtacatc atattaatgc aaagaactta  36720

gtgtaaactt agtaagtgct agagaaataa ctacaagctc ttaggcatgt cacttgtgga  36780

aagaaactta cttgtgctct gattcatctt gaacaaatgc atgaagagct tccacagcta  36840

aggagaacga catgaacata agaaacagct gtctacacat atgtcaatac tgaacatatc  36900

aatgtgttaa cccaaaagat aaaatgaatg agacagtgaa ggcaaaatga aaagataatc  36960

aacattttaa acgagctgta agattattct attctatcaa caacagtaaa ggaaagtgtg  37020

caaacactat cgacactatt ttctgaaaga tattaagcca gttttattgc atggcacatc  37080

agccattaga ccctcaaatt aaaaccggaa atgacatcca acaaacttaa agaacatact  37140

tacagcatta gtgaaagcag aaagaacttc aagtcttttg tacctggaag aaaagccaac  37200

gattactaag tcacaactga ttcagcatta tgcaatgtca gtatcagcag caaagaagca  37260

aacagacaag gtttcatatt tagtaattat aaaaactgga tcctatgaaa acaacggcgg  37320

atctacttta ggaatgctcc agagaaagaa aagaaaaagt aatttaacaa attgggaaat  37380

caaccgtaaa gtaccacaaa ccatgcattc caacatatat ctccagcaaa tacaagcacc  37440

aactaatcgg atcaaatttg aaaaatttct cacccgtatg agtaagcatg atcaggcttc  37500

ttccttgaag tcgccattgc aaataaagaa aacgtcagga gaccacatcc aaatgtcaaa  37560

tggaatgcat cagaaaccaa acctgcaaga gtcacatcaa acatcaaaca tcaaaaaaga  37620

gagcaagtaa acaacaacag taaacatggg aatctaaaca aatctcaaac caattttgat  37680

atttacaaaa cctcagctgc aacagaagac aatatcttaa aaattaaaac tccataacca  37740

aaaggtctct acatacgcat aggatctact atccatgcgg tttagttccc aaatttaaaa  37800

gattatatta accaaaaaaa aatcaacttt agctgttttg tttcatctaa atctctagtc  37860

actacccgaa gtaaggatgt gaagctcaca tcgacctgga gtcttattcc tccaacaaat  37920

ccaactctct ccctctaaca aagttatcaa gaactaaaac caagcaacaa ccaaatcgta  37980

cctacacgcc cagtcaatag cccaatcaac agctctgtag tagagtacgc cacgttaagc  38040
```

```
gaaatcaaca taaacaatct cttcatctgc cgatttccat ttctcagcac cccaaaaacc  38100
accaaaacca tacgcaaaac cgacaccttc ccaatcgccg ccgccgcttt cccttccccg  38160
aagaaaacat catccccgtc gacagagtat atctccggcg gcatatcgat ggtggagacc  38220
gtcctatcga gaaaaggctt agccgccggc gttcgcgggc cgtgggagtg gtgaaaggag  38280
cgggagtaag cgagcctccg atcattggcg gcgtatccga cgtcgctgct ccgatcattc  38340
gggagttcgt tatcgccgcg aagatcgaag gaaacggatc tctccatact tagctttctg  38400
tttgctcctc aaatgtgtaa ttcaacgagt cttaaaagta cactgcgtct actagaatga  38460
ccttaatggg ccactgatgt aagcccatat aagagctcaa gtcatgaagc gttgaccgca  38520
tttaacgcct tattggactt gattgcctct cgagtagggc ttttaacgcc ttattggact  38580
tgattgcctc tcgagtaggg ctgggacttt taaccgaacc cgaaccggat ccgactcgaa  38640
atagaccagt tcggttcggt tttggacatg gccatattat ccaatagatc attgcttcta  38700
atatcacggg tcggttccgg ttattaccca aaacctgatc aggtatttat ttaaaccaaa  38760
atggatagtg taaaacctag aatattttaa aaagtattat caccacgact caaacccggg  38820
taaaagtggc tatgttacca ccagaccact tcaacttata tgtattcttc tatattgtaa  38880
atatctatag tatttcaata ttattttta taaaattaat attttagaga ttttgaatcc  38940
gggttggcca cactacaaat agagtatgta accactgaac catttcaatt tacacgtaat  39000
tattttattt aaaaaatatg tatatgattt acataataaa tgagtacccg aaactgactt  39060
ggaatcagag atatccgatc cgaaacctga accgaaattt atctagtacc tattggatag  39120
ataattcatt tatctgaaag atccagaccc gaatggatct tacccgacct gatccggata  39180
accgaagtcc cggatctact ctcgagtctt gtgatatgtt ttctcccata acaacaaaaa  39240
tacagtatag tataatactt cagataaata aactttatta aaattagtag ggttaacata  39300
tcacattcaa gcatttttca gcccgttaat atcaataatt aactttttat tcaagcattt  39360
ttcagcccgt taatattaat aactaatttt tggttggatt tgtctcttta aggaggattt  39420
gtctcatgat ttacaaataa caatattcat atttttagtc tcgtaagatt ttatactaca  39480
aaatattaac tattataatt tataaataat acattattta ttattataat ataattatct  39540
agactgtttg taaggtaatc acctagagct ttagaacact ttcatagtga tgtggaatca  39600
ttgtttcagg cattgtgttg gattctggag atggtgtgag tcacactgtt ccaatctacg  39660
aaggatatgc tctcccacac gccattctgc gtcttgatct cgcaggtcgt gacctcactg  39720
attacctcat gaagatctta accgaacgtg gttactcatt caccaccaca gcagagcgtg  39780
agatcgtgag agacgtgaaa gagaaactcg cttacatagc acttgactac gagcaagaga  39840
tggagacggc aaacactagc tcatcggtcg acaagagcta cgagttgcct gatggacagg  39900
tgatcaccat cggaggggag aggttcaggt gtcccgaggt tcttttccag ccgtctttgg  39960
tcggaatgga agctgctggt atccacgaga cgacttacaa ttcgatcatg aagtgtgatg  40020
ttgatatcag gaaggatttg tatggaaaca ttgtgcttag tggtggaacc acgatgttcc  40080
ctggaattgc tgataggatg agtaaagaga ttactgctct tgctccaagt agtatgaaga  40140
ttaaggtggt tgctccaccg gagaggaagt atagtgtctg gatcggagga tccattctag  40200
catcactcag taccttccaa caggtaaatc atcttttctg cttgttactc gttttgtaag  40260
ctgactatga tacacaatgt tggtattgca gatgtggata gcaaaggctg agtatgatga  40320
ggcagggcca tcgatagtcc acaggaaatg cttctaagat tacgctcgcc gttggatgaa  40380
```

```
agattttttc gtattatttt atatgttcaa cgagttggtt tcagacaatt ttttttcttt  40440
ggtttttcct cactacaatt gtttcttgtt gtcacactct ctttggttgt ttctgccatt  40500
aatgagaaaa aaaaagattc atttgtctta ttttcttttg ttccctcaca aatctgaaag  40560
caaataaata tgaagaaatg aatttggctt atgttgacag gtttctacaa attaaaagag  40620
aagaatagag ttttttacaa agagactgaa ccacatgagt agtaaaggtg atctgccaac  40680
caaacaacgc aataactcaa actaacttaa ctgtaacgaa gattagattt atggttcact  40740
tcaggtgagt aaaacatttt tcttaaagca ttggtatgtc ttgaaacgac aagttgcttt  40800
atgtcaagat tcactagaac ataatagtag tttcagagga agctaagcca ttacactgtt  40860
cagggatcca cattaagata gttcgagaac aagagttcac tagtccgaaa gtcacatttc  40920
aacgatccca aacataacag cgatgagaag aagaacaata cagacacaag acattttaga  40980
cactaacttc caacatcaca taattttagc caaaatgtca gaaaacacaa caaaatggat  41040
aattaaagat tattgaaaca gaaacatagc ttcttaaaac aaagacaatc atagatgaga  41100
aaggttcagt ttcttctttg cttcataact tattgttgta ccagaacaca cctttcttct  41160
caccttgcct gtccggttcc acatagatac actccttcgc ctccctccac atcgccttaa  41220
ccaccggcgt cccatcgaac tgataatact ctcccagtat cggctttatc gccttcgtag  41280
cttccatcgc gtgataatgc ggcatggtcg agaacaggtg atgcgccacg tgcgtgtccg  41340
tgatattgtg gaagaccttg ttcaagattc cgtagtctct gtcaacggtg gccaaagctc  41400
ccctcaacca atcccactca gacgagtcat agtgaggcag ggaaggatgc gtgtgctgca  41460
agtaagtgat caaaactaag aacccgttga caatcagaag aggaactccg tagaagcaga  41520
ccatcgaggc aactccttgg acagcagcgt agcggtagag accgtagcag acggcgagga  41580
tgccagcgtc ggagatgtat atctggagac gctcacggtc gttgtagatg ggagcgttgg  41640
ggtggaaatg gcaagcgaag ccgccgtcgt aaggtctccc cgagacgttg aaggctaagt  41700
acaaaggcca gccgagagtg aactgaaccg ttaacatcac ggtgcgtccc aaagggttgt  41760
tgaggtactt gccgtaccac ttgatgtctg acttcttctt ggggacaaac acttcgtctc  41820
tctcgaggga gccagtgttg gaatggtggc gtcgatgact gtacttccag gagaagtaag  41880
ggacgaggag gaaggagtgg aagatgaggc cgacggtgtc gtccagccac tggtagtcgc  41940
tgaaggcgtg gtggccgcac tcgtgggcta tgacccagac gccggttagg acgcagccct  42000
ggcaggccca gtagagaggc caggcgaagt aggagagagg gtgagggagg agagggaagt  42060
aagtggtggc gacgtagtag aagcaggagg ctatgatgat gtcccagatg aggtaggaga  42120
aagagcgagg gatcgagcgt ttgaaacagt gcggtgggat tgctttcttg agttctccga  42180
cagtgaaggg cggtgtctcg cagggtacgc gcttgatgtt gtcggtttca gactttttgg  42240
agggaggaga cacttgcatt cttccacctg cacccatgtt tctgcataaa ccaaaagcaa  42300
agactcaaag ttaattaaac caacaaatta atattcagtg ttacgttatt aaagtttcaa  42360
aaaaatggac taccacaaaa aaaatggata gtacgtggga taaagagcag agaagcggca  42420
tatagtggca aaccaaagaa agaaataaac gatagcgttg agaatactac tagttattaa  42480
tgagatttga tacgttacag cttacatctc tttcttgtgg atatcaattt ctttcgtctt  42540
ttattactaa actacgttag agaagacaag tcataatcac aatgtctctt agaataagca  42600
acttgacaaa aacataaacc taaatgaaac agttgatagc aactctattg tcaacatata  42660
gacttttaaa cataaacaaa caaacaaaaa tacaatcttt ttactatcat gaatcctatt  42720
attttcttca tgcaaatcta ttgcatctga atctatgaag gagcatctaa tccaattaat  42780
```

ttgcaagaaa aagtttataa gcatgaagtg agcataggcc aaatgaaact ttttcatgta 42840
ttaggtaact acagaatcca gagccaatag gaatcggtca aatctctcag caaattttac 42900
ccagagacat aagtttttac ccaaagattc aacaaatatg tacttacatg tctcaggtcc 42960
agatctaaaa caaaagtaaa caaatatata taactttgaa taggaaggat atttctaaga 43020
ccaggacgtg agactgctat ggtgattttt caactccacc aacccatcaa aaatatatat 43080
ataattttaa aaacgattga aagtcaaaca gtttgtattc ggacaaatga aaatgcaaca 43140
tttcatattc tccacggtat agacaatata atcagattaa tggttaagac agcatcaaga 43200
tttcacacat gaaaacagag aatcaagacc agatctatag tttaatgcaa taaatattaa 43260
cagatctaga aataaatcga ctgaaatgca aaaatgatag atagaacaga aaagcgataa 43320
gaaaagaaca gaccaagatt gaaaacaacg taaaaatgag aagaaatgga agaagaaagg 43380
gaccttgagc tggctgacgt aggggggat gaagatttaa cgttaataac gatgaaccct 43440
acgaagaagc tcctcctcaa actctctctc tgtctcctct ctttctctct ctctctatct 43500
ctttggtaat gaatctctct ggttctggta agatgcgatt gggcagaagg caggccgttt 43560
aaattgacgg gggcccgtgt gagacgattg agtgacatct cttttctttc ttttttttaca 43620
agtgggcccc tccattattt cctctcttca tatttctttt tttttatta tttttctact 43680
ccaaatatct gatatttaca ccacttatat atatttacgg aaaagtgaaa aagatgccgt 43740
gatcatataa ttgcttttat aaagtttatc acgtttcttt ttgtattttg tttttaaaat 43800
gtaaatattg gtttacccaa tcctaatgtt cacaaagact agtttgggtt atgttataga 43860
actcatccgt tacgttaatt agcattaaga ttatggtatt tgatgtcttt actttaatat 43920
gaggaaacgt ccttgccgac tcacaagtag aactgtagaa gttagtggta gccggaaaga 43980
aaagaaaaaa atgctataaa gttgaggatg gaggatcgtg cttggcttct tcttctccca 44040
tgtgagaaga aaacttaaaa aaatatctgc agacattgtg gttgagatca cgtgaatagc 44100
cccgagtgtg tgtgatgtac tttggagatt cgtcatatat tataataaat taatttaggt 44160
ggtacacaag taggcagcga ctgccgacta gtaattaatt taagtacttt attaaagcta 44220
tcgctctctc ttatgttaag atgattagag tttttctatg cattaccgct tataacgaca 44280
cacattattt ttaacattct ttaaagatca tcacctacca tgatttcatt tcatttattc 44340
agctgttact atcagcgacg gctattaata acatgaattt ttcgttatat agtctatcaa 44400
acattataag agaactataa catcgacaac gattagttat acagtctagc atactcacaa 44460
aataatctaa gctgataatc acacacacat cagagaaaca catgaacttg ctgaccaaaa 44520
taaagcagag aaaacatgaa gtattaagta gagacagcac acaaatccta tccactgttt 44580
tgccaatcat tcatcaagcc tgccccatct caaattcaaa ctagattcta aaaaaacacc 44640
aaatggggaa aacttacact gacaatgaaa actaaacatt gtagtttcaa aaaacaaaga 44700
caactaaaaa caagtaggag aagatgatat taggaatcac cacaacaaat gaaagagact 44760
tgtttcacca gtaactctag gagcaattca tgacctgcgt agctctgctt ccccgtgagc 44820
aaagtgacat ctatcaccaa atgtacagct tcctttagag aatctctcac acatcttcgt 44880
cttgaagttg cttcctggat gtggtttccc ttcagaacca agcccacccc cgccaccacc 44940
gccaccaggt ggtctcctag atgcggaatt aagcctccca atcagctctc taaccattgc 45000
gctcgcttcg tttatctgct cgaatgttcc ttcaagctca atgttcttca ggttgggatc 45060
tctctcgtga tcttggatcg atagctttgc tcctgtctga cgacatatct gtttcgaaca 45120

```
gactccacct tttccaatga ttgcgccggc caaggaagca tccacactga tcttggctgt  45180
ggctgaggca ccaaagctag agacatggcc aggccctgac tctcctctcc ccgaaaaccg  45240
acctccacca ccaccaccac cagatccttg catgtttctg gaaacttgag acatgggtga  45300
tcccatgttt gtcatctgtg ccataggatt gtatcctccg ggaacaaagt gcaagaaatg  45360
gcagttctca ccaaaaggac agccagaagt gctgcaacag acgcataata aatatgtcaa  45420
gagagttaaa aaccattggc attgagaaga cacaagagaa caaacagttg aaacacagaa  45480
gaaatggcac atagcaacta tgctaactgc ttgtctatga cggacatgtt caccagtatt  45540
cagtaatgca acaaccttac tagacactat atgaccatga tgagacaacc ccaaaataac  45600
taatatctta ccaccaaaca gagaattaca acacatatct ttactgccac agctcaaaca  45660
aaaggtgtgg attgattttc tacgctataa tcaccagttg aggctaatat atttctaaat  45720
ttataatcga atatcatatt tgttatattg aaactttttt ttaactggtt cagcatgaat  45780
aataatacat acctgtaata agagctaatc acttacatta gcatacattt tttagttgtc  45840
aatttgaagc tcagactata aataacaatt ttgaatatta atttagttaa gaaaaaggat  45900
tataacctga aaaattttgt gcatggcttc gatttgcttc ctaaaccaga ttccatctct  45960
gttccaaaga ttaagtgttt ttctttagtt aagactttgc tgatgttcaa taataattgc  46020
ttttagaatc atacatatca ttcataaatt ctcatctata tggaacttca cacttaaatc  46080
aaagctgcta ctctagaatt ttcaggatta tttaccaaca actaccacat gaataactaa  46140
cacataaaaa agctaattca atcacagcaa actcaagctt tgggcatggt gataaatatgt  46200
tacaagaggg actaaactaa agcaataatt aaaactcaag ataactataa gcttgattta  46260
actttaagat cacttatcaa aagctcatcc atcattaaac tgaaaaatta atggacttta  46320
gatttgcatc agatcaaaga ctgcagcaat ctctctactt agccagagaa gtgagcacga  46380
aagaaagatc caaacttgaa tttactagag aatacgaagc tcgaattgaa gaaatcatcg  46440
ctaccccaaa tcaaattgac aacaaaggaa ctattcatcc atcaattaag atctaaagtt  46500
tcaaccttta acagagcaag tgaagcaaaa cagaaactgt aacagctaaa acactctttc  46560
gagacaataa agtaagagga agagcgaaag agctaacctt gcttcgactt cttgaatccg  46620
ccgccattgg agttgaatga gccagcttca ggccgtcccc tcttacgagc atccatggct  46680
aaaggtgtac agatccgaat tagaaaccct actgtgtgag tgtctagaga gcgaatcgga  46740
gaagacaaat cgaaatcgga attaaaggga gaaggaacga gtagagagaa gagaataata  46800
ataagataaa taaaaccttt ttaaccctaa gggtggtgtt gtcttgtcgt cgaggggggtg  46860
agatgagatt ttcctttttt tcctaactct tcccgatttt tttttaattc gatttaaacc  46920
ggagtggcgt aacaaataaa caaaaaggta aaccggaatg tcctgaaaaa aggataaaag  46980
ataaccggat tcgcaagatg aggctgtttc gattcctttg atacggttaa catgtataat  47040
gacgttgatt gttccttatt cgacatctta cgacgtaaga cgaaaaataa attgcgtacc  47100
ggtctagtaa gttcggattc tattatgttt tccataccga ggagacagac acacaaccaa  47160
tgtttatcat ttaccttaag gctgggcgtt tttaacttaa accggtgtcc acaccttaaa  47220
ccgaaccaaa ataatgagtc cggttcggta acgggaccat gcaaataccg aatgggtttt  47280
tagctctaag cacttcggac accgggtcgg tttggttagg taccaaacca aaaaatttta  47340
aaagaggaaa atcatcttac aaaattactg tatatttatg tagaaactaa attattttgt  47400
tgaaaacgaa gcggtgaaag tcagtataaa tattatatat atatatatat atatatatat  47460
atcttacaag aaataataat tgttctaagt aca                                47493
```

<210> SEQ ID NO 2
<211> LENGTH: 40174
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 2
gggggtgggg tatagatttt ggagtttttt ataatttggg tagactttgg aagttgttta 60
aacgattttg gtgaagtttt gaaaatacat ttaaacaaca ccattgttgc ttctgagtta 120
tctctaacat tatgaattct aatgatatta tcacctccta ggatgcttac agtaaaagaa 180
acaacagttt taattttttt cttactggtc ttaataagcc cattcagaaa tatctcccaa 240
taatctcttc actgaaggtc cctacaggca cacgagacac tgctatatgc ttctgcatat 300
ctttggcgaa tatagagctc atcacataaa aacaaaaaga tgatgaacct aaatcttcaa 360
attgcaatgc gatctctcgc ggaagaatca aaaccttgaa gttgctgtac ttttcttttc 420
tgtatggttc tctgagtggg actaagtatt atttataata tttttttgta attactacta 480
tttttatttt ttattttttt tattttaaaa acataatata acttgataat attttgtttc 540
tttttataaa agatatcaaa tttgaaataa cacaatccta ttggttggtg aacctaaaga 600
ttcaaaataa acccaagaat aagtcaataa agaacaacaa tatttatttg atatatgttt 660
tcataaatta tatgtagata aaatacaaag cacaacggtg cacaccagca tatgcaacgt 720
taaagtttag attttaaaat aataaaaaac cataatacat ttttaaccgt agattttaag 780
ttacataggg ccggcccgct gcggaagcaa cgtaagcgac ggcgtagggc acacaacgtg 840
tttcaatttt tttttacagc taaatttgtt cactaacttt taaaaaaaaa tcatccagct 900
gattaaaatg cacattttaa ttttggatta gggcatctaa tagtaatgga actcgtacga 960
tgaaactttg aattttgtga aagaaaactc caataagtta atataatcat gttattggat 1020
aatgtacata aattttaaag gtgactgttt atgaggaaac aaatcagata tgcacgattt 1080
tgtttcctac aaatggctaa ttttaccaat ttatatttaa gttgtttaga ttgttttcct 1140
tcgagtgtgt attaaaaatt tattcaaaag tatgtggttc attgaatatt gatatttaca 1200
atgaacacgt ttcatacata gatgaaatat agatattaac ctaaaataac cttaacaaaa 1260
attaaaatac aataactttc aaatcaatat tcatattatt agtatatata ataatactta 1320
gtcccactca catttacaat cggctttcca aaactttgtg ctacattatg tttcatcttt 1380
caatggccaa cactaaacaa aaaccagttt caatcttatt gcttactaca ttttgcttct 1440
tgtcgttata ctttgtgaaa aatcaagcct tctcaaaagt ctcatatcca tctaccttag 1500
gtctaaacca agagaaacta acacatcttc acttttactt ccacgacatg tatggttaca 1560
acccaacatc agtggaagta gcagaagccg cacaaacaaa cacatctaaa acatattttg 1620
gttccatgtt cgtaatggat tgtcctataa ctacacttcc taatataagc tccaatataa 1680
tagggtatgc acagggtatg acagcatctg catctcaaac cgaattggga ttgttgatga 1740
ttctccattt tgtgtttacg gaaagagaat ataatggaag cacgattagc attcttggac 1800
gtaaccttgt gtttgagaat gttagggaga tgcctgttgt tggaggcagt ggcctgtttc 1860
gattcgctag aggatatgct gagggaaaga cgtattcatt agatgtgaaa tctggaaatg 1920
caactcttga atataatgta tttatcttgc atccttgatg tattatacaa taatgttaaa 1980
gctaaactat tttattatcg ttgattccgc taattttttt gataattaca gtgatgatat 2040

```
ttcataattt ataaatttgt tttacgtaaa ttaatgtcac tatgtcctaa tttggagaac   2100
aatagtcaca ttgagaaaat gtagatcaac ttttttacta cagagttaaa ccgcaatata   2160
agaactacca catgtaatgt gagagactca aagtttagaa tccaaatgtt tttcgattaa   2220
tttgtttgtt ttgatatgga tctttacaat acaatttctt aaacactaat catttacaaa   2280
actggttgtt aacttttcat tttttgttgg tccaagatgt gaccgagaca cttcaaatct   2340
ctacttatat atctctttaa atttttgtaa tcaaccaagt tttagctatc tttgtaatac   2400
aattttcact tcatgaatat tcgcattctc gtgaatcttg attggttgca ataaaataaa   2460
aacaaaatcc ttggcatcaa ctgccaaagt cgatgttaga aaataatttt ttttttttaa   2520
acgctagaat tttatagaag gataacagaa caaaggttct acaaggatca tcttcaatca   2580
aaagagacaa agagaggtag aaatattgac ctaacaaaat aggtaactaa gccaacatgg   2640
atatcctcta gcaatataag attgaaaaaa atcctcctgg atcacacttt ttgcaataag   2700
tgttgctcct ttaatgttat gataagagtg gaattgagtc ttccaatccg ggaattcatt   2760
cagtaatggt aagacctttg aagagtagaa ccttatagaa ggccatgcag atggtttaga   2820
gatggcgcca atcaggtcat gatcatcact agcaaagatg atggagctga aatggagagt   2880
cttcaatatc tcaataggcc atctctagtt ttctagagag gcatcctgtt tgcacgaagt   2940
gtcagagaag gatcttcttc catggaggag aattttacct tcgctgctac gaagaatcct   3000
agagtaacct tgagtcgtca gtaggtatca ctgcttcttt gtgtgttgat tgatttttgt   3060
actcatcttc ttcattcatt gttctggagg tttaacttcg actttgtgat ggcatctaga   3120
aaaggatcaa agctgaggaa agcagggtat accaatttaa agggtgctga ttctactgct   3180
tcctcagcga cctcgtcttc aaagctttat caggagacat ctattgatga tggccatagc   3240
tcccctgctt cttcatctgc tcaaagcaag cagcagttct tctcatcaga ttcgtttcca   3300
caaagctcta agccttctaa agaaaacgtc acagtgacag ttcgctttcg cccactcagg   3360
ttcagagtga aatacttgta tatgcttgca aatataaggt tgatgtttgt tctgtgaatt   3420
tgacatatat tttttccttg acgtagtcca agggaaatcc gcaatgggga ggaggttgca   3480
tggtatgcag atggggaaac aatcgtaaga aatgagaata atccgacaat agcttatgcc   3540
tatggttagt ctttaacaat ttaattagtg tcatggtgaa cacatcactc aaaaacaaca   3600
aaactaagga caaatagtat tgttcttatg tgatattcat tttcacttgt aatcatgtct   3660
taaaatagga ggactaagat taaattggat attctttttt ttttgatatt ttgatttccc   3720
atgttgtttt cttgaagttg tctttcaatc tgttaatgat tgattctctt tctggcagat   3780
cgtgtctttg gacctacgac cacaacacgc aatgtctacg atgttgctgc acaccaagtt   3840
gttaatggag ctatggaggg gattaacggt atgaagtgac cagttttaat gataagtcta   3900
ttttaaaata gaagaaacga agagcagcga cacttgccgg cggcaattct gtaacaacac   3960
tccactgtaa ttcctctctc atgcttgtta tttttggtc gctgttctct gacgcgcgtt   4020
agagaaacga acagggcttt tgtatttttt tttgtcacag attatttgtt gaaagactgt   4080
tcttagtgtg ttattcttca gaacagttga tttgaatata atgacatcaa tgttaatcca   4140
ctacagggac catttttgca tatggagtga caagcagtgg aaagactcac acgatgcatg   4200
taagattccc taataccgtt tgatttcaac acaccctact gttgaaaact tgaaaccatg   4260
tttgcattta actttagaat gtccatgact tacgattaat attatctgat agttttggtt   4320
aattttttgg ttcaaatgtc agggtgacca aagatctcct ggtattatac cgttagcagt   4380
```

```
gaaagatgct ttcagcatta tccaagaggt acttttgtag gatattggtt cgtccagatt   4440
ccttggctta agtactagca gcctgacata ttaatctttt acagacacca aatcgagagt   4500
ttctcctgcg tatctcctac ttggaacttt ataatgaggt gctattattt acctattgtc   4560
ttgtctgctt tatattcatt ttcaatagta gcagagagtg atagaaataa ttttcctttg   4620
agattactat ctttaaggtc caccttattt caggttgtca atgatttatt gaatccagaa   4680
ggacacaatt tgaggatcag agaagacaaa caggtatgtg actcactttc agatcacctt   4740
ttgatacatg caactacttc tcttgttgac tcgtaatata tttgttgtgt ttacgagtaa   4800
tatattttgc ttatcataga atcttttatt gggaaccatg gttaggctat ttggtacctg   4860
aaaatatata ttggttccat tatgaggact ctgctattag aatgctttca tatgtggccc   4920
tttgtttcat tgcaatgctc tatgtcacaa tgttttcaag cacatttgaa gttgatcctc   4980
ctaattatca tttgaaatga gaattgtata atgagcttct catggctttt attcaatttt   5040
ttttaattga acccattttt gttgattcca gggaactttt gtagaaggga taaaataact   5100
tcctctttaa gatatttcgt ccttcaactc tgtcatgatt tggtaaattt ccatattatt   5160
caatgcatgc ttagtaaatc tttttcctca tgacagagca acgccatgtt ggatcaacaa   5220
actttaattt gctcagcagc cggagtcata caatattaac gttggtatgt taataatctc   5280
tttgaagcaa gggagaaatt gctatctgtg tgcagttgat atatcatttt tttctcctga   5340
caagattaaa agtgaagctg tacacctctc acagctggta agctactctt ataaccagtg   5400
atatagttag ttatgattag ctctttcgtc tacgctaaag cgaattcaaa taatattaac   5460
tacccataat ttctctcata tttgcagaac ctcgttgatc tggcaggttc cgagagttca   5520
aaggttgaaa ctagtggctt aagacgcaag gaaggatcat atataaataa aagtttgctg   5580
actttagaaa ctgtgagttt ttttcttacc acacagtttt ctcttagtca acaataggtt   5640
ttggagtcaa ttcagatagt acttttgtga tgttgtaggt gatacaaagc tcagggatgt   5700
gaaggcttcg catgtaccat acagagactc taagctaact aggatccttc actcctcact   5760
gagtggtcat ggccgagtat ctgtaagtcc ttttagatct gttctcaatc cccttttctta   5820
tgaaatccac aacatgatta aaaacatctt gataacctta agcacatact ttgctagtta   5880
tgtactttac tgattagttg tccctttgtg gatatggtag ctcatttgta cagtaactcc   5940
tgcatcaaga agttcggaag aaacacacaa cacattgaaa tttggtcatc gtgcaaagca   6000
tattgagatt cagcccgaac aaaacaaggt tttactcgca tatcttctac ctgcctttat   6060
ttttttggta ctaacactac aaaactgcag ataactgatg agaaatcact aatcaagaag   6120
taccaacatg agattcggcg actgagggag gagttggaac agcttaaaca ggacattgta   6180
ccagttcctc cactgaagga tatgggtgca catgatacta ttctcctgaa ccagaaggta   6240
tgctcgaaag ataccttcca tccccattta tacttttgta gtgattaagg gatgtttttt   6300
ttctgaatag agttccaatt ttgaaaactt aaaatcttgt ttttaattgt cattcatgca   6360
ttttcctgtc agtgataaaa gtttaatatg aactgataat agttgaaacc cacttatacg   6420
ttggattaga caagtaggag gacattttgt gtcattgtgt tttagttaca atcacgcatt   6480
tgagagaatc tgtagtaatt ttgttgtttc cttttttttgg ctatataacg tgataataga   6540
agctagaaga tggtcaagcc aagctataat caagactaga ggaagaggaa gaagctagag   6600
cagctctctc gagccgaatc caacagttga cgaaactaat attggtgtct actaaaactt   6660
cactgacata tcgcttacct catcgcttta atcctcggag aaaacactca tttgaggaag   6720
aagaggtaga atcactgata tagcttgaat agtataaatt gtttacacgt tcctgtggag   6780
```

```
ggaagtcctg agattagaga tgttccatgt agagaagaaa agaagagccg gaagcatggg   6840
ttgttaaatt ggctaaagcc taaggtatac aaatgtctga ctttttgttt aaagaataat   6900
gctataagta atagtagaaa tcaccacaca gccttgtctc ctcttaggtg cagtttcttc   6960
ttttaattat tctctggtca actccccttt gttgatccga gcttactttt acctatcaga   7020
aaagggataa cagttcaagt gctagcgacc agtcgagtgt ggtaaaatcc aacagcacgc   7080
catcgactcc tcaaggggga ggaagttatc tttacacaga atcaagactt tcagaaggat   7140
ggcctttgat ggaaggaaca actctcagag tctagagaag acagagaagc tcctgaagac   7200
atggagactc tggaggtaca taagagatac tttcacatct gtaatggcgc caaagtaact   7260
aaatcattca tatgtgctct tgttcccaga ctagcaataa aatcatcgat gagttggatc   7320
ttatgagagt gcagaaaaag attttatctg agggggtggc gcttcaatca agttcattga   7380
aaaggttgtc agatgaagct gtgctttaaa tctaccaaat attcaccttc ttggttctct   7440
aatgttactt aggaggagat taatgcccta catgatggca tcaaggcaaa gagtgaccag   7500
attgccacct tggagaaatt aacaaatctt ggattatgtt atgacaacac atgaggcatt   7560
ggataaatct gacatcctga aggtaggttg ttgacattgc aaagtattat gcagtgagtt   7620
ctttttccgt tgctcatttc acaagcggtg ctctattatc ttcaggcagt tgctgagctg   7680
agggatcaac ttaatgagaa atcttttgaa ttcgaggtga tcgaattgtt tatgtgttta   7740
catacaatac ttcttcatct attgatccag cacctagagc tagctttgct attgattaga   7800
taatatatgt tcacacctta gtaaagttgt ttctctgcaa atattagtgg tcaaatgcca   7860
gactatttaa cgaagaagcc aaatcatatg ctctacgttt cgactcatca ttacatcttg   7920
tttacaggtt aaaagctgca gaaaatcgca tcattcgggg aaaactcaat caaaaggtca   7980
gaggctttgt ctttggagaa gcttgtaaac taggtttgta atgtgtagtg gaattgaata   8040
actgatgaat tattttccgc agacatgtga acgtgaagta ttgcaagaag aagttagaaa   8100
cctaaagcag cagctctcta attcccgcaa actagcacag gtctatctac atacatttta   8160
ttcacgcctt acaccaatct tctagcttaa tagcttcatg actctcaaca taaaatctct   8220
ctactttctg ttatgaaagg aaacaaagat cgaagagctg aaatggaaaa cttaaggaac   8280
taaacgaatc taaggagcaa ctagaacacc gtaacaagaa actcgcggaa gagagctcat   8340
attcaaaacg ccttgcatca gcagccgcag ttgagctcag ctcaaggcat tagccgaaga   8400
agttgcaaaa ctaatgaatc aaaacgagag actatcagct gagctagcaa cacagaagaa   8460
ctcagtcaca cagcgaagca acaagacagg aacaacaaca acaaatgtaa ggaacggacg   8520
aagagagagt cttgcaaaga gaaatgaaca agacaactcg tgggagctaa agaaagaact   8580
aagaatgagc aaagagcgtg aactatcata cgaagccgca ctcgttgata aagatcaaag   8640
agaagctgag cttgaaagaa tcgtaaaaga ctcaaaacat agagaacgag ctcgctagca   8700
tgtggattct tgtttcctgt gttttaaaag gcgatcgcct tttgcgccaa ggcgcaaggc   8760
gcaccggggc gatggcccta atgcctcagt cctctaaggc gagccctagt tactcaaggc   8820
gctcgccatg gtgcgccatt ggcttaaata taagcgcctt tgaacctctt aaggcgcttg   8880
tagtttccgt taaacactac tttgacggaa tccttaaaac atcttggaac tctatcacta   8940
ctttgtcgac catttaaata tcctaaaaac ataatgctta gatcttcaga gttataggtt   9000
ttgttggatt tgagcaattg aatttagctt tttagtttca agttctttgt tttgatttga   9060
tgttttcggg tttatatatg tgtacatagc tgactatatt agtgtgcatg actaactcgt   9120
```

-continued

```
tgctgactat attagtgtgt ataaataaga cagtttggta tagctgactg tactagtgtt   9180
atatacgagt ctactctata acttatcttc tgtacgtaac catagaaata gttacacgtc   9240
tgtagcttac acatacactt ctaacctaag aacatctatc aatgcatatc taagttcctc   9300
taaagctgta tataactaaa ccacgtttga atgcatccta accataaggc gagcgccttg   9360
gagcgccatg gcgcaaggcg catggctcca acctcctcgc cttagagcgc catgcgccat   9420
ttaaaacaca gcttgtttct aagctgagaa gatcacaaag aagctgattc tgttaccata   9480
tcagagacac cgccacaaaa acttaacaaa gacgaatcca aacaaataca taatcatcac   9540
aactttaaat tgtttcttat tccgaagaat taaaaataaa acaaaaggat agaacaatga   9600
tcaatactaa cggatcagtc agttagtctt gggatcaggc atggggaaca aaccagcacc   9660
agcagcgcca cgtggcggag aaaaccctag aaacttctgc agattcgtcc ttatactaat   9720
cgaacacagc aaatacaaaa acgccatgga acaatccgtg gcatcatctc ccttcaaccc   9780
cctgtgactc atcttcttca cgatcgcgat cggatggaac gggagcttcg cgacgacctt   9840
accttcgaag agcgagttca acagcccgaa gacgacgaag aggacgaggg ccacgacggc   9900
gccggatttg aacttgaaga gggacagatc tcggctcgac tccttgaggc tcgtctcgac   9960
gcggtccatc ttcttggtct tcgatttctt gacggtgagc ttggaggaag ggttctcggt  10020
cttcatcgtc tccagcttct tggcggcttt gtcgattgag tattttaggg atttgtagga  10080
ggtggtgcgg tagattagga tccacgagat ggcttcgcag actagcgccg tgcagaagga  10140
gatgccgacg acggttaggc tgtcggcgta cttgaaggag gcgaagagtg ggatcgtcgt  10200
cgccattggg atttagtttc ttctgctttc gcttctgttc tctctctctc actgtggaga  10260
tctgattagg aattgggtaa aataaaagtc aatagagggt acaataagta aataaggaaa  10320
agtttggggg acttttagaa atacttttta attttacttg taaccaatac ctttcgaatt  10380
attagaattt accccagctg tttttttat tccttgctat gcaaaaccca aattacaatt  10440
tttaacatta gcataaacac tgtggtgcac atcaaatagt gtaaacttgt aatcatgcag  10500
atgtatgttt ttactcacag aaaagaagaa gcaagggaaa aaaagattgg taagtttgta  10560
ccaaactcat tagttgtatg ggttttatgt actagattat tttttctagg tttgatttga  10620
atcagagttt atttgggttt tgattagaaa aatgtggagt aaaagagagt aaataataaa  10680
gtggaaaatg gagaaaactt tggaaattga aatgaaaaga gaacaaaaaa ttagaataaa  10740
actcgtttca cttataaatc ccaaaataaa tatgtgagtg ttttttttta atttcatccc  10800
tcaacttaat gatgctacat agttaacatc acgaatttat tttcattcat ctaaaaattg  10860
atgtagattt tagaaaccgt ttaaatctta tgtttttatt aattaaaata tgatgtacat  10920
ggcggtaatt taactaaata tgaaagttac ataagatatt atttaatttt ggttttcaat  10980
tattttaata tgttttctta ttaactctta ataaaatttt tgtaatttat ttgattaatt  11040
gtgtggaata tacttatttg atcatttttt ttattataaa acttatttca tgtcaaatta  11100
ctgactctaa cattttattt gtttgatata aaattaaata actaatgaat tattttattt  11160
atatattcat aaaaaaaaat tgcatacatt ttaaaatgta tcaaataagt atatatcaga  11220
caattaatca aatgaattac atattttta ttaaaatttc ataagaaaat ggattaaaat  11280
aatttaaaaa caaaattaca taatatctta tagaattttc atatttaata taaataaaaa  11340
taatataata atatattttc atatacacaa aaataaaaat gttaaaacac tacttataaa  11400
aaaatgttaa aacatattga ttttgtaaaa tcaattatgt taaaaatatt cttacacttt  11460
taaaatgtgg gtcaaaatct catttagtta aattacggcc gggtcggtca tattttaatt  11520
```

```
gatgaaacga gatatttaaa cggtttctaa catttacatc aatttttgga tgaacgaaat  11580
taaacttatg atgttaatga gatatgttat catgcataat atataattcg cgtagctagg  11640
tatacattag tttagtttgc atggttaacc atgtgaatga ctaatacttc aggtagttag  11700
caaatatttt tttccttctt ttaatcaatg aacctaaatc cggattgaaa tcctgataat  11760
tgaattcaac ccaatagaac aatagtgtta tcatagttac aactaaaaaa aaacttaaca  11820
gacaaatcta aaatttagaa atggaaatat gagaaggaat ggaaaaactt aacagacaaa  11880
gcgtttcaag aagaaaaaaa aattctagag gcttcgtttt gcgttagttc attataatgc  11940
aagtagagcg aattcgatga tttatttatt ttgaagtacc atctcattag atggtatttg  12000
tttctagtgg attttgtatg taaaatcaac taggtgatta tccactcaca tgtgtggagt  12060
aaaatgtata tattctaata attgttgaat atgaactttg tccgtataac cataattata  12120
ttattcataa gcctatatat gtattaattt gaatatctat taaatgttag tttactcgta  12180
tggtttttat gatcatttat attttattat aataaaaaat ttaaactata gatcataaaa  12240
ttttcagtgt gagagtttta acaattttca ttatttatag tcgtttttaa acattcaaaa  12300
tataatatat acgaaaaatc tattttttat tatatggtta atatgattgt ttaatttatt  12360
ttaatactat aacattaaaa aataatgaag atatgtgaat tgttgtcaag tctttattat  12420
taaaattatt aattgtcaaa tatatatttt agtcacgttt ggtaattccg taaattttat  12480
ttaagaaaaa aaaacaataa ttatatattg ttaattaatt tcatggttat tctaagtaga  12540
agtatataat acatgtttaa tagaccaaaa tatttcttta gagactttaa gaaacattat  12600
agtgatgaca cgtgttatag ttaaaatgtt gtaatgctta tcttttaata tatagaagat  12660
tatctaataa tttccaataa ctcttgataa atactaggaa aagaacccgt gcgatatcgc  12720
acggtaactc attttgtaaa aaatacaata caaataaaat tacaataatt tttgaagata  12780
attttttaa attctttata agagtgtata tatatatata tgaaaataaa tgaaaagcca  12840
atttcatata ttttgataaa aaatttaaaa acaaaggcaa tttcatgtag tgatctttga  12900
tgatctaaat aatgaatctc tttcttttt agtttatttg tgattgttgt gattttctaa  12960
ttttatttgg tgtttattgt ggttgttatt tgtcattttc gacaactatt tatatatatg  13020
actaaggatt gcaatagttg acaatcaacc tttgcaaagg tttaactaag ggttacactg  13080
gttaacacca aaagttgcaa cagttcacaa ctaaaaacaa taatcactaa taattgtaat  13140
ttttttatca tcaaagaatg taatggttca acactaacag ttgcatcatc taaccaattg  13200
taactattca ctaagacaac atactccact taaacagtct caaagattca cttaaatctc  13260
taacaattat ttcttattta attattatca gagattcaca aaataaatat cactcgtatc  13320
aaactcatgc acgaataaaa atgtacgtaa catcaattcg aaaaacatca taaatgtcta  13380
tttatttgat agataacaaa atggatcata tatttttata aaaaaatagg atcatatatg  13440
cgttgtacgt atataatttg acatatcatt aaaccttgta tcagatgtga tgtcaaagtt  13500
actaatatgg tagatagatt attctttgaa aaagtatttg taaaatggga tgaccgatga  13560
ttaatagtag cttaacagat ctctcttcac aaaaataaat aaattaatag actatttaga  13620
agaaataaaa tatcagatgt aaaagttgga atcttcgatg tataaatgtt ttcaaagagg  13680
tgtctttgga agaggtttaa gccgttttga tttgaaggaa tgcattgatt cgagaaaggc  13740
aaaagcgttc tttggtttaa taaatgatga tgtcatctat ttaaaggaaa tctaattttt  13800
aaccattaga ttattataaa ataaagcaaa tctaacagtt agatatatct tttttcccta  13860
```

```
taaaaaatga tgatattatc agttaacaaa aaaacaggtt tcctattatg tatagaaaat  13920
ttaaaaaaga agtaagaaaa acttgctttg atagtagcaa atgtcatttt atttgcataa  13980
cttcttgtat atctgccaag aagaagcaag gttggtttca aggtgactct ttaataaaaa  14040
caaataaaca cgaaccaaaa acaaaaaatc agtttaatac ccagcgagtt gattattgat  14100
catccatggt ctccagttat caataaccga atagttgaga gatcttatcc aagcttgagt  14160
cccaatgtaa ggtactgtca tatcgtgatc accaatgttc acacaaaacc acacaaatat  14220
ttacataaag attttgaatc ttggtgggag aaaaaaactc tgacctgaag atgagagaac  14280
gatagccatt gatgctatta tccatatggt aaggtacatt acttataatg tcgttactgt  14340
aaggaatatc caaattacat cgtatccatc tccctatgct ctactacaat tatagatctt  14400
cttaaaaaac ttgacagcgc ttctttacta aactctttga aatgaacagt cttatatacc  14460
ttcttgattt gaagagcttt gcgtacgctt tcgctttcgt catttgccca gtaggtagct  14520
agcaaatacc tataaatctg caaaagcaac cttatatatg ctttgtttcc tgaatggttt  14580
aacggtaaag aaagaaggtt aaaaatttat aacagtagtt attttaaaat tatacttata  14640
ataatagtca caacttttca ctttttaaaa gatatctata cataatagca aactccacat  14700
tctgtgtttg atgacatcaa catttttat agcaaaataa aattgaaatc ggacggttga  14760
gattattgcg gttatgtaat ctagtggata ttatttaagt ttcatttagt atatgatgtc  14820
atccgttatt atatctaaac gatgtctttt tctttttgaa acgttgcatt tttgaaacat  14880
tgcttctgaa gagacacgac cctctcaaaa taataattct tatatctaac ggtgtcttgt  14940
ttttgaaacg ttgcattttt gaaacgttgc atttttgaaa agatacgacc ctctcaaaat  15000
aatagttctt aaatcttaac aaatttatat attcattctt tatgacttcc ctacttcccg  15060
tcatcattgt tcttttttct ccttcactta ccatggattt cttttgttct ggaaataacc  15120
gtctctctct aagaattttc atgtctgttt tcaccaccac cgccatcctc ttttctgttt  15180
gttatgttaa tctccatcct cattttctgt ctccccaacc cactactata ttaatttact  15240
cataaccgtt gaaatattag aacatgtgtt gtcctcatga aaccatttga tgatatttta  15300
accgggagat tcaagagact gaaatttata aaagggaaat atgatttcat gtttcaagaa  15360
ggaactgaca atcataatca atttaactta caaattagcg agaaaagctt tagcgagaga  15420
attccgatga ttctccctcc actgtttcca ggccttatga gaatataatc catcctagga  15480
aaattaattg taccaaaaat ttaacaaaaa aattcaccga gcatctttcc acaaatcctg  15540
tatatctgaa gaaaataata attgtgttga attctttata attgtgtttt ttcacaattc  15600
tttttgcacc atcaaatcat catatatcac tctcactaat acgcatctct tcgctctcaa  15660
ctggctattt tcagccaatt gttaaacaat ttttttgatt tccggctgac attgatccta  15720
gcactggttg ttttctcttt ttatttactt ttgtttttaa tacatttaga tctcggttta  15780
ctaccattaa aatcagtgga agagacttat aattgaaaaa tgcatggcgg agactattta  15840
tagattttta aaatctattt gaatagtcac atcccttcaa tctgaatagt tgcattcttc  15900
taatactcac aacttttcac tttttaaaaa atacttatga atagtcacaa cttttaaaca  15960
atttttagaa aagacacaac cttacaacat agaactttta gaaaagacac aaccctttac  16020
acatcttttt caaaagatac aacctttcaa tataagtgag attcacaacc tttggaatta  16080
atgaggattg ctattattag tagattatga gtgaaatctt tgttttccag taaggagaga  16140
ttcgaaagag ttttaataaa tgattaattc aataagagtg gatttgatag aacttttata  16200
aatactaaga ggagatttga acaaaaacta gaattctctt aaatcataag cccccttttgt  16260
```

```
tcctatctgt tttttggtca ccattccatt ccagaaaatg cttttaaaga taacaatcac  16320
aacattccaa atgtagaaaa ggcacaatct caacattcta aacctgcgtc cacctaacaa  16380
aaaacaattg ccttctcgta gtttactcca aatacaaagg gtgtaatata acaacagaaa  16440
cactcaacac tttaccgaac acacacgttg ccttctctcc taactcctta aagttcaatc  16500
ttcataatct ctctctgtct ctctctctct ctctctctct ctctgacaac agagagactc  16560
ttcacgtgcc aacaaaaaaa aactgagcac cttcctctcg cccatggcca cggactccgt  16620
caagcacgtg cctacattcg gcggcgcagc catctctgaa atgaaaagct tcttctccgc  16680
catgaaacca agaaaaacga tcataacttt tgtctacgcc ttcgtcataa cctttgttgc  16740
cttcactgtt tacttagcct tcgccccttc cctcatcact atctctaatt cagtttcttc  16800
ctatatcctc cctaatgtca gtgccgtgac ttcagcgtcc agtaacatca cattacaagc  16860
aaccacgccg gaaagtctca ctccggctgt tataaacaca acctttgagc ctcccctagg  16920
taatgaaaca aacccacatt ctagaaacaa cgcttcacgg tctcatgcaa gtgtacactt  16980
atgtcctaac aacaacactg ctcgaaattc ggacaaacaa gcacctctgt ccgtgaattc  17040
aagtgcttct tctccgatga gaaaacaaag taggaagtca ggggctaaac gagagatcaa  17100
gtctctgaag gactgcgatt ttttccaagg agaatgggtc aaagacgaat cctacccgct  17160
ttacaaaccc ggcacgtgta atctcatcga cgaacagttt agctgtttaa ccaacggaag  17220
accagacgtt gagttttaca aactgaagtg gaaacctaaa gaatgcactt taccaaggct  17280
gaacggaggc aagttgctgg agatgattag aggaagaagg ctcgtgttcg ttggagactc  17340
gctgaataga aacatgtggg agtctttggt ttgtattctt aaaggatcag ttaaagatga  17400
gagacaagtc tttgaagctc atggaaggca tcagtttcgt cgggaagctg agtacacttt  17460
ggtcttcaaa gtaagtttgc aatctgtttc ggtgaggcct gcgggtttgg ctagtttggg  17520
ctgggtcgtt cggttcgacc aaaatatcgc ccaactgaac cgaacagagt ttggttcggt  17580
ttaggtagtt cggtttttca acttctttta ccgaaactaa tcaaagtttt tggtttcaat  17640
tatatgttgg tttaaaattt ctttaaattc ggggtaattt ggttaattcg gtttgtcggt  17700
tattttgatt cgaatttttg attagtttag ttagcttttt tttggaaaac ccgagctaac  17760
caattactga agtgaaaacc gaagtatttt ataagcttgc cgaattgaac caaactaacc  17820
aaaaattttc gttcggttcg gttatcaacg aggcctagtt tgactaccta gttgttattg  17880
gagacttgat ttgtgtggtt gatatgatag gaatataatt gcactgtgga gttctttgcg  17940
tctcctttct tggttcgaga atgggaagtt acggacaaga acgggacgaa gaaggaaact  18000
ttgcgtctag atatgatggg aagctcatca aagcagtaca taggagcgga tgtacttgtg  18060
ttcaataccg gagcttggtg gactgatgac ataacatcca aagggtagag ttctgtcagc  18120
tattttttat ttttttatat ggaggatttg tctcattggc tttttggtgt ttggatggtt  18180
ttgattagtg aggactattt tcaagaaaga agcactgttt acccgaaact caacgttgat  18240
gaagctttta gaaaagcatt gactacttgg ggtcgatggg ttgataagta tgtgaatcca  18300
aagaagtctc ttgtcttctt ccgcggattc tccctgtcac atttcaggta tgtacagttc  18360
tttcatggta gtcttaagat tctgtttaaa aaaataaata aatgggtttg gtctggttgc  18420
atgcagtggt gggcgatgga atgcgggagg ggcgtgcgat gatgaaacag aaccgatcaa  18480
gaacgaggca tacctaatgc cttacccttc caagatggag attcttgaaa gagttctaag  18540
gggaatgaag acaccggtca cgtatctcaa catcacgagg ttaacagatt acaggaagga  18600
```

```
tgctcacccg tctgtttata ggaaacagaa atttactgca gaagaaagca aatcaccgtt  18660
gttgtaccaa gactgcagtc actggtgcct cccaggtgta cctgattctt ggaacgagat  18720
tctctatgcc gagatgctgg taaagctcga ccagctccgt ggcaacagac ggcggaaacc  18780
tgaagggcta ctataggagg agttgaatca tattcttgtt ttagatgaaa tacacaatat  18840
atattttcaa tggatgaaaa gaaaagaaac acttagaagc aattatatgt tttcaaaggc  18900
atagagaaag taagagatga gaatcatatt actgccttgc tcatcacttt tcttggttgt  18960
aaactatgtt catgggagag gtttgagatt gtaaatggtt aatttttatt ttactcaatt  19020
taatagtaag gtttgtcaaa tcataactga accggaaatg gaagcaatca tttggttaaa  19080
agaatccggt tgatgacatc gactggcaaa gcataggcag gatcaatttg gtttgactcc  19140
aggatactcc agccctgcac cagttttgga tcattaagtt ctctttagct ttgaagacct  19200
taacagtatg tactaatgag acgcaaattt tagtcacctg caactccaaa gtaagtgtga  19260
aagatatcaa cagcatcgtc aggtccattc tccatatctt attcaaatta cacctgaaac  19320
tcagggaagg ctctaaagag atgtgagttt tatcaaccaa tgtttgagaa aaacctgaca  19380
gtccaagatg aactttacaa gctttgattt gtcaatccaa tggactctgt tggtcatgat  19440
aaaactcgat aaaacccacc aagagtggca aacctggtga taattaagca agaacaatca  19500
gtgtggtaag tgttaggata atgacgtatc attatagaga taatcatagt ttaagataac  19560
tgttgtattt atcttataga taactatgag catgtgataa gatcaacttg actctatcac  19620
atgatctcga cttgtataaa tagagagctg cagacatcaa taaacttaag ctttccacaa  19680
tacaaatctt atatggtatc agagcaattc tcgatccaaa tcgtttaaat ttttcttttc  19740
tcttcacgca aacacaaaca tcgttaacat gtctgatcaa aacagctctc tcacaactgc  19800
cactgctaca cgcaccgcag tctatgatcc cgcaaaccct gcaaactcgc ttcttgcggt  19860
taacatgtcg aacgttacac gtttgacaaa caccaattac ctcatgtgga gcagaaaaat  19920
tcaagccctc cttgaaggtc atgaactcca cacttttctt gagaaaacag aatccactcc  19980
agaggcggtc ctcatcaaca atggcctcgc agaacctaac ccggcgtatc taccgtggag  20040
acgtcaggac aggctcctat acagtgccat cattggtgct atatcccttc cagttcaacc  20100
actcgttgca agtgctacaa ccactcatga agtctggagc acacccaatc tcatctttgg  20160
cacaccaact cgcggacaca tcaaacaatt gaagttccaa gtcaagagct gcaccaaagg  20220
aacaaaaacc atcagtgagt atctgcgtct tatcaagacc aaagcagatg aactagcact  20280
ccttggcaag cccattgacc ctgaagatct gatagagcag attctagcgg gtctctctga  20340
ggaatacaaa gccgaagttg atgcaatcaa cggccgagat catctgatct ccttctctga  20400
acttacagag aaacttctta accgagaagc catgattgtc tgcgatcaac cagcaacacc  20460
gacgtttcca gttacagcta acaacaccac aagaagcaac accaacaaca ataaccgcaa  20520
taacaacaac aactggcgtc catcctttgt cccacgacaa ggcaacaact cgcctcgccc  20580
atctcgtccc taccttggaa gatgtcaggc ctgcggaatt caaggacata gcgcccaacg  20640
gtgtccatca ttcaaagtca ttgcaaccaa ctcaatgcag caaaacaccc aacacgctca  20700
gtggcgacca catgccaatg caacgtacat gacaaaccaa caccctgatg cttggcttat  20760
ggacagtgca gcctctcacc atgtcacgag tgatctcaac aacatggctg cacacatgcc  20820
atatgcagga ccagatggca tagtgattgg gaatggagcc aatcttccca tcacacacac  20880
cggttcactt tctcttccaa cttcatctaa aagtttcaat cttaatgatg ttctttatgc  20940
tccatctatg caaaagaatt tgatctctgt taaccggttc tgtaaaacta acaatgcctc  21000
```

```
tgtggaattc tttccaacta tgtttcaggt gaaggatctt ccaacgggga caccggtgct  21060
gaccgcgcca gttaatggca acctctatga atggcctacc aatgactcac gcactcctct  21120
tgctttctct gctgtatcat catcgtcctt agactggcat cacagactag gacatccggc  21180
ttttccgatt ttacagcata tttcttcttg tttttctcct ggtttttctt gtcgttctcc  21240
aaactctctt cattgcaatg cttgttctat taataagagt cacaaattgc cattccataa  21300
aacatctatt acttcctctc gtccgttaca aattcttttc tcagatgttt ggtcctctcc  21360
catcttttct tttgatggtt acaaatacta tttactcata gttgaccact atacaagata  21420
tatgtggttc tttcctttga aactaaagtc acaggtcgca gccacattca ccagatttaa  21480
ggagctcgtc gaaacacagt tccaaacaaa gatcacaaca ctctatagcg acactggcgg  21540
tgaatacatt gcactccgac cattccttgc gcagcacggc atctctcacc tcacaacacc  21600
accacacaca cctgaacaca atggcctatc cgagagacga catcgacaca ttgtagagac  21660
aggtctttcg cttctcactc acgcttccat ccctactgaa tattggacat atgcctttgc  21720
tgcagctgta tacctgatca ataggatgcc aacgaaagta ctttcaatgg acacccctta  21780
caatcggctc tttggaactg ctcccaacta ctccaaactg aagatctttg ggtgtctctg  21840
ctacccgtgg ctgcgaccgt acacatccaa taagttggaa ccacgctcca ctccatgtgt  21900
ctttcttggt tattctctta ctcaaagtgc ttatttctgt tttgatccct ccacttctcg  21960
agtctttgtc tcacgacatg taacttttgt tgaacataag ttttcctttg tttctttaag  22020
tgccaatgtc tcttccactc cagcaacaga ggagctagcg tgggttccta cggtggaacc  22080
tttaggtcag caacaggtac tcgtggagga gccctcaccg gaaactggac ctgcaccaac  22140
aacggcatct ccaacaccaa cagcacctgc ttcaccaaca gcacctgctt caccaacagc  22200
gcttgctcag tccacagctg cccctcctgc tacaagctct cagccaacac aacatgccat  22260
gacaacacga tcacgcaaca acattgtcaa acccaaccca aagtatggct tgacaacagc  22320
acttgccccg tacgttgagc cacatacaat cacacaagct ctggctgatg agcgctggcg  22380
gaagtctgca actgcagagt tcaatgctca ggttgtcaac aacacatggg atctagttcc  22440
agctgaagaa gcgacaaacc tagttggcaa caggtggatc ttccggtaca aatacaaccc  22500
tgatgggact gagaaatcac tgaaatccag actggtagca aagggatatc atcaacgtcc  22560
aggaatagat tatcatgaaa cattcagtcc agttatcaag tctccaacaa tccgacttct  22620
acttgggctc gcagcaaaat atgactggcc tcttaagcaa ctagacatca acaatgcctt  22680
cctccaaggg actctcaatg aagatgtcta catggtccaa ccagcaggct tcatcgacaa  22740
ggacaaacca aatcatgtgt gcaaactcaa caaagccctc tatggcttga aacaggcgcc  22800
acgtgcttgg tacacggagt taaaaacata tcttctcagc cttggattca aaaattctgt  22860
tgcagatgca tctctgttct ttttacatga tcgagggatc gtcatcttca tgctaattta  22920
tgtcgatgac attgtggtta ctggtaactc tctttctcgg atccgtgaca tcatcaacaa  22980
cttgtctagg cgattctctc ttaaagacct cgatgacttg ggatacttct taggcattga  23040
ggtcatgcgc tcgtctcagg gtattgatct ctctcagaga aagtacattg ctgacctact  23100
tcatcggacc aacatgacac acgccaagcc agtaccaact cccatgtgcg cctccacgtc  23160
gctctctata cgagatggta ctaccttgga taatccttca gagtacagaa atgttgtcgg  23220
cagcctacaa tatcttcttc tcacgcgacc tgatattgca cttgctgtca acaaactctc  23280
acaattcatg cacaagccct cagatactca ttggatggcg gctaagagag tgctacgtta  23340
```

```
cttggctggc acgtatacct ctggcatctt cctctctcgt cagtgttctc tctccctcca  23400
tgcctattct gatgcggatt gggctggcaa caaggatgat tatacctcca ctggtgcgta  23460
tgtcgtcttc tttggtcaac accctatatc atggtctgct aagaaacaaa cgggaatagc  23520
acgatcgtca actgaggctg aatatcgagc tgtctcagct gctgctgctg aggtacgttg  23580
gctctactcg ttactgcgag aactacacat tccaatcatc tccaccccga cgatctactg  23640
cgacaacgtt ggagctacct accttagtgc caaccctgtg tttcattcac gcatgaaaca  23700
tctagcactt gactttcatt tcatacgtga acaagtgcag aatggagaca cgtctcatca  23760
aaggatcagc ttgctgatgg tttaaccaaa ccgctaccaa ggaaccggtt tcaactcctc  23820
tttaccaaga tcggcctcaa taaccgtgct ccgtcttgag gggggatgtt aggataatga  23880
cgtatcatta tagagataat catagtttaa gataactgtt gtgttttcac tctctaactc  23940
cagttcgccc tagctggttc tctctcaggc acggagtcca aggcagccgc acagcttgca  24000
tctccgccag aatgaaggtc tctttccggt gcagctcctc ctgtcctaat cacgagcctc  24060
tcttccgctg ctgatgacgt ttcgctcacc atcccgaagc tctccctctt ctcctccaat  24120
gggttcctct gcaactgtcc cgtttggttc tcctcccctg ccgcctgaac caccagatcc  24180
ggatcttgtc gtggtgtttc cgataaatcc tccagaccct ccaccggtcc tgctggtttg  24240
tccctttctc cgccagttct cgccgtctta caccgctcct ctcaatcaaa aggaaatcga  24300
atctcttatg ccatgggatc tctgcttttc aaccggttgc ttgctcaagc ctctctgccc  24360
agacgtcgat gtgctatcca cgcagcctgc tctgctgcat ctttcgttgg ctggaatttc  24420
tccctccgga gctctcaact ctggcctgag ttactcctcc tttcgacatt atcccgtttc  24480
aaagccgata attattacct cttgtgtgga acatgttttg ttaaagtcag ccttaagggc  24540
atcaacgatt tatcatcaag agtcgtgtgt ggtttcctta tctgttgcaa gattattggt  24600
atcaatagct gagtgcaagc tgacttccct tcattactca tctcttcaaa gtcttgagga  24660
ctgggcttgg aaggttgaaa tattggtggt gattttctct ctgttggcag ctcttaatac  24720
cgcaatgcag cattttgaag tggagctctc tactgcttta tgcagttctc agtcaaggcc  24780
tatcttctct tgcttcaagc tctcgcaagg tatggtgttt ttaatttgct ggagtgagtc  24840
acgattgttc gatccttgcc tcctagtaga tcttagttat ctcaatacga accccatttt  24900
aattcggaat gaagaggtaa tgctatcctg gattagctct gtacctcttt ttgaggatgt  24960
tacactccct ttgagtttca ggttgaagct ctctttacct cagtatgagg aagttactcg  25020
ttgtgatact actttgttac ctcagtgtga ggattttatt tggactgctg tctctgtgga  25080
catggtttca cttatctcag gcgtgtttag gctatggtgg ttctcctcac agctctcagt  25140
ctcttcaaag aggtgtttgg tcgcctttga gcttgtagct gggtctttcc caattggtta  25200
ctttcagatt tgcccggcaa agggaatgtg gatgcaaggc cgtgtcctcc atcgcttatt  25260
gagtagagtg ggctctggac acgtcgtcaa agcggtgatg attcacaaag cctctcaacc  25320
agcaatatca actggactct caagacttca gattcttccg gactcaatcg tccccttctg  25380
ttccctgcgc ttagggatgg acttgaatga gattacaggt ttcttgagct tcaaaaacct  25440
tgttcctctc ttcactccgt tatcatgtgt ttataatcta cgcacagcat tatgtttagc  25500
tgttgctttt gcaaagggtg ttgtacccag actttgtatt tcaagtactc tgctttgagt  25560
tggatatgaa ataaaattgt tgacaaaaaa aaaaaagata actgttgtat ttatcttata  25620
gataactatg agcatgtgat aagatcaact tgactctatc acatgatctc gacttgtata  25680
aatagagagc tgcagacatc aataaactta agctttccac aatacaaatc ttatagtaag  25740
```

```
aacaattgga ataatgtttt gtgtttgtag agagaagctc cgttccctca aatggacacc  25800
tattgtttat tcatctgcga taaactggtc atggcgttga caagtacgtt tccttacctt  25860
tacagttttg ttttaactta ttctatttga tgttatatat gaacatttat acatgtagta  25920
ttgtggttgc tgctgcgact gttcaaaagg agagatcaag aagactttgt acagccatat  25980
taaaccaagt gataagagaa ttagctgttg catttaaacc aagtgatatg aaattattct  26040
cttcttctct cttttgttct tcacattctt cagtttccag caagtaaaaa agctcatatt  26100
ctcacactcc tattcgtctt ctttggctca gcccttaaaa gatcgacaag aatggaggag  26160
gtacatagtt ttttagcact aaaactatta ttcttagttt gtattgaaaa aaaaatgttg  26220
ctggtgaagg aacaatgtca agtctttcac gtgagagaaa tcttgcaacc aaaggggggg  26280
cataataaac tgagactata taagtttcgt ttagttatgt atttcttgag aaataatgta  26340
attctttgtt tttttttttg ttaaagggtt ttataattca cgtttgtgtg ttgagcgtaa  26400
ataaaaggga ccgctttata cgattcagtg atgtttttag tttaatttca gcttctttct  26460
tttcatgaaa ttcaagctac ttcacaaatc aaagatgcat gcatatttgc gtggggaact  26520
acatagacac ccattcaaca agaactctat ttataatcac gtcctaatga atcggtcatt  26580
tgaacaaaaa aaaaccactt cctaatgaat cggtcatact tttatttttta aaatagatac  26640
aaagacaccc attcaacaag aactctattt ataatcacgt ccttatgaat cggtcatttg  26700
aacaaaaaaa aatcacttcc taatgaatcg gtcatacttt tattttggag attaatgttt  26760
cataaccaag ttgctttggt ctagtggtat aggagctcca gctggagtgc ccgcccctgg  26820
gttcgagcct tggccactgc ggaatttaac atatgggctg cagcatccga gaccgaaaac  26880
cgttacacgg tgagccacat ggtgacgccc tggcagcgtc catgctcact tcggtctcta  26940
gtctggacca cctcggtgga gccaggatac tcggttagca aaaaaaaaat gtttcataaa  27000
taaaaacaga tatcagtgta cgtagtatcc tcccttatct ttaggattcg attcccacct  27060
tcaacattcc actttttctt catttcagtt tgttatttaa agggtttcaa aacatacaac  27120
aattatccaa aactagattg tttcaaattt ctcaaaagat atttaattcg aagctaatta  27180
tcacgagaac tacaaattaa ttccaaaaat gaagttaatt tcattgatgt gcatcgcctt  27240
tgtcatactc ttgacatcat tcccggctac ggctattacg ttcaaccctg cttgcattaa  27300
aaatcatgat acctgcggcc ccctagttgc tgtaaagggc cggcggtgga gacccgaatg  27360
ttgtaaaatt tggagcggga atgtacttcc agaaacaaga caatgtgcat gttatgtact  27420
gaaacattct ttatttggca atggtgttct tccccttatt ttagctaagt gtaaattagg  27480
tggtatcgaa caattcaaat gttcggaggt ggaaacataa aatagttaac taaccagaat  27540
cgtgaaaacc aaactggaga taataagata aagtaatcaa ttgggtattt ctttatttct  27600
ttctaatcat tttaataatg ttactgttca ataaggagag agaaatggtt tgtttttgtt  27660
catgctcgtg tgaattacga ttccatgttt ttttgtttcc atgtattttc ttatatattt  27720
agtaaaaaaa tgaaaaggta taatctagtc tggattaagt accataaata aatatttgtt  27780
cttaatctta gtgctttgga cttgtaacac caactttatg cgtaataagc atggggagaa  27840
gaagcaaatg aagaattctt cttattcacc aagttttgta atataataat tttcattcta  27900
ccaaaaaagc ctctctctag tattttctct aacttctttc taaaaaagct tccgaccaaa  27960
tagatttgct catgtggcca gtgggctctt tgctgccggt cacccataat ctttttgttt  28020
ttgtttttgc tttgtattat atttcttctc ttcgcggtgg cgataaaccg tggcaaattt  28080
```

```
ttgttgtgta ttcaaaatct taattgaagc aaaacttgat gattgtgttg tgttattctt  28140
cgattgagat tgatctttta tgtatgcttc tcctctttca cagttgctct ttaaatcccg  28200
ttcgctttaa tggagttttc ttcttctcta ttggattcgc atgtactctt ttcttaaggg  28260
agtcaatttt cactctttaa aagatgaagc cgatgaatag gctcttaggt ggaggtgatg  28320
ttagagtaat ctcgatgaag atttagatga atcggcatcc tctcggagat ggtccgataa  28380
agatctttaa ttttattgga ttgattgagt aatcccagag ttattaccca atgaagttga  28440
tggtggctct cattgaagcg acagccggat gaaagatagc agatcgcagt ctcatcccat  28500
gtcagatcca gaagtttaaa gactcatgca aaggaggatg agggcgcgtg tcacgtcttt  28560
cccgtgcatg gaactcgaag agcctaatgg accacgaatt aggcctaata aaatttattt  28620
tatgatgatg agtttcaagc ttgttgcttc tcttgtaatg ttcattggta ggcatggaca  28680
ttcggggtcc caatcgggtt tcgattttat ccattcgggt ttcggttttt cgggtttatc  28740
aaaatcaacc ccattcgggt tatataaaag ttcggttcgt gaccggttcg ggttctatcg  28800
ggttcgggtc ggggttagta aatcttcaaa gaaccggtat aacccattgt actttcgggt  28860
tcgggtccca atcggttctt cagtttaaaa atacatgatt tgtacctatt ttgtaactaa  28920
aacataaata aaatcggttc ttcggattta aaatacatga tttgtacata ttttaatagc  28980
caaaacataa gtaaaatcga ttcaaaaata agaaaaaaca tcaaacgtga tcattcaaaa  29040
tcaaacgaaa gataaacata gttagtgata taaaaaaaac cttataaatg aaatcataaa  29100
acaaaatata agttctcatg aaatgagaaa cattattcaa taaaaacaaa accaaaatct  29160
aaaaactcca ggcatcaacc gccacattcc accatcaacc ttcatgtaac agataattat  29220
tttagaagtt caataatatc ttaaagtatt ttggatacat attaagaatt aagatcatat  29280
ttggtagaag ttctttttgt gattttaaat gtttcgggtt ctatcggata tccatttagg  29340
tccgggttcg gttcggataa tacccataac ccaaaatacc aaaaaacagg atccattcgg  29400
tatttatgtc gggttcggat cggttcggat tcatttttat cggatcgggt tcggttcgga  29460
ttttcgggtt cggtttattt gcccagccct attcattggg cctttctaaa ggaaagaaac  29520
agttgacaaa aaaaaaagaa aaaaattcta cctacttagg cccttcttaa ttcctcaaat  29580
ccctcttttt ccaatattac aatttcttcc tcttgactat caacaacaga cctcaatggg  29640
ttcatatcct atggcctctt gggagtcttt tttggatagt catccatact gtgaaggagc  29700
attggggtgt gataaggaaa ccaaatccct ttgtaccagt caactgctga atggttagct  29760
tccatgtgag ctaatcatta ctcatcctcg caagttttta gatgactgct tctttttatc  29820
aggtggttga gtataatcta ttttgaatta gcctgttgga ctagtttctc ttattcaaga  29880
aatccacttg ctcagtgaca caagagcagc taagcgggtc cgtaactttg ttggtaatat  29940
aaagggaaaa ctcagatctt ctgttttgat ctttgcttgt gcgcgtctca gacatgtatt  30000
gcacatcttt gtttcttaca agcgtcaaat cgtttataca tttttagtga aacaaaggtg  30060
agcaggtagc caggtagtac ctttccttgc aactcacgca tgaatataat aaatcaacta  30120
tttcattgtt gatgactgga tgattcacaa tcaagttgct gggtatagta tttacactaa  30180
attttttttt cttttgttta ctcgtgagat catcaaagat gttttagata tatgaaaagc  30240
acatttcata gtctatattc atcttccatg tatgtttctt tgatgattta aaaaaaacag  30300
aagtacatca acacttctta tctttgtgtt ttcttaatct caagttggta aatagaaaaa  30360
aatgatgaaa agaagaagaa aaacaaatta ctacgaggct ctcagtaaag ctgttctttc  30420
ttttcatgcc accatctcca cctgtaaaca caaaattgct agaaacatta gtgaactttt  30480
```

```
atataatttt atataatata aaaaatatat aaaaaattat tttaaaaaat gaattttaat  30540
ataattttgt gccaaatctt gcattctgag atcatcaagt caatgtagta tacgtaccag  30600
taatattccc aacgaggacg gactttggtc atgcggttat catcagatgg gtgataagga  30660
tgagcagcgt ggtgagtgtt gtggaaagcg cagcaacctg cagcgtagac ggatgttgac  30720
aaccgataac tttctccagt caagacggat ctcttcaaga acaccagctt tacaagcatc  30780
acactcgtag cataacgttt caataccatt gttccatcta tagcaatctt ctcctccgac  30840
tattactcca gtctcgtacg tgcacgccgt tggtggctta caacatcccg actacaatca  30900
aagacaggtt agttactaaa caaactgatg aagatgctag ttcatatcat aggacacaag  30960
cggagtttat aaccaaaccg gaaaaaaaaa caaaatccga tatgaacagt tatacaaaaa  31020
tacctgaacg gacctaaaat cattagatat ttttggattc cgaaataata tctgaaatta  31080
gctaaatttg ttaaactttt acatatttaa ggtaatttag atattatcga aagataagga  31140
tgatgatacc tgaacagaag tcatatccct ttggaaataa tcaagtgtgg tccaagattc  31200
aatcttagaa caagtctttg aagtcaagat acagcttcta atggagttcc aatactcttg  31260
atctctaact cttgatctca gccacggatg ataatctcca agtctatact ctttgtaaac  31320
ccacaccacc tccttggcta gtcaccacaa gaccaaagag cgttagaccc atgagagtcg  31380
ctatgaggaa gatcatgaca actaagtaca cccacagagc ccatgccacg ttgaaacaag  31440
ctcctatgaa accagcaagg gatactaaca gtatgatgaa tcctatcacg agaagcggtg  31500
tctggaggaa gttctcgcaa gttttactgc ttcttgcctt ccatagagca gttcctttga  31560
ttggtattga agctagtaag ctgagaaggt ttatgacccc aatcactgtg ttgctgaacc  31620
tgtacatagt aggattgtta tcaagaagaa accagagaac tttgcagtgt ttctcttctc  31680
taatcagatt ctctcttatc aattaggaat cccctggact atatttgcga agtgattttg  31740
ccacaagtca tttctacaat caatttcaca aaacaagtat gacattgcta ctgaaattga  31800
tgatatgtct tatagcttaa tatgacatgg acaattgcat ttaatgttaa tttatatttt  31860
tggtaaactt tttaaaatat ggtaataact catataatac atttaatgtc aatttatatt  31920
ttagaaattt ttttagaata tgaaaataac tcataaatca tcattaaaat aaatatattc  31980
aaatatgaca ttataaattt cgaaatataa tataattata tatttttaaa ttatataatt  32040
ttattactaa aattttcaaa aatgtatata attttttttag aaaattataa aaatttaatc  32100
gtaaaatcat tattttctta tatatctaca aattttataa atattgttta attttaattg  32160
ttggtgatta tgcaactttt acaaatgtat ttaatatatt taattaaaat aaatagatag  32220
aaaaatctat ctaagattat aatttcaaat ataaacatgc atatttttaa atataatttt  32280
tatgtttaat taaatcaaat ttatattaaa atattgatac gaaaaagaaa atttacaata  32340
ttaaaaaaac ttattttaaa atataattta tatttatctg ttaaaaaata ttttaatttt  32400
ttttactgca catggtgcag gaagacacct agttttaatt aagggaaaaa gttaagagtt  32460
aattgtttaa tgattcatgc tcatattctc ttgtcgtttc ttgatttatt tttatttttg  32520
tcaagaggtc gtttcttgat ttgaatcaac taaacaacaa cattaaaatt gtattttttt  32580
tcaaataaaa gcgtcttttt ggacaattgt ttcttgttta atagtatttt atacgcttat  32640
gtcgtttaaa ccagaccaca agtagtgcct tgaataaaat atgtacataa aattaaacta  32700
tattgtatat agaatcagat aaattcacaa tgatcaatga aaggtaagca aagaataata  32760
tagaggacgg atggtgaatt ttctttttaa gatgctttta ctggccccat aacttggcat  32820
```

```
attaggttct gtaggtagag cacaatatga tgtttgattc ccacattcac tatttttttaa  32880
gcaagaaaaa tgctaaaaca tacttaattt aagccaaaat gtcataaaac aacaaaataa  32940
gacaataata acattactgc aacaaataca tagtttttaa taccgaaagc tagatcgaat  33000
caaaataaaa aaaacatgag tggcaactct aaggttttgg cgaatggtga gaatagggtt  33060
caaaagtcgg gagatcagga tgtgaccatg atggatgtgg gggagagagc gagaccaccc  33120
ggagaccctc cggacatagg gctttcatgg gtagccaagg tagcgggtac gagtgaaggg  33180
ggtatgtcgg taccagagag cttgattgat gatgctttcg tgtcggaaag gctccgagtc  33240
gagttcccga atggagagga tggtgaaccg tgtatcacga tcgagacaga ggttttggaa  33300
gcgatgaacg ggatgtggaa gcagtgcatg atcgttaggg tgttgggaag gagtgttgcg  33360
atctctgcct tgagcaagaa gttacgagag ttatgggatc cgaagggagc aatgtatgtg  33420
atggacctgc ccaggcagtt tttcatggtc tgtttcgaga aagaggatga atacttaggg  33480
gcactgacag gaggcccatg gagagtcttt ggcagttacc tcatggtgag ggcttggtcg  33540
tcggagtttg atcctttaag agatgacatt gtcacaacac cggtttggtg ggttagatta  33600
acaaatatac cagtgaatct ctatcatcga tcgatcctta tgggaatcgc caagggattg  33660
gggcagccag ttcgagtaga catgaccaca ctgaagtttg aaagagcgag gtttgcaaga  33720
atctgtgtgg aggttaatct agcaaagccg ttgaaaggga cagtgctaat taatggtgag  33780
agatacttcg tagcttatga agggttatct gaaatctgtt caaggtgtag aatttacggg  33840
catttggttc atggatgccc aaaaacgatt gcggagaagg tggctaactt ggcaatacag  33900
acggagacgc cgacacttac caatccagtg cctaaacaag tcccaccaag gcaggaagat  33960
ggttttactc aagcaaaggg atcaagaaga ggaacgcaag ccccgcgatc ggtgaatgtt  34020
gtgaccggag aatcaaatgg ggtgactaat cggaagctcc aagagattct taattttaaa  34080
gaggctaatg agattgcact atcgaataag tatggaagtc tggagatggc tacgaatgtg  34140
gatggatcaa aggaggatgt ggttgctggt gaagagaata aggagaatca tgatatgaat  34200
atccagaaca gtaagggaaa gggtctcccg caaggaaaag aagctttaat ctttagtggg  34260
aaaacaagta cgtcgactag cttgaaaggg atgactaagg agaagtgggc tgcgaacaag  34320
agaataatgg agggaggtag aggaaagccc aaaagggtaa ataacaggcc cattaggggc  34380
ttggtgttta gtccgacgaa gggtgaaatc agtccggtaa aagactgaga gtggataaca  34440
ttgatgcagg gagatccagg ggtgtgttta gtgatggtgt ggaggaagtc agaagtatgt  34500
ctaaacctct gctactacga gatgaagcgt tggacaacct gatggagagt actatcagcg  34560
aggtggatca gagagtggct gatatacaga cgagctcaca aggagatggt aggatcgtgc  34620
cccttgcatg acagcgtgcc ccggtaattc gtatagacct taacagatta attatgatga  34680
attgcttatt ctggaattgc cggggggcaa aaaaactcaa tttcagacgc tctattcgat  34740
acatattgaa gaagtttaat actgatgttc ttgcactttt tgagactcat gcgggtggag  34800
aaaaaacgag aaggatttgc cagaatttgg ggtttgagta ctcctttcgg gtagatgccg  34860
ttggtcaaag tggtggaatt tggctcttgt ggagagacca agcgggcgtg attacggttt  34920
tggaatcgtc agagcagttt gttcatgcta gggtggttaa tgggacagag actatccatc  34980
tcatcgccgt atacgcagca cctacagtta gtcgtagaag tagactttgg gggcagctaa  35040
aaaggatatt ggagtatata gatgaaccgg tgctggttgg tggagacttt aatactatct  35100
tgaggttgga tgagaggaca tgggggaatg ggaggctttc atcagactct ctggactttg  35160
gggaatggat taatgagatt gccttggtgg atatgggttt taaaggcaat acatttacat  35220
```

```
ggaaacgagg aaaagagacg cggaactttg tggcgaagca tttggacagg gttttatgta  35280
atgcacaggc gcgggttaga tggcaggagg cggtggtgtc ccaccttccg ttcctagcgt  35340
ctgatcatgc accactctat atgcaactaa aacctgagca gagaagtaac ccaaggagga  35400
gaccgtttag atttgaggca gcgtggctga agcatgaagg atttaaagag ctgttattgg  35460
cttcctggaa tggtcaaatg cgtactcctg atgcattggt atctctacaa ctgaaactta  35520
aaaaatggaa taaagagatt tttggaaatg tgattcaacg taaagaaaaa cttctcggtg  35580
agatcaaggg tattcaggag cagttggaaa ggaatccgaa tgatgatcta ctgtcgaggg  35640
agggggtgct tcagaaggag cttgatgtgg tcctagaaca agaggaagta ttatggtatc  35700
agaagtctcg ggaaaaatgg atagttcttg gagacaggaa tacgaactat tatcatacga  35760
gtactatagt gaggcggaag agaaatagga ttgagatgct gaaagacgac gatggccgtt  35820
ggatagatca gtcggaagag ctggagaagc tagcaataaa ctattacaag agactgtatt  35880
caaccgagga cctcaaccta gacacggaaa agctcccccc gcaaggcttt accgagctgg  35940
agattttgaa tgaacctttc tcgaaactag atatcgagac ttctgttcga tctatgtgga  36000
aatataagtc ccctgggcca gatggctttc aacctgtttt ctatcaagat tcatgggatg  36060
tggtgggga gtcggtaact aggttcgggt tggagttctt tgaatcggga gttctaccgg  36120
aaggcacgaa tgatgcaatg ttagtcctca taccgaaggt tcttaaacct gaaagaataa  36180
tgcagttccg gcctataagt ctatgtaatg ttcttttcaa gatcataaca aaggccatgg  36240
tgttgagact gaagaaacta atgctgaagc tcataggccc agcgcaagca agttttatcc  36300
ttggtcgact caattctgat aatattgtta ttgttcaaga agcggttcac tcaatgagaa  36360
ggaagaaagg acgaagagga cggatgctcc ttaaactaga cctcgagaaa gcttatgata  36420
gaatcaggtg ggacttctta gaggatacac tctatgcagc aaagctacca cggagttgga  36480
ttaaatggat tatggaatgt gtcacaaatc cgggaatgag tctattggaa tggagagaga  36540
acataggcgt ttacgcctca acgtggactt cgacagggtg atcctctgtc cccgtaccta  36600
tttgtgctat gcatggagag actatgtcac caaattgaat tttcggtggc aaacaaggag  36660
tggaagccga tcagattatc tagaggtgga ccggctctat cacatgtttg tttcatggat  36720
gatctaattt tgtttgttga ggcctcacta tcgcaaattc gtgtaatacg cagggtactt  36780
gagtggtttt gtggagcttc tcggcagaaa gttaatctgg agaaatctgt tatcttcttc  36840
tctgagaatg ttcatcggga cctagtgaac ttaataagca atgagagtgg cattaaagga  36900
actaaggagt tgggaaaata cctgggtatg ccgatcctgc aaaagaggat taataaggag  36960
acttttggag aagtgattga gaaggtttcc tcaaaacttg ctggatggaa gaagagattc  37020
ttgagtttgg cgggaagaat cactctcacc aaatctgttc tctcatctat cccagtccac  37080
acgatgagta ctatagctct gccggcgtca actctaaacc aactggataa gattgctcga  37140
gcttttatct ggggcagtag cgaaggtaac agaaagcagc atttggtttc ttgggataaa  37200
atttgcaaac ctaaaagaga agggggcctt ggtataaggt tggaaaagga aatgaatgtt  37260
gctttattag caaaacttag atggagattg ctgaatacat atgatactct atgggtcaag  37320
gtgctgcgga aaaagttccg agtggggagc tatatgaccc aacatggttg atagtccagg  37380
ggacctggtc accgacttgg agaagcctag tggtgggtat cagagaagtt gttattctgg  37440
gaacgtgttg gatcttgggg gacggccgcc gggttcgttt ctggaaagac aattggttgt  37500
tgaacgagcc cctatacgaa tcaagtatgg tgcatatccc agagccgatc ttagaagcaa  37560
```

```
gggcccgaga cttatggcag aatggaacca gttggctact tcaagctatt gagccgtata  37620
tgtcagtata gaatcagtta agactagctg aagtagtgat tgatgatgtt actggagtcc  37680
gagatagaat gtcgtgggaa gagagcaaag atggattgtt ttctgttaaa tatgcgtatg  37740
ccttactgac tagagatgaa gtactgagac caaacatgga atccctatac agcctggtgt  37800
ggtgtctagt tgctccagaa cgagtccgag tcttcttatg gttggtaaca catcaggtta  37860
tcatgacgaa catggaacgg aagcgtagac atttgagtga taatgttgtg tgcccgttgt  37920
gtagagatgg agacgaaacc attctccatg ttcttcgaga ctgtcaggca gcagttggaa  37980
tatgggtgaa aatcatgatt ccgagtagac aacagcattt ctttagctta cctctattgc  38040
aatggctcta cgagaatctg gggagggaca agccgggtaa tggagaccaa tggccaacac  38100
tttttgcctt cactgtgtgg tggtgctgga aatggtgatg tggctatgta tttggtgaaa  38160
caaggacatg tcgagacaga gtgcagtttg ttaaagaaaa gtccagagaa gtgttggaag  38220
caaataagca tttgcgagat cgttcttgtg ctaggggccg ggtggagaag caaatcgcat  38280
ggcagcgacc cgttaatggc tggcttaaat tgaacattga tggagcatct aggggtaacc  38340
ctggactggc cacagcggga ggagctgtgc gagacgaatt tggaatgtgg aaaggaggtt  38400
ttgcgattaa tataggtatt tgtttggctc cgttggcaga actgtggggt gtttactatg  38460
gactgtgcat agcatgagat tgtggtattc ggaggctaga ggtggaagtt gattcagaga  38520
gtgtggcggg ttttcttcag acagggattc atgattctca tcccatatcc ttcctagtac  38580
gtttgtgcta tgacttcatt tcaagagact ggatagtcaa aatttctcac gtgtataggg  38640
aggctaattg tctagcagat ggattagcta actatgcgtt ttctttaccg tttggtttac  38700
attattttga gtcggctcca gagcatgttg cttcagtttt gttagaagat tgtaacggag  38760
tgtccagaac tcgacaaatt tgcctgtagt tgttttgttt ttgatttgaa taaaaagtag  38820
gcctgcagcc taccaaaaaa atacatagtt tctaattaga acaaagacta aaccagacca  38880
agagaaaagt cgacaacatc ttttaactct gtccttccac tatcatcatc atcatcatca  38940
tcctcataac ttattgttgt accagaacac acctttcttc tcaccttgcc tatccggttc  39000
aacatagata cactccttcg cctccctcca catcgcctta accgccggcg ttccatcaaa  39060
ctggtaatac tctccaaagt atcggcttta tcgccttggt cgcttccatc gcgttataat  39120
gcggcatcgt cgagaacaga tgatgcgcca cgtgcgtgtc cgtgatgtta tggaacacct  39180
tgttcaagat tccatagtct ctatccacag tagccaaagc tcctctcaac caatcccact  39240
cggaagaatc atagtgaggc agcgaagggt gcgtgtgctg caagtaagtg atcaagacga  39300
ggaaacagtt gacaattaga agcggaactc cgtagacaca gaccacagag gctactcctc  39360
gcgaagcagc gtaacggtag agaccgtaac atacggagag gacgccagcg tcagagatgt  39420
atatctggag acgctcgcgg tcgttgtaga tgggagcgtt cgggtggaaa tggcaagcga  39480
aaccgtcgct gtaaggtctt cccgagacgt tgaaggctaa gtacaacggc cagccgagct  39540
tgaactggac ggttagcatc accgtgcgtc ctagcgggtt gttgaggtac ttgccgtacc  39600
acttgatgtc ggatttcttc ttggggacga acacttcgtc cctatcgagg gatccggtgt  39660
tggaatggtg gcgtcatgga tgtacttcca ggagaagtac gggacgagga ggaaggagtg  39720
gaagacgagg ccggcggcgt cgtccagcca ctggtggtcg ctgaaggcgt ggtggccgca  39780
ctcgtgggct atgacccaga ggcccgttag gacgcagcct tggcaggccc agtagagggg  39840
tcaggcgagg taagggagag ggaagtaggc tgtggagagg tggtagaggg aggagccgag  39900
gaggagatga tgatgtcgaa gaggagaagg agcgtgggat ggagcgtttg aagcagtgag  39960
```

gtgggattgc tttcttgagg tctccgagag tgaatggtgg tgtctcgcag gggacgcgtt 40020
tgagggtgtt ggttccgggg gagctggagg gaggagagac ttgcattctt ccacctgcgc 40080
ccatgtttgt ttctgtagag aaaaccaaaa aaaaagaaaa gaaagtaata agttagttag 40140
taggaagaac ggaaggggta aggttttttt taac 40174

<210> SEQ ID NO 3
<211> LENGTH: 28527
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3
acacaagtat ttgaaatatt cgaaatctta gatttatcta gtaaaacatt acatacacaa 60
ttccaaatta tcttaaagta cttaaaacca aaaaactggt atgaaaataa ttcaaattta 120
taaaatttat aaaatattca aaatatataa atcatgaaaa ctgaataaaa attgggaaat 180
tctcctaaat tgatcatttt caagttttgg tcacaaaaat agaccacagg gaggaaaatg 240
accaaaatgt tttatttaat aggtaaaaag accttaatac actggatata taaaaaataa 300
aaaaagtaaa aaataaaaaa atcataaaaa aatttatagt tttagattat atgttttcaa 360
attcgaaatt tttataaaaa attatttttt ttgaattttt tttcgaaatt ttctttttt 420 tcaaatttta tttttgtaat tcgaaaatat tttttgaaac tattttaaaa atttttattt 480
ttaaattttt aacatttatt ttttatttta taaaatttta aacctcaatc ccaaatctct 540
atcccttaac tctaaaccct aaagtttgaa ttagttaacc atacgtgtat aaatgtatat 600
ttacctcttt catgaaacag tttggtcatt ttgatcatta gagtctatat ttgtgacaaa 660
ataaaattag tgctatcctc tggtatttct cataaaaatt taataaattt atttaattta 720
attttttaat attagtttga gtttagaatc ttatccaaaa gccgaattat catattattt 780
aaatatttcg taaaatcaga tgaatcaact ttttttgtat ggattttggg ttctaaatat 840
tgtcgcccaa gttgacaaaa aaaaaagtat tgtcgcccaa tccacatgac acaatagtat 900
tcttttaatc aatgaaccct aaatcccgat tgaaatccta ataattgaat tcaacccaat 960
agaacaatag taggcctgcg atttcggttt tccgaaaccg aaccgaacca atttttcggt 1020
tttcggttaa acggtttttt ttggaaaaaa ctccgaagaa aaccgaattt gaattcggtt 1080
cagtttttgg ttatttccga tttttgattt tattccaaaa aaatcgaaat caaacatttt 1140
caataaaaaa atcggatcac acgattaatt tcgggtattt acggttactg ttgggtttcg 1200
gttacctaag gttgtttcgg ttatgcctct attttcacct gccaaatcaa ataatcatgc 1260
aatcaacaac ggaaaaataa tctccaacat caaaaccaat ttataatcga ttcaccaagt 1320
taaaacattt aaaagagatc actctcaaac atgaaaatcc aaaaaaagat aacaatctga 1380
atctatattt cttttgcaaa tatcagactt tgaaagatac attcatacat agattcatga 1440
agttcaaaaa gataagttgt ccaaaagaga gtgataggct aagttggttt tggcttcctc 1500
gacattccaa cctacaagtt tatgaagtaa gaaaatcagt aaaaacaggg agaagaacaa 1560
actacaagaa actatacaaa taatagagca acaaattacc tttaatgatc ggattcactc 1620
ggaatttgca aagactctac ataatgtcaa aggcagttag gaatatatga ctgtggacat 1680
ataaaaattg aaggaaaata gttaaatgat tacctaatga ctcatgaaaa tcgagttctt 1740
caaacatctg aaccaagctt gcaaccttct cagcctggat gttgtttcga agccactgtt 1800

```
gtaggcagac aagagcttca atcatgtatg gagtcagaca actacgaaac ggatctaaaa   1860
tcctaccact tgtactgaat gctgactctg aagcaacaaa ggagacttga acagctagca   1920
catcttctgc tagttcagac aagattggaa acttacaaga gttcttcctc caccaagata   1980
acacattgta atccaagccg aagttgtttg agcctcgtgg tactggtttt tccatcaagt   2040
agatgtcaag ttcactgctt ccttcttcat ttgctgcctc tgaaaccatc tttgaataca   2100
aagaatctct cctctcaaag tcttcatcat cgtcatcaga gatatcaaac atggttccaa   2160
cttcaccttc cccattatca ataacgttgc tgagactatc accttgagat gaagagccga   2220
gcttgctcac atactcctca tacaacgatt tcatcagtgc cctgattgat gttctgagat   2280
gaccactctc cagactatcc ttcccgtaca gcttatcaaa acatatagaa gcaaattgca   2340
tcttgttcct tggatcgaac acacttgcaa tgatgaccag tgggttcata ttgataagcc   2400
catcccagta tttctcaaat ttgttcctca tctcctttgc ttgaatctgt agaatcccat   2460
ctttgctatt gctcaatgca atcaagttcc tctcgataat cacaatctca ttctaacaaa   2520
tggtggacgt gactgtcttc gatgctgaga acgctaaagt gcagccaaag aagattttca   2580
gaaacttcac taacctctgc acctcttccc acccttccgt agtaggaggt ccaactctct   2640
tctgtccatt ctcctcttct tccagaaaat aatcattata caacatgtct tcggctttga   2700
gcttctcaaa agcaacctta aacttcaaag cggcagacaa catgagatat gtggagttcc   2760
aacgagttat gcagtccaaa gacaagctcc ctctactaac cattcttgtc agcaccctta   2820
actgaaacga ctgcaatctt gtacccgatg atctaacata cttcacagca tttctaatag   2880
ccattacact atctttgacc tcagataaac catccctaac tatcaagttg agaatatggg   2940
cacagcaacg catatgcaac aatgcaccat ccttaactaa tgcatttggt cctatctccc   3000
tacatgtttc tgtaaacagc cgtagggcct tgtcattcgc cttagcattg tctactgtaa   3060
ccgtaaagac cttctatatt ccccaatcag agagacatag actcaaatgc tcagaaatat   3120
tgtcaccttt atgatccgtg ataggtttga agctgatgat tctcttctgc atattccagt   3180
ttcgatcaat ccaatgagct gtgacgacca tgtagctgta ggatgttgta ggagcaaccc   3240
aaatattggt ggtaagagac actctctgct tctcagaatt aaacaactgc tttaagctag   3300
ctttctccct tagaaacatt ccaaatatgt cttttgttgt tgttctcctg cagtgaactg   3360
tgtacatagg caagacgttg tgacagaacc tcctaaaccc ttcagattcg acaaaagaaa   3420
atggctcctc attcagcact atcatctcat tcactgatct cctaaacaag gcagcatcat   3480
acttaatggt tgtcaataca ccactactat ctccacctag cacctgctgt tttccaaatt   3540
ctttgtagag ctggtacatc ttacatcgag caatgtgatt cttcatcgca ctcgtcccac   3600
tcttcttcga gtcacatcca atcccttggg cacaataatg gcagttgctg atgcttggat   3660
catcttctct ttgaatgaaa tgttgccaaa cttctgctct gtgagcttgc tttttctttg   3720
caacaggagg catatcagtg cttgatctct cagaagcaga tcttttcttt cccccacctt   3780
gatctatata tgcttcaacg tcttctgcga ggaagttacc attatcttca caagctgaca   3840
tctacaaata caatcagaaa ataaacactt aagatcagac aaatatatat acaaaacgaa   3900
ccaaatgaac acaaaatcat acgctatttc agaaaactca ttcgctaaac tctgttcaaa   3960
atcaacagaa atcgttccta accaaagctg ataaattgat aaactataac tgactcatta   4020
agcgacacac acacaaaccc taacaattaa aatcccaatt cgattatcac acaaagtcac   4080
aaaccctaaa ttcgatttac acataaactt agaaagaaga gaagacatat acgaaaacta   4140
```

-continued

```
accttctacc ttgtgctcca aattatgtaa ggaagaagag aaattggtct ggtctgagaa   4200
tcagacaagg attgatcgga gatcgtattt gagaaagaga gattaagaga ggcgattagg   4260
gtaaaccgtt tacgacttta ggtttgtcgg cacttaggtt aaggatgact taggttaggc   4320
atacatagtt aggttaaaat ttcggttatc cgttcggtta tcacgaaccg aaccgaggaa   4380
aaaaccgata tatttgaaaa cttgtaccga tcgatttctc tgttatttct gaatcataac   4440
cgatatccga cgtttttggt tcggttcgga tcggaccgat cggttcggtt cggaatacca   4500
ggcctaaaaa atagtgttat catagttaca actaaaaaga aagttaacag acgccgtaaa   4560
aaaagaaaaa aagaaaaaaa agaaaaaaaa gttaacagac aagtctaaaa catagaaaag   4620
gaaatacgag aaggagacta gacgcttcct ctactaaagc gttttaagag catgtacaac   4680
ggtataaatc aggaaatcct taggaaagat ccttaatgct ttttgattaa agaaatatta   4740
aaagaggagg gcaaagttaa ggatgatcct taattaagga ttaaaatacc gaagtcctta   4800
tcgtgcttgc acactttgat tggtccgttt tgtgttgtct ctcgttaggg gagagaaaaa   4860
acacgggacc caacctcatt gtatctcgaa cccgaaaaaa aagcagagga gaaggagagg   4920
cgacagagag gcgatttgcg atcccgactt gtgaaggtaa aatccgatct taatcttttt   4980
tttccttctc gagtttatgc atgttgattt catcacgttt tagggttcga ttgaggtgtt   5040
ttataaaatc tagggtttga aatcagattg ggatttttta tcgatttagg gttttcgtct   5100
tggtttgatt tttttttgca ttttcgcatc ggttctttgt tgttatcgtc tggattagag   5160
gttctggatt gagttcacaa tcgatttagg gttttggttc ttgatttcaa ttttttttta   5220
ataagaatcg tctcggtttg ttttttttttc attttgcttt tggttgtttg ttgttaacgt   5280
ctcgattaga ggtttaatca attgagttca caatcgatta aggttttggt tcttgatttg   5340
aaattttttt ttaataagaa tcgtctcggt ttttttttca tttttgcttc ggttgtttgt   5400
tgtgatcgtc tcgattagag gtttaatcga ttgagttcac aatcgattaa ggttttggtt   5460
cttgatttga attttttttt ttgcaggttc tgaaatggat gaagaacagc gagatatgaa   5520
agcacacaaa gcatactacc aaagggttga tttcgtatca aattcgctgc aggggattcc   5580
ccaactgtgc ccctgtggat caatcacgaa ggaaattgta gatgaagagg atacacatga   5640
ctacctccct gggaaaacat acttcatctg caaagacttc gaggtatgaa ctttgtttct   5700
atctctttca tttattacgg gttatatgtt tgctatttga caattttttt ccctttggca   5760
gaatgacggt ctgcattaca ggaaaccatg ggttattggt gtgcaagaag aggttgagag   5820
gctcaaactg aaagttctcc gccatgagaa ccttcttaga gagtgagagg cacttaaggt   5880
gagtttattt tttttcggta tcataaaaat tgtgtttcta ctatctttct aaccaatgtg   5940
ttttggtttg tcttatgtct gttaaggaac atgttaaaat gttggtcaag cgggtttctg   6000
aacttgaggt tagtcttaaa actcaaccgc aatagtttcc tggttagaga acatagctgt   6060
tagaattgaa acggatagga ctgtcggtaa ctgtgtagtt aggaaaaaat tacttcatta   6120
aatagaccct aactgcattt tggatagtaa aacttcatta aattgtttgt agctgttctg   6180
ataagacagt tttctactag gattcaatgt agaatctctt atttaatcct agtagaatac   6240
tagtagagaa tcacacttca tcttaaatgg caagctctag ttttgttaat ctcttagcga   6300
gccaagggtc agttgacctt aactctgcag agactccatt gtttagtacc caaactccta   6360
cccaaactcc gcaagaacca agtgtcaaag agaggagaaa gtggtctgtg aaggaggatt   6420
taatcctggt gggtgtttgg ctcaacacta gcaaagattc aatcgttggt aacgaacaaa   6480
aaggtgttgc cttctggaag aggattgtag agtactacaa ctccagtcct cttctcgttg   6540
```

```
ggacagtgcc aagagaacta gggcaatgca agcaaagatg ggctaggatc aatgatttgg   6600
tctgcaagtt tgctggctgc tacgacacga cattgaggga gcacagaagt ggtcaaaatg   6660
acaacgatgt gatgaaggct gccttggata tcttcaacag tgaccagaac atgaagttca   6720
acttggaaca tgcgtggagg gagcttaggc atgatgtgaa atggtgctcc acctatcagg   6780
agaaggacaa ggataagcgc aaaaccgcgg atacttcggt tgcagaacca gaagatagac   6840
caatatgggt taaggctgcg ggtaagagga agaaaacagg aaaagatgaa gaattaacca   6900
agcttgaagg gctggtggac attaaaaagc aaatctcaag gcaaagtttg cttgaaagtt   6960
tgcttgcaaa gcctgagcca ctgtctgata tggaattagc actgaaaaca aaactgttgt   7020
ctgaaatgtt gtcttgatgg tttgttagct ttagattaac ttgtttgctt tattactttg   7080
ctttgtttac tttactgact cgtttggttg ttgctttgtt tcaggatcag taaagacatg   7140
tgcaagatga agacaaaaga tggtgtccct tcctttttca gtcactggtc atttcgtttg   7200
ctttttctgt atgttggatg tgtcacgggt tgtatgtgtc acgggttgct ttgtttttgt   7260
tgttgctttc tattttgaac ttctatttat aagtcagtgt ctgttgcttt gtaatttgaa   7320
cttcccttgt atcatttcat caatgaaatc tctttcctct tattccaagc tttgaagcaa   7380
acttcccttg tatcatctcc aagcttttct cctcttctac ttccataaat gtcacgaaca   7440
taaaaccaac aagtgaagaa agttaaacca ttctccaatc tttcctcctc ttctacttct   7500
ctaaattcac gacaataaaa ccaacaattc aagacacttc aaccattctc caagctctcc   7560
tctacttcaa gtaatttttt tattctaaaa ttagtaattt ttttatattc taaaacgtga   7620
ttagtaattt tttttattct aaaattattc taaaacctga ttagtatttt ttttttggca   7680
gtatgggaga tgaagtcgat cgaagattga atgcggcatt ggataaggct gtcgatgaat   7740
attttgaaga cacatacaac aacatcgtca agaaccaaac aaagaaacaa accaaacgtg   7800
catatgtcga acgaaacagc gaagagggcc acagaagtct atggaattac tacttcagtg   7860
aaaatcctac atttctgcct catttattca gacgacgttt ccgcatgaac aaggcggtgt   7920
tcatgcgtat cgtcgatcgc ctctcaaaaa attttccctc ctttcaacaa agaaaagatg   7980
caactgggag gttaggtcta tctccactac aaaagtgtac ggcggctctt cgtatgcttg   8040
cttatggttg tgctgttgac gccgttgacg agtatctccg acttggagaa agcacaacac   8100
tttcatgttt aaccaatttc acagaaggtg taatacagtt atttggagat gagtatctac   8160
gaaggcccac tctagaggat cttcaacgac tactcgatat tggagagata cgcggctttc   8220
ctgggatgat aggaagcatc gactgtatgc attgggagtg gaaaaattgc ccaaccgcct   8280
ggaaaggaca gtacacacgt ggatcaggaa agccaaccat tgtcttggag gctgtagctt   8340
cacaagatct ttggatatga cacgtttttt ttgtcctcca ggtaccttaa acgatattaa   8400
cgtcctcgat cggtctcctg tttttgatga cattttacaa ggtcgagctc caagggtaca   8460
atatgtggtc aacgggcacc agtatgattt ggtgtactac ctcacagacg acatatatcc   8520
aaaatggtaa acatttatcc aatctatctc aaaccctcaa ggtcctgaag cagaattatt   8580
tgctaaagtt caagaagaaa tccgaaaaaa tgtggagcgt gcttttggag ttttgcaaac   8640
tcgatttgca atagtgaaaa acccggctat tttgtgggac aagagacaaa tagggatgat   8700
tatgcgaaca tgtatcatac tgcacaatat gatagtagaa aatgaacgca atggatacac   8760
tcagtatgat acatcagagt ttgaagaagg agagtcgagt agaagttcac aggtggatat   8820
gtcatattat ctgaagcctt caaatctcct tactatgctt gacatacgaa gtcgtgtgcg   8880
```

```
tgacccgcac atacatagac aattgaaata tgatttgatt caaaatattt gtaacaagtt   8940
tggtaatgat gaagatgttt aattattgta tgtttacatt ttgtttttca ataaatgaaa   9000
attttaaatt tcaaatttta aaattttaaa tttttaagat taaaaaaaaa aaaatcaaag   9060
tactccttgt tggataacac aattggacct atggttatgt taaaagtcct taactattga   9120
agaaaaaaga aattataata taactaagga ttccataccc accattggag ttgctataag   9180
aagaagaaaa aaaattgtct agaggcttcg ttttgcgtta cttcatcata taggtaagta   9240
gagaaccaca tcttatcgaa ttcgacctct ctgcttcgct ctcagtactt gaaagctcaa   9300
tcaaccctct cttgtagtag gcaatttcaa atccacggac atggcaaagt tcgtcgaagg   9360
cgacaagcga tggatcgtgg aagacagacc cgacggcacc aacgtccaca actggcactg   9420
ggccgaaaca aactgcctcg aatggtctcg caacttcttc aacaaccaat tctccgacgc   9480
cgtgatcctc tccggcgagt ccaacctctt cctcaaaatc aacaaggtgg agaagctcga   9540
aggcgaggcc tacgtgaacg tgcgcaaggg gaagatcatc cccggctacg agctcaacgt   9600
ctctctatcg tggcaaggcg aggcgaagga ctctgaagga agacgatctc gaaggcggaa   9660
gggttggtgg agatgccgta catctccgat gagaatgccg atgagaatcc agagattagg   9720
tattagacgg tacttatagg tgtaattcgg tttagtatat accggtagtt atggtggttt   9780
aagtttactt tagtatatta cggtacatat aggtttaatc cggtttatta tatacagatg   9840
gttatggtgg ttaagattcc tttagtatat ttcggcatag gtttaatccg gtttagtata   9900
tacaggtagt tatggtggtt aagtttactt tagtatatta cggtacatat aggtttaatc   9960
cggtttagta tgtaccggta gttatggtgg ttaagtttcc tttagtatat tacggtacat  10020
ataggtttaa tccggtttag tatatacagg tggttatggt ggttaagttt cctttagctt  10080
tccacttgta tttaaacttt gatgtgtaca tttgagaaat atatacattt caatgttagg  10140
gtttcggtta aggacgacgg ggagattggg aagacgttga aggaagcgat ggtgacaaaa  10200
gggaaggtgg ttgttcagga gaaggttagg gtttacgtgg aggcgatggc tagaggtggg  10260
ccgtgtaggg atgagttgga gtttaagaag gttgcgccaa aggcaaagga gaagtctagt  10320
ggtttaccgg ttgtatctga tgcgaaggag agtaaggtag tgaaagagaa gaaggggaag  10380
acgaaggaag ggtttaagat gattagtatg accgagaagt ttagttgtag agtgaaagat  10440
ttgtatgaga ttctgatgga tgagaatcgt tggaaggggt ttactcaaga gtaatgccaa  10500
gattagtaga gatgtgagtg gtgcgattag tttgtttgat gggtcggtta ctgggatgaa  10560
tttggagttg gaagaaggga agttgattgt tcagaagtgg aggtttggga gcaggcctga  10620
tggtcttgat ttaacggttg gtttactgat tgtttttgtt gtggttcaga aacatggtgc  10680
tttgatttgg atctggttgc gattgatgtg ttggctttct ttgctttgac attttaggtg  10740
agaatcactt tcgaggaacc tgaaccagga gtcaccattg ttaatcttac ccagtgacat  10800
tcctgaagaa gataggttag tctcacttac cgaattgatg tatgtagttg ttcgactcat  10860
taagtctttg ctttagtgaa tggattcttt ggaatttggg tgtgctgtat tggttagtag  10920
tatatgatat agaatactca acgcacaggc cgagaaccat tggactatta gagattagag  10980
aggatcttaa atatcttagc cgcccaaacg tctttgacta tctatgttaa tcatttcctc  11040
taattgactc ttagtatttg ctgcgcattt ggagcttatt tgtttgtcca tgcgctcgtt  11100
ttcttctttt ttgttaagca aatatactta agagttattc gctcgatatt ggctcctttg  11160
atgttatctg atgggtttcc attgacatac gggaatgcga ctgtggtgga aaacacggag  11220
agaggatgga gagaccttat attccacatg atccgtgctg tttttgggtt tggaatatga  11280
```

```
tatgtgattc taattttcaa acaaacaaaa ccagcattgc ttttatctat ggttatgatt  11340
tcaattccaa aacaaggggg actagtgaca agcagcgcaa atgtatgatt tctaagtttt  11400
ttgtttatgc attttcatgt aactatttgc tcacttctat atttatttag gaatggacaa  11460
ttatccgtaa attttgattc gattttttgt ttcgatctga aaaatcttga tataatcaag  11520
caaaaaacta aaatattata tccgtaaaaa aatgaaacaa atcacaaata ctatttgtaa  11580
tatatatata tatatatata attatatctt tttctaaatt ttataatatt tttaaagtaa  11640
ctatttagtt attaattttt taaataatag gtaatttttt aaaaaatcgt aataaaatat  11700
tattatttat atcagatttt tttattattc ttttttcgga tcaatcggac attcatgtcc  11760
cgtaaaatac agatttttca gatatctgaa aagttacaga ttaaattgaa tctgaaaatc  11820
gattatctgt acggagtaga atggatatct taaaaaaatt atatctgatt tgcgccgacc  11880
ctacttttgt tgagattgtt tagatcaatg gcacacaccg atctatgtta aaactgttgt  11940
tatcagtatt ctatcaatca ttaaattcag atgggacaag aacttccagt gtaataatac  12000
tgcaggtcaa ctacgttgaa ataatctatg ctcaaaagat atagttataa accccacaat  12060
ttgacatgta agagcatatg taagagcatg ttcaacgcag acatggaacc atatgtaact  12120
tttttgtttt tagtattatt tttttagttt gaaaaaaaaa ttaatttaaa accgaaccaa  12180
tcgcgggtcg ccacgtgtca gtgaagtccg caaacagtga taaaaacaga gaaagatcga  12240
tctttatttg cttacttttg tgatcggttt taaaagtttt ggtgggactc ttgcattaag  12300
aaacccagtt ataaccatgg ataaacatgg tctaagcata tgagcctgat gccttgctaa  12360
ttattagcat taatttgtta aacctgtagg ttgggcagaa attaagtact ttacaattat  12420
catatttatt gaaactagca ataaattagt taaacatcgt tcaccaaata atttaatttt  12480
ctaacatcag atcccaaaat tcaaatttcg aagattataa cctctgtcgg tttcgtgctt  12540
ccgcgccaga ctaaacagcc acatacacaa atactttgtg gagcttgttg gaatagagat  12600
ttggaaaaat gttaaaagat ttcatatatg atagaattta gctgaatcta tttagattta  12660
aggatttaac agagatttgt atgagaaatt tggtagattt tggtcatttt ggtctccctc  12720
tataacctag ctaaagggag tgaactatcc ctaatactaa gcattcacgt tacaacttct  12780
cttgatcagg aaatagcaaa tatcaaagtt agaagacgat gtttacagtt tcagattgat  12840
tcttccacaa gctatcgttg gtccgtcagt ttcggcaaga gaagaagcat ttcttcgaga  12900
gaattggtag gaggttcttt cacaagatca catactttaa tcatgtgtaa gaaaaatttg  12960
tgatatttgt ctctgttttg tttcaaccat cgttggagag tgaggaagga agataattgt  13020
tttatttatt ttgaaatacc atctaggtga ttatccgttc acatgcacga aatgaaatgt  13080
atattctaat aattgttgaa tatgaacttt gtccgtataa ccataattat atcattcata  13140
agcctatata tattaatttg aatatctatt aaatgttatt ttactcatat ggtttttatt  13200
atcatttata ttttattata acaaaaaatt taaactatag atcataaaat tttcagtgtg  13260
agagttttaa caattttcgt tatttatagt catttttaaa cattcaaaat ataatatata  13320
tatgaaaatc tattttttat tatatggtta atatgattgt ttaatttatt ttaataatat  13380
aacattaaaa aataatgaag atatgtgaat tgttgtcaaa tctttattat taaaatcatt  13440
aattgtcaaa tatatatttt attcacgttt ggtaattccg taaattttat ttaagaaaag  13500
aaagaaaaac aataattgta gattgttaat taatttcatg gttagtccaa gtagaagtat  13560
ataatatatg tttaatggac caacatattt ctttagagac tttaagaaac attttattga  13620
```

```
tgacacgtgt caaagttaaa atgttgtaat gcttatcttt taatatatag atgattatct  13680
aataattcca ataactcttg ataaatatta tgagtgaaat ctttgttttc caataaggag  13740
aaatttgaaa gagttttaat aaatgattaa ttcaataata gtggatttga tagaactttt  13800
ataaatacta agaggagatt tgaacaaaaa ctagaatttt cttaaatcat aagcctccta  13860
taagcccccct ttgttcctat ctctttttgg tcaccattcc attccagaaa atgcttttaa  13920
agataacaat cacaacattc caaatgtaga aaagtcacaa tctcaacatt ctaaacctgc  13980
ttccacctaa caaaaaacaa ttgccttctc gtagtttact ccaaatacaa agggtgtaat  14040
ataacagaaa cactcgacac tttaccgaac acacacattg ccttctcttc taaataagtt  14100
caatcttcct aatctctctc tgtctctctc tgacaacaga gagactcttc acgtgccaaa  14160
caaaaaaaac tgagcacctt cctctcgcca tggccacgga ctccgtcaag cacgtgccta  14220
cattcggcgg ggcagccatc tccgccgaaa tgaaaagctt cttctccgcc gtgcctactt  14280
ttgtctacgc cttcgtcgta acctttgttg ccttcactgt ttacttagcc ttcgcccctt  14340
ctctcatcac tgtctctaat tcagtttctt cctatatcct ccctaatgtc agtgccgtga  14400
cttcagcgtc cagtaacatc acattacaag caaccacgcc ggaaagtctc actccggctg  14460
ttataaacac aacctttgag cctcccctag gtaatgaaac aaacccactt tctagaaaca  14520
acgcttcacg ggatcatgca agtgtacact tatgtcctaa caacaatact gctcgaaatt  14580
cggacaaaca agcacctctg tccgtgaatt caagtgcttc ttctccgatg agaaaacaaa  14640
gtaggaagtc aggggctaaa cgagagatca agtctctgaa ggactgcaat tttttcgaag  14700
gagaatgggt caaagacgaa tcctacccgc tttacaaacc cggcacgtgt aatctcatcg  14760
acgaacagtt tagctgttta accaacggaa gaccagacgt tgagttttac aaactgaagt  14820
ggaaacctaa agaatgcact ttaccaaggc tgaacggagg caagttgctg gagatgatta  14880
gaggaagaag gctcgtgttc gttggagact cgctgaatag aaacatgtgg gagtctttgg  14940
tttgtattct taaaggatca gttaaagatg agagacaagt ctttgaagct catggaaggc  15000
atcagtttcg tcgggaagct gagtacactt tggtcttcaa agtaagtttg caatctgttt  15060
tggtgaggcc tgcgggttcg ggtagtttgg gctgggtcgt tcggttcgac caaaatattg  15120
cccaactgaa ccgaacagag tttggttcgg tttaggtagt tcggtttttc aacttctttt  15180
accgaaacta atcaaagttt ttggtttcaa ttatatgttg gtttaaaatt tctttaaatt  15240
cagggtaatt ttggttagtt cggtttgtca gttattttga tttgaatttt tgattaattt  15300
agttagcttt tttttgaaaa cccgagctaa ccaattactg aagtgaaaac cgaagtattt  15360
tataaacttg ccgaattgaa ccaaactaac caaaaaaatt tggttcggtt cggttatcaa  15420
cgcaggccta gtttgactac ctagttgtta ttggagactt gatttgtgtg gttgatatga  15480
taggaatata attgcactgt ggagttcttt gcgtctcctt tcttggttcg agaatgggaa  15540
gttacggata agagcgggac gaagaaggaa actttgcgtc tagatatgat gggaagctca  15600
tcaaagcagt acataggagc ggatgtactt gtgttcaata ccggagcttg gtggactgat  15660
gacataacat ccaaagggta gagttctgtc agctattttt tgtttttttt atatggagga  15720
tttgtctcat tggcttttttg gtgtttaaat ggttttgatt agtgaggatt attttcaaga  15780
aagaagcact gtttacccga aactcaacgt tgatgaagct tttagaaaag cattgactac  15840
ttggggtcga tgggttgata agtatgtgaa tccaaagaag tctcttgtct tcttccgcgg  15900
attctccctg tcacatttca ggtatgtaca gttctttcat ggtagtctta agattctgtt  15960
taaaaaaata aataaatggg tttggtctgg ttgcatgcag tggtgggcga tggaatgcgg  16020
```

```
gaggggcgtg cgatgatgaa acagaaccga tcaagaacga ggcataccta atgccttacc  16080
cttccaagat ggagattctt gaaagagttc taaggggaat gaagacaccg gtcacgtatc  16140
tcaacatcac gaggttaaca gattacagga aggatgctca cccgtctgtt tataggaaac  16200
agaaatttac tgcagaagaa agcaaatcac cgttgttgca ccaagactgc agtcactggt  16260
gcctcccagg tgtacctgat tcttggaacg agattctcta tgccgagatg ctggtaaagc  16320
tcgaccagct ccgtggcaac agacggcgga aacctaaagg gctactatag gaggagttaa  16380
atcagatttt tgttttagat gaaatacact atatatattt tcaatggatg aaaagaaaag  16440
aaacacttag aagcaattat atgttttcaa aggcatagag aaagtaagag gtgagaatca  16500
tattagtgcc ttgctcatca cttttctagt ttttagattg taaatggtta atttttattt  16560
tactcaattt aatagtaaag gtttgtcaaa tcataactga accggaaatg gaagcaatca  16620
tttggttaaa agaatccagt tgatgacatc gactggcaaa gcataggcag gatcaatttg  16680
gtttgactcc aggatactcc agccctgcac acagttttgg atcattaagt tctctttagc  16740
tttgaagacc tgaacagtat gaactaatga gaagcaaatt ttagtcacct gcaactccaa  16800
agtaagtgtg aaagatatca acagcatcgt caggtccatt ctccatatct tattcaaatt  16860
acacctgaaa ctcaggaaag actctaaaga gatgtgagct ttataaacca atgtttgaga  16920
aaaacctgac agtccaagat gaactttaca agctttgatt tgtcaatcca atgtactcta  16980
ttggtcatga taaagctcga taaaacccac caagagtggc aaacctggtg ataattaagc  17040
aagaacaatc agtgtggtaa gaacaattgg aataatgttt tgtgtttgta gagagaagct  17100
ccgttccctc aaatggacac ctattgttta ttcaactgcg ataaactggt catggcgttg  17160
acaagtacgt ttccttacct ttacagtttt gttttaactt attctatttg atgttatata  17220
tgaacattta tacatgtagt attgtggttg ctgctgcgac tgttcaaaag gagagatcaa  17280
gaagactttg tacagccata ttaaaccaag tgataagaga actagctgtt gcatttaaac  17340
caagtgatat gaaattattc tctccttctc tcttttgttc ttcacattct tcagtttcca  17400
gcaagtaaaa aagctcatat tctcacactc ctattcgtct tctttggctc agcccttaaa  17460
agatcgacaa gaatggagga ggtacatagt tttttagcac taaaactatt attcttagtt  17520
tgtattgaaa aaaaatgttg ctggtgaagg aacaatgtca agtctttcac gtgagagaaa  17580
tcttgcaacc aaaggggggg gcataataaa ctgagactat ataagtttcg tttagttatg  17640
tatttcttga gaaataatgt aattctttga tttttttttt tggttaaagg gttttataat  17700
tcacttttgt gtgttgagcg taaataaaag ggaccgcttt atacgattca gtgatgtttt  17760
tagtttaatt tcagcttctt tcttttcatg aaattcaagc tacttcacaa ataaagatgc  17820
atgcatattt gcgtggggaa ctacatagac acccattcaa caagaactct atttataatc  17880
acgtcctaat gaatcggtca tttgaacaaa aaaaaaacca cttcctaatg aatcggtcat  17940
acttttattt ttaaaataga tacaaagaca cccattcaac aagaactcta tttataatca  18000
cgtccttatg aatcggtcat ttgaacaaaa aaaaaatcac ttcctaatga atcggtcata  18060
cttttatttt ggagattaat gtttcataaa taaaaacaga tatcagtgta cgtagtatcc  18120
tcccttatct ttaggattgg attcccacct tcaacattcc actttttttct catttcagtt  18180
tgttatttaa gggtttcaaa acatacaaca attatccaaa actagattgt ttcaaatttc  18240
tcaaaagata tttaattcga agctaattat cacgagaact acaaattaat tccaaaaatg  18300
aagttaattt cattgatgtg catcgccttt gtcatactct tgacatcatt cccggctacg  18360
```

```
gctattacgt tcaatacttc gttcaacccct acagattgcc ttaaaaatca tgatacctgc  18420
ggccccctag ctgctgtaaa gggccggcgg tggagacccg aatgttgtaa attttggagc  18480
gggaatgtac ttccagaaac aagacaatgt gcatgttatg tactgaaata ttctcttggc  18540
gatggttatc ttccccttat tttaggtaag tgtaaattag gtggtatcga acaattcaaa  18600
tgttgggagc tgcgaacata taactaacca gaatcgtgaa aaccaaactg gagataataa  18660
gataaagtaa tcaattgggt atttctttat ttctttctaa tcattttaat aatgttactg  18720
ttcaataagg agagagaaat ggttttgttt ttgttcatgc tcgtgtgaat tacgattcca  18780
tgttttttg tttccatata ttttcttata tatttagtaa aaaaaatgaa aaggtataat  18840
ctactctgga ttaagtacca taaataaata tttgttctta attaatctta gtgctttgga  18900
cttctaacac caactttatg cgtaataagc atggggagaa gaagcaaatg aagaattctt  18960
cttattcacc aagttttgta atataagaat tttcattcta ccaaaaaagc ctgtctctag  19020
tattttccct aacctctttc taaaaaagct tccgaccaaa tagatttgct catgtggcca  19080
gtgggctctt tacagccggt caccataatc tttttgtttt tgtttttgct ttgtattata  19140
tttcttctct tcgcagtggc gattatgtta tgattatgtt attcgcggtg ccgataaacc  19200
gtggcaaatt tttgttgtgt attcaatctt aattgaagca aaacttcatg attgtgttct  19260
gttattcttc gattgagatt gatcttttat gtatgcttct cctctttcac agtttttttt  19320
ttttggtaat ccagggttcc cagtttcgcg ggtcattccc tgggtccggt caggcagcgg  19380
gtcggcttca cccgggaggg tatgtcctga gcccgaaggt ccagtacccg cttcgtgaca  19440
tggatgagca gttcggctcc ggctggcgtc gaacccgcaa gcatgacaat tggccctcaa  19500
ggttctaact agtagaactg actcatcccg tctcctcttt cacagttgct ctttaaatcc  19560
cgttcgcttt aatggagttt tcttcttctc tattggattc gcatgtactc ttttcttaag  19620
ggagtcaatt ttcactcttt aaaagatgaa gccgccgatg aataggctct gagtgaagtt  19680
tcctggatag aaaggtggag taatctcgat ttgatttgat gaagatttag atgaatcggc  19740
atcctctcgg agatggtccg ataaagatct ttaattttat tgagtaatcc cagagttatt  19800
acccaatgaa gttgatggtg gctctcattg aagcgacagc cggatgaaag atagcagatc  19860
gagaagttca aagcttgttc ggtgaccatg agcagtctct gccgccggcg aggtgtaccg  19920
acttcctctc atcccatgcg ttggtgcgac agatgcatgt cagatccaga agtttaaaga  19980
ctcatgcaaa ggaggatgag ggcgcgtgtc acgtctttcc cgtgatgaag acacatgcac  20040
tattaggcct aataaaattt attttatgtc gagttgtatg atgagtttca agcctgttgc  20100
ttctcttgta atgttcattg ggcctttcta aaggaaagaa acatttgaca aaaaaaagaa  20160
aaaaattcta cctttaggcc cttcttatca acaactttga caacagacct caatgggttc  20220
atatcctatg gcctcttggg actctttttt ggatagtcat ccatactgtg aaggagtatt  20280
cggggtgtga taaggaaacc aaatcccttt gtaccagtca actgctgaat ggttagcttc  20340
catgtgagct aatcattact catcctcgca agtttttaga tgattgcttc tttttgatca  20400
gatggttgag tataatctat tttgaattag cctgttggac tagtttctct tattcaagaa  20460
atccacttgc tcagtgacac aagagcagct aagcgggtcc gtaactttgt tggtaatata  20520
aagggaaaac tcagatcttc tgttttgatc tttgcttgcg tctcagacat gtattgcaca  20580
tctttgtttc ttacaagcgt caaatcgttt atacattttt agtgaaacaa tggtgagcag  20640
gtagccaggt agtacctttc cttgcaactc acgcatgaat ataataaatc aactatttca  20700
ttgttgatga ctggatgatt cacaatcaag ttgctgggta tagtatttac actaattttt  20760
```

```
tttcttttgt ttactcgtga gatcatcaaa gatgttttag atatatgaaa agcatatttc  20820
atagtctata ttcatcttcc atgtatgttt ctttgatgat ttaaaaaaaa acagaagtac  20880
atcaacactt cttatctttg tgttttctta atctcaagtt ggtaaataga aaaaaatgat  20940
gaaaagaaga agaaaaacaa attactacga ggctctcagt aaagctgttc tttcttttca  21000
tgccaccatc tccacctgta aacacaaaat tgctagaaac attagtgaac ttttatataa  21060
ttttatataa tataaaaaac atataaaaaa ttattttaaa aatgaatttt aatataattt  21120
tgtgccaaat cttgcattct gagatcatca agtcaatgta gtatacgtac cagtaatagt  21180
cccaacgagg acggactttg gtcatgcggt tatcatcaga tgggtgataa ggatgagcag  21240
cgtggtgagt gttatggaaa gcgcagcaac ctgcagcgta gactgtgatg aggaggacta  21300
ggactagaat gttgacaacc gataactttc tccagtcaag acggatctct tcaagaacac  21360
cagctttaca agcatcacac tcgtagcata acgtttcaat accattgttc catctatagc  21420
aatcttctcc tccgactatt actccagtct cgtacgtgca cgccgttggt ggcttacaac  21480
atcccgacta caatcaaaga caggttagtt actaaacaaa ctgatgaaga tgctagttca  21540
tatcatagga cacaagggga gtttataacc aaaccggaaa aaaaaacaaa atccgatatg  21600
aacgggccta aaatcagata tttttggatt ccgaaataat atctgaaatt agctaaattt  21660
gttaaacttt tacatattta aggtaattta gatattatcg aaagataagg atgatgatac  21720
ctgaacagaa gtcatatccc tttggaaata atcaagtgta gtccaagatt caatcttaga  21780
acaagtcttt gaagtcaaga tacagcttct aatggagttc caatactctt gatctctaac  21840
tctctctctc agccacggat gataatctcc aagtctatat tctttgtaaa ccctccctgg  21900
tacttccaca ccacctcctt ggctagtcac cacaagacca aagagcgtta gacccatgag  21960
agtcgctatg aggaagatca tgacaactaa gtacacccac agagcccatg ccacgttgaa  22020
acaagctcct atgaaaccag caagggatac taacagtatg atgaatccta tcacgagaag  22080
cggtgtctgg aggaagttct cgcaagtttt actgcttctt gccttccata gagcagttcc  22140
tttgattggt attgaagcta gtaagctgag aaggtttatg accccaatca ctgtgttgct  22200
gaacctgtac atactaggat tgttatcaag aagaaaccag agaactttgc agtgtcttct  22260
ctcttctcta agcagattct ctcttatcaa ttaggaatct attggactat atttgcgaag  22320
tgattttgcc acatgttctt tctacaatca atttcacaaa acaaatatga cattgctact  22380
gaaattgatg acatgtatta tagcttaata tgacatggac aattgcattt aatgttaatt  22440
tatatttttg gtaaattttt taaaatatgg taataactca tatagtacat ttaatgtcaa  22500
tttatatttt agaaattttt tagaatatga aaataactca taaatcatca ttagaataaa  22560
tatattcaaa tatggcatta taaatttcga aatataatat aattatatat tttaaaatta  22620
tacaatttta ttactaaaat tttcaaaaat gtatacaatt ttcttagaaa attataaaaa  22680
tttaatcgta aaatcattat tttcttatat atctataaat tttataaata ttgtttaatt  22740
ttaattgttg gtgattatgc aacttttaca aatttattta atatatttaa ttaaaataaa  22800
tagatagaaa aatctatcta agattataat ttcaaatata tacaagcata ttcttaaata  22860
taatttttat gtttaattaa attaaattta tattaaaatg ttgatacgaa aaaagaaaat  22920
ttacaatatt aaaaaaaaaa tttaaaatat aatttatatt tatctgttaa aaaatatttt  22980
aattttttta cacacctagt tttaattaag ggaaaaggtt aagagttaat tgtttaatga  23040
ttcatgctca tattctcttg tcgtttcttg atttattttt atttttgtca agaggtcgtt  23100
```

-continued

```
tcttgatttg aatcaactaa acaacaacat taaaattgta tatttttttt caaataaaag  23160
cgtctttttg gacaattgtt tcttgtttaa tagtatttta tacgcttatg tcgtttaaac  23220
cagaccacaa gtagtgcctt gaataaaata tgtacttaaa attaaactat attgtatata  23280
tagtggaaca tatcatatat agaatcagat aaattcacaa tgatcaatga aaggtaagca  23340
aagaataata tagaggacgg atggtgaatt ttctttttaa gatgctttta ctggccccat  23400
aacttagcat attaggttct gtaggtagag cacaatatga tctttgattc ccccattcac  23460
attttttttg gtttaagcaa gaaaaatgct aaaacatact taatttaagc caaaatgtca  23520
taacacaaca aaatgagaca ataataacat tactgtaaca aatacatagt ttctaattag  23580
aacaaagact aaaccagacc aagagaaaag tcgacaacaa cttttaactc tgtccttcca  23640
ccatcatcat catcatcatc atcatcatca tcatcatcat catcctcata acttattgtt  23700
gtaccagaac acacctttct tctcaccttg cctatccggt tcaacataga tacactcctt  23760
cgcctccctc cacatcgcct taaccaccgg cgttccatca aactggtaat actctccaag  23820
tatcggcttt atcgccttgg tcgcttccat cgcgttataa tgcggcatcg tcgagaacag  23880
atgatgcgcc acgtgcgtgt ccgtgatgtt atgaaacacc ttgttcaaga ttccatagtc  23940
tctatccaca gtagccaaag ctcctctcaa ccaatcccac tccgaagaat catagtgagg  24000
cagcgaaggg tgcgtgtgct gcaagtaagt gatcaagacg aggaaacagt tgacaatcat  24060
aagcggaact ccgtagacac agaccatcga ggccactcct cgcgaaccag cgtagcggta  24120
gagaccgtaa catacggaga ggacgccagc gtcagagatg tatatctgga gacgctcgcg  24180
gtcgttgtag atgggagcgt tcgggtggaa atggcaagcg aaaccgtcgc tgtaaggtct  24240
tccagagacg ttgaaggcta agtacaacgg ccagccgagc gtgaactgga cggttagcat  24300
caccgtgcgt cctagcgggt tgttgaggta ctttccgtac cacttgatgt cggatttctt  24360
cttggggacg aacacttcat ccctctcgag ggatccggtg ttggaatggt ggcgtcgatg  24420
gctgtacttc caggagaagt aagggacgag gaggaaggag tggaagacga ggcccacggc  24480
gtcgtccagc cactggtggt cgctgaaggc gtggtggccg cattcgtggg cgatgaccca  24540
gaggcccgtt aggacgcagc cttggcaggc ccagtagagg ggccaggcga ggtaagggag  24600
agggtggggg aggagaggga agtaggctgt ggagaggtgg tagagggagg aggagacgag  24660
gatgtcgaag aggaggtagg agaaggagcg agggatggag cgtttgaagc agtgaggtgg  24720
gattgctttc ttgaggtctc cgagagtgaa gggtggtgtc tcgcagggga cgcgtttgag  24780
ggttttggtt tcgggggagc tggagggagg agagacttgc attcttccac ctgcgcccat  24840
gtttgtttct gtagagaaaa ccaaaaaata ataataatgt tatggaggac ggagactttt  24900
tatcctttaa tcaaagttgt atatgcaact cttcatgcat ttgaatctat aaaagaacat  24960
ctaaaccctg aagtacctac ctactttaaa tcatccgttt tatttgtaca aagttgatga  25020
gcttataagt caatgaaacg ttcttccatt tattaagaaa taacagtagc aagaaccagt  25080
aggaatcggt caaatctatc aaaggttcaa caataagtga tttttatatt gaaaaaaaac  25140
aaaaatagca ctaaaccaag tttttgttcc caaactagca ctcaaggtca aaagtcacaa  25200
aaatatcact taatatttta tcaaaagtca caaacttatg gtttagagtt aaagggtggg  25260
gtttagggtt tagggtttag ggtttagagt ttagggttta gggtttatgg ttcagagttt  25320
agggtttaga gttgagaaat gaggttttgg ggataagatt tcaaattttg aaaaataaaa  25380
aattaaaatt ttcaaaagat aaaataatat tttggtcatt ttaatttttg agtgctattt  25440
ttgtgatata aacttagaaa gttgctattt tggagatttg acctttttcta tttcaccaac  25500
```

```
ctattgaata aaaagatttc tgaatagata gaaagttgca acatttcata tgctagacca  25560
tagacagtaa tcattattta acggtgagat gaaagaaaca tgacacaaga tttgtcaaat  25620
ggaaacagag gaacagatct ttagttgaat gcaataaaga ctggcagatc tatcgattta  25680
aatgccaaat gctagactgc tagagagatg gacgagatga acacagacca ggaattcata  25740
aaaataagag gaaaatgaga agaagaagaa gaagaagggg accctgaaag ctgctgacgt  25800
agggtggggg gagagagatt ttacgttaat aacgatgaac cctacaatga agctcctcca  25860
aagaatctat ctctctctct tctctttctc tctctctctc tcttgtctcg gcacttctct  25920
caatctgttg tggtttgtct ggtcagatgc gagtggcaat aggcagggcc gtttttaaat  25980
tgatgagaga caggaaggca tttgaatgac atctcttatt cttacaactg gcccctcttt  26040
tctcttattt ttacaactgg gcccctctgt tcaaaatatc tgatatttaa ctcaaggaac  26100
gaccattaat ttagaattta ccaaaatgta aaagttagag tgatgaaaag gtgatattac  26160
tacgacgttc tctcttttc tcgtccacgt tatcttggtt atgtatgtaa tgtaataaaa  26220
aaggtcgtat catgttattg acttaatcac tttggaacgc aatgacacat gcggtacttg  26280
tttgaatcag tttttctcta cgtaagtcaa tcatgtatca tttcttaata tgacattaga  26340
aacaacttga taaagaagaa gaagaagaag atggtagttg atgcctgaaa atggagtatc  26400
gtgtttggct tcttctcact tttgcccatg tgaacacaca agaacttaca gaaatatgta  26460
acagacaaat tgtggtgatg ctcacgtgag gatttctctc tcttttcttt ttcttattac  26520
aatttgttat gtatgtgtaa tcatctttga tacttataat aatcaaattt gttggcagac  26580
gaaaagaaac tagtaattga ttagattgag atctcttgta ttatactaga cttagaagat  26640
gattagagtt tgatttgtct aagcattacc tctaacaaca acacactttt ctttcaaaat  26700
tttttgttta agatcacaca cccaccatta ggaatgttat atttattcag ctgattgtta  26760
ctaccagtga cgggttttat aacatgtttt tttggtatca aagatgatgt gtctgactca  26820
cgcacaacag acaaatcaga gcaagcatga ctgtaagaaa attaaggcag catacaaatc  26880
ctaaccaccg tctgtcaatc catccaccaa gtctctcatc aattcaaact caatttaaca  26940
gcaaaaaaac tatattctaa gaatcaccac acagagagaa agaaaactta caaagacaat  27000
gaaactaaca ttgtattttc ataaaacaaa agcaaaatag atgaagaaga tggatgatat  27060
tagagatcac caccacacac aaaagaaaag acagcaaact ccacaaacag caacttaggc  27120
aattcctgac ctgcgcagct ctgcttcccc gtgcgcaaag tgacacctat ccccaaacgt  27180
acagttccct ttcgcgaacc tctcacacat cttcgtcttg aagttgctcc ctggatgtgg  27240
tttcccttcc gaaccaaccc caccaccaat cccaccacca ccaccaggtg gtctcctact  27300
agctgcagag ttaagcctcc caatcagctc tctaaccatc acactcgctt cgtttatctg  27360
ctcaaacgtc ccttcaagct caatgttctt caggttcggg tccctctcgt gatcttgaat  27420
cgacagcttc gcccccgtct gacgacatat ctgcttcgaa ctgactcctc ctttaccgat  27480
gatggctccg gccaacgaag cgtccacgct gattttcgca gtggctgagg cgccaaagct  27540
agacacatgg ccaggtccag actctcctcc tctccctgag aatctccctc ctccaccacc  27600
accaggtcct tgcatgtttc tggaagcttg aggcatgggt agtgccatgt ttgtcagctg  27660
tgctacagca ttgtatcctc cgggtacata gtgcaagaag tggcagttat ctccaaaagg  27720
acagccagaa gtgctgcaat agagcataat aaagacatca gatagttaaa accatttccc  27780
ttaagatgac acaagagaag ttgagaacaa acggttaaaa tacagaggaa gtatcaattg  27840
```

ctatacacaa ggaaccaatt agtcaccacc agtaatgtaa taaacttacc tgaacctgac 27900
catatatgac catgttataa acacaacatc actaacacct taccaccaaa cagaaaatta 27960
tagcaatttt ctaaacaagt tatagtttga tttcgaacgt tatgatcacc aattgagttg 28020
aacgtttcta tgattataat ccagatgcac ttatctctta ttgaaacttt tttttaactt 28080
gtttaggatc aatgatttat aagtacctgt aataacaatt aaccacttca ttagcataca 28140
gttttacttg ttaatttgac aattaacaat tttcaatatt aatccagtta agaaaaaaaa 28200
ggattataaa tttataacct gaaaaattta gtgcaaggct tggatttgct gcctaaacca 28260
gttgaatatg attccatctc tgttccaaac atttaagtgt gtttttattc tttagttaag 28320
agttttctca agttcaataa tatgacacca ttcatacttt tcatccatat gaaacttgag 28380
acttaagaat taaagctgca tgataccttc tgtaaatttt caggacacat caatccgaca 28440
aaggaaaaga catgggctgt cttactcaac tgaacatggt ttactaaaag caaaattgga 28500
actaaagtaa cttcgaaaaa aaaacat 28527

<210> SEQ ID NO 4
<211> LENGTH: 26095
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4
acatcttcct cggaatatac cgagggacac ctttccttgg aatataccga gggacatgtt 60
cctcggaata ttttgaggaa gatgtccctc ggtatatttc gaacgttttt ttataaacgg 120
atcgatcgat ggatatatgt ccaaaaacgc atcgatcgat gaacttccga ggaaatatcc 180
cgacgaagtt ctccctcggt atattccgag gagattttcg acaaactagt gatcctcgga 240
atttcctcgg aaatttgttt cctcggaatt ccgtcggaaa attccgaggg atttccgagg 300
aaagaagaaa ttccgaggaa ttatttccga ggacttgttt cgtcggtatg tcgtcggaat 360
aacgttattc cgacgaaatt ccgacgattt tttccctcag tatccttgct gttttcttgt 420
agtgcaagaa agctaataga tattagcaag taagaagaca taagtacttg atggccaagc 480
aaaagcctag aattggaata tcacgacatt caagcaaaag gagaagacat attccaacag 540
agccagagcc atgttcaaga tgagacaaac aaatgtgggt ctataagggg acataaagca 600
aaaactcaat aaaaagttag gctagtgcct atatcagctg gacacatggg agaaccaggt 660
ccatgctata taacaatatt atcaaaagca gtgttttcat ataagtagga gtaactttct 720
tccctagtcc actctgtggt ctaaataacc accagaggca ctacacagga tacaaacaaa 780
agttgaaaac acacacagaa tctatgtata gagagtgaca aagaaaagga taagaaggta 840
cttccattga aagtacggag tgtctgatat atattgaatg tataactatt gtaattatca 900
gtcaacaaag tcctcacaaa gtcaagcctt tccatagagt cttttttcgg tagactcttg 960
ttagcaatgg atgaatcttc caagtgccct ggcgcaatat gtttcgagat cgcttgccaa 1020
acccaacact ccagctgatc caccatgact ctctccatcc tccactctac aaccctacaa 1080
cccgctcgac accgtctccg acgttctcaa cgccgctttc ttccgttaaa tctcccgttc 1140
ccgtctttac ccaaccaaaa gcaatctcaa gtgctgtcca atctcaaacg gaggcgaata 1200
cttcatgagt atctcaatcg gtactcgacc aacagccttc agatcgtcaa ataacataag 1260
agagttagac gacgcttgga ttaagccgct tctatcatgt tctatgcttg gactcagaca 1320

```
gagtatatga cgactatttc ttatcaatac atataggccc aaacaattta aactcaacaa   1380
ctgagcccaa taaaaaactt cgaataaatg aaacgatgag tttcataata ctgggacacg   1440
tggcacaatg atgtaaagtg actttcctaa ctggaatcct atgtgtcaca atgaggaggg   1500
agtaaaacac ttatttatat aattagataa ctatgtatat aacacataat cggttgaatc   1560
gaatgttttg gttcagatct cagtacataa ccaaaccgac ccggtgtccg aagtgcttag   1620
agctaaaaac ccattcggta tttgcctggt cccgttaccg aaccggaccc attattttgg   1680
ttcggtttaa ggtgtggact ccggtttaag ttaaaacccc cagccctagg gtaaatgata   1740
aaacatttgg ttgtgtatct cctcggtggt atggaaaacg taatagaatc cgaacttact   1800
agaccggtac gcgatttatt tttcgtctta cgtcgtaaga tgtcgaataa ggaaaaagca   1860
acgtcattat acatgttaat ccggttatct ttgatccttt tcgaggacat ttcggtttac   1920
ctttttgttt gttcaatacg ccactccggt ttaaaaaaaa aatcgggaag agttaggaaa   1980
aaaggaaaat ctcatctcac cccctcgacg acaagacaac caccaccctt agggttaaaa   2040
aggtttattt atctgattat tattctctct actcgttcgt tctcccttta attccgattt   2100
cgatttcgat ttgtcttctc cgatttgctc tctagacact cacagtaggg tttctaattc   2160
ggatctgtac accttttgcc atggatgctc gtaagagagg acggcctgaa gctggctcat   2220
tcaactccaa tggcggtgga ttcaagaagt cgaagcaagg ttagctcttt cgcctcgtcc   2280
tcttactttt ctatctcaaa agagtgttat agttctgttg tgcttcactt gctctgttaa   2340
aggttgaaac tttagatctt tattgcttga tggatagttt ctctgtgtca attggatttg   2400
gggtagcgat gatttcttca attcgagctt cgtaatattt tttgctcaac aaaagttttt   2460
gtttttagtt atgagattct ctaggattca agtttggatc tttctttcgt gctcacttgc   2520
tgcagtcttt gatctgatgc aaatctaaag tcaattaatt tttcagttta attgtggatg   2580
agcttttgat aagtgatgtt aaagttagtt tgagtgctgt tcgtagcaag cttattgtta   2640
tttgactttc tcttgagttt cattattgct ttagtttaat cccttttgca ttagctagta   2700
acatcttatc accatgccca aagcttgagt ttgctgtgat tgaattagcc tttttatgtg   2760
ttagttattc atgtgtctag ttgttggtaa ataatcctga aaattctaga gaatatatct   2820
tgcagctttg atttatgtgt gaagttacat atagatgaat ttgatatgta tgattctaaa   2880
agcaaatatt attgaacatc agcaaagtct taactaaaga aaaacactta atctttggaa   2940
cagagatgga atctggttta ggaagcaaat cgaagccatg cacaaaattt ttcaggttat   3000
aatccttttc ttaactaaat taatatttaa aattgttatt tatagtctga gctttaaatt   3060
gacaagtaaa aatgtatgct aatgaagtag ttagttgtta ttacaggtat gcatcatcct   3120
tcatgctaaa caagttaaaa aaaagtttca gtataacaaa tatgatattc actaggaacg   3180
gaaaaacaaa tctggattat aaatttagaa atattaagct caactggtga ttatagctta   3240
gaaaatcaat ccacaccttt tgtttgagct gtggcagtag ttaagatatg tgttgtaatt   3300
ctctgtttgg tggtaagata ttagttattg tgtttgtatc atcatggtca tatagtgtct   3360
agtaaggttg ttgcattact gaatactggt gaacatgtcc gtcatagaca agcagttagc   3420
atagttgcta tgtgccaatt cttctgtgtt tcaactgttt gttctcttgt gtcttctcaa   3480
tgccaatggt ttttaacttt ctgacgtatt tgttatcctt cttttgcagc acttctggct   3540
gtccttttgg tgagaactgc catttcttgc actttgttcc cggaggatac aatcctatgg   3600
cacagatgac aaacatggga tcacccatgt ctcaagtttc cagaaacatg caaggtggtg   3660
gtggtggtgg gggccgattt tcggggagag gagagtctgg acctggccac gtctctagct   3720
```

```
ttggtgcctc agccacagcc aaaatcagtg tggatgcttc cttggcaggc gcaatcattg   3780
gaaaaggtgg agtctgttcg aaacagatat gtcgtcaaac aggagcaaag ctatcgatcc   3840
aagaccacga gagagatccc aacctgaaga acattgagct tgaaggaaca ttcgagcaga   3900
tcaacgaagc gagcgcaatg gttagagagc tgattgggag gcttaattct gcatctagga   3960
gaccacctgg tggtggtggc ggtggacttg gttcagaagg gaaaccgcat ccagggagca   4020
acttcaaaac gaagatgtgt gagagattct cgaaaggaag ctgtacattt ggtgatagat   4080
gtcactttgc acacggggaa gcagagctac gcaggtcatg aattgcgcct agagttgctg   4140
gtggagttag agagtttgct ggcgaaacaa gtctctttca tttgttgtgg tgattcctaa   4200
tatcatcttc tcctacttgt ttttagttgt ctttgttttt tgagactaca atgtttagtt   4260
ttcattgtca gtgtaagttt tccccatttg gtgttttttt agaatctagt ttgaatttga   4320
gatgggggga tgcttgatga atgattgaca aaacagtggt taggatttgt atgctgtttc   4380
tacttaatat ttcatgtttt ctctgcttta ttttggtcag taagttcatg tgtttctctg   4440
acatgtgtgt gattatcagc tttgattatt ttccgagtat gtagatgtta tagttctctt   4500
atgatagaca atataactaa aaattcatgt taataatagc cgtcgctgat agtaacagct   4560
gaataaatga aatgaaatca tggtaggtga tgatcttaaa aaaaatgttg aaaataatgt   4620
gcgttgttac aatagcatct cctaaccact tttatatatg tctctataat agcatttaga   4680
tttagaagta aaatcactgc aatcctactt tatttcttcc tctaaaataa aaattgttat   4740
tttcacggaa atacattcct ttataataaa aacatacttt tttattcaca aaataatctt   4800
ttaatttttt attttaacaa ttataaccaa aataaatatt ttttaatgaa aatgtactgt   4860
ttatataaat atataatcat actttttatt tacataatag tttctataaa aatattcagt   4920
ataaataata tcatagtttt atgaatgtta cactaaattg gattggtttt caactttcac   4980
aaataaaaag tactatttat aaaattagaa aaaaatatat caagactatt ctttttttaga  5040
ggaagaaata gaagaataca ttggaaacaa atctatctct attatatagt tttcctattt   5100
tagaaaaaaa aatagagaaa tacattggag atggtttaag cggtagtaac acaaagaaaa   5160
actctaaata tcttaagagc atctctaatg tacacttctg taatttcttc taaaatagag   5220
atctctatta tagaggtgaa aatgctccaa tgtatgcctc tataatagaa ttcatctatt   5280
ttaaaagaaa atatagagaa aaattacttt ttgcttttat atttaaaggt ggaaataaaa   5340
tatctctata taaataaata aactctatta tacatgtata cattggagca ttttcacttt   5400
tataatagag ttttttttatt ttaagaaaaa atatagagat agaaatagaa atagaaatag  5460
agatgagttg gagattagaa atagagatga gtttgagatg ttgttacgta agaaagagct   5520
agagctttaa taaagtactt aaattaatta ctagtcggca gtcgctgcct acttgtttac   5580
cacctaaatt aatttattat aatatatatt acgaatctcc aaagtacaca tcacacacac   5640
tctactcacg tgatctcaac cacaatgtct gcagatattt tttatagttt tttctcacat   5700
gggagagaag aagccaagca cgatcctcca tcctcaactt tatagcattt ttttcttttc   5760
tttccggcta ccacttgtga gtcgagtcgg caagggcgtt tccttatatt aaagtaaaga   5820
catcaaatac catcgtctta atgctaatta acgtaattga tgagttctat aacataatcc   5880
aaactagtct ttgtgaacat taggattggg taaaccaata tttacatttt aaaaacaaaa   5940
tacaaaaaga aacgtgataa actttataaa agcaattata tgatcactgc atcttttcca   6000
cttttccgta aataaataca taaaagtgcc gtaaatatca gatatttgga gtagaaaagt   6060
```

```
aataaagaaa agaaatatga ggagagggaa taatggaggg ggcccacttg taaaaaagaa   6120
agaaaagaga tgtcactcaa tcgtctccca cgggcccccg tcaatttaaa cggcctgcct   6180
tctgcccaat cgcatcttat cagaaccaga cagattcatt accaaagaga tagagaagag   6240
agagagagag agagagagag agagtgagtt tgaggaggag cttcttcgta gggttcatcg   6300
ttattaacgt taaatcttca cccctacgt cagccagctc aaggtccctt tcttcttcca   6360
tttcttttca ttctacgttg ttttcaatct tatgaaactt tctggtctgt gcttttctta   6420
tcgcttttct attctatcta tcatttttgc atttcagtcg atttaattct agatctgtta   6480
atattaaact atagatctgt tcttgattct ctgttttcat gtgtgaaatc tgatgctgta   6540
ttaatctgat tatattgtct ataccgtgga gaatatcaaa tgttgcattt tcatttgtcc   6600
gaatacaaag tgtttgactt tcaatcgttt ttaattatat atatatatat attttttgat   6660
gggttggtgg agttgaaaaa tcaccatagc agtctcacgt cctggtttta gaaatatcct   6720
attcaaaatt atatatttgt ttacttgttt tagatctgga cctgagacat ataagtacct   6780
atttgttgaa tctttgggta aaaacttatg tctctgggta aaatttgctg ggagatttga   6840
ccgattccta ttggctcttg attctgtagt tacgtaatac atgaaaaagt ttcatttggc   6900
ctatgctcac ttcatgctta taaacgtttt cttgcaaatt aattggatta gatgttattt   6960
catagattca gtcattcaga tacaatggag ttgcatgaag aaaataatag aattcgtgac   7020
agtaaaaaag attgtatttt tgtttgtttg tttatgttta aaagtctata tgttgacaat   7080
agagttgctc tcaactgttt catttagctt cttttttgt caagttgctt attcttagag   7140
acattgtgat tatgacttgt cttctttaac gtagtttagt aataaaagac gaaagaaatt   7200
gatatccaca agaaagagat gtgagctgta gcgtatcaaa tctcgttcat ttactagtag   7260
tattctcaac gctatcgttt atttattttt ctttcgttgg tttgccacta tatgccactt   7320
ctctcctctt tgtcccacgt actatccatt ttttttgtgg tagtccattt tcttgtaact   7380
tataataacg taactctgaa tcttttgtct gtagattaat ttgttggttt aattaacttt   7440
taagtctttg cttttggctt atgcagaaac atgggtgcag gtggaagaat gcaagtgtct   7500
cctccctcca agaagtctga aaccgacacc atcaagcgcg taccctgcga gacaccgccc   7560
ttcactgtcg gagaactcaa gaaagcaatc ccaccgcact gtttcaaacg ctcgatccct   7620
cgctctttct cctacctcat ctgggacatc atcatagcct cctgcttcta ctacgtcgcc   7680
accacttact tccctctcct ccctcaccct ctctcctact tcgcctggcc tctctactgg   7740
gcctgccaag ggtgcgtcct aaccggcgtc tgggtcatag cccacgagtg cggccaccac   7800
gccttcagcg actaccagtg gcttgacgac accgtcggtc tcatcttcca ctccttcctc   7860
ctcgtccctt acttctcctg gaagtacagt catcgacgcc accattccaa cactggctcc   7920
ctcgagagag acgaagtgtt tgtccccaag aagaagtcag acatcaagtg gtacggcaag   7980
tacctcaaca accctttggg acgcaccgtg atgttaacgg ttcagttcac tctcggctgg   8040
ccgttgtact tagccttcaa cgtctcggga agaccttacg acggcggctt cgcttgccat   8100
ttccacccca acgctcccat ctacaacgac cgcgagcgtc tccagatata catctccgac   8160
gctggcatcc tcgccgtctg ctacggtctc ttccgttacg ccgccgcgca gggagtggcc   8220
tcgatggtct gcttctacgg agtcccgctt ctgattgtca atggtttcct cgtgttgatc   8280
acttacttgc agcacacgca tccttccctg cctcactacg attcgtccga gtgggattgg   8340
ttgaggggag ctttggctac cgttgacaga gactacggaa tcttgaacaa ggtcttccac   8400
aatattaccg acacgcacgt ggcgcatcat ctgttctcca cgatgccgca ttatcacgcg   8460
```

```
atggaagcta ccaaggcgat aaagccgata ctgggagagt attatcagtt cgatgggacg   8520
ccggtggtta aggcgatgtg gagggaggcg aaggagtgta tctatgtgga accggacagg   8580
caaggtgaga agaaaggtgt gttctggtac aacaataagt tatgaggata tgatgatggt   8640
gaaagaacaa agaagatatt gtcacgaacc tttctcttgc tgtctctggt cgtctttgtt   8700
ttaagaagct atgttttcgt ttcaataatc ttaactatcc attttgttgt gttttctgac   8760
attttggcta agttatgtga tgtgggacac gttagtgtct aaaatgtctc tgtgtctgta   8820
ttgttcttct catctgtgac tttcggacaa ctaaactctt gttctcgaac tacctcaatg   8880
tggcattaat gaaagtgtta ttgttgattt taatctgaaa ctgctattat ttagtgaatt   8940
tttacatcag ccaacttgtt tgtttaagac ctaccaatgg tataagaagg tttgtgtact   9000
aatgttcacc atgtccatag tgttaagaca taaccatgat cttctgtcca attaatttgc   9060
gtcgagttat cgtgttattt ggcaccttta ctatgttttt ttgtaaagaa ctccttacag   9120
aatagctttt tgtaaagaac tacgttttat ctttttgtaa gaacctttta acaaaagcca   9180
aattcattat tacctggcac aagaaaaaac tctggtttct tcctctttct ctgtttttag   9240
atttgaggag gaacatgaag atgaagaaaa agaaacaaat aaataacaaa tctctttttt   9300
tccattaacg gcagaaacac caaaacagag tgacaacaag aaacaaatgt agtgaggaaa   9360
aaccaaagaa aaaagaatat tctgaaacca actcgttgaa catattcaaa tacgaaacaa   9420
tctttcatcc aacggcgagc gtaatctaga agcatttcct gtggactatc gatggccctg   9480
cctcatcata ctcagccttt gctatccaca tctgcaagac caacattgtg tatcatagtc   9540
agcttaaaaa cgagtaacaa gcagaatcga caattttacc tgttggaagg tactgagtga   9600
tgctagaata gatcctccaa tccaaacact atacttcctc tccggtggag caaccacctt   9660
aatcttcata ctactcggag ccaaagcagt aatctcctta ctcatcctat cagcaatccc   9720
agggaacatc gtggtaccac cactaagcac aatgtttcca tacaaatctt tcctaatatc   9780
cacatcacat ttcatgatcg aattgtaagt cgtctcgtgg ataccagcag cttccattcc   9840
gaccaaagac ggctggaaaa gaacctcagg acacctgaac ctctcccctc cgatggtgat   9900
cacctgtcca tcaggcaact cgtagctctt gtcgacggat gagctagtgt tcgccgtctc   9960
catctcttgc tcgtagtcaa gtgctatgta agcgagtttc tctttcacgt ctctcacgat  10020
ctcacgctct gctgttgttg tgaacgagta gccacgctcg gttaaaatct tcatgaggta  10080
gtcagtgagg tcacgacctg cgagatcaag acgcagaatg gcgtgtggaa gagcatatcc  10140
ttcgtagatt ggaacagtgt gactcacacc atctccagag tccaatacaa tacctgaaac  10200
aatgattcca catcaataaa agtgttctac cttttttta tcaacaaaag tgttcttcta  10260
ccttataaac tctctagata attataacat aataataata aataatttat aattataata  10320
attaatattt tttagtataa aatcttatga gaataaacaa tataaatatt attatttgta  10380
aatatttaaa ctcttatatt attatttttt tccaaccact acactcttat attacatata  10440
ttgttataat tggtaaacaa ctaggtcgaa gataggcatt gagttaccgt ctcagcgcta  10500
aaatgtctac taaaattata ttacattaca ttgagaaagc taagatgaac atcataaacc  10560
aatggtgttt gaagatctta ccagtagtac gaccactggc gtagagggac aaaacagctt  10620
ggatagcgac atacatagcg gggtgttga acgtttcaaa cataatctga gtcattttct  10680
cacgattagc tttaggattg agaggagcct ctgtgagaag aacgggatgc tcttcaggtg  10740
caacacgcag ctcgttgtag aaagtgtgat gccaaatctt ctccatgtca tcccagttgc  10800
```

```
tgacaatacc atgctcaata gggtacttga gagtcaagat acctctcttt gactgagcct  10860
cgtcaccaac gtaagcatct ttttgcccca taccaaccat cacaccagtg tgacgtggtc  10920
taccaacaat gcttgggaac acagctcttg gtgcatcgtc tcccgcgaat ccagcctttc  10980
atatagagat ttggaggtaa gaaaattaaa agattttcag acagcattat attaaacaaa  11040
gttgttacgt ttatgattga ttaccttaac cattcctgtt ccattgtcac acactagtgg  11100
ctgaatgtcc tctccatctg ccattttcta atgattctga aactatatat atatatatat  11160
atatatatat atgtcaatga ttcaattgat tacaaaaaca caataacatt cttgaaaaaa  11220
atcaaatgaa catgaactca aacaaagatc tctgattcac tcacattgtt acaaaataca  11280
aaaaatcaat ttaacatttt accaaagaaa aacaaaaaat cgagaaaagt ctggtaattt  11340
atttttacct gatagtttgc gaggagagga aaaatagtac gaagagaaca aagagaagag  11400
cgaacgaaga agagaatata taggaagagt ctttctgaga aaagaagttt tattttattt  11460
taatggtgga agaagatccg agccgttgat atttgtaaga tgtgaccgaa gaaggacccc  11520
acgacgagtc atgttgatgg tggatacagc tgtctcataa agagtaacga cactccattt  11580
aattatttta ttaatctttc gaaatttggt aacgtaactg aaagtatcta ctctgtaaag  11640
tattaaatgg gctggaaaat gttccttaag ggacaaatcc aaccaaaaat tagttattaa  11700
tattaacggg ctgaaaaatg cttgaataaa aagttaatta ttaatattaa cgggctgaaa  11760
aatgcttgaa tgtgatatgt taaccctact aattttaata aagtttacta gattctgcca  11820
gtatatttgt ttttattcag aaactagggc tggcccgccc tacggacgga atgaatattt  11880
aaaaataatt taaattgtta aaataagtat ttaatgaaaa tttttattaa ttaaaaatat  11940
aaatattagt tatatttctt tttcttgggg tggcattaca tataataact tatgtggtgc  12000
attattaata ttgtgtaagt tgtgattgag atgtaagagt gaagttgtga tcgagaagtt  12060
attaatattg tgtaagtgag aagttattaa tattgataat ttatattatt tatttaaaat  12120
cttagggggt tttaacttgt ttttgttttt tccatttttg ttatgttttt aactttaaaa  12180
gtgtttataa attataaact gctaaattcc cattgaaatt ttgtgattga aatttaaata  12240
tttataacaa aatacaaata attacaaaaa catacgtaag atatatttgt attgtatttt  12300
ttaataacat ataccatata aaaccaacta attatttaaa tttagatttt aatagctgca  12360
ttgtattttt taataacaat tatgaattac taaaaacata tactatttga atttttatta  12420
atatatagtg atttccaaca gaatatgcga atgattattt ttatctgaaa atgagaaaca  12480
ttttgactaa aatattgtgt ctcgatacat gtgaccacgt caatttaata tatcggatca  12540
ttaagtgtcc aaatattttg taatgttatt ttctcagttt cataagataa tttgaatata  12600
taactttatt tctaatgtta ttggttagtg tattttaata gatttagaaa tccaaattaa  12660
atatattatt attagttata taattgtaaa atatatattg aaatcatgtg ttactggtgg  12720
catgatttaa aaattctaat tcaaaacaag tgttattcaa tcatactatt tattaataga  12780
tttgatttca taatggattt gaatagattt gtatatattt ctttgttaaa atataaattc  12840
tcaaatctga aggtaacccg aaagaaaacc atcggatttg taaatactaa tttttttttt  12900
tttttgaca gcaagaaatt tacagactca tgttgactct gtaaaccata ttggtaactc  12960
cgcatccatg tgaacgacaa aggacagttg cttgcgtgca ctacgtgcta agctatccgc  13020
ccgaaggttc gccgtccgag gtacatggac gatgtctgag ttgaggaagt ttcctttgag  13080
gagtttgata tcttccaagt agcttccaaa tgctggccat tcttctggtt ccgaaaccat  13140
cttcaccaat tgagaacaat ccgttgcaaa cgtaacctgg acctgtctta aattcctcat  13200
```

```
acatttcatt gcccaaatca aagcctctat ctccgaatgc aggggagaga ggcatgccct  13260
tacattcctt gcccccagta gaccctcgaa ccccggtaaa gtactatgcc agccttgccc  13320
tgacattaat tctttatcct tccatgatcc atcaataaaa caccatcgac ctgatgtctc  13380
taaaggagga atggtttgta ccgaaagccc cctccttggt tcatttctca cttgtgcgtc  13440
tgcccagagt gatgattcca cttcagccaa tttaagagta tcccgcggat caatatccaa  13500
attactataa actttgttat ttcgggcttt ccatatatac cataaaatcc atgcaaaatg  13560
gtggtcatcc atttgcggtt gtactctcca aaaaagatga tccatattaa caaataaaga  13620
gctgataggg aagatattat gcggtgaagg aatcttggat agtgcccaca cttgacgtgc  13680
aggaggacat tcaaaaaata catgatttat tgattcttcc ggatctccac aacgagcaca  13740
acatatatct cctctgatcc ctcgtgcctt taaatttttc atcaccgata tacatcctga  13800
taccatttgc cacaagaaat gccgtatctt tggtggacac cgcactttcc agcagaaagc  13860
tttaagtata tccactgtgg ggccattaaa aacaggaggt tttaacctat cagggtaaat  13920
acgttcaacc tgataacctg attggaccga atattttcca ttattagtaa aatgccatcc  13980
atccttatcc tccatctgaa tcctacttaa agggatactt tcaataattc ttacatcctt  14040
cggatccact agagccctga ttgcctgtat attccatgaa cgagattcct gattgatgag  14100
ggaatccact gtgagttccg gataaaagtt gtgaaatttt ttatttgctg gtctcgggcg  14160
agtggctggg atccaaggat cattccatac agagatagat gatcctgttc ccaccctttt  14220
aattagtcct ttacaaacca gagatctagc agaagtaata ctcttccagc catatgacgg  14280
ggagtaagat cggatcggtt ccaggggtga agcattcctg taataccgtc ctttgaaaac  14340
tcttgaaaaa agagtatttg gtttctcaat tagcctccat agttgcttac caagcattgc  14400
tgtattaaaa tccataagat ccttaaagcc caaaccacca ttatctttgg tttcacacac  14460
tttatcccat gatttccaat gcatacctct tgcactaccc cctggactcc accaaaattg  14520
tgctacagca cccgtcagct tcttaactgt agcttttggt aacctataca cagacatcac  14580
atggtttggt aaggccgtaa tcaccgattt aataatcacc tcctttccac cttttgtaaa  14640
aaaacgaaag gtccatccat taaccctttt attcaaccgc tcttgaacaa atccaaacac  14700
ttgtaccttt atgtatattt aaatttgata ctaatttaaa tttgtatatt aaattttaac  14760
tttatgaaca aatccaaata ctaatttaaa tttgtatatt aaattttaac atatgtatat  14820
tttactttga tttgtaaata ttatttggat ttctgaatca actaaaatac ataaactaaa  14880
taataatata ttttctttgg aaattttaaa tgtatggact attaaatcat gcaaatacta  14940
tgaaaaacaa attgatctac aattggtata aaactatttc catgtatgag atacaatatt  15000
gttacgaacc taaaattata gtttattata ctatcaccta ttactgttat ttttgtaaaa  15060
caatatttta attttagata gaacttcaag attactcttt tggtaactgt tgccttaata  15120
ttcccggttc tattacatca gccattgaaa taaaatgtta ctaataaagt aagttactgc  15180
tggtaactaa aattcagaaa ccgagatgac ttaactcttc tattataacg tagatttata  15240
catttataaa acagatctta cataatcaac ttcttcacat cagactcact tacgtgacct  15300
ttttctagga tttccttgtg agattgggtt tgttcagttc ctagactcag tttcttcgcc  15360
tttgaccctt ctattcttct tccataaatt ctcctttcca ttttctcaac tcttgttcta  15420
cgcctaactc ttcttcttta gctttctcaa tttcttctgc aagtgttttt tgcttcttcc  15480
tctccaagtt accttgtcta tttctctagc ttcctcgatc tcagaacaac tgttgcaacc  15540
```

```
attgtattgg cttcttcttc agcatcatga gcacgctagc taagcagacg gcggctaatg  15600
ccaacctctc tgaaccctta gcagccttag tttattccta agttgcaaat aaaatggtct  15660
ccattgtact tgccccagcc tttgcttgct ctgcttcttc ttgagacttt cgaagctctt  15720
cagtgaatga ttttgcactg tgacagtgaa aattttttct tcatcagcct ttgtgttgct  15780
ttctgcggct gcttcggtag ctccgctatt tatcttatgg cttcttttcc ttggactcag  15840
aaatagctat tctcatgtta tacgaccatc actcgccagc aaaacaaacc tggataaaca  15900
taaggcattg tttactaaaa gcatgagaaa tgaaactaaa aatcatcttt cttggctttt  15960
tttcaaaaaa aaatatggta acaaaaccat aaactccgaa ttatcacaat atgcttaatt  16020
ctatggaggg acatcaagag aatctacgaa tgatatcttt tttgaattct ctgtaatccg  16080
taaccataag ctatcagtat tgtgaaacac taacatctaa caacctaaaa tcagacaaca  16140
accccacaaa gttgtagttt tatgacaata caatgaagca tttctctccc accaaccatc  16200
aaagagtatg caaacctaaa gccaactgaa gcatacacct taagattaaa acttgggaga  16260
actgtaaagt agacctctgg ttttggggtg actttaacag caacctcctg acccttgagc  16320
tctctttctt gaacttaggc tagcagagca agtgcaacca aaatgacctc tcccgagctc  16380
tcccatctga aactgcatac ctctgtattc agaaaacata ctgacaacac gttagtttgt  16440
agtaactaaa ataaagagag cccagcaaat aattattatt ttacagaacc agacaacatc  16500
aaaatcagat atatttttt gttaggtaga acttgttgca gttttgaaaa atagtaataa  16560
gaatttgctc actctttatg atgaagatgt actaagacac cgtccctctg caaactgctg  16620
ttgatgtcca taatacttgt attgtatcca tccttcaccg tgaagtttgt ttatgtttgg  16680
cagaatgacg gttagaatgg aaaagtgttt ggttattcaa actctaaggc agctgtatct  16740
tctttttagg cttgttgagc tttttcttct tctttctaca aaaacatgtc acagactcag  16800
agttagccaa gttcggtatt actaaagcaa gaggcctaaa caacacagaa ctgcagataa  16860
gttaattgac ccaccaactt ccactcatct gcctagcact cctcatcctt tactcgtgtg  16920
tagcttcttc agcctatgcc agacagtatg aagaaatttt tattaggaaa acgttgccac  16980
gtactaacgc tacaatctta aactttcaca gttagggcct gtaactgttc gactgatatt  17040
catgtagttt cccatccttg ctacttggtt acatatgtga attagataga acaatcaaca  17100
aacaaataaa taatcaacaa aaaaataaaa aatctgtaaa acttggttaa atgattcaac  17160
acaacgcata agttcaataa cataatcaag gataaaaaaa gttggtaagt ggattcacac  17220
ggcggagtcg ttacaaatat aatcaaattt tttttaatag attgatagga tgctttagat  17280
tgtagggatg ctaaccttat tatagtggaa cctccactga ttgatttcta gattggatca  17340
gtaggaaaaa gatgaataaa ttgctccaaa ctctagattc gctactgcgc agattgattg  17400
atggatcagt gaatggatag aaactttaga atttcttact gcggagaaga gagagcgtga  17460
aacgataaaa taagaaaagc ggcgtttcaa acccatcata ttatgcttta tatcgatatg  17520
ggctttaata aagtaaaata cacatacgaa gccaagccca acggaatccg atgaaaaaac  17580
aaatgaaacg gagcgtttaa taaggtggac acatgttaac gcgagagagc tcgactttcc  17640
tagctggaat ctgacgtgga gccctcagga gtgaggtgac tctactttat atataaagat  17700
ttagaaattt aattttcatg tttgtctttt tctttgtaat catatttgtg tttttctttg  17760
agatcatatt tgtgtataaa ttttaatcaa aatctattta taaaataata tcaatttaaa  17820
agttgatctg acatacgctc gtatttttgt aatcatatat gttcgtatgc tcgttttttt  17880
gtaaccatct gtgtctattc tagattttga tctccacttt taaagtgtat atttatttgc  17940
```

```
taaacaaatc aaatttattt gatataaatt tgtatttttg atttttaatt acatttaaat  18000
gttacaaata aagcattata attgtgcaga ttgtaatatg ttttctaata gaaataattt  18060
tgatgatgaa atatgtaacc aagttttact aaaatcaaga tatttttgca tttttagtat  18120
tttgaattat taacgtaatt tataatattt gtactcgaaa acctatgtag catctacctg  18180
taagtctagc cccgaatccg attaaatacg acctatatac tcaaaaatat tggtttcttg  18240
tattgatcta aattttgcta aatttaattt ataatataat tttcatatat tttctcgcta  18300
tttttatatt tgatcataat ccacgataaa aatggtaaat taagtgatct gcatataatt  18360
tatctcagat tttggattaa attataaaat ttatttttaa aaactccata aaattcggtt  18420
aaacccaaaa aaaattattg acatgtgatc cgataatggt tgacccgaaa aaaactagat  18480
aaatctaatg gtcacctata tgaaaatatt atcactacaa gaaaacataa cattaacgac  18540
ggcgaaattc gtagtaaatt cgtcgtaaaa caggttttac gaggaattag cgaggaaaca  18600
agtttcgtcg ttattcgttc gtcgtaacgc atatttcctc gctaattcgt cgtaaaatag  18660
cgagaaacac aattcgtcgt aaagacgaag aacaatattc gtcgtaaaaa ccatgtaacc  18720
tttccacgta aggaggacgc tagatttcct cgtaaatacc tcgaaagtaa ttcctcgtaa  18780
attacacata aacctttcca cgtaatatac tcgttaagct ttcctcgtag tgttgccgta  18840
aaagttttcc tcgtaacttc ttcgcaaact ttccacgtaa cgtagtcgtg ctttaggcgg  18900
atttgaatgc taccagcaaa tttatagatt ttaagtgttg ttatacatac gtagacatgt  18960
tctctattta ttaaataaat agtaacaatg tcaattaggt atagaccatg gccatatttt  19020
tagctaacag ataaaaaaaa tatttgagaa aaataatata tatgtatttc tggtcatgag  19080
aaaataatat gtgggttaaa tcatttatca tatagtagaa gggagtgggt tccgccggtt  19140
acaaggaaaa tgatcacctc gtttgtttcg agtaaaaaag ttaggtaact gtcatacctt  19200
ttataatgtg gtggttacat tcggaaatta aaaaaaggtt gcagttatca tataaaaatg  19260
tatgtgttgt tgaaataata gtttgaccct acgtttatca attggttaca ctaatagaat  19320
agatttatca agagtagtat actgtatttt tgttgttacg tttgtttccc gacaaactta  19380
aattttatta atacgaaagc ataatatctg aatacaaagt tggagttaac cacttaggtg  19440
gataaacttt acaattttca aaaatagaat ttgttggaca atgtcgaaca attttatgga  19500
cggcttgatt tccattacgt ttgacaaaaa aaaatgttgt tgtagaaaac ttattcctca  19560
agctagtaat ttcttcaaga agattttgaa tggttgaatt cgttagttga gcattgatca  19620
ttttaaccaa gatttctgag tctccttcga aaatcatatt gctatatcct cctatccaaa  19680
cattctgcat tgccacaagt aaagccaact aaactggaat tagagaaccc caaattagct  19740
gaaccccaca tataaggatg accataacag ttccaaataa tccatgcacc tcgaacttgg  19800
ttcgaattta aatcatatgc tgcatcgtaa ttacatttta gaaaaccttg atctcgtcgt  19860
gtccatgacg ataaagcagg aaaagaagaa attgtgcttg tattgcttac attaggagat  19920
gataaacata aatgagatat ccattctcta acgtcagcac aagcattgtc cactgtgaca  19980
tttgggggca gtatttgttt cctaaagaga agaaaattcc tctttttcca tatacgccat  20040
agcaaccaaa aaggtaacaa ccgttgataa agcgaaagag attgtatgct ttgaatatgc  20100
agcagaaacc gattttattg tccatataat catttgttaa taatggagcc gtaaaaggta  20160
gatatgaaaa tctccaaata catattgaat ctgagcacgt acaaaaacaa tggtcaattg  20220
tctcttctgc caaactacat ctctgacaaa tagaatctaa attcattcct cttgaattta  20280
```

```
gtcgtgtagt tgttccaata gcctttgata gaatacgcca aaaaaatggt taagtttggg  20340
cattatattt aatttcctaa tcttatcctt tagaatagga tcaccataag gaattggagg  20400
agcttcaatc aaaaactctg gtgcatgcct agcaacctta tatccagaag acacaggata  20460
gttttcatct cgtgtatgac tccaaatcaa cttatcttct ttttttgttt ggcttaaata  20520
tatctggctt acgagacgtt gatcctcatc gcataaataa gactgtagcg ccaccgtatt  20580
ccaatgtttg taaggtgata ctgtaatcat attactaaca cgtaaatcac aattaattgt  20640
tgtagaagca ggtcgaggtg gaataacagg taaccaatta tctttggaag ctcgtatatt  20700
tttgccattt cccacaatat agctacatcc tttctttaaa acctcaatac cagcgagcag  20760
agttgcctat ccatatgact gcttgcgaca tgtttttcct tctagaaatt gttttccttt  20820
aagatatcga gctttataaa gtttggaaaa gaggcaattt ggttttgagt agattcacca  20880
tgcttgtttg gcaagcaaag catcattaaa ttttggtaaa tctttgaatc caaatcttcc  20940
ttcttttttc gtatactgta gttttttca agtcatccat ggtaaacctt taagatcatt  21000
tttaccccac cagaatccca ttaagatggc atctatcttt tgtgttgttg caacagggag  21060
tttaaaatgt gacatagaat agataggggt tgatacagca accgatttga tcgtaacttc  21120
tttaccagct gatgaaaaca tacataatta caagactcga gagccaatca agtccaataa  21180
ggcgtttaat gcggtcaacg cttcttgact tgaggctctt atatgggctt acatcagtgg  21240
cccattaagg tgattcttgt gtacttttaa gacttgttga atttacacat ttgaggatca  21300
aacagaaagc taagtatgga gagatccgtt tccttcgatc ttagcggcga taacgaactc  21360
ccgaatgatc ggagcagcga cgtcggatac accgccaatg atcggaggct cgcttactcc  21420
cgctcctttc accactccca ctcccacggc ccgcgaacgc ccgcagctaa gccttttctc  21480
gataggacgg tctccaccat cgatatgccg ccggagatat actctgtcga cggggatgat  21540
gttttcttcg gggaagggaa agcggcggcg attgggaaag cgtcggcttt gcgtatggtt  21600
ttggtggttt ttggggtgct gagaaatgga aatcggcaga tgaagagatt gtttctgctg  21660
atttcgctta acgtggcgta ttctaccaca gagctgttga ttgggttatt gactgggcgt  21720
gtaggtacga tttggttcca gcttttaaca ttttgttaca cttagttttt agttcgtggt  21780
aactttgtgt gtgtgggaga gacttttgga tttgttgaag aactaaggtt ttagtagtgg  21840
ctagagatat agatggaaag tgaaatgaat cagctaaagc cccaagattt tgattccaag  21900
tcttaatttg atataatctg aatcatgaaa ctaaaccacc acatggatag tagatcttgt  21960
gcgtgtatcc agggaacttg gctatgcagc tgtaatttct gattatttat taaccttact  22020
ctcttttttt ggctgtttta tttgactctt acaggtttgg tttccgatgc attccatttg  22080
acatttggat gtggtctctt gacgttttct ttgtttgcaa tggcgacttc aaggaagaag  22140
cctgatcatg cttactcgta cgggtaagaa atatgtaaaa tttgatccgc ttagtttgtt  22200
ttgtattagg gatataggtt ggaatgcatg ctttgtggta gttaacggtt gatttctcaa  22260
tttgtcaaat tattttttct tttctttctc tctggagcaa ttcctaaagt agattcgcta  22320
atgttttcgt aggatatagt atttatagtt gctgaatatg aaaccttttc tgtttgattt  22380
ttttgctgct aatactgtaa ttgcataatg ctgaattggt tggaacttag aaatcgttgc  22440
ctttttttggt taccaggtac aaaagacttg aagttctatc tgctttcact aatgctgtaa  22500
gtatgttctt aaagtttgtt ggatcatgga tgtcatttcc agttttaatt tgaaggtcta  22560
atggctgatg tgccatgcaa taaaactggt ttaatatcgt atagaaatta gtgtcctgag  22620
cttatctcag tgtttgcaca ctttccttta ctgttgttgg tagaatagaa taatcttaca  22680
```

```
gctcgttaaa aatgttgatt atcttttcat tttgccttca tcactgtctc attcatttta  22740
tcttttgggt taacacattg atatgttcag tattgacata tgtgtagaca gctgtttctt  22800
atgttcatgt cgttctcctt agctgtggaa gctcttcatg catttgttca agatgaatca  22860
gagcacaagt aagtttcttt ccccaagtga catgcctaag agagctcgta gttatttctc  22920
tagcacttac taagtttaca ctaagttctt tgcattaata tgatgtattg aaattgactt  22980
catgcaggca ttatcttatt gtatcagcgg taacaaatct gctggtgaac ctacttggtg  23040
tttggttctt ccggaattat gctcgtatga atattggtat gtattctctg ttttataatt  23100
atgcttaagt tctggttaga cttgaatgaa ctgatgccaa tactggtgat ttatatcata  23160
tagccctgtt tggcggcttt ggtatatttc gtttgtaaaa actggccacc cctgtcaatg  23220
taaagcaaca aagaagcaaa gggtttctaa ttaagataga ataagtagga ggattagtta  23280
aaatagagag acagaagcat gatgactgaa tctggccttc tgtacatatt caaaactcac  23340
atttttcttg aatgtgtttc ttaaattcat aaaatgatgc agtgtacaga aaagcagaag  23400
atatgaacta ccactccgtt tgcttgcatg tcatatcaga ttccatccgc aggtgtgata  23460
ttctttttgg ctttctttat ctcaagcaga gccgcagata gctagataga aaaatgtttc  23520
tctttgcatg gaatttacat acatcccaca tgacatattc gctgcttctg tcttttcagt  23580
gcaggtctga tactggcatc ctggctcctc tctctggggt aatgctcact tcctttaaaa  23640
ggaacaaaat gaataaaaat gtcttattac ctgacctctt acattttcca tttttctcct  23700
ccggtctttg gatttttcag ggttgaaaat gcagaggtcc tatgtttggg attggtatca  23760
gttacagtgt ttatgcttgt tatgccactc ttcaaagcca ctggtggcgt tttgcttcag  23820
atggcacctc caaacattcc ttcttccgca ttaagtaaat gcttgcgtca ggttcgctct  23880
gttccataaa gtgtttcctg aacgtgtaca tatagatcga tcaacctggg tttctcttca  23940
actatcttta tttacagatt acttctcgag aggatgtcat agaggtttta caggcacgtt  24000
tctgggaggt tgtgcccggt cacactgttg gctcactcag aatccaggta ctagcttcct  24060
tactgttttc atatcggtta aaacacgaat ccataataag aattgtactg attttgagct  24120
ggttatttgt gtttaggtga agagcgggat agatgaaagg cctttactgc aatatgtgta  24180
tgatgtatac catgatttgg gtgtacaaga cttgacgctg caaacagact acagctgagc  24240
tgcatctact tctatgtttt caaatactga ggactttgga tgtatactag tagagattat  24300
ggttctataa gaagatagca cttggtttca agcttgcgag tttcttgtta catttgttta  24360
gttttatttt ttttaattcc ttttcccatt cgtcttttga accacacaca caaggaccac  24420
aatctttgta aactctttta gtctttcaag tttgtgcgtc tttttggctc aaattctcct  24480
ttttaatcct ttttcatgta aaaaaatcat ctgcaaaatg taaaatcaaa acggtagcac  24540
gtaaaattgt cagctgaaac aagattttat tgttcttctt gtttacacag aaaaaactaa  24600
gtggaggaat caaagatcat attgtgctcc tcaacctaca cagcctaata ttctgcaagt  24660
tatggggaca gtacaagcat cttaaaaagc aaattcatcc gtccatgtct atgttattct  24720
ttgcttaccc ccgtttgctt cgttgatcat tgtaaattta acatagttta ctaaacgata  24780
caaaaatttg taaacataaa aaaaatgata caaaaattta atatagttta ctaattgact  24840
acgtgcacat gacaaaggaa tttttattaa tggaacttga aaatatattt tggatttaac  24900
tgaactacaa aaacgcaaga tatatatgaa aagtatctca attatttccc gtaacgagtc  24960
aacaatttca aagtatacaa tacccacata tgatacgatc cattatataa tccatgattg  25020
```

cgttttttgg actctaagct agaaaaatgt atattaataa tatggtatat catatttaat 25080
taaggcacta cttgtgtggt ctgctttatt gttagttaaa cgtataaaat agaataataa 25140
acaagaacca attgtccaaa aagacacttt tatttgaaaa aatactattt ttaatgttat 25200
tgtttggatg attcaaatca agagacgacc agagaatatg agcatgaatc atcaaaccat 25260
taactcttaa cctttcccct taaaaaaaat tcccagttga taagatagaa tcaaaagcag 25320
aaaaaaggta gagttaaaca atataataac taaaaaacaa agaagattgt aagataaagc 25380
tgatgaagtt cacattacaa gaagagaatc tgcttattac aaaagagaga gatataagag 25440
aatacactgc taagtctctg gtttcttctt gataacactt tcactatgta cagattcagc 25500
aacacagtga ttggagtctt aaacctcctc agcttactag cttcaatacc aatcatagga 25560
gccgctctat ggaaggcaag aagcagcaca acttgcgaaa acttcctcca gactcctcta 25620
ctcgttatag gtttcatcat actcttagta tctctcgccg gattcatagg agcctgtttc 25680
aacgtggcat gggctctttg ggtttactta gtggtcatga tcttcctcat cgcgactctt 25740
atgggtctaa ctctgtttgg tctggtggtg acgagccaag gaggcggtgt ggaagtacca 25800
gggagggttt ataaagagta taggcttggt gattatcatc catggttgag agagagagtt 25860
agagatcctc agtattggat ctctataaga agctgtatct tgagttccaa gacttgtgct 25920
aagattgaat cttggactac acttgattat ttccaaagag acatgacttc tgttcaggta 25980
tcatcctcag tgcctagagc catgttaaaa aaaattaacc gtagattttt atatatgtct 26040
aaagttttta ttgatttata agtattaata actccagtta tatatgtttt ttttt 26095

<210> SEQ ID NO 5
<211> LENGTH: 1161
<212> TYPE: DNA
<213> ORGANISM: Brassica napus

<400> SEQUENCE: 5
atgggtgcag gtggaagaat gcaagtgtct cctccctcca aaaagtctga aaccgacaac 60
atcaagcgcg taccctgcga gacaccgccc ttcactgtcg gagaactcaa gaaagcaatc 120
ccaccgcact gtttcaaacg ctcgatccct cgctctttct cctacctcat ctgggacatc 180
atcatagcct cctgcttcta ctacgtcgcc accacttact tccctctcct ccctcaccct 240
ctctcctact tcgcctggcc tctctactgg gcctgccagg gctgcgtcct aaccggcgtc 300
tgggtcatag cccacgagtg cggccaccac gccttcagcg actaccagtg gctggacgac 360
accgtcggcc tcatcttcca ctccttcctc ctcgtccctt acttctcctg gaagtacagt 420
catcgacgcc accattccaa cactggctcc ctcgagagag acgaagtgtt tgtccccaag 480
aagaagtcag acatcaagtg gtacggcaag tacctcaaca accctttggg acgcaccgtg 540
atgttaacgg ttcagttcac tctcggctgg cctttgtact tagccttcaa cgtctcgggg 600
agaccttacg acggcggctt cgcttgccat ttccacccca acgctcccat ctacaacgac 660
cgtgagcgtc tccagatata catctccgac gctggcatcc tcgccgtctg ctacggtctc 720
taccgctacg ctgctgtcca aggagttgcc tcgatggtct gcttctacgg agttcctctt 780
ctgattgtca acgggttctt agttttgatc acttacttgc agcacacgca tccttccctg 840
cctcactatg actcgtctga gtgggattgg ttgaggggag ctttggccac cgttgacaga 900
gactacggaa tcttgaacaa ggtcttccac aatatcacgg acacgcacgt ggcgcatcac 960
ctgttctcga ccatgccgca ttatcacgcg atggaagcta cgaaggcgat aaagccgata 1020
ctgggagagt attatcagtt cgatgggacg ccggtggtta aggcgatgtg gagggaggcg 1080

```
aaggagtgta tctatgtgga accggacagg caaggtgaga agaaaggtgt gttctggtac   1140

aacaataagt tatcttgcta a                                              1161


<210> SEQ ID NO 6
<211> LENGTH: 1134
<212> TYPE: DNA
<213> ORGANISM: Brassica napus

<400> SEQUENCE: 6

atgggtgcag gtggaagaat gcaagtctct cctccctcca gctcccccgg aaccaacacc     60

ctcaaacgcg tcccctgcga gacaccacca ttcactctcg gagacctcaa gaaagcaatc    120

ccacctcact gcttcaaacg ctccatccca cgctccttct cctcttcgac atcatcatct    180

cctcctcggc tcctccctct accacctctc cacagcctac ttccctctcc cttacctcgc    240

ctgacccctc tactgggcct gccaaggctg cgtcctaacg ggcctctggg tcatagccca    300

cgagtgcggc caccacgcct tcagcgacca ccagtggctg gacgacgccg ccggcctcgt    360

cttccactcc ttcctcctcg tcccgtactt ctcctggaag tacatccatg acgccaccat    420

tccaacaccg gatccctcga tagggacgaa gtgttcgtcc ccaagaagaa atccgacatc    480

aagtggtacg gcaagtacct caacaacccg ctaggacgca cggtgatgct aaccgtccag    540

ttcaagctcg gctggccgtt gtacttagcc ttcaacgtct cgggaagacc ttacagcgac    600

ggtttcgctt gccatttcca cccgaacgct cccatctaca acgaccgcga gcgtctccag    660

atatacatct ctgacgctgg cgtcctctcc gtatgttacg gtctctaccg ttacgctgct    720

tcgcgaggag tagcctctgt ggtctgtgtc tacggagttc cgcttctaat tgtcaactgt    780

ttcctcgtct tgatcactta cttgcagcac acgcaccctt cgctgcctca ctatgattct    840

tccgagtggg attggttgag aggagctttg gctactgtgg atagagacta tggaatcttg    900

aacaaggtgt tccataacat cacggacacg cacgtggcgc atcatctgtt ctcgacgatg    960

ccgcattata acgcgatgga agcgaccaag gcgataaagc cgatactttg gagagtatta   1020

ccagtttgat ggaacgccgg cggttaaggc gatgtggagg gaggcgaagg agtgtatcta   1080

tgttgaaccg gataggcaag gtgagaagaa aggtgtgttc tggtacaaca ataa         1134


<210> SEQ ID NO 7
<211> LENGTH: 1161
<212> TYPE: DNA
<213> ORGANISM: Brassica napus

<400> SEQUENCE: 7

atgggcgcag gtggaagaat gcaagtctct cctccctcca gctcccccga aaccaaaacc     60

ctcaaacgcg tcccctgcga gacaccaccc ttcactctcg gagacctcaa gaaagcaatc    120

ccacctcact gcttcaaacg ctccatccct cgctccttct cctacctcct cttcgacatc    180

ctcgtctcct cctccctcta ccacctctcc acagcctact tccctctcct cccccaccct    240

ctcccttacc tcgcctggcc cctctactgg gcctgccaag gctgcgtcct aacgggcctc    300

tgggtcatcg cccacgaatg cggccaccac gccttcagcg accaccagtg gctggacgac    360

gccgtgggcc tcgtcttcca ctccttcctc ctcgtccctt acttctcctg gaagtacagc    420

catcgacgcc accattccaa caccggatcc ctcgagaggg atgaagtgtt cgtccccaag    480

aagaaatccg acatcaagtg gtacggaaag tacctcaaca acccgctagg acgcacggtg    540

atgctaaccg tccagttcac gctcggctgg ccgttgtact tagccttcaa cgtctctgga    600
```

agaccttaca gcgacggttt cgcttgccat ttccacccga acgctcccat ctacaacgac 660
cgcgagcgtc tccagatata catctctgac gctggcgtcc tctccgtatg ttacggtctc 720
taccgctacg ctggttcgcg aggagtggcc tcgatggtct gtgtctacgg agttccgctt 780
atgattgtca actgtttcct cgtcttgatc acttacttgc agcacacgca cccttcgctg 840
cctcactatg attcttcgga gtgggattgg ttgagaggag ctttggctac tgtggataga 900
gactatggaa tcttgaacaa ggtgtttcat aacatcacgg acacgcacgt ggcgcatcat 960
ctgttctcga cgatgccgca ttataacgcg atggaagcga ccaaggcgat aaagccgata 1020
cttggagagt attaccagtt tgatggaacg ccggtggtta aggcgatgtg gagggaggcg 1080
aaggagtgta tctatgttga accggatagg caaggtgaga agaaaggtgt gttctggtac 1140
aacaataagt tatgaggatg a 1161

<210> SEQ ID NO 8
<211> LENGTH: 1137
<212> TYPE: DNA
<213> ORGANISM: Brassica napus

<400> SEQUENCE: 8
atgggtgcag gtggaagaat gcaagtgtct cctccctcca agaagtctga aaccgacacc 60
atcaagcgcg taccctgcga gacaccgccc ttcactgtcg gagaactcaa gaaagcaatc 120
ccaccgcact gtttcaaacg ctcgatccct cgctctttct cctacctcat ctgggacatc 180
atcatagcct cctgcttcta ctacgtcgcc accacttact tccctctcct ccctcaccct 240
ctctcctact tcgcctggcc tctctactgg gcctgccaag ggtgcgtcct aaccggcgtc 300
tgggtcatag cccacgagtg cggccaccac gccttcagcg actaccagtg gcttgacgac 360
accgtcggtc tcatcttcca ctccttcctc ctcgtccctt acttctcctg gaagtacagt 420
catcgacgcc accattccaa cactggctcc ctcgagagag acgaagtgtt tgtccccaag 480
aagaagtcag acatcaagtg gtacggcaag tacctcaaca accctttggg acgcaccgtg 540
atgttaacgg ttcagttcac tctcggctgg ccgttgtact tagccttcaa cgtctcggga 600
agaccttacg acggcggctt cgcttgccat ttccacccca acgctcccat ctacaacgac 660
cgcgagcgtc tccagatata catctccgac gctggcatcc tcgccgtctg ctacggtctc 720
ttccgttacg ccgccgcgca gggagtggcc tcgatggtct gcttctacgg agtcccgctt 780
ctgattgtca atggtttcct cgtgttgatc acttacttgc agcacacgca tccttccctg 840
cctcactacg attcgtccga gtgggattgg ttgaggggag ctttggctac cgttgacaga 900
gactacggaa tcttgaacaa ggtcttccac aatattaccg acacgcacgt ggcgcatcat 960
ctgttctcca cgatgccgca ttatcacgcg atggaagcta ccaaggcgat aaagccgata 1020
ctgggagagt attatcagtt cgatgggacg ccggtggtta aggcgatgtg gagggaggcg 1080
aaggagtgta tctatgtgga accggacagg caaggtgaga agaaaggtgt gttctgg 1137

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
atgggtgcag gtggaagaat g 21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
agcgtctcca gatatacatc 20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
atgtatatct ggagacgctc 20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
tagatacact ccttcgcctc 20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
tctttctcct acctcatctg 20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
ttcgtagctt ccatcgcgtg 20

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
gacgccacca ttccaacac 19

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
acttgccgta ccacttgatg 20

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 17
cccaaagggt tgttgaggta cttgccgt 28

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 18
cgcaccgtga tgttaacggt tcagttca 28

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 19
taagggacga ggaggaagga gtggaaga 28

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 20
ttctcctgga agtacagtca tcgacgcc 28

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 21
gtcgctgaag gcgtggtggc cgcactcg 28

<210> SEQ ID NO 22

<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 22
cagtggctgg acgacaccgt cggcctca 28

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
gagaagtaag ggacgaggag gaaggagt 28

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 24
gaagtacagt catcgacgcc accattcc 28

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25
tcccaaaggg ttgttgaggt acttgccg 28

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 26
accgtgatgt taacggttca gttcactc 28

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
gagaagtaag ggacgaggag gaaggagt 28

<210> SEQ ID NO 28
<211> LENGTH: 28

<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 28
tggaagtaca gtcatcgacg ccaccatt 28

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 29
gtagagaccg tagcagacgg cgaggatg 28

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 30
gctacgctgc tgtccaagga gttgcctc 28

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 31
gaggccaggc gaagtaggag agagggtg 28

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 32
actgggcctg ccagggctgc gtcctaac 28

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 33
gagaggccag gcgaagtagg agagaggg 28

<210> SEQ ID NO 34
<211> LENGTH: 28
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 34
actgggcctg ccagggctgc gtcctaac 28

<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 35
aggcccagta gagaggccag gcgaagta 28

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 36
ccagggctgc gtcctaaccg gcgtctgg 28

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 37
tagtcgctga aggcgtggtg gccgcact 28

<210> SEQ ID NO 38
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 38
agtggctgga cgacaccgtc ggcctcat 28

<210> SEQ ID NO 39
<211> LENGTH: 57
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
acactctttc cctacacgac gctcttccga tctacgtacc ctctcycyta cytcgcc 57

<210> SEQ ID NO 40
<211> LENGTH: 57
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
acactctttc cctacacgac gctcttccga tctcgtaccc ctctcycyta cytcgcc 57

<210> SEQ ID NO 41
<211> LENGTH: 57
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
acactctttc cctacacgac gctcttccga tctgtacgcc ctctcycyta cytcgcc 57

<210> SEQ ID NO 42
<211> LENGTH: 59
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
acactctttc cctacacgac gctcttccga tcttacgtgt catagcccac gagtgcggc 59

<210> SEQ ID NO 43
<211> LENGTH: 59
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
acactctttc cctacacgac gctcttccga tctctgacgt catagcccac gagtgcggc 59

<210> SEQ ID NO 44
<211> LENGTH: 59
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
acactctttc cctacacgac gctcttccga tcttgactgt cggcctcatc ttccactcc 59

<210> SEQ ID NO 45
<211> LENGTH: 59
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
acactctttc cctacacgac gctcttccga tctgactggt cggcctcatc ttccactcc 59

<210> SEQ ID NO 46
<211> LENGTH: 59
<212> TYPE: DNA
<213> ORGANISM: Artificial Sequence
<220> FEATURE:

<223> OTHER INFORMATION: Description of Artificial Sequence: Synthetic primer

<400> SEQUENCE: 46
acactctttc cctacacgac gctcttccga tctactgagt cggcctcatc ttccactcc 59

<210> SEQ ID NO 47
<211> LENGTH: 58
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
acactctttc cctacacgac gctcttccga tctgctagca gacatcaagt ggtacggc 58

<210> SEQ ID NO 48
<211> LENGTH: 58
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
acactctttc cctacacgac gctcttccga tctctagcca gacatcaagt ggtacggc 58

<210> SEQ ID NO 49
<211> LENGTH: 59
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
acactctttc cctacacgac gctcttccga tcttagctat ctccgacgct ggcatcctc 59

<210> SEQ ID NO 50
<211> LENGTH: 62
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
cggtctcggc attcctgctg aaccgctctt ccgatctacg tactggtagt cgctgaaggc 60
gt 62

<210> SEQ ID NO 51
<211> LENGTH: 62
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
cggtctcggc attcctgctg aaccgctctt ccgatctcgt acctggtagt cgctgaaggc 60
gt 62

<210> SEQ ID NO 52
<211> LENGTH: 62

<212> TYPE: DNA
<213> ORGANISM: Artificial Sequence
<220> FEATURE:
<223> OTHER INFORMATION: Description of Artificial Sequence: Synthetic primer

<400> SEQUENCE: 52
cggtctcggc attcctgctg aaccgctctt ccgatctgta cgctggtagt cgctgaaggc 60
gt 62

<210> SEQ ID NO 53
<211> LENGTH: 63
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
cggtctcggc attcctgctg aaccgctctt ccgatcttac gtggacgagg aggaaggagt 60
gga 63

<210> SEQ ID NO 54
<211> LENGTH: 63
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
cggtctcggc attcctgctg aaccgctctt ccgatctctg acggacgagg aggaaggagt 60
gga 63

<210> SEQ ID NO 55
<211> LENGTH: 63
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
cggtctcggc attcctgctg aaccgctctt ccgatcttga ctagtgttgg aatggtggcg 60
tcg 63

<210> SEQ ID NO 56
<211> LENGTH: 63
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
cggtctcggc attcctgctg aaccgctctt ccgatctgac tgagtgttgg aatggtggcg 60
tcg 63

<210> SEQ ID NO 57
<211> LENGTH: 63
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
cggtctcggc attcctgctg aaccgctctt ccgatctact gaagtgttgg aatggtggcg 60
tcg 63

<210> SEQ ID NO 58
<211> LENGTH: 63
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
cggtctcggc attcctgctg aaccgctctt ccgatctgct agcccgagac gttgaaggct 60
aag 63

<210> SEQ ID NO 59
<211> LENGTH: 63
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
cggtctcggc attcctgctg aaccgctctt ccgatctcta gccccgagac gttgaaggct 60
aag 63

<210> SEQ ID NO 60
<211> LENGTH: 63
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
cggtctcggc attcctgctg aaccgctctt ccgatcttag ctgaaggatg cgtgtgctgc 60
aag 63

<210> SEQ ID NO 61
<211> LENGTH: 13472
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 61
gaaatatcct tcctattcaa agttatatat atttgtttac ttttgtttta gatctggacc 60
tgagacatgt aagtacatat ttgttgaatc tttgggtaaa aacttatgtc tctgggtaaa 120
atttgctgag agatttgacc gattcctatt ggctctggat tctgtagtta cctaatacat 180
gaaaaagttt catttggcct atgctcactt catgcttata aactttttct tgcaaattaa 240
ttggattaga tgctccttca tagattcaga tgcaatagat ttgcatgaag aaaataatag 300
gattcatgat agtaaaaaga ttgtattttt gtttgtttgt ttatgtttaa aagtctatat 360
gttgacaata gagttgctat caactgtttc atttaggttt atgtttttgt caagttgctt 420
attctaagag acattgtgat tatgacttgt cttctctaac gtagtttagt aataaaagac 480

```
gaaagaaatt gatatccaca agaaagagat gtaagctgta acgtatcaaa tctcattaat    540
aactagtagt attctcaacg ctatcgttta tttctttctt tggtttgcca ctatatgccg    600
cttctctgct ctttatccca cgtactatcc attttttttg tggtagtcca ttttttttgaa    660
actttaataa cgtaacactg aatattaatt tgttggttta attaactttg agtctttgct    720
tttggtttat gcagaaacat gggtgcaggt ggaagaatgc aagtgtctcc tccctccaaa    780
aagtctgaaa ccgacaacat caagcgcgta ccctgcgaga caccgccctt cactgtcgga    840
gaactcaaga aagcaatccc accgcactgt ttcaaacgct cgatccctcg ctctttctcc    900
tacctcatct gggacatcat catagcctcc tgcttctact acgtcgccac cacttacttc    960
cctctcctcc ctcaccctct ctcctacttc gcctggcctc tctactgggc cggtaccgcc   1020
ttttgcagtt tatctctatg cccgggacaa gtggagtcca tgctcaacac cgtgcaggat   1080
gaggatgacc accgcggtag cgacttcgtg ggcgaggaaa gcctttcgtc caaggtggtc   1140
cctcctcgca atcttgttgg atggtgaata ttataaaagc ctgcccttct cgcgggtgtt   1200
taaacgtcga cctgcaggtc aacggatcag gatattcttg tttaagatgt tgaactctat   1260
ggaggtttgt atgaactgat gatctaggac cggataagtt cccttcttca tagcgaactt   1320
attcaaagaa tgttttgtgt atcattcttg ttacattgtt attaatgaaa aaatattatt   1380
ggtcattgga ctgaacacga gtgttaaata tggaccaggc cccaaataag atccattgat   1440
atatgaatta aataacaaga ataaatcgag tcaccaaacc acttgccttt tttaacgaga   1500
cttgttcacc aacttgatac aaaagtcatt atcctatgca aatcaataat catacaaaaa   1560
tatccaataa cactaaaaaa ttaaaagaaa tggataattt cacaatatgt tatacgataa   1620
agaagttact tttccaagaa attcactgat tttataagcc cacttgcatt agataaatgg   1680
caaaaaaaaa caaaaaggaa aagaaataaa gcacgaagaa ttctagaaaa tacgaaatac   1740
gcttcaatgc agtgggaccc acggttcaat tattgccaat tttcagctcc accgtatatt   1800
taaaaaataa aacgataatg ctaaaaaaat ataaatcgta acgatcgtta aatctcaacg   1860
gctggatctt atgacgaccg ttagaaattg tggttgtcga cgagtcagta ataaacggcg   1920
tcaaagtggt tgcagccggc acacacgagt cgtgtttatc aactcaaagc acaaatactt   1980
ttcctcaacc taaaaataag gcaattagcc aaaaacaact ttgcgtgtaa acaacgctca   2040
atacacgtgt cattttatta ttagctattg cttcaccgcc ttagctttct cgtgacctag   2100
tcgtcctcgt cttttcttct tcttcttcta taaaacaata cccaaagagc tcttcttctt   2160
cacaattcag atttcaattt ctcaaaatct taaaaacttt ctctcaattc tctctaccgt   2220
gatcaaggta aatttctgtg ttccttattc tctcaaaatc ttcgattttg ttttcgttcg   2280
atcccaattt cgtatatgtt ctttggttta gattctgtta atcttagatc gaagacgatt   2340
ttctgggttt gatcgttaga tatcatctta attctcgatt agggtttcat agatatcatc   2400
cgatttgttc aaataatttg agttttgtcg aataattact cttcgatttg tgatttctat   2460
ctagatctgg tgttagtttc tagtttgtgc gatcgaattt gtcgattaat ctgagttttt   2520
ctgattaaca gatggcttca tctgagaacg ttatcactga gttcatgagg ttcaaggtga   2580
ggatggaagg tactgttaac ggacatgagt tcgagatcga gggtgagggt gaaggtagac   2640
cttacgaggg acataacacc gttaagctta aggttacaaa gggtggacct cttcctttcg   2700
cttgggatat cctttctcct caattccaat acggaagcaa ggtaagtttg tggattcttc   2760
gtccatgtga tctttgagtt tctttagagc ttgtgaggga ttagtaagta acaatgcttg   2820
```

```
agttttttgc tgctgggctt cgaaaagttt gtcacttgtt ggtttgatcc acaaggtctt   2880
cttctccata gctactagac atgttttagc ttaagattca agtttatata tgccttgtgg   2940
attaatcatt gcctgattct tccgtgtcat ctctgagttt atttagagct tggaagtggt   3000
gtagtaataa ctaacaatac tcttgataag ttgtagcaat gctcttgatt agtggatgta   3060
atatgatgtt gataagatat atgaggcaca gaaccaaaag tggtgcttcc actagacccg   3120
tttttagcct aaggttcaag tttatacctt gtagatgttt ctgtattgtc tgattcttcc   3180
ctgtgatatt tgaatttctt agagctttgg aagtgatata ggaacaatgc tcttgtgtgt   3240
ttgtctctat gaagattatc gctgtcgtgt ttcatccgag tgtgcgggat tttttgctgc   3300
tgggtttagc ctttcttcaa aaagttatta cttgttagtt ttattgtttt ggtcttgata   3360
agagatgtta ggacagacat ggtgcttctt gtctatagcc actagaccta ttttagcata   3420
aggttaacga aattctctct acataccttg tggatttgtt tacattgcct gatctttcct   3480
gtgatcgctg tcatgtttct ttggaatgat tgatgtttat aaatggaaaa atctttgtgc   3540
agaagactcc cgcccatctc tctatgcccg ggacaagtgc caccccacag tggggcagga   3600
tgaggatgac caccatgggg tcgcagcgtg tgcgtgtccg tcgtacgttc tggccggccg   3660
ggccttgggc gcgcgatcag aagcgttgcg ttggcgtgtg tgtgcttctg gtttgcttta   3720
attttaccaa gtttgtttca aggtggatcg cgtggtcaag gcccgtgtgc tttaaagacc   3780
caccggcact ggcagtgagt gttgctgctt gtgtaggctt tggtacgtat gggctttatt   3840
tgcttctgga tgttgtgtac tacttgggtt tgttgaatta ttatgagcag ttgcgtattg   3900
taattcagct gggctacctg gacattgtta tgtattaata aatgctttgc tttcttctaa   3960
agatctttaa gtgctgttta aacaaccgac aaccactttg cggacttcct ttcaagagaa   4020
ttcaataagg ttaattccta attgaaatcc gaagataaga ttcccacaca cttgtggctg   4080
atatcaaaag gctactgcct atttaaacac atctctggag actgagaaaa tcagacctcc   4140
aagcatgaag aagcctgagc ttactgctac ttctgttgag aagttcctca tcgagaagtt   4200
cgattctgtg tctgatctta tgcagctctc tgagggtgag gaatcaagag ctttctcttt   4260
cgatgttggt ggaagaggat acgttctcag agttaactct tgcgctgacg gattctacaa   4320
ggatagatac gtgtacagac acttcgcttc agctgctctc cctatccctg aagttcttga   4380
tatcggagag ttctctgagt ctcttaccta ctgtatctca agaagggctc agggtgttac   4440
tcttcaagat cttcctgaga ctgagcttcc tgctgttctt caacctgttg ctgaggctat   4500
ggatgctatc gctgctgctg atctttctca aacttctgga ttcggacctt tcggtcctca   4560
gggaatcgga cagtacacta cttggagaga tttcatctgc gctatcgctg atcctcatgt   4620
ttaccattgg cagaccgtta tggatgatac cgtttctgct tctgttgctc aagctcttga   4680
tgagcttatg ctttgggctg aggattgtcc tgaggttaga catcttgttc acgctgattt   4740
cggatctaac aacgttctca ccgataacgg aagaatcacc gctgttatcg attggtctga   4800
ggctatgttc ggagattctc aatacgaggt ggccaacata ttcttttgga ggccttggct   4860
tgcttgtatg gaacaacaga ctagatactt cgagagaagg catcctgagc ttgctggatc   4920
tcctagactt agagcttaca tgcttaggat cggacttgat cagctttacc agtctctcgt   4980
tgatggaaac ttcgatgatg ctgcttgggc tcagggaaga tgtgatgcta tcgttagatc   5040
tggtgctgga actgttggaa gaactcaaat cgctagaaga tctgctgctg tttggactga   5100
tggatgtgtt gaagttctcg ctgattctgg aaacagaagg ccttctacta gacctagagc   5160
caagaagtga agatcggcgg caatagcttc ttagcgccat cccgggttga tcctatctgt   5220
```

```
gttgaaatag ttgcggtggg caaggctctc tttcagaaag acaggcggcc aaaggaaccc   5280
aaggtgaggt gggctatggc tctcagttcc ttgtggaagc gcttggtcta aggtgcagag   5340
gtgttagcgg gatgaagcaa aagtgtccga ttgtaacaag atatgttgat cctacgtaag   5400
gatattaaag tatgtattca tcactaatat aatcagtgta ttccaatatg tactacgatt   5460
tccaatgtct ttattgtcgc cgtatgtaat cggcgtcaca aaataatccc cggtgacttt   5520
cttttaatcc aggatgaaat aatatgttat tataattttt gcgatttggt ccgttatagg   5580
aattgaagtg tgcttgcggt cgccaccact cccatttcat aattttacat gtatttgaaa   5640
aataaaaatt tatggtattc aatttaaaca cgtatacttg taaagaatga tatcttgaaa   5700
gaaatatagt ttaaatattt attgataaaa taacaagtca ggtattatag tccaagcaaa   5760
aacataaatt tattgatgca agtttaaatt cagaaatatt tcaataactg attatatcag   5820
ctggtacatt gccgtagatg aaagactgag tgcgatatta tggtgtaata catagtttaa   5880
acgggcccaa gactcccgcc catctctcta tgcccgggac aagtgccacc ccacagtggg   5940
gcaggatgag gatgaccagt cagttttact tcccttaatt ttctatgtac tttcataatt   6000
acttatgtta ttttcttcat gagttttaat gcaaattact atatggactc tagtgaaaac   6060
gttcagaatc ctataaacat gactactgag acgaacttga gagtagtttt gatcatacac   6120
acgtttcatg tggtacttga gagttactaa tttttgtcat cttcgtataa gtagtaaaag   6180
atactacaag aatagtttag tagaaaatac tagcggtagg tgaagatttg tcgctatgta   6240
ctattattgt ctagtaactt gagtaacaat ttcgtggtct aaatatcaaa taaaaatgga   6300
tgagtggttc accaaatcta ggcatcaaaa ctattaatgt cattgtctag atcttaggtg   6360
acaccacatt tcgaatattt attggtaatt gagatgttaa agtaccaata tttgacttaa   6420
taaactaaaa gattttggct ttatcaaatg tagacattga tgacatatcg ttgtcattat   6480
cttgagtata tacaagtcga tcaattaggt gaaagtttag tgtctcgtgg ttggtaaacg   6540
attaatacag tagtatattt tatccaaaga caaaatccaa atcatttcac cagtatgaat   6600
agtattattt tatcttaaaa gctaaaatct taaaaaccaa ggtagcaccc acgttgagct   6660
agacgatcaa atcgatttct gctttgtcca atttaccaag ctatttaaag ccaaataatt   6720
gaaatatagg taggtcgtta tattaggcta agatttatct caaatgctta actaaaggaa   6780
taacaaggga ttctagttgt gtggttttat aagattggtc caatttcact taagtttgtt   6840
tattgtagaa ttttatatgt gaataatttg aattccaatt gaaaagatat tatagtaaaa   6900
gaaaaaatag tgcgaacaaa aactttaat cccataaaaa gaaaaagaaa aatgaaaagt   6960
tcttctaaca tccatatttt gcatcatatc ataaagataa gaaagataca tatcatagac   7020
gtacagataa acaaacatat catcatttgt gaaatacata gtacaataat ttgcttttaa   7080
atagagttta agtcacacac actgacacac acgataaaac gataatgtct gcaaaaacac   7140
tttaatccca ttgcctagag gacagcttct ccactttgtc tttaaggttg gttttgccgt   7200
gttgttttta tctttatata atgatctatt ttttggatta tgaaatgaat tcacacattt   7260
taattattta agaagatcca tatacaggtt tataacagta ctaagtgatg attattttt   7320
gtttttgcat agtttagttt attgggtaaa cattcattac gtgtctcttt atacgaatca   7380
cccatccaaa atttcaagta gtcttttagt tcatttatta tttcataact atttgactta   7440
ttgatttgac aagaaacaac aaaagtgttg acttattgat agattgtggg atcataaaag   7500
taattaagcg tcaaccacga cccacaacaa caaagcacat gttatacatt aatatctcgt   7560
```

```
ttacttaatt acagttttca gaatgccgtt tcatgtcttg tcactggcga tgttattatc   7620
atgttggaca atattcgact gttgtcgttt ttacattttc gtattgacta aaactaaaaa   7680
aacaaaactc tgtttcaggt tgggcctagg atccacattg tacacacatt tgcttaagtc   7740
tatggaggcg caaggtttta agtctgtggt tgctgttata ggccttccaa acgatccatc   7800
tgttaggttg catgaggctt tgggatacac agcccggggt acattgcgcg cagctggata   7860
caagcatggt ggatggcatg atgttggttt ttggcaaagg gattttgagt tgccagctcc   7920
tccaaggcca gttaggccag ttacccagat ctaatatcaa aatctattta gaaatacaca   7980
atattttgtt gcaggcttgc tggagaatcg atctgctatc ataaaaatta caaaaaaatt   8040
ttatttgcct caattatttt aggattggta ttaaggacgc ttaaattatt tgtcgggtca   8100
ctacgcatca ttgtgattga gaagatcagc gatacgaaat attcgtagta ctatcgataa   8160
tttatttgaa aattcataag aaaagcaaac gttacatgaa ttgatgaaac aatacaaaga   8220
cagataaagc cacgcacatt taggatattg gccgagatta ctgaatattg agtaagatca   8280
cggaatttct gacaggagca tgtcttcaat tcagcccaaa tggcagttga aatactcaaa   8340
ccgccccata tgcaggagcg gatcattcat tgtttgtttg gttgcctttg ccaacatggg   8400
agtccaaggt tgtttaaaca tttaaatacc ctgccaagct tgaggtagcc tccaatttga   8460
cggtgccgcc agcgacgccg tctggaactg tcctttttga ggaccactcc gtttgtggag   8520
atcatgagag tccatgctca acaccgtgca ctagggacag gattgaagac tcccgcccat   8580
ctcactaggg acaggattgc caccccacag tggggcctag aaagactgga gttgcagagt   8640
ttgtgtcttc tagattaatc ctccaaactt ttgattaacc aaaaaaatta tcaaactaac   8700
atgttctcct tttttcttta gaaattctaa cgaatttatc tttatactga tttgaatata   8760
cttaatttgg tcatttggat gccctttaca acctccttac caaactattg atcacagttt   8820
ctattgctaa aatcaccaac aaaacgcatg tcgccattca taattatggt ttcacaccta   8880
caactaggct aataagtaaa taagtagaca actagactca ggtttgaaaa aaccataaaa   8940
gccatatagc gttttctcat tgaaactgcg aacacgatcg tgtgaatgtt gcagtttcta   9000
gttttgatac aaacaaacaa aaacacaatt taatcttaga ttaaaaagaa aaaagagaac   9060
ggagcccact agccactcct tcaaacgtgt cttaccaact ctcttctaga aacaaattag   9120
gcttcacctt cctcttccaa cctctctctc tctctctctc tctttttctc aaaccatctc   9180
tccataaagc cctaatttct tcatcacaag aatcagaaga agaaagatgg acctgcatct   9240
aattttcggt ccaacttgca caggaaagac gacgaccgcg atagctcttg cccagcagac   9300
agggcttcca gtcctttcgc ttgatcgggt ccaatgctgt cctcaactat caaccggaag   9360
cggacgacca acagtggaag aactgaaagg aacgacgcgt ctctaccttg atgatcggcc   9420
tctggtggag ggtatcatcg cagccaagca agctcatcat aggctgatcg aggaggtgta   9480
taatcatgag gccaacggcg ggcttattct tgagggagga tccacctcgt tgctcaactg   9540
catggcgcga aacagctatt ggagtgcaga ttttcgttgg catattattc gccacaagtt   9600
acccgaccaa gagaccttca tgaaagcggc caaggccaga gttaagcaga tgttgcaccc   9660
cgctgcaggc cattctatta ttcaagagtt ggtttatctt tggaatgaac ctcggctgag   9720
gcccattctg aaagagatcg atggatatcg atatgccatg ttgtttgcta gccagaacca   9780
gatcacggca gatatgctat tgcagcttga cgcaaatatg gaaggtaagt tgattaatgg   9840
gatcgctcag gagtatttca tccatgcgcg ccaacaggaa cagaaattcc cccaagttaa   9900
cgcagccgct ttcgacggat tcgaaggtca tccgttcgga atgtattaga aatcaccagt   9960
```

```
ctctctctac aaatctatct ctctctattt ttctccagaa taatgtgtga gtagttccca  10020
gataagggaa ttagggttct tatagggttt cgctcatgtg ttgagcatat aagaaaccct  10080
tagtatgtat ttgtatttgt aaaatacttc tatcaataaa atttctaatt cctaaaacca  10140
aaatccagtg tttaaacgag tccatgctca acaccgtgca ctagggacag gattgaagac  10200
tcccgcccat ctcactaggg acaggattgc caccccacag tggggcctag aaagactgga  10260
gttgcagaca ttaaggatga ccagttcgta aaggtcctgc ggtgtctatt gcttttcata  10320
ggttaataag tgtttgctag actgtggtga aaggcctatc cgaagtaagg ccggccggat  10380
ccttcatctt tggacaaggg aataaagact ccccacttgc tactaagaac aatacctaag  10440
ttgcccagac atgactgtac ccattcagag acctaccacc cattagggct atgacactaa  10500
cactagcccc tggaggttga ccatgctagg cagtgggggt ctcacctatg acccactcag  10560
ataggggttt aaaccagtgg gtgggatctc agcctcatat aggtgtttgt ggtgagcttt  10620
ctcctagaca agagaaccct gaagaacagc aagaaccagc taatatgata tgtagacata  10680
gtgggttgct caaattttgt gtttagtcat attagaattg acctcagtga ccactcagaa  10740
agtgcccaag cccatctata ggggccaaag tgctattgac tggtgtgtct gtgaattgtt  10800
cctccctaca gagttggtgc tgatatatcc tagcattctt tggaaaacct agctagggac  10860
tgtcaagtgt aagatacctc ctgaattgga gggaacacta gctgccctgt accttctggc  10920
tagtacctta caccctgaat gggttagggg gtctattatt tgctggaaat ataccagttt  10980
cagtagggct gctgccttag gtcccacaag gtgtaacatg tgctcaatag ttgcactacc  11040
acatgcacgt gaacttaatg atgttatagc cacaacacca accttggttt gcagtttgac  11100
atccctctgg aatgggtgta gtcatcttgc tctggatctg cctgaatcat tggggctgta  11160
tgcagcctgg gcttaaagtg aagaatggga tgtcccagaa atattttggg tgagaagaat  11220
cctggagtag atggtgacct gactatccct gtcctatggg cacaatctat catcagatat  11280
tgcattcaaa gggctatcat gggatcaagt cctaagtcaa ctgttgttta cctggcagac  11340
attcatctag gagttctctt ttatgccacc ccacagtgat ccgccttttg cagtttatcc  11400
actagggaca ggattgccac cccacagtgg ggcctctatg cccgggacaa gtgtaaaata  11460
tagagtatag gggttatcat cacagagaag ctattgctgg agggcctctg ttatttcctc  11520
tccatgccac tcccattttt aacctaccaa ctgaaatccc aagggagact ccaccctgta  11580
actagagtcc tcagaggtga gccatcccat attaacaaat gggcattagg gctaggatgc  11640
caagggatac ctgaaatggg aagttgtggg gctgagtcct cctgggaatc agagataata  11700
tgtaaacagt ttgttgagag attgatgaga gctgactttg agaggtggcc atgctccctg  11760
gtcctcaata gggaaggcac tacacaagaa acctgggttt gatcaactgc actgtgtcct  11820
actcacacat tgtgtgcctg gaaaaatgtt acttagtatt tggagggcct ccagaacccc  11880
cctgggtgca agactgggtg ctagtgactg ggtgaatgag tcttggacac agtggccttg  11940
tctaggttgt gtgaggtggc taggcatcat ggcaatacct cataattgat gagtgaggaa  12000
acaagactaa gtccttgact cctcttatta catgacctgg tggatattat gtttaaactc  12060
tgcaagctgg aatgagtact gggtgcagat cccctgggat tctggctaca aaggtgaatg  12120
atagctagtc tgtttattag tagccaaaaa agtcagtgag gggtgagtgc cctgggatgt  12180
tgttaagttc acattgcaca cttggagacc ctctccatcc agtaacatac cagagaaaac  12240
tgaccaagcc ctcatgggtg tatgggaaca acaaacctcc tggctacttc aagggcacat  12300
```

```
aacaccagca aggagcctgt cataaccacc atctcaaaca atagaacttc ctaagtgaag  12360

caatgacttc aaatctactt gaaggcatgg agtataagcc atgttccttt cagaggggac  12420

tgtacttctg tagattactt tccctcatta accagatctg gccggccgca tgccagggct  12480

gcgtcctaac cggcgtctgg gtcatagccc acgagtgcgg ccaccacgcc ttcagcgact  12540

accagtggct ggacgacacc gtcggcctca tcttccactc cttcctcctc gtcccttact  12600

tctcctggaa gtacagtcat cgacgccacc attccaacac tggctccctc gagagagacg  12660

aagtgtttgt ccccaagaag aagtcagaca tcaagtggta cggcaagtac ctcaacaacc  12720

ctttgggacg caccgtgatg ttaacggttc agttcactct cggctggcct ttgtacttag  12780

ccttcaacgt ctcggggaga ccttacgacg gcggcttcgc ttgccatttc caccccaacg  12840

ctcccatcta caacgaccgt gagcgtctcc agatatacat ctccgacgct ggcatcctcg  12900

ccgtctgcta cggtctctac cgctacgctg ctgtccaagg agttgcctcg atggtctgct  12960

tctacggagt tcctcttctg attgtcaacg ggttcttagt tttgatcact tacttgcagc  13020

acacgcatcc ttccctgcct cactatgact cgtctgagtg ggattggttg aggggagctt  13080

tggccaccgt tgacagagac tacggaatct tgaacaaggt cttccacaat atcacggaca  13140

cgcacgtggc gcatcacctg ttctcgacca tgccgcatta tcacgcgatg gaagctacga  13200

aggcgataaa gccgatactg ggagagtatt atcagttcga tgggacgccg gtggttaagg  13260

cgatgtggag ggaggcgaag gagtgtatct atgtggaacc ggacaggcaa ggtgagaaga  13320

aaggtgtgtt ctggtacaac aataagttat gaagcaaaga agaaactgaa cctttctcat  13380

ctatgattgt ctttgtttta agaagctatg tttctgtttc aataatcttt aattatccat  13440

tttgttgtgt tttctgacat tttggctaaa at                                13472
```

```
<210> SEQ ID NO 62
<211> LENGTH: 5521
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
```

```
tggcaggata tattgtggtg taaacaaatt gacgcttaga caacttaata acacattgcg     60

gacgttttta atgtactgaa ttaacgccga attgaattcg agctcggtac cggggacaac    120

tttgtataga aaagttgggt ggtttaaact atgtattaca ccataatatc gcactcagtc    180

tttcatctac ggcaatgtac cagctgatat aatcagttat tgaaatattt ctgaatttaa    240

acttgcatca ataaatttat gtttttgctt ggactataat acctgacttg ttattttatc    300

aataaatatt taaactatat ttctttcaag atatcattct ttacaagtat acgtgtttaa    360

attgaatacc ataaattttt atttttcaaa tacatgtaaa attatgaaat gggagtggtg    420

gcgaccgcaa gcacacttca attcctataa cggaccaaat cgcaaaaatt ataataacat    480

attatttcat cctggattaa aagaaagtca ccggggatta ttttgtgacg ccgattacat    540

acggcgacaa taaagacatt ggaaatcgta gtacatattg gaatacactg attatattag    600

tgatgaatac atactttaat atccttacgt aggatcaaca tatcttgtta caatcggaca    660

cttttgcttc atcccgctaa cacctctgca ccttagacca agcgcttcca caaggaactg    720

agagccatag cccacctcac cttgggttcc tttggccgcc tgtctttctg aaagagagcc    780

ttgcccaccg caactatttc aacacagata ggatcaaccc gggatggcgc taagaagcta    840
```

-continued

```
ttgccgccga tcttcacttc ttggctctag gtctagtaga aggccttctg tttccagaat    900
cagcgagaac ttcaacacat ccatcagtcc aaacagcagc agatcttcta gcgatttgag    960
ttcttccaac agttccagca ccagatctaa cgatagcatc acatcttccc tgagcccaag   1020
cagcatcatc gaagtttcca tcaacgagag actggtaaag ctgatcaagt ccgatcctaa   1080
gcatgtaagc tctaagtcta ggagatccag caagctcagg atgccttctc tcgaagtatc   1140
tagtctgttg ttccatacaa gcaagccaag gcctccaaaa gaatatgttg gccacctcgt   1200
attgagaatc tccgaacata gcctcagacc aatcgataac agcggtgatt cttccgttat   1260
cggtgagaac gttgttagat ccgaaatcag cgtgaacaag atgtctaacc tcaggacaat   1320
cctcagccca aagcataagc tcatcaagag cttgagcaac agaagcagaa acggtatcat   1380
ccataacggt ctgccaatgg taaacatgag gatcagcgat agcgcagatg aaatctctcc   1440
aagtagtgta ctgtccgatt ccctgaggac cgaaaggtcc gaatccagaa gtttgagaaa   1500
gatcagcagc agcgatagca tccatagcct cagcaacagg ttgaagaaca gcaggaagct   1560
cagtctcagg aagatcttga agagtaacac cctgagccct tcttgagata cagtaggtaa   1620
gagactcaga gaactctccg atatcaagaa cttcagggat agggagagca gctgaagcga   1680
agtgtctgta cacgtatcta tccttgtaga atccgtcagc gcaagagtta actctgagaa   1740
cgtatcctct tccaccaaca tcgaaagaga aagctcttga ttcctcaccc tcagagagct   1800
gcataagatc agacacagaa tcgaacttct cgatgaggaa cttctcaaca gaagtagcag   1860
taagctcagg cttcttcatg cttggaggtc tgattttctc agtctccaga gatgtgttta   1920
aataggcagt agccttttga tatcagccac aagtgtgtgg gaatcttatc ttcggatttc   1980
aattaggaat taaccttatt gaattctctt gaaaggaagt ccgcaaagtg gttgtcggtt   2040
gtttaaacca acttttgtat acaaagttgt cccctctaga gtcgacctgc aggcatgcaa   2100
gcttagcttg agcttggatc agattgtcgt ttcccgcctt cagtttatca caagtttgta   2160
caaaaaagca ggctgtcgac ctgcaggtca acggatcagg atattcttgt ttaagatgtt   2220
gaactctatg gaggtttgta tgaactgatg atctaggacc ggataagttc ccttcttcat   2280
agcgaactta ttcaaagaat gttttgtgta tcattcttgt tacattgtta ttaatgaaaa   2340
aatattattg gtcattggac tgaacacgag tgttaaatat ggaccaggcc ccaaataaga   2400
tccattgata tatgaattaa ataacaagaa taaatcgagt caccaaacca cttgcctttt   2460
ttaacgagac ttgttcacca acttgataca aaagtcatta tcctatgcaa atcaataatc   2520
atacaaaaat atccaataac actaaaaaat taaaagaaat ggataatttc acaatatgtt   2580
atacgataaa gaagttactt ttccaagaaa ttcactgatt ttataagccc acttgcatta   2640
gataaatggc aaaaaaaaac aaaaaggaaa agaaataaag cacgaagaat tctagaaaat   2700
acgaaatacg cttcaatgca gtgggaccca cggttcaatt attgccaatt ttcagctcca   2760
ccgtatattt aaaaaataaa acgataatgc taaaaaaata taaatcgtaa cgatcgttaa   2820
atctcaacgg ctggatctta tgacgaccgt tagaaattgt ggttgtcgac gagtcagtaa   2880
taaacggcgt caaagtggtt gcagccggca cacacgagtc gtgtttatca actcaaagca   2940
caaatacttt tcctcaacct aaaaataagg caattagcca aaaacaactt tgcgtgtaaa   3000
caacgctcaa tacacgtgtc attttattat tagctattgc ttcaccgcct tagctttctc   3060
gtgacctagt cgtcctcgtc ttttcttctt cttcttctat aaaacaatac ccaaagagct   3120
cttcttcttc acaattcaga tttcaatttc tcaaaatctt aaaaactttc tctcaattct   3180
ctctaccgtg atcaaggtaa atttctgtgt tccttattct ctcaaaatct tcgattttgt   3240
```

```
tttcgttcga tcccaatttc gtatatgttc tttggtttag attctgttaa tcttagatcg   3300
aagacgattt tctgggtttg atcgttagat atcatcttaa ttctcgatta gggtttcata   3360
gatatcatcc gatttgttca aataatttga gttttgtcga ataattactc ttcgatttgt   3420
gatttctatc tagatctggt gttagtttct agtttgtgcg atcgaatttg tcgattaatc   3480
tgagtttttc tgattaacag atggcttcat ctgagaacgt tatcactgag ttcatgaggt   3540
tcaaggtgag gatggaaggt actgttaacg gacatgagtt cgagatcgag ggtgagggtg   3600
aaggtagacc ttacgaggga cataacaccg ttaagcttaa ggttacaaag ggtggacctc   3660
ttcctttcgc ttgggatatc ctttctcctc aattccaata cggaagcaag gtaagtttgt   3720
ggattcttcg tccatgtgat ctttgagttt ctttagagct tgtgagggat tagtaagtaa   3780
caatgcttga gtttttttgct gctgggcttc gaaaagtttg tcacttgttg gtttgatcca   3840
caaggtcttc ttctccatag ctactagaca tgttttagct taagattcaa gtttatatat   3900
gccttgtgga ttaatcattg cctgattctt ccgtgtcatc tctgagttta tttagagctt   3960
ggaagtggtg tagtaataac taacaatact cttgataagt tgtagcaatg ctcttgatta   4020
gtggatgtaa tatgatgttg ataagatata tgaggcacag aaccaaaagt ggtgcttcca   4080
ctagacccgt ttttagccta aggttcaagt ttataccttg tagatgtttc tgtattgtct   4140
gattcttccc tgtgatattt gaatttctta gagctttgga agtgatatag gaacaatgct   4200
cttgtgtgtt tgtctctatg aagattatcg ctgtcgtgtt tcatccgagt gtgcgggatt   4260
ttttgctgct gggtttagcc tttcttcaaa aagttattac ttgttagttt tattgttttg   4320
gtcttgataa gagatgttag gacagacatg gtgcttcttg tctatagcca ctagacctat   4380
tttagcataa ggttaacgaa attctctcta catacettgt ggatttgttt acattgcctg   4440
atctttcctg tgatcgctgt catgtttctt tggaatgatt gatgtttata aatggaaaaa   4500
tctttgtgca ggtttacgtt aagcaccctg ctgatatccc tgattacaag aagctttcat   4560
tccctgaggg attcaagtgg gagagagtta tgaacttcga ggatggtggt gttgctactg   4620
ttactcagga ttcttcactt caggacggat gcttcatcta caaggttaag ttcatcggag   4680
tgaacttccc ttctgatgga cctgttatgc agaaaaagac tatgggatgg gaggcttcta   4740
ccgagagact ttaccctaga gatggtgttc ttaagggtga gactcacaag gctcttaagc   4800
ttaaagatgg tggacactac ctcgtcgagt tcaagtctat ctacatggct aagaagcctg   4860
ttcagcttcc tggttactac tacgttgacg ctaagcttga tatcacctct cacaacgagg   4920
actacactat cgttgagcaa tacgagagaa ctgagggtag acatcacttg ttcctctgat   4980
atcaaaatct atttagaaat acacaatatt ttgttgcagg cttgctggag aatcgatctg   5040
ctatcataaa aattacaaaa aaattttatt tgcctcaatt attttaggat tggtattaag   5100
gacgcttaaa ttatttgtcg ggtcactacg catcattgtg attgagaaga tcagcgatac   5160
gaaatattcg tagtactatc gataatttat ttgaaaattc ataagaaaag caaacgttac   5220
atgaattgat gaaacaatac aaagacagat aaagccacgc acatttagga tattggccga   5280
gattactgaa tattgagtaa gatcacggaa tttctgacag gagcatgtct tcaattcagc   5340
ccaaatggca gttgaaatac tcaaaccgcc ccatatgcag gagcggatca ttcattgttt   5400
gtttggttgc ctttgccaac atgggagtcc aaggtttacc cagctttctt gtacaaagtg   5460
gtgataaact atcagtgttt gacaggatat attggcgggt aaacctaaga gaaaagagcg   5520
t                                                                   5521
```

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
cttacatgct taggatcgga cttg 24

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
agttccagca ccagatctaa cg 22

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
ccctgagccc aagcagcatc atcg 24

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
cggagagggc gtggaagg 18

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
ttcgatttgc tacagcgtca ac 22

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: Synthetic probe

<400> SEQUENCE: 68
aggcaccatc gcaggcttcg ct 22

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
cttccactcc ttcctcctcg tc 22

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
gcgtcccaaa gggttgttga g 21

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
tctctactgg gcctgccagg gc 22

<210> SEQ ID NO 72
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
ccccgagacg ttgaaggcta agtacaaa 28

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
ttgcgctgac ggattctaca agga 24

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
tccatcagtc caaacagcag caga 24

<210> SEQ ID NO 75

<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
catagcagtc tcacgtcctg gtc 23

<210> SEQ ID NO 76
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
ggaagctaag ccattacact gttcag 26

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
catagcagtc tcacgtcctg gtc 23

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 78
cctgatccgt tgacctgcag 20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 79
gtgtgaggtg gctaggcatc 20

<210> SEQ ID NO 80
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 80
ggaagctaag ccattacact gttcag 26

<210> SEQ ID NO 81
<211> LENGTH: 22

<212> TYPE: DNA
<213> ORGANISM: Artificial Sequence
<220> FEATURE:
<223> OTHER INFORMATION: Description of Artificial Sequence: Synthetic
primer

<400> SEQUENCE: 81
agagaggaga cagagagaga gt 22

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 82
agacagcatc aagatttcac aca 23

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 83
caacggcgag cgtaatctta g 21

<210> SEQ ID NO 84
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 84
gttccctgga attgctgata gg 22

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 85
tgttggtgga agaggatacg 20

<210> SEQ ID NO 86
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 86
atcagcagca gcgatagc 18

<210> SEQ ID NO 87
<211> LENGTH: 6342
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 87

```
agcttcaggg ctgcgtccta accggcgtct gggtcatagc ccacgagtgc ggccaccacg     60
ccttcagcga ctaccagtgg ctggacgaca ccgtcggcct catcttccac tccttcctcc    120
tcgtccctta cttctcctgg aagtacagtc atcgacgcca ccattccaac actggctccc    180
tcgagagaga cgaagtgttt gtccccaaga agaagtcaga catcaagtgg tacggcaagt    240
acctcaacaa ccctttggga cgcaccgtga tgttaacggt tcagttcact ctcggctggc    300
ctttgtactt agccttcaac gtctcgggga gaccttacga cggcggcttc gcttgccatt    360
tccaccccaa cgctcccatc tacaacgacc gtgagcgtct ccagatatac atctccgacg    420
ctggcatcct cgccgtctgc tacggtctct accgctacgc tgctgtccaa ggagttgcct    480
cgatggtctg cttctacgga gttcctcttc tgattgtcaa cgggttctta gttttgatca    540
cttacttgca gcacacgcat ccttccctgc ctcactatga ctcgtctgag tgggattggt    600
tgaggggagc tttggccacc gttgacagag actacggaat cttgaacaag gtcttccaca    660
atatcacgga cacgcacgtg gcgcatcacc tgttctcgac catgccgcat tatcacgcga    720
tggaagctac gaaggcgata aagccgatac tgggagagta ttatcagttc gatgggacgc    780
cggtggttaa ggcgatgtgg agggaggcga aggagtgtat ctatgtggaa ccggacaggc    840
aaggtgagaa gaaaggtgtg ttctggtaca acaataagtt atgaagcaaa gaagaaactg    900
aacctttctc atctatgatt gtctttgttt taagaagcta tgtttctgtt tcaataatct    960
ttaattatcc attttgttgt gttttctgac attttggcta aaatggcgcc acccagcttt   1020
cttgtacaaa gtggtcccct taattaactg ggcctcatgg gccttccgct cactgcccgc   1080
tttccagtcg ggaaacctgt cgtgccagct gcattaacat ggtcatagct gtttccttgc   1140
gtattgggcg ctctccgctt cctcgctcac tgactcgctg cgctcggtcg ttcgggtaaa   1200
gcctggggtg cctaatgagc aaaaggccag caaaaggcca ggaaccgtaa aaaggccgcg   1260
ttgctggcgt ttttccatag gctccgcccc cctgacgagc atcacaaaaa tcgacgctca   1320
agtcagaggt ggcgaaaccc gacaggacta taaagatacc aggcgtttcc ccctggaagc   1380
tccctcgtgc gctctcctgt tccgaccctg ccgcttaccg gatacctgtc cgcctttctc   1440
ccttcgggaa gcgtggcgct ttctcatagc tcacgctgta ggtatctcag ttcggtgtag   1500
gtcgttcgct ccaagctggg ctgtgtgcac gaaccccccg ttcagcccga ccgctgcgcc   1560
ttatccggta actatcgtct tgagtccaac ccggtaagac acgacttatc gccactggca   1620
gcagccactg gtaacaggat tagcagagcg aggtatgtag gcggtgctac agagttcttg   1680
aagtggtggc ctaactacgg ctacactaga agaacagtat ttggtatctg cgctctgctg   1740
aagccagtta ccttcggaaa aagagttggt agctcttgat ccggcaaaca aaccaccgct   1800
ggtagcggtg gtttttttgt ttgcaagcag cagattacgc gcagaaaaaa aggatctcaa   1860
gaagatcctt tgatcttttc tacggggtct gacgctcagt ggaacgaaaa ctcacgttaa   1920
gggattttgg tcatgagatt atcaaaaagg atcttcacct agatcctttt aaattaaaaa   1980
tgaagtttta aatcaatcta aagtatatat gagtaaactt ggtctgacag ttaccaatgc   2040
ttaatcagtg aggcacctat ctcagcgatc tgtctatttc gttcatccat agttgcctga   2100
ctccccgtcg tgtagataac tacgatacgg gagggcttac catctggccc cagtgctgca   2160
```

-continued

```
atgataccgc gagaaccacg ctcaccggct ccagatttat cagcaataaa ccagccagcc   2220
ggaagggccg agcgcagaag tggtcctgca actttatccg cctccatcca gtctattaat   2280
tgttgccggg aagctagagt aagtagttcg ccagttaata gtttgcgcaa cgttgttgcc   2340
attgctacag gcatcgtggt gtcacgctcg tcgtttggta tggcttcatt cagctccggt   2400
tcccaacgat caaggcgagt tacatgatcc cccatgttgt gcaaaaaagc ggttagctcc   2460
ttcggtcctc cgatcgttgt cagaagtaag ttggccgcag tgttatcact catggttatg   2520
gcagcactgc ataattctct tactgtcatg ccatccgtaa gatgcttttc tgtgactggt   2580
gagtactcaa ccaagtcatt ctgagaatag tgtatgcggc gaccgagttg ctcttgcccg   2640
gcgtcaatac gggataatac cgcgccacat agcagaactt taaaagtgct catcattgga   2700
aaacgttctt cggggcgaaa actctcaagg atcttaccgc tgttgagatc cagttcgatg   2760
taacccactc gtgcacccaa ctgatcttca gcatctttta ctttcaccag cgtttctggg   2820
tgagcaaaaa caggaaggca aaatgccgca aaaaagggaa taagggcgac acggaaatgt   2880
tgaatactca tactcttcct ttttcaatat tattgaagca tttatcaggg ttattgtctc   2940
atgagcggat acatatttga atgtatttag aaaaataaac aaataggggt tccgcgcaca   3000
tttccccgaa aagtgccacc taaattgtaa gcgttaatat tttgttaaaa ttcgcgttaa   3060
atttttgtta aatcagctca ttttttaacc aataggccga aatcggcaaa atcccttata   3120
aatcaaaaga atagaccgag atagggttga gtggccgcta cagggcgctc ccattcgcca   3180
ttcaggctgc gcaactgttg ggaagggcgt ttcggtgcgg gcctcttcgc tattacgcca   3240
gctggcgaaa gggggatgtg ctgcaaggcg attaagttgg gtaacgccag ggttttccca   3300
gtcacgacgt tgtaaaacga cggccagtga gcgcgacgta atacgactca ctatagggcg   3360
aattggcgga aggccgtcaa ggccgcatgg cgcgccgggg acaagtttgt acaaaaaagc   3420
aggctgcggc cgcgaaatat ccttcctatt caaagttata tatatttgtt tacttttgtt   3480
ttagatctgg acctgagaca tgtaagtaca tatttgttga atctttgggt aaaaacttat   3540
gtctctgggt aaaatttgct gagagatttg accgattcct attggctctg gattctgtag   3600
ttacctaata catgaaaaag tttcatttgg cctatgctca cttcatgctt ataaactttt   3660
tcttgcaaat taattggatt agatgctcct tcatagattc agatgcaata gatttgcatg   3720
aagaaaataa taggattcat gatagtaaaa agattgtatt tttgtttgtt tgtttatgtt   3780
taaaagtcta tatgttgaca atagagttgc tatcaactgt ttcatttagg tttatgtttt   3840
tgtcaagttg cttattctaa gagacattgt gattatgact tgtcttctct aacgtagttt   3900
agtaataaaa gacgaaagaa attgatatcc acaagaaaga gatgtaagct gtaacgtatc   3960
aaatctcatt aataactagt agtattctca acgctatcgt ttatttcttt ctttggtttg   4020
ccactatatg ccgcttctct gctctttatc ccacgtacta tccatttttt ttgtggtagt   4080
ccattttttt gaaactttaa taacgtaaca ctgaatatta atttgttggt ttaattaact   4140
ttgagtcttt gcttttggtt tatgcagaaa catgggtgca ggtggaagaa tgcaagtgtc   4200
tcctccctcc aaaaagtctg aaaccgacaa catcaagcgc gtaccctgcg agacaccgcc   4260
cttcactgtc ggagaactca agaaagcaat cccaccgcac tgtttcaaac gctcgatccc   4320
tcgctctttc tcctacctca tctgggacat catcatagcc tcctgcttct actacgtcgc   4380
caccacttac ttccctctcc tccctcaccc tctctcctac ttcgcctggc ctctctactg   4440
ggccaagctt aaccgacaac cactttgcgg acttcctttc aagagaattc aataaggtta   4500
attcctaatt gaaatccgaa gataagattc ccacacactt gtggctgata tcaaaaggct   4560
```

```
actgcctatt taaacacatc tctggagact gagaaaatca gacctccaag catgaagaag   4620

cctgagctta ctgctacttc tgttgagaag ttcctcatcg agaagttcga ttctgtgtct   4680

gatcttatgc agctctctga gggtgaggaa tcaagagctt tctctttcga tgttggtgga   4740

agaggatacg ttctcagagt taactcttgc gctgacggat tctacaagga tagatacgtg   4800

tacagacact tcgcttcagc tgctctccct atccctgaag ttcttgatat cggagagttc   4860

tctgagtctc ttacctactg tatctcaaga agggctcagg gtgttactct tcaagatctt   4920

cctgagactg agcttcctgc tgttcttcaa cctgttgctg aggctatgga tgctatcgct   4980

gctgctgatc tttctcaaac ttctggattc ggacctttcg gtcctcaggg aatcggacag   5040

tacactactt ggagagattt catctgcgct atcgctgatc ctcatgttta ccattggcag   5100

accgttatgg atgataccgt ttctgcttct gttgctcaag ctcttgatga gcttatgctt   5160

tgggctgagg attgtcctga ggttagacat cttgttcacg ctgatttcgg atctaacaac   5220

gttctcaccg ataacggaag aatcaccgct gttatcgatt ggtctgaggc tatgttcgga   5280

gattctcaat acgaggtggc caacatattc ttttggaggc cttggcttgc ttgtatggaa   5340

caacagacta gatacttcga gagaaggcat cctgagcttg ctggatctcc tagacttaga   5400

gcttacatgc ttaggatcgg acttgatcag ctttaccagt ctctcgttga tggaaacttc   5460

gatgatgctg cttgggctca gggaagatgt gatgctatcg ttagatctgg tgctggaact   5520

gttggaagaa ctcaaatcgc tagaagatct gctgctgttt ggactgatgg atgtgttgaa   5580

gttctcgctg attctggaaa cagaaggcct tctactagac ctagagccaa gaagtgaaga   5640

tcggcggcaa tagcttctta gcgccatccc gggttgatcc tatctgtgtt gaaatagttg   5700

cggtgggcaa ggctctcttt cagaaagaca ggcggccaaa ggaacccaag gtgaggtggg   5760

ctatggctct cagttccttg tggaagcgct tggtctaagg tgcagaggtg ttagcgggat   5820

gaagcaaaag tgtccgattg taacaagata tgttgatcct acgtaaggat attaaagtat   5880

gtattcatca ctaatataat cagtgtattc caatatgtac tacgatttcc aatgtcttta   5940

ttgtcgccgt atgtaatcgg cgtcacaaaa taatccccgg tgactttctt ttaatccagg   6000

atgaaataat atgttattat aatttttgcg atttggtccg ttataggaat tgaagtgtgc   6060

ttgcggtcgc caccactccc atttcataat tttacatgta tttgaaaaat aaaaatttat   6120

ggtattcaat ttaaacacgt atacttgtaa agaatgatat cttgaaagaa atatagttta   6180

aatatttatt gataaaataa caagtcaggt attatagtcc aagcaaaaac ataaatttat   6240

tgatgcaagt ttaaattcag aaatatttca ataactgatt atatcagctg gtacattgcc   6300

gtagatgaaa gactgagtgc gatattatgg tgtaatacat aa                      6342
```

<210> SEQ ID NO 88
<211> LENGTH: 5103
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 88

```
tatgtattac acataatatc gcactcagtc tttcatctac ggcaatgtac cagctgatat     60

aatcagttat tgaaatattt ctgaatttaa acttgcatca ataaatttat gtttttgctt    120

ggactataat acctgacttg ttattttatc aataaatatt taaactatat ttctttcaag    180

atatcattct ttacaagtat acgtgtttaa attgaatacc ataaattttt atttttcaaa    240
```

```
tacatgtaaa attatgaaat gggagtggtg gcgaccgagc tcaagcacac ttcaattcct    300
ataacggacc aaatcgcaaa aattataata acatattatt tcatcctgga ttaaaagaaa    360
gtcaccgggg attattttgt gacgccgatt acatacggcg acaataaaga cattggaaat    420
cgtagtacat attggaatac actgattata ttaatgatga atacatactt taatatcctt    480
acgtaggatc aacatatctt gttacaatcg gacacttttg cttcatcccc gctaacacct    540
ctgcacctta gaccaagcgc ttccacaagg aactgagagc catagcccac ctcaccttgg    600
gttcctttgg ccgcctgtct ttctgaaaga gagccttgcc caccgcaact atttcaacac    660
agataggatc aacccgggat ggcgctaaga agctattgcc gccgatcttc agatctgggt    720
aactggccta actggccttg gaggagctgg caactcaaaa tccctttgcc aaaaaccaac    780
atcatgccat ccaccatgct tgtatccagc tgcgcgcaat gtaccccggg ctgtgtatcc    840
caaagcctca tgcaacctaa cagatggatc gtttggaagg cctataacag caaccacaga    900
cttaaaacct tgcgcctcca tagacttaag caaatgtgtg tacaatgtgg atcctaggcc    960
caacctttga tgcctatgtg acacgtaaac agtactctca actgtccaat cgtaagcgtt   1020
cctagccttc cagggcccag cgtaagcaat accagccaca acaccctcaa cctcagcaac   1080
caaccaaggg tatctatctt gcaacctctc gagatcatca atccactctt gtggtgtttg   1140
tggctctgtc ctaaagttca ctgtagacgt ctcaatgtaa tggttaacga tatcacaaac   1200
cgcggccata tcagctgctg tagctggcct aatctcaact ggtctcctct ccggagacat   1260
tacaaactta caaatttctc tgaagttgta tcctcagtac ttcaaagaaa atagcttaca   1320
ccaaattttt tcttgttttc acaaatgccg aacttggttc cttatatagg aaaactcaag   1380
ggcaaaaatg acacggaaaa atataaaagg ataagtagtg gggataaga ttcctttgtg   1440
ataaggttac tttccgccct tacattttcc accttacatg tgtcctctat gtctctttca   1500
caatcaccga ccttatcttc ttcttttcat tgttgtcgtc agtgcttacg tcttcaagat   1560
tcttttcttc gcctggttct tctttttcaa tttctacgta ttcttcttcg tattctggca   1620
gtataggatc ttgtatctgt acattcttca tttttgaaca taggttgcat atgtgccgca   1680
tattgatctg cttcttgctg agcttacata atacttccat agtttttccc gtaaacattg   1740
gattcttgat gctacatctt ggataattac cttctggtct agagtcgaat cacaagtttg   1800
tacaaaaaag caggctgtcg acctgcaggt caacggatca ggatattctt gtttaagatg   1860
ttgaactcta tggaggtttg tatgaactga tgatctagga ccggataagt tcccttcttc   1920
atagcgaact tattcaaaga atgttttgtg tatcattctt gttacattgt tattaatgaa   1980
aaaatattat tggtcattgg actgaacacg agtgttaaat atggaccagg ccccaaataa   2040
gatccattga tatatgaatt aaataacaag aataaatcga gtcaccaaac cacttgcctt   2100
ttttaacgag acttgttcac caacttgata caaaagtcat tatcctatgc aaatcaataa   2160
tcatacaaaa atatccaata acactaaaaa attaaaagaa atggataatt tcacaatatg   2220
ttatacgata aagaagttac ttttccaaga aattcactga ttttataagc ccacttgcat   2280
tagataaatg gcaaaaaaaa acaaaaagga aaagaaataa agcacgaaga attctagaaa   2340
atacgaaata cgcttcaatg cagtgggacc cacggttcaa ttattgccaa ttttcagctc   2400
caccgtatat ttaaaaaata aaacgataat gctaaaaaaa tataaatcgt aacgatcgtt   2460
aaatctcaac ggctggatct tatgacgacc gttagaaatt gtggttgtcg acgagtcagt   2520
aataaacggc gtcaaagtgg ttgcagccgg cacacacgag tcgtgtttat caactcaaag   2580
```

```
cacaaatact tttcctcaac ctaaaaataa ggcaattagc caaaaacaac tttgcgtgta   2640
aacaacgctc aatacacgtg tcattttatt attagctatt gcttcaccgc cttagctttc   2700
tcgtgaccta gtcgtcctcg tcttttcttc ttcttcttct ataaaacaat acccaaagag   2760
ctcttcttct tcacaattca gatttcaatt tctcaaaatc ttaaaaactt tctctcaatt   2820
ctctctaccg tgatcaaggt aaatttctgt gttccttatt ctctcaaaat cttcgatttt   2880
gttttcgttc gatcccaatt tcgtatatgt tctttggttt agattctgtt aatcttagat   2940
cgaagacgat tttctgggtt tgatcgttag atatcatctt aattctcgat tagggtttca   3000
tagatatcat ccgatttgtt caaataattt gagttttgtc gaataattac tcttcgattt   3060
gtgatttcta tctagatctg gtgttagttt ctagtttgtg cgatcgaatt tgtcgattaa   3120
tctgagtttt tctgattaac agatggcttc atctgagaac gttatcactg agttcatgag   3180
gttcaaggtg aggatggaag gtactgttaa cggacatgag ttcgagatcg agggtgaggg   3240
tgaaggtaga ccttacgagg gacataacac cgttaagctt aaggttacaa agggtggacc   3300
tcttcctttc gcttgggata tcctttctcc tcaattccaa tacggaagca aggtaagttt   3360
gtggattctt cgtccatgtg atctttgagt ttctttagag cttgtgaggg attagtaagt   3420
aacaatgctt gagtttttg ctgctgggct tcgaaaagtt tgtcacttgt tggtttgatc   3480
cacaaggtct tcttctccat agctactaga catgttttag cttaagattc aagtttatat   3540
atgccttgtg gattaatcat tgcctgattc ttccgtgtca tctctgagtt tatttagagc   3600
ttggaagtgg tgtagtaata actaacaata ctcttgataa gttgtagcaa tgctcttgat   3660
tagtggatgt aatatgatgt tgataagata tatgaggcac agaaccaaaa gtggtgcttc   3720
cactagaccc gtttttagcc taaggttcaa gtttatacct tgtagatgtt tctgtattgt   3780
ctgattcttc cctgtgatat ttgaatttct tagagctttg gaagtgatat aggaacaatg   3840
ctcttgtgtg tttgtctcta tgaagattat cgctgtcgtg tttcatccga gtgtgcggga   3900
tttttgctg ctgggtttag cctttcttca aaaagttatt acttgttagt tttattgttt   3960
tggtcttgat aagagatgtt aggacagaca tggtgcttct tgtctatagc cactagacct   4020
attttagcat aaggttaacg aaattctctc tacatacctt gtggatttgt ttacattgcc   4080
tgatctttcc tgtgatcgct gtcatgtttc tttggaatga ttgatgttta taaatggaaa   4140
aatctttgtg caggtttacg ttaagcaccc tgctgatatc cctgattaca agaagctttc   4200
attccctgag ggattcaagt gggagagagt tatgaacttc gaggatggtg gtgttgctac   4260
tgttactcag gattcttcac ttcaggacgg atgcttcatc tacaaggtta agttcatcgg   4320
agtgaacttc ccttctgatg gacctgttat gcagaaaaag actatgggat gggaggcttc   4380
taccgagaga ctttacccta gagatggtgt tcttaagggt gagactcaca aggctcttaa   4440
gcttaaagat ggtggacact acctcgtcga gttcaagtct atctacatgg ctaagaagcc   4500
tgttcagctt cctggttact actacgttga cgctaagctt gatatcacct ctcacaacga   4560
ggactacact atcgttgagc aatacgagag aactgagggt agacatcact tgttcctctg   4620
atatcaaaat ctatttagaa atacacaata ttttgttgca ggcttgctgg agaatcgatc   4680
tgctatcata aaaattacaa aaaaatttta tttgcctcaa ttattttagg attggtatta   4740
aggacgctta aattatttgt cgggtcacta cgcatcattg tgattgagaa gatcagcgat   4800
acgaaatatt cgtagtacta tcgataattt atttgaaaat tcataagaaa agcaaacgtt   4860
acatgaattg atgaaacaat acaaagacag ataaagccac gcacatttag gatattggcc   4920
gagattactg aatattgagt aagatcacgg aatttctgac aggagcatgt cttcaattca   4980
```

gcccaaatgg cagttgaaat actcaaaccg ccccatatgc aggagcggat cattcattgt 5040
ttgtttggtt gcctttgcca acatgggagt ccaaggttta cccagctttc ttgtacaaag 5100
tgg 5103

<210> SEQ ID NO 89
<211> LENGTH: 8802
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtggccgct acagggcgct cccattcgcc attcaggctg cgcaactgtt 180
gggaagggcg tttcggtgcg ggcctcttcg ctattacgcc agctggcgaa agggggatgt 240
gctgcaaggc gattaagttg ggtaacgcca gggttttccc agtcacgacg ttgtaaaacg 300
acggccagtg agcgcgacgt aatacgactc actatagggc gaattggcgg aaggccgtca 360
aggccgggga caagtttgta caaaaaagca ggcttacttc gcctggcctc tctactgggc 420
ctgccagggc tgcgtcctaa ccggcgtctg ggtaccgtc gacaagcttc ttgcctcaat 480
tccggaggtg tttctagtgt tcaacatgac aaacaaaacc catctctttc agtatatgtc 540
tctcagttgt gcttaattca aatttcaact cagagaactt cttggcatac ttatccagat 600
tatctaatga tctcatctaa tggtaattca actttcagta tatgtctcgc agcaaactat 660
ctttacatca aatttttaac aactcaatgc acaaaatact tttcctcaac ctaaaaataa 720
ggcaattagc caaaaacaac tttgcgtgtg aacaacgcgt tacacgtccc tacacatacg 780
tgtcaattta taattggcta ttgcttccac gccttagctt tctcgtgacc gaccgagtcg 840
tcctcgtctt ttttgcttct ataaatcaaa tacccaaaga gctcttcttc ttcacaattc 900
agattccaat ttctcaaac tctaaaatca atctctcaaa tctctcaacc gtgatcaagg 960
tagatttctg agttcttatt gtatttcttc gatttgtttc gttcgatcgc aatttaggct 1020
ctgttctttg attttgatct cgttaatctc tgatcggagg caaattacat agtttcatcg 1080
ttagatctct tcttatttct cgattagggt tcgtattttt cgcagatctg tttattttct 1140
tgttgtttcc ttgtatttga tccgatttgt tgaaagaatt tgtgtgttct cgattattta 1200
cgctttgatc tgtgattttt atctagattt ggtgttagtt tcttgtttgt gcgatcgaat 1260
ttgtcgatta atctcggttt ttctgattaa cagatggctc aatctagcag aatctgccac 1320
ggtgtgcaga acccatgtgt gatcatttcc aatctctcca aatccaacca gaacaaatct 1380
cctttctcag tcagcctcaa gactcaccag cagcagcgtc gtgcttacca gatatctagc 1440
tggggattga agaagtcaaa caacgggtcc gtgattcgtc cggttaaggc agctgcaaga 1500
gggatgccag ccttgtcttt acctggatca aagagtatca cagctagggc actctttctt 1560
gctgctgctg ctgatggggt tactactttg gtgaggccat tgagaagtga cgacacagaa 1620
ggattcgctg aggggttagt tcgtttaggc tatcgtgtag ggaggacacc cgatacttgg 1680
caagtcgatg gcagaccaca aggaccagca gtggctgagg ctgacgtcta ctgtagagac 1740
ggagcaacca ccgctagatt cttgccaacc ttagcagctg ctggtcacgg aacatacaga 1800
tttgatgctt caccacagat gaggagacgt cctcttttgc ccttaagcag agccttgagg 1860

```
gatttgggtg tcgatcttag acacgaagaa gctgaaggtc atcaccctct gactgtccgt   1920
gctgctgggg ttgaaggagg agaggttact ttggatgctg gtcagtcaag tcagtatctc   1980
actgccttgt tgctccttgg tccccttaca agacaaggac tgaggataag ggttactgat   2040
ttggtgtcag caccatacgt ggagattacg cttgcaatga tgagggcttt cggagttgaa   2100
gtggcaaggg agggagatgt gttcgttgtt ccacctggtg gatatcgtgc aactacgtat   2160
gctatagaac ccgacgcaag tactgcttct tacttcttcg cagctgctgc tttgactcct   2220
ggagctgaag tgactgtacc tgggttaggc acgggagcac ttcaaggaga tttgggattt   2280
gtagatgtct taaggagaat gggagccgag gtgtccgtag gagctgatgc aaccactgtt   2340
agaggaactg gtgaattgcg tggccttaca gccaacatga gagacataag tgatacgatg   2400
ccgaccctcg ctgcaatagc accctttgct agtgctccag ttagaatcga ggatgttgcc   2460
aacactcgtg tcaaagaatg tgacagactt gaggcttgtg cagagaacct taggaggttg   2520
ggagtaaggg ttgcaacggg tccggactgg attgagatac accctggtcc agctactggt   2580
gctcaagtca caagctatgg tgatcacaga attgtgatgt catttgcagt gactggactt   2640
cgtgtgcctg ggatcagctt cgacgaccct ggctgtgttc gtaagacttt tcctgggttt   2700
cacgaggctt tcgcagaatt gaggcgtggc attgggagct gatgagtagt tagcttaatc   2760
acctaagatc ggcggcaata gcttcttagc gccatcccgg gttgatccta tctgtgttga   2820
aatagttgcg gtgggcaagg ctctctttca gaaagacagg cggccaaagg aacccaaggt   2880
gaggtgggct atggctctca gttccttgtg gaagcgcttg gtctaaggtg cagaggtgtt   2940
agcgggatga agcaaaagtg tccgattgta acaagatatg ttgatcctac gtaaggatat   3000
taaagtatgt attcatcact aatataatca gtgtattcca atatgtacta cgatttccaa   3060
tgtctttatt gtcgccgtat gtaatcggcg tcacaaaata atccccggtg actttctttt   3120
aatccaggat gaaataatat gttattataa tttttgcgat ttggtccgtt ataggaattg   3180
aagtgtgctt gcggtcgcca ccactcccat ttcataattt tacatgtatt tgaaaaataa   3240
aaatttatgg tattcaattt aaacacgtat acttgtaaag aatgatatct tgaaagaaat   3300
atagtttaaa tatttattga taaaataaca agtcaggtat tatagtccaa gcaaaaacat   3360
aaatttattg atgcaagttt aaattcagaa atatttcaat aactgattat atcagctggt   3420
acattgccgt agatgaaaga ctgagtgcga tattatggtg taatacatac ggccgccaga   3480
aggtaattat ccaagatgta gcatcaagaa tccaatgttt acgggaaaaa ctatggaagt   3540
attatgtaag ctcagcaaga agcagatcaa tatgcggcac atatgcaacc tatgttcaaa   3600
aatgaagaat gtacagatac aagatcctat actgccagaa tacgaagaag aatacgtaga   3660
aattgaaaaa gaagaaccag gcgaagaaaa gaatcttgaa gacgtaagca ctgacgacaa   3720
caatgaaaag aagaagataa ggtcggtgat tgtgaaagag acatagagga cacatgtaag   3780
gtggaaaatg taagggcgga aagtaacctt atcacaaagg aatcttatcc cccactactt   3840
atccttttat atttttccgt gtcatttttg cccttgagtt ttcctatata aggaaccaag   3900
ttcggcattt gtgaaaacaa gaaaaaattt ggtgtaagct attttctttg aagtactgag   3960
gatacaactt cagagaaatt tgtaagtttg taatgtctcc ggagaggaga ccagttgaga   4020
ttaggccagc tacagcagct gatatggccg cggtttgtga tatcgttaac cattacattg   4080
agacgtctac agtgaacttt aggacagagc cacaaacacc acaagagtgg attgatgatc   4140
tcgagaggtt gcaagataga taccccttggt tggttgctga ggttgagggt gttgtggctg   4200
```

```
gtattgctta cgctgggccc tggaaggcta ggaacgctta cgattggaca gttgagagta   4260
ctgtttacgt gtcacatagg catcaaaggt cagttttact tcccttaatt ttctatgtac   4320
tttcataatt acttatgtta ttttcttcat gagttttaat gcaaattact atatggactc   4380
tagtgaaaac gttcagaatc ctataaacat gactactgag acgaacttga gagtagtttt   4440
gatcatacac acgtttcatg tggtacttga gagttactaa tttttgtcat cttcgtataa   4500
gtagtaaaag atactacaag aatagtttag tagaaaatac tagcggtagg tgaagatttg   4560
tcgctatgta ctattattgt ctagtaactt gagtaacaat ttcgtggtct aaatatcaaa   4620
taaaaatgga tgagtggttc accaaatcta ggcatcaaaa ctattaatgt cattgtctag   4680
atcttaggtg acaccacatt tcgaatattt attggtaatt gagatgttaa agtaccaata   4740
tttgacttaa taaactaaaa gattttggct ttatcaaatg tagacattga tgacatatcg   4800
ttgtcattat cttgagtata tacaagtcga tcaattaggt gaaagtttag tgtctcgtgg   4860
ttggtaaacg attaatacag tagtatattt tatccaaaga caaaatccaa atcatttcac   4920
cagtatgaat agtattattt tatcttaaaa gctaaaatct taaaaaccaa ggtagcaccc   4980
acgttgagct agacgatcaa atcgatttct gctttgtcca atttaccaag ctatttaaag   5040
ccaaataatt gaaatatagg taggtcgtta tattaggcta agatttatct caaatgctta   5100
actaaaggaa taacaaggga ttctagttgt gtggttttat aagattggtc caatttcact   5160
taagtttgtt tattgtagaa ttttatatgt gaataatttg aattccaatt gaaaagatat   5220
tatagtaaaa gaaaaaatag tgcgaacaaa aaactttaat cccataaaaa gaaaaagaaa   5280
aatgaaaagt tcttctaaca tccatatttt gcatcatatc ataaagataa gaaagataca   5340
tatcatagac gtacagataa acaaacatat catcatttgt gaaatacata gtacaataat   5400
ttgcttttaa atagagttta agtcacacac actgacacac acgataaaac gataatgtct   5460
gcaaaaacac tttaatccca ttgcctagag gacagcttct ccactttgtc tttaaggttg   5520
gttttgccgt gttgttttta tctttatata atgatctatt ttttggatta tgaaatgaat   5580
tcacacattt taattattta agaagatcca tatacaggtt tataacagta ctaagtgatg   5640
attatttttt gtttttgcat agtttagttt attgggtaaa cattcattac gtgtctcttt   5700
atacgaatca cccatccaaa atttcaagta gtcttttagt tcatttatta tttcataact   5760
atttgactta ttgatttgac aagaaacaac aaaagtgttg acttattgat agattgtggg   5820
atcataaaag taattaagcg tcaaccacga cccacaacaa caaagcacat gttatacatt   5880
aatatctcgt ttacttaatt acagttttca gaatgccgtt tcatgtcttg tcactggcga   5940
tgttattatc atgttggaca atattcgact gttgtcgttt ttacattttc gtattgacta   6000
aaactaaaaa aacaaaactc tgtttcaggt tgggcctagg atccacattg tacacacatt   6060
tgcttaagtc tatggaggcg caaggtttta agtctgtggt tgctgttata ggccttccaa   6120
acgatccatc tgttaggttg catgaggctt tgggatacac agcccggggt acattgcgcg   6180
cagctggata caagcatggt ggatggcatg atgttggttt ttggcaaagg gattttgagt   6240
tgccagctcc tccaaggcca gttaggccag ttacccagat ctaatatcaa aatctattta   6300
gaaatacaca atattttgtt gcaggcttgc tggagaatcg atctgctatc ataaaaatta   6360
caaaaaaatt ttatttgcct caattatttt aggattggta ttaaggacgc ttaaattatt   6420
tgtcgggtca ctacgcatca ttgtgattga gaagatcagc gatacgaaat attcgtagta   6480
ctatcgataa tttatttgaa aattcataag aaaagcaaac gttacatgaa ttgatgaaac   6540
aatacaaaga cagataaagc cacgcacatt taggatattg gccgagatta ctgaatattg   6600
```

```
agtaagatca cggaatttct gacaggagca tgtcttcaat tcagcccaaa tggcagttga   6660
aatactcaaa ccgccccata tgcaggagcg gatcattcat tgtttgtttg gttgcctttg   6720
ccaacatggg agtccaaggt tgcatgctac ttcgcctggc ctctctactg ggcctgccag   6780
ggctgcgtcc taaccggcgt ctggacccag ctttcttgta caaagtggtc cccggcctca   6840
tgggccttcc gctcactgcc cgctttccag tcgggaaacc tgtcgtgcca gctgcattaa   6900
catggtcata gctgtttcct tgcgtattgg gcgctctccg cttcctcgct cactgactcg   6960
ctgcgctcgg tcgttcgggt aaagcctggg gtgcctaatg agcaaaaggc cagcaaaagg   7020
ccaggaaccg taaaaaggcc gcgttgctgg cgtttttcca taggctccgc ccccctgacg   7080
agcatcacaa aaatcgacgc tcaagtcaga ggtggcgaaa cccgacagga ctataaagat   7140
accaggcgtt tccccctgga agctccctcg tgcgctctcc tgttccgacc ctgccgctta   7200
ccggatacct gtccgccttt ctcccttcgg gaagcgtggc gctttctcat agctcacgct   7260
gtaggtatct cagttcggtg taggtcgttc gctccaagct gggctgtgtg cacgaacccc   7320
ccgttcagcc cgaccgctgc gccttatccg gtaactatcg tcttgagtcc aacccggtaa   7380
gacacgactt atcgccactg gcagcagcca ctggtaacag gattagcaga gcgaggtatg   7440
taggcggtgc tacagagttc ttgaagtggt ggcctaacta cggctacact agaagaacag   7500
tatttggtat ctgcgctctg ctgaagccag ttaccttcgg aaaaagagtt ggtagctctt   7560
gatccggcaa acaaaccacc gctggtagcg gtggtttttt tgtttgcaag cagcagatta   7620
cgcgcagaaa aaaaggatct caagaagatc ctttgatctt ttctacgggg tctgacgctc   7680
agtggaacga aaactcacgt taagggattt tggtcatgag attatcaaaa aggatcttca   7740
cctagatcct tttaaattaa aaatgaagtt ttaaatcaat ctaaagtata tatgagtaaa   7800
cttggtctga cagttaccaa tgcttaatca gtgaggcacc tatctcagcg atctgtctat   7860
ttcgttcatc catagttgcc tgactccccg tcgtgtagat aactacgata cgggagggct   7920
taccatctgg ccccagtgct gcaatgatac cgcgagaacc acgctcaccg gctccagatt   7980
tatcagcaat aaaccagcca gccggaaggg ccgagcgcag aagtggtcct gcaactttat   8040
ccgcctccat ccagtctatt aattgttgcc gggaagctag agtaagtagt tcgccagtta   8100
atagtttgcg caacgttgtt gccattgcta caggcatcgt ggtgtcacgc tcgtcgtttg   8160
gtatggcttc attcagctcc ggttcccaac gatcaaggcg agttacatga tcccccatgt   8220
tgtgcaaaaa agcggttagc tccttcggtc ctccgatcgt tgtcagaagt aagttggccg   8280
cagtgttatc actcatggtt atggcagcac tgcataattc tcttactgtc atgccatccg   8340
taagatgctt ttctgtgact ggtgagtact caaccaagtc attctgagaa tagtgtatgc   8400
ggcgaccgag ttgctcttgc ccggcgtcaa tacgggataa taccgcgcca catagcagaa   8460
ctttaaaagt gctcatcatt ggaaaacgtt cttcggggcg aaaactctca aggatcttac   8520
cgctgttgag atccagttcg atgtaaccca ctcgtgcacc caactgatct tcagcatctt   8580
ttactttcac cagcgtttct gggtgagcaa aaacaggaag gcaaaatgcc gcaaaaaagg   8640
gaataagggc gacacggaaa tgttgaatac tcatactctt cctttttcaa tattattgaa   8700
gcatttatca gggttattgt ctcatgagcg gatacatatt tgaatgtatt tagaaaaata   8760
aacaaatagg ggttccgcgc acatttcccc gaaaagtgcc ac                      8802
```

<210> SEQ ID NO 90
<211> LENGTH: 10272
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 90
ttgtacaaag tggtgattcg acctgcaggc atgcaagctt ggcgtaatca tggtcatagc 60
tgtttcctgt gtgaaattgt tatccgctca caattccaca caacatacga gccggaagca 120
taaagtgtaa agcctggggt gcctaatgag tgagctaact cacattaatt gcgttgcgct 180
cactgcccgc tttccagtcg ggaaacctgt cgtgccagct gcattaatga atcggccaac 240
gcgcggggag aggcggtttg cgtattgggc gctcttccgc ttcctcgctc actgactcgc 300
tgcgctcggt cgttcggctg cggcgagcgg tatcagctca ctcaaaggcg gtaatacggt 360
tatccacaga atcaggggat aacgcaggaa agaacatgtg agcaaaaggc cagcaaaagg 420
ccaggaaccg taaaaaggcc gcgttgctgg cgtttttcca taggctccgc ccccctgacg 480
agcatcacaa aaatcgacgc tcaagtcaga ggtggcgaaa cccgacagga ctataaagat 540
accaggcgtt tccccctgga agctccctcg tgcgctctcc tgttccgacc ctgccgctta 600
ccggatacct gtccgccttt ctcccttcgg gaagcgtggc gctttctcat agctcacgct 660
gtaggtatct cagttcggtg taggtcgttc gctccaagct gggctgtgtg cacgaacccc 720
ccgttcagcc cgaccgctgc gccttatccg gtaactatcg tcttgagtcc aacccggtaa 780
gacacgactt atcgccactg gcagcagcca ctggtaacag gattagcaga gcgaggtatg 840
taggcggtgc tacagagttc ttgaagtggt ggcctaacta cggctacact agaaggacag 900
tatttggtat ctgcgctctg ctgaagccag ttaccttcgg aaaaagagtt ggtagctctt 960
gatccggcaa acaaaccacc gctggtagcg gtggtttttt tgtttgcaag cagcagatta 1020
cgcgcagaaa aaaaggatct caagaagatc ctttgatctt ttctacgggg tctgacgctc 1080
agtggaacga aaactcacgt taagggattt tggtcatgag attatcaaaa aggatcttca 1140
cctagatcct tttaaattaa aaatgaagtt ttaaatcaat ctaaagtata tatgagtaaa 1200
cttggtctga cagttaccaa tgcttaatca gtgaggcacc tatctcagcg atctgtctat 1260
ttcgttcatc catagttgcc tgactccccg tcgtgtagat aactacgata cgggagggct 1320
taccatctgg ccccagtgct gcaatgatac cgcgagaccc acgctcaccg gctccagatt 1380
tatcagcaat aaaccagcca gccggaaggg ccgagcgcag aagtggtcct gcaactttat 1440
ccgcctccat ccagtctatt aattgttgcc gggaagctag agtaagtagt tcgccagtta 1500
atagtttgcg caacgttgtt gccattgcta caggcatcgt ggtgtcacgc tcgtcgtttg 1560
gtatggcttc attcagctcc ggttcccaac gatcaaggcg agttacatga tcccccatgt 1620
tgtgcaaaaa agcggttagc tccttcggtc ctccgatcgt tgtcagaagt aagttggccg 1680
cagtgttatc actcatggtt atggcagcac tgcataattc tcttactgtc atgccatccg 1740
taagatgctt ttctgtgact ggtgagtact caaccaagtc attctgagaa tagtgtatgc 1800
ggcgaccgag ttgctcttgc ccggcgtcaa tacgggataa taccgcgcca catagcagaa 1860
ctttaaaagt gctcatcatt ggaaaacgtt cttcggggcg aaaactctca aggatcttac 1920
cgctgttgag atccagttcg atgtaaccca ctcgtgcacc caactgatct tcagcatctt 1980
ttactttcac cagcgtttct gggtgagcaa aaacaggaag gcaaaatgcc gcaaaaaagg 2040
gaataagggc gacacggaaa tgttgaatac tcatactctt cctttttcaa tattattgaa 2100
gcatttatca gggttattgt ctcatgagcg gatacatatt tgaatgtatt tagaaaaata 2160

-continued

```
aacaaatagg ggttccgcgc acatttcccc gaaaagtgcc acctgacgtc taagaaacca   2220
ttattatcat gacattaacc tataaaaata ggcgtatcac gaggcccttt cgtctcgcgc   2280
gtttcggtga tgacggtgaa aacctctgac acatgcagct cccggagacg gtcacagctt   2340
gtctgtaagc ggatgccggg agcagacaag cccgtcaggg cgcgtcagcg ggtgttggcg   2400
ggtgtcgggg ctggcttaac tatgcggcat cagagcagat tgtactgaga gtgcaccata   2460
tgcggtgtga aataccgcac agatgcgtaa ggagaaaata ccgcatcagg cgccattcgc   2520
cattcaggct gcgcaactgt tgggaagggc gatcggtgcg ggcctcttcg ctattacgcc   2580
agctggcgaa agggggatgt gctgcaaggc gattaagttg ggtaacgcca gggttttccc   2640
agtcacgacg ttgtaaaacg acggccagtg aattcgagct cggtacccgg ggatcctcta   2700
gagtcgaatc acaagtttgt acaaaaaagc aggctgtaag tttgtggatt cttcgtccat   2760
gtgatctttg agtttcttta gagcttgtga gggattagta agtaacaatg cttgagtttt   2820
ttgctgctgg gcttcgaaaa gtttgtcact tgttggtttg atccacaagg tcttcttctc   2880
catagctact agacatgttt tagcttaaga ttcaagttta tatatgcctt gtggattaat   2940
cattgcctga ttcttccgtg tcatctctga gtttatttag agcttggaag tggtgtagta   3000
ataactaaca atactcttga taagttgtag caatgctctt gattagtgga tgtaatatga   3060
tgttgataag atatatgagg cacagaacca aaagtggtgc ttccactaga cccgttttta   3120
gcctaaggtt caagtttata ccttgtagat gtttctgtat tgtctgattc ttccctgtga   3180
tatttgaatt tcttagagct ttggaagtga tataggaaca atgctcttgt gtgtttgtct   3240
ctatgaagat tatcgctgtc gtgtttcatc cgagtgtgcg ggattttttg ctgctgggtt   3300
tagcctttct tcaaaaagtt attacttgtt agttttattg ttttggtctt gataagagat   3360
gttaggacag acatggtgct tcttgtctat agccactaga cctattttag cataaggtta   3420
acgaaattct ctctacatac cttgtggatt tgtttacatt gcctgatctt tcctgtgatc   3480
gctgtcatgt ttctttggaa tgattgatgt ttataaatgg aaaaatcttt gtgcaggttt   3540
aaacgtttac gttaagcacc ctgctgatat ccctgattac aagaagcttt cattccctga   3600
gggattcaag tgggagagag ttatgaactt cgaggatggt ggtgttgcta ctgttactca   3660
ggattcttca cttcaggacg gatgcttcat ctacaaggtt aagttcatcg gagtgaactt   3720
cccttctgat ggacctgtta tgcagaaaaa gactatggga tgggaggctt ctaccgagag   3780
actttaccct agagatggtg ttcttaaggg tgagactcac aaggctctta agcttaaaga   3840
tggtggacac tacctcgtcg agttcaagtc tatctacatg gctaagaagc ctgttcagct   3900
tcctggttac tactacgttg acgctaagct tgatatcacc tctcacaacg aggactacac   3960
tatcgttgag caatacgaga gaactgaggg tagacatcac ttgttcctct gatatcaaaa   4020
tctatttaga aatacacaat attttgttgc aggcttgctg gagaatcgat ctgctatcat   4080
aaaaattaca aaaaaatttt atttgcctca attattttag gattggtatt aaggacgctt   4140
aaattatttg tcgggtcact acgcatcatt gtgattgaga agatcagcga tacgaaatat   4200
tcgtagtact atcgataatt tatttgaaaa ttcataagaa aagcaaacgt tacatgaatt   4260
gatgaaacaa tacaaagaca gataaagcca cgcacattta ggatattggc cgagattact   4320
gaatattgag taagatcacg gaatttctga caggagcatg tcttcaattc agcccaaatg   4380
gcagttgaaa tactcaaacc gccccatatg caggagcgga tcattcattg tttgtttggt   4440
tgcctttgcc aacatgggag tccaaggttg ccttttgcag tttatctcta tgcccgggac   4500
aagtgaagac tcccgcccat ctcactaggg acaggattgg agtccatgct caacaccgtg   4560
```

```
caggatgagg atgaccaaca actttgtata caaaagttgt atccgaagta aataaaacca   4620
tcggactctc gtataagact gtcgacaagc ttcttgcctc aattccggag gtgtttctag   4680
tgttcaacat gacaaacaaa acccatctct ttcagtatat gtctctcagt tgtgcttaat   4740
tcaaatttca actcagagaa cttcttggca tacttatcca gattatctaa tgatctcatc   4800
taatggtaat tcaactttca gtatatgtct cgcagcaaac tatctttaca tcaaattttt   4860
aacaactcaa tgcacaaaat acttttcctc aacctaaaaa taaggcaatt agccaaaaac   4920
aactttgcgt gtgaacaacg cgttacacgt ccctacacat acgtgtcaat ttataattgg   4980
ctattgcttc cacgccttag ctttctcgtg accgaccgag tcgtcctcgt ctttttttgct   5040
tctataaatc aaatacccaa agagctcttc ttcttcacaa ttcagattcc aatttctcca   5100
aactctaaaa tcaatctctc aaatctctca accgtgatca aggtagattt ctgagttctt   5160
attgtatttc ttcgatttgt ttcgttcgat cgcaatttag gctctgttct ttgattttga   5220
tctcgttaat ctctgatcgg aggcaaatta catagtttca tcgttagatc tcttcttatt   5280
tctcgattag ggttcgtatt tttcgcagat ctgtttattt tcttgttgtt tccttgtatt   5340
tgatccgatt tgttgaaaga atttgtgtgt tctcgattat ttacgctttg atctgtgatt   5400
tttatctaga tttggtgtta gtttcttgtt tgtgcgatcg aatttgtcga ttaatctcgg   5460
tttttctgat taacagatgg ctcaatctag cagaatctgc cacggtgtgc agaacccatg   5520
tgtgatcatt tccaatctct ccaaatccaa ccagaacaaa tctcctttct cagtcagcct   5580
caagactcac cagcagcagc gtcgtgctta ccagatatct agctggggat tgaagaagtc   5640
aaacaacggg tccgtgattc gtccggttaa ggcagctgca agagggatgc cagccttgtc   5700
tttacctgga tcaaagagta tcacagctag ggcactcttt cttgctgctg ctgctgatgg   5760
ggttactact ttggtgaggc cattgagaag tgacgacaca gaaggattcg ctgaggggtt   5820
agttcgttta ggctatcgtg tagggaggac acccgatact tggcaagtcg atggcagacc   5880
acaaggacca gcagtggctg aggctgacgt ctactgtaga gacggagcaa ccaccgctag   5940
attcttgcca accttagcag ctgctggtca cggaacatac agatttgatg cttcaccaca   6000
gatgaggaga cgtcctcttt tgcccttaag cagagccttg agggatttgg gtgtcgatct   6060
tagacacgaa gaagctgaag gtcatcaccc tctgactgtc cgtgctgctg gggttgaagg   6120
aggagaggtt actttggatg ctggtcagtc aagtcagtat ctcactgcct tgttgctcct   6180
tggtcccctt acaagacaag gactgaggat aagggttact gatttggtgt cagcaccata   6240
cgtggagatt acgcttgcaa tgatgagggc tttcggagtt gaagtggcaa gggagggaga   6300
tgtgttcgtt gttccacctg gtggatatcg tgcaactacg tatgctatag aacccgacgc   6360
aagtactgct tcttacttct tcgcagctgc tgctttgact cctggagctg aagtgactgt   6420
acctgggtta ggcacgggag cacttcaagg agatttggga tttgtagatg tcttaaggag   6480
aatgggagcc gaggtgtccg taggagctga tgcaaccact gttagaggaa ctggtgaatt   6540
gcgtggcctt acagccaaca tgagagacat aagtgatacg atgccgaccc tcgctgcaat   6600
agcacccttt gctagtgctc cagttagaat cgaggatgtt gccaacactc gtgtcaaaga   6660
atgtgacaga cttgaggctt gtgcagagaa ccttaggagg ttgggagtaa gggttgcaac   6720
gggtccggac tggattgaga tacaccctgg tccagctact ggtgctcaag tcacaagcta   6780
tggtgatcac agaattgtga tgtcatttgc agtgactgga cttcgtgtgc ctgggatcag   6840
cttcgacgac cctggctgtg ttcgtaagac ttttcctggg tttcacgagg ctttcgcaga   6900
```

```
attgaggcgt ggcattggga gctgatgagt agttagctta atcacctaag atcggcggca   6960
atagcttctt agcgccatcc cgggttgatc ctatctgtgt tgaaatagtt gcggtgggca   7020
aggctctctt tcagaaagac aggcggccaa aggaacccaa ggtgaggtgg gctatggctc   7080
tcagttcctt gtggaagcgc ttggtctaag gtgcagaggt gttagcggga tgaagcaaaa   7140
gtgtccgatt gtaacaagat atgttgatcc tacgtaagga tattaaagta tgtattcatc   7200
actaatataa tcagtgtatt ccaatatgta ctacgatttc caatgtcttt attgtcgccg   7260
tatgtaatcg gcgtcacaaa ataatccccg gtgactttct tttaatccag gatgaaataa   7320
tatgttatta taatttttgc gatttggtcc gttataggaa ttgaagtgtg cttgcggtcg   7380
ccaccactcc catttcataa ttttacatgt atttgaaaaa taaaaattta tggtattcaa   7440
tttaaacacg tatacttgta aagaatgata tcttgaaaga aatatagttt aaatatttat   7500
tgataaaata acaagtcagg tattatagtc caagcaaaaa cataaattta ttgatgcaag   7560
tttaaattca gaaatatttc aataactgat tatatcagct ggtacattgc cgtagatgaa   7620
agactgagtg cgatattatg gtgtaataca tacggccgac gcataggttc atttgaagct   7680
gctattctat ttagattgaa gtttaaaccc agaaggtaat tatccaagat gtagcatcaa   7740
gaatccaatg tttacgggaa aaactatgga agtattatgt aagctcagca agaagcagat   7800
caatatgcgg cacatatgca acctatgttc aaaaatgaag aatgtacaga tacaagatcc   7860
tatactgcca gaatacgaag aagaatacgt agaaattgaa aaagaagaac caggcgaaga   7920
aaagaatctt gaagacgtaa gcactgacga caacaatgaa aagaagaaga taaggtcggt   7980
gattgtgaaa gagacataga ggacacatgt aaggtggaaa atgtaagggc ggaaagtaac   8040
cttatcacaa aggaatctta tcccccacta cttatccttt tatatttttc cgtgtcattt   8100
ttgcccttga gttttcctat ataaggaacc aagttcggca tttgtgaaaa caagaaaaaa   8160
tttggtgtaa gctattttct ttgaagtact gaggatacaa cttcagagaa atttgtaagt   8220
ttgtaatgtc tccggagagg agaccagttg agattaggcc agctacagca gctgatatgg   8280
ccgcggtttg tgatatcgtt aaccattaca ttgagacgtc tacagtgaac tttaggacag   8340
agccacaaac accacaagag tggattgatg atctcgagag gttgcaagat agataccctt   8400
ggttggttgc tgaggttgag ggtgttgtgg ctggtattgc ttacgctggg ccctggaagg   8460
ctaggaacgc ttacgattgg acagttgaga gtactgttta cgtgtcacat aggcatcaaa   8520
ggtcagtttt acttccctta attttctatg tactttcata attacttatg ttattttctt   8580
catgagtttt aatgcaaatt actatatgga ctctagtgaa aacgttcaga atcctataaa   8640
catgactact gagacgaact tgagagtagt tttgatcata cacacgtttc atgtggtact   8700
tgagagttac taatttttgt catcttcgta taagtagtaa aagatactac aagaatagtt   8760
tagtagaaaa tactagcggt aggtgaagat ttgtcgctat gtactattat tgtctagtaa   8820
cttgagtaac aatttcgtgg tctaaatatc aaataaaaat ggatgagtgg ttcaccaaat   8880
ctaggcatca aaactattaa tgtcattgtc tagatcttag gtgacaccac atttcgaata   8940
tttattggta attgagatgt taaagtacca atatttgact taataaacta aaagattttg   9000
gctttatcaa atgtagacat tgatgacata tcgttgtcat tatcttgagt atatacaagt   9060
cgatcaatta ggtgaaagtt tagtgtctcg tggttggtaa acgattaata cagtagtata   9120
ttttatccaa agacaaaatc caaatcattt caccagtatg aatagtatta ttttatctta   9180
aaagctaaaa tcttaaaaac caaggtagca cccacgttga gctagacgat caaatcgatt   9240
tctgctttgt ccaatttacc aagctattta aagccaaata attgaaatat aggtaggtcg   9300
```

```
ttatattagg ctaagattta tctcaaatgc ttaactaaag gaataacaag ggattctagt   9360

tgtgtggttt tataagattg gtccaatttc acttaagttt gtttattgta gaattttata   9420

tgtgaataat ttgaattcca attgaaaaga tattatagta aaagaaaaaa tagtgcgaac   9480

aaaaaacttt aatcccataa aaagaaaaag aaaaatgaaa agttcttcta acatccatat   9540

tttgcatcat atcataaaga taagaaagat acatatcata gacgtacaga taaacaaaca   9600

tatcatcatt tgtgaaatac atagtacaat aatttgcttt taaatagagt ttaagtcaca   9660

cacactgaca cacacgataa aacgataatg tctgcaaaaa cactttaatc ccattgccta   9720

gaggacagct tctccacttt gtctttaagg ttggttttgc cgtgttgttt ttatctttat   9780

ataatgatct attttttgga ttatgaaatg aattcacaca ttttaattat ttaagaagat   9840

ccatatacag gtttataaca gtactaagtg atgattattt tttgtttttg catagtttag   9900

tttattgggt aaacattcat tacgtgtctc tttatacgaa tcacccatcc aaaatttcaa   9960

gtagtctttt agttcattta ttatttcata actatttgac ttattgattt gacaagaaac  10020

aacaaaagtg ttgacttatt gatagattgt gggatcataa aagtaattaa gcgtcaacca  10080

cgacccacaa caacaaagca catgttatac attaatatct cgtttactta attacagttt  10140

tcagaatgcc gtttcatgtc ttgtcactgg cgatgttatt atcatgttgg acaatattcg  10200

actgttgtcg tttttacatt ttcgtattga ctaaaactaa aaaaacaaaa ctctgtttca  10260

gacccagctt tc                                                      10272
```

```
<210> SEQ ID NO 91
<211> LENGTH: 9958
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91

ttgtacaaag tggtgattcg acctgcaggc atgcaagctt ggcgtaatca tggtcatagc     60

tgtttcctgt gtgaaattgt tatccgctca caattccaca caacatacga gccggaagca    120

taaagtgtaa agcctggggt gcctaatgag tgagctaact cacattaatt gcgttgcgct    180

cactgcccgc tttccagtcg ggaaacctgt cgtgccagct gcattaatga atcggccaac    240

gcgcggggag aggcggtttg cgtattgggc gctcttccgc ttcctcgctc actgactcgc    300

tgcgctcggt cgttcggctg cggcgagcgg tatcagctca ctcaaaggcg gtaatacggt    360

tatccacaga atcaggggat aacgcaggaa agaacatgtg agcaaaaggc cagcaaaagg    420

ccaggaaccg taaaaaggcc gcgttgctgg cgtttttcca taggctccgc ccccctgacg    480

agcatcacaa aaatcgacgc tcaagtcaga ggtggcgaaa cccgacagga ctataaagat    540

accaggcgtt tccccctgga agctccctcg tgcgctctcc tgttccgacc ctgccgctta    600

ccggatacct gtccgccttt ctcccttcgg gaagcgtggc gctttctcat agctcacgct    660

gtaggtatct cagttcggtg taggtcgttc gctccaagct gggctgtgtg cacgaacccc    720

ccgttcagcc cgaccgctgc gccttatccg gtaactatcg tcttgagtcc aacccggtaa    780

gacacgactt atcgccactg gcagcagcca ctggtaacag gattagcaga gcgaggtatg    840

taggcggtgc tacagagttc ttgaagtggt ggcctaacta cggctacact agaaggacag    900

tatttggtat ctgcgctctg ctgaagccag ttaccttcgg aaaaagagtt ggtagctctt    960

gatccggcaa acaaaccacc gctggtagcg gtggtttttt tgtttgcaag cagcagatta   1020
```

```
cgcgcagaaa aaaaggatct caagaagatc ctttgatctt ttctacgggg tctgacgctc   1080
agtggaacga aaactcacgt taagggattt tggtcatgag attatcaaaa aggatcttca   1140
cctagatcct tttaaattaa aaatgaagtt ttaaatcaat ctaaagtata tatgagtaaa   1200
cttggtctga cagttaccaa tgcttaatca gtgaggcacc tatctcagcg atctgtctat   1260
ttcgttcatc catagttgcc tgactccccg tcgtgtagat aactacgata cgggagggct   1320
taccatctgg ccccagtgct gcaatgatac cgcgagaccc acgctcaccg gctccagatt   1380
tatcagcaat aaaccagcca gccggaaggg ccgagcgcag aagtggtcct gcaactttat   1440
ccgcctccat ccagtctatt aattgttgcc gggaagctag agtaagtagt tcgccagtta   1500
atagtttgcg caacgttgtt gccattgcta caggcatcgt ggtgtcacgc tcgtcgtttg   1560
gtatggcttc attcagctcc ggttcccaac gatcaaggcg agttacatga tcccccatgt   1620
tgtgcaaaaa agcggttagc tccttcggtc ctccgatcgt tgtcagaagt aagttggccg   1680
cagtgttatc actcatggtt atggcagcac tgcataattc tcttactgtc atgccatccg   1740
taagatgctt ttctgtgact ggtgagtact caaccaagtc attctgagaa tagtgtatgc   1800
ggcgaccgag ttgctcttgc ccggcgtcaa tacgggataa taccgcgcca catagcagaa   1860
ctttaaaagt gctcatcatt ggaaaacgtt cttcggggcg aaaactctca aggatcttac   1920
cgctgttgag atccagttcg atgtaaccca ctcgtgcacc caactgatct tcagcatctt   1980
ttactttcac cagcgtttct gggtgagcaa aaacaggaag gcaaaatgcc gcaaaaaagg   2040
gaataagggc gacacggaaa tgttgaatac tcatactctt cctttttcaa tattattgaa   2100
gcatttatca gggttattgt ctcatgagcg gatacatatt tgaatgtatt tagaaaaata   2160
aacaaatagg ggttccgcgc acatttcccc gaaaagtgcc acctgacgtc taagaaacca   2220
ttattatcat gacattaacc tataaaaata ggcgtatcac gaggcccttt cgtctcgcgc   2280
gtttcggtga tgacggtgaa aacctctgac acatgcagct cccggagacg gtcacagctt   2340
gtctgtaagc ggatgccggg agcagacaag cccgtcaggg cgcgtcagcg ggtgttggcg   2400
ggtgtcgggg ctggcttaac tatgcggcat cagagcagat tgtactgaga gtgcaccata   2460
tgcggtgtga aataccgcac agatgcgtaa ggagaaaata ccgcatcagg cgccattcgc   2520
cattcaggct gcgcaactgt tgggaagggc gatcggtgcg ggcctcttcg ctattacgcc   2580
agctggcgaa agggggatgt gctgcaaggc gattaagttg ggtaacgcca gggttttccc   2640
agtcacgacg ttgtaaaacg acggccagtg aattcgagct cggtacccgg ggatcctcta   2700
gagtcgaatc acaagtttgt acaaaaaagc aggctgtaag tttgtggatt cttcgtccat   2760
gtgatctttg agtttcttta gagcttgtga gggattagta agtaacaatg cttgagtttt   2820
ttgctgctgg gcttcgaaaa gtttgtcact tgttggtttg atccacaagg tcttcttctc   2880
catagctact agacatgttt tagcttaaga ttcaagttta tatatgcctt gtggattaat   2940
cattgcctga ttcttccgtg tcatctctga gtttatttag agcttggaag tggtgtagta   3000
ataactaaca atactcttga taagttgtag caatgctctt gattagtgga tgtaatatga   3060
tgttgataag atatatgagg cacagaacca aaagtggtgc ttccactaga cccgttttta   3120
gcctaaggtt caagtttata ccttgtagat gtttctgtat tgtctgattc ttccctgtga   3180
tatttgaatt tcttagagct ttggaagtga tataggaaca atgctcttgt gtgtttgtct   3240
ctatgaagat tatcgctgtc gtgtttcatc cgagtgtgcg ggattttttg ctgctgggtt   3300
tagcctttct tcaaaaagtt attacttgtt agttttattg ttttggtctt gataagagat   3360
```

```
gttaggacag acatggtgct tcttgtctat agccactaga cctattttag cataaggtta   3420
acgaaattct ctctacatac cttgtggatt tgtttacatt gcctgatctt tcctgtgatc   3480
gctgtcatgt ttctttggaa tgattgatgt ttataaatgg aaaaatcttt gtgcaggttt   3540
aaacgtttac gttaagcacc ctgctgatat ccctgattac aagaagcttt cattccctga   3600
gggattcaag tgggagagag ttatgaactt cgaggatggt ggtgttgcta ctgttactca   3660
ggattcttca cttcaggacg gatgcttcat ctacaaggtt aagttcatcg gagtgaactt   3720
cccttctgat ggacctgtta tgcagaaaaa gactatggga tgggaggctt ctaccgagag   3780
actttaccct agagatggtg ttcttaaggg tgagactcac aaggctctta agcttaaaga   3840
tggtggacac tacctcgtcg agttcaagtc tatctacatg gctaagaagc ctgttcagct   3900
tcctggttac tactacgttg acgctaagct tgatatcacc tctcacaacg aggactacac   3960
tatcgttgag caatacgaga gaactgaggg tagacatcac ttgttcctct gatatcaaaa   4020
tctatttaga aatacacaat attttgttgc aggcttgctg gagaatcgat ctgctatcat   4080
aaaaattaca aaaaaatttt atttgcctca attattttag gattggtatt aaggacgctt   4140
aaattatttg tcgggtcact acgcatcatt gtgattgaga agatcagcga tacgaaatat   4200
tcgtagtact atcgataatt tatttgaaaa ttcataagaa aagcaaacgt tacatgaatt   4260
gatgaaacaa tacaaagaca gataaagcca cgcacattta ggatattggc cgagattact   4320
gaatattgag taagatcacg gaatttctga caggagcatg tcttcaattc agcccaaatg   4380
gcagttgaaa tactcaaacc gccccatatg caggagcgga tcattcattg tttgtttggt   4440
tgcctttgcc aacatgggag tccaaggttg ccttttgcag tttatctcta tgcccgggac   4500
aagtgaagac tcccgcccat ctcactaggg acaggattgg agtccatgct caacaccgtg   4560
caggatgagg atgaccaaca actttgtata caaaagttgt atccgaagta aataaaacca   4620
tcggactctc gtataagact gtcgacgaga tttttcaaat cagtgcgcta gacgtgacgt   4680
aagtatccga gtcagttttt atttttctac taatttggtc gtttatttcg gcgtgtagga   4740
catggcaacc gggcctgaat ttcgcgggta ttctgtttct attccaactt tttcttgatc   4800
cgcagccatt aacgactttt gaatagatac gtctagggtc gagggggggat ccgtcgaggg   4860
ggtccaccaa aaacgtaagc gcttacgtac atggtcgagg gggtccacca aaaacgtaag   4920
cgcttacgta catggtcgag gggggtccacc aaaaacgtaa gcgcttacgt acatggtcga   4980
gggggtccac caaaaacgta agcgcttacg tacatgctcg actagagcgt gacgctcgcg   5040
gtgacgccat ttcgcctttt cagaaatgga taaatagcct tgcttcctat tatatcttcc   5100
caaattacca atacattaca ctagcatctg aatttcataa ccaatctcga tacaccaaat   5160
cgatggctca atctagcaga atctgccacg gtgtgcagaa cccatgtgtg atcatttcca   5220
atctctccaa atccaaccag aacaaatctc ctttctcagt cagcctcaag actcaccagc   5280
agcagcgtcg tgcttaccag atatctagct ggggattgaa gaagtcaaac aacgggtccg   5340
tgattcgtcc ggttaaggca gctgcaagag ggatgccagc cttgtcttta cctggatcaa   5400
agagtatcac agctagggca ctctttcttg ctgctgctgc tgatggggtt actactttgg   5460
tgaggccatt gagaagtgac gacacagaag gattcgctga ggggttagtt cgtttaggct   5520
atcgtgtagg gaggacaccc gatacttggc aagtcgatgg cagaccacaa ggaccagcag   5580
tggctgaggc tgacgtctac tgtagagacg gagcaaccac cgctagattc ttgccaacct   5640
tagcagctgc tggtcacgga acatacagat ttgatgcttc accacagatg aggagacgtc   5700
ctcttttgcc cttaagcaga gccttgaggg atttgggtgt cgatcttaga cacgaagaag   5760
```

```
ctgaaggtca tcaccctctg actgtccgtg ctgctggggt tgaaggagga gaggttactt   5820
tggatgctgg tcagtcaagt cagtatctca ctgccttgtt gctccttggt ccccttacaa   5880
gacaaggact gaggataagg gttactgatt tggtgtcagc accatacgtg gagattacgc   5940
ttgcaatgat gagggctttc ggagttgaag tggcaaggga gggagatgtg ttcgttgttc   6000
cacctggtgg atatcgtgca actacgtatg ctatagaacc cgacgcaagt actgcttctt   6060
acttcttcgc agctgctgct ttgactcctg gagctgaagt gactgtacct gggttaggca   6120
cgggagcact tcaaggagat ttgggatttg tagatgtctt aaggagaatg ggagccgagg   6180
tgtccgtagg agctgatgca accactgtta gaggaactgg tgaattgcgt ggccttacag   6240
ccaacatgag agacataagt gatacgatgc cgaccctcgc tgcaatagca ccctttgcta   6300
gtgctccagt tagaatcgag gatgttgcca acactcgtgt caaagaatgt gacagacttg   6360
aggcttgtgc agagaacctt aggaggttgg gagtaagggt tgcaacgggt ccggactgga   6420
ttgagataca ccctggtcca gctactggtg ctcaagtcac aagctatggt gatcacagaa   6480
ttgtgatgtc atttgcagtg actggacttc gtgtgcctgg gatcagcttc gacgaccctg   6540
gctgtgttcg taagactttt cctgggtttc acgaggcttt cgcagaattg aggcgtggca   6600
ttgggagctg atgagtagtt agcttaatca cctaagatcg gcggcaatag cttcttagcg   6660
ccatcccggg ttgatcctat ctgtgttgaa atagttgcgg tgggcaaggc tctctttcag   6720
aaagacaggc ggccaaagga acccaaggtg aggtgggcta tggctctcag ttccttgtgg   6780
aagcgcttgg tctaaggtgc agaggtgtta gcgggatgaa gcaaaagtgt ccgattgtaa   6840
caagatatgt tgatcctacg taaggatatt aaagtatgta ttcatcacta atataatcag   6900
tgtattccaa tatgtactac gatttccaat gtctttattg tcgccgtatg taatcggcgt   6960
cacaaaataa tccccggtga ctttctttta atccaggatg aaataatatg ttattataat   7020
ttttgcgatt tggtccgtta taggaattga agtgtgcttg cggtcgccac cactcccatt   7080
tcataatttt acatgtattt gaaaaataaa aatttatggt attcaattta aacacgtata   7140
cttgtaaaga atgatatctt gaaagaaata tagtttaaat atttattgat aaaataacaa   7200
gtcaggtatt atagtccaag caaaaacata aatttattga tgcaagttta aattcagaaa   7260
tatttcaata actgattata tcagctggta cattgccgta gatgaaagac tgagtgcgat   7320
attatggtgt aatacatacg gccgacgcat aggttcattt gaagctgcta ttctatttag   7380
attgaagttt aaacccagaa ggtaattatc caagatgtag catcaagaat ccaatgttta   7440
cgggaaaaac tatggaagta ttatgtaagc tcagcaagaa gcagatcaat atgcggcaca   7500
tatgcaacct atgttcaaaa atgaagaatg tacagataca agatcctata ctgccagaat   7560
acgaagaaga atacgtagaa attgaaaaag aagaaccagg cgaagaaaag aatcttgaag   7620
acgtaagcac tgacgacaac aatgaaaaga agaagataag gtcggtgatt gtgaaagaga   7680
catagaggac acatgtaagg tggaaaatgt aagggcggaa agtaacctta tcacaaagga   7740
atcttatccc ccactactta tccttttata tttttccgtg tcatttttgc ccttgagttt   7800
tcctatataa ggaaccaagt tcggcatttg tgaaaacaag aaaaaatttg gtgtaagcta   7860
ttttctttga agtactgagg atacaacttc agagaaattt gtaagtttgt aatgtctccg   7920
gagaggagac cagttgagat taggccagct acagcagctg atatggccgc ggtttgtgat   7980
atcgttaacc attacattga gacgtctaca gtgaacttta ggacagagcc acaaacacca   8040
caagagtgga ttgatgatct cgagaggttg caagatagat acccttggtt ggttgctgag   8100
```

```
gttgagggtg ttgtggctgg tattgcttac gctgggccct ggaaggctag gaacgcttac   8160
gattggacag ttgagagtac tgtttacgtg tcacataggc atcaaaggtc agttttactt   8220
cccttaattt tctatgtact ttcataatta cttatgttat tttcttcatg agttttaatg   8280
caaattacta tatggactct agtgaaaacg ttcagaatcc tataaacatg actactgaga   8340
cgaacttgag agtagttttg atcatacaca cgtttcatgt ggtacttgag agttactaat   8400
ttttgtcatc ttcgtataag tagtaaaaga tactacaaga atagtttagt agaaaatact   8460
agcggtaggt gaagatttgt cgctatgtac tattattgtc tagtaacttg agtaacaatt   8520
tcgtggtcta aatatcaaat aaaaatggat gagtggttca ccaaatctag gcatcaaaac   8580
tattaatgtc attgtctaga tcttaggtga caccacattt cgaatattta ttggtaattg   8640
agatgttaaa gtaccaatat ttgacttaat aaactaaaag attttggctt tatcaaatgt   8700
agacattgat gacatatcgt tgtcattatc ttgagtatat acaagtcgat caattaggtg   8760
aaagtttagt gtctcgtggt tggtaaacga ttaatacagt agtatatttt atccaaagac   8820
aaaatccaaa tcatttcacc agtatgaata gtattatttt atcttaaaag ctaaaatctt   8880
aaaaaccaag gtagcaccca cgttgagcta gacgatcaaa tcgatttctg ctttgtccaa   8940
tttaccaagc tatttaaagc caaataattg aaatataggt aggtcgttat attaggctaa   9000
gatttatctc aaatgcttaa ctaaaggaat aacaagggat tctagttgtg tggttttata   9060
agattggtcc aatttcactt aagtttgttt attgtagaat tttatatgtg aataatttga   9120
attccaattg aaaagatatt atagtaaaag aaaaaatagt gcgaacaaaa aactttaatc   9180
ccataaaaag aaaaagaaaa atgaaaagtt cttctaacat ccatattttg catcatatca   9240
taaagataag aaagatacat atcatagacg tacagataaa caaacatatc atcatttgtg   9300
aaatacatag tacaataatt tgcttttaaa tagagtttaa gtcacacaca ctgacacaca   9360
cgataaaacg ataatgtctg caaaaacact ttaatcccat tgcctagagg acagcttctc   9420
cactttgtct ttaaggttgg ttttgccgtg ttgtttttat ctttatataa tgatctattt   9480
tttggattat gaaatgaatt cacacatttt aattatttaa gaagatccat atacaggttt   9540
ataacagtac taagtgatga ttattttttg tttttgcata gtttagttta ttgggtaaac   9600
attcattacg tgtctcttta tacgaatcac ccatccaaaa tttcaagtag tcttttagtt   9660
catttattat ttcataacta tttgacttat tgatttgaca agaaacaaca aaagtgttga   9720
cttattgata gattgtggga tcataaaagt aattaagcgt caaccacgac ccacaacaac   9780
aaagcacatg ttatacatta atatctcgtt tacttaatta cagttttcag aatgccgttt   9840
catgtcttgt cactggcgat gttattatca tgttggacaa tattcgactg ttgtcgtttt   9900
tacattttcg tattgactaa aactaaaaaa acaaaactct gtttcagacc cagctttc     9958
```

<210> SEQ ID NO 92
<211> LENGTH: 10735
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 92

```
ctaaattgta agcgttaata ttttgttaaa attcgcgtta aatttttgtt aaatcagctc     60
atttttaac caataggccg aaatcggcaa aatcccttat aaatcaaaag aatagaccga    120
gatagggttg agtggccgct acagggcgct cccattcgcc attcaggctg cgcaactgtt    180
```

```
gggaagggcg tttcggtgcg ggcctcttcg ctattacgcc agctggcgaa agggggatgt    240
gctgcaaggc gattaagttg ggtaacgcca gggttttccc agtcacgacg ttgtaaaacg    300
acggccagtg agcgcgacgt aatacgactc actatagggc gaattggcgg aaggccgtca    360
aggccgcatg gcgcgccggg gacaagtttg tacaaaaaag caggctgcgg ccgcgaaata    420
tccttcctat tcaaagttat atatatttgt ttacttttgt tttagatctg gacctgagac    480
atgtaagtac atatttgttg aatctttggg taaaaactta tgtctctggg taaaatttgc    540
tgagagattt gaccgattcc tattggctct ggattctgta gttacctaat acatgaaaaa    600
gtttcatttg gcctatgctc acttcatgct tataaacttt ttcttgcaaa ttaattggat    660
tagatgctcc ttcatagatt cagatgcaat agatttgcat gaagaaaata ataggattca    720
tgatagtaaa aagattgtat ttttgtttgt ttgtttatgt ttaaaagtct atatgttgac    780
aatagagttg ctatcaactg tttcatttag gtttatgttt ttgtcaagtt gcttattcta    840
agagacattg tgattatgac ttgtcttctc taacgtagtt tagtaataaa agacgaaaga    900
aattgatatc cacaagaaag agatgtaagc tgtaacgtat caaatctcat taataactag    960
tagtattctc aacgctatcg tttatttctt tctttggttt gccactatat gccgcttctc   1020
tgctctttat cccacgtact atccattttt tttgtggtag tccatttttt tgaaacttta   1080
ataacgtaac actgaatatt aatttgttgg tttaattaac tttgagtctt tgcttttggt   1140
ttatgcagaa acatgggtgc aggtggaaga atgcaagtgt ctcctccctc caaaaagtct   1200
gaaaccgaca acatcaagcg cgtaccctgc gagacaccgc ccttcactgt cggagaactc   1260
aagaaagcaa tcccaccgca ctgtttcaaa cgctcgatcc ctcgctcttt ctcctacctc   1320
atctgggaca tcatcatagc ctcctgcttc tactacgtcg ccaccactta cttccctctc   1380
ctccctcacc ctctctccta cttcgcctgg cctctctact gggccggtac cgtcgacaag   1440
cttcttgcct caattccgga ggtgtttcta gtgttcaaca tgacaaacaa aacccatctc   1500
tttcagtata tgtctctcag ttgtgcttaa ttcaaatttc aactcagaga acttcttggc   1560
atacttatcc agattatcta atgatctcat ctaatggtaa ttcaactttc agtatatgtc   1620
tcgcagcaaa ctatctttac atcaaatttt taacaactca atgcacaaaa tacttttcct   1680
caacctaaaa ataaggcaat tagccaaaaa caactttgcg tgtgaacaac gcgttacacg   1740
tccctacaca tacgtgtcaa tttataattg gctattgctt ccacgcctta gctttctcgt   1800
gaccgaccga gtcgtcctcg tctttttgc ttctataaat caaataccca aagagctctt   1860
cttcttcaca attcagattc caattttctc aaactctaaa atcaatctct caaatctctc   1920
aaccgtgatc aaggtagatt tctgagttct tattgtattt cttcgatttg tttcgttcga   1980
tcgcaattta ggctctgttc tttgattttg atctcgttaa tctctgatcg gaggcaaatt   2040
acatagtttc atcgttagat ctcttcttat ttctcgatta gggttcgtat ttttcgcaga   2100
tctgtttatt ttcttgttgt ttccttgtat ttgatccgat ttgttgaaag aatttgtgtg   2160
ttctcgatta tttacgcttt gatctgtgat ttttatctag atttggtgtt agtttcttgt   2220
ttgtgcgatc gaatttgtcg attaatctcg gtttttctga ttaacagatg gctcaatcta   2280
gcagaatctg ccacggtgtg cagaacccat gtgtgatcat ttccaatctc tccaaatcca   2340
accagaacaa atctcctttc tcagtcagcc tcaagactca ccagcagcag cgtcgtgctt   2400
accagatatc tagctgggga ttgaagaagt caaacaacgg gtccgtgatt cgtccggtta   2460
aggcagctgc aagagggatg ccagccttgt ctttacctgg atcaaagagt atcacagcta   2520
gggcactctt tcttgctgct gctgctgatg gggttactac tttggtgagg ccattgagaa   2580
```

```
gtgacgacac agaaggattc gctgaggggt tagttcgttt aggctatcgt gtagggagga   2640
cacccgatac ttggcaagtc gatggcagac cacaaggacc agcagtggct gaggctgacg   2700
tctactgtag agacggagca accaccgcta gattcttgcc aaccttagca gctgctggtc   2760
acggaacata cagatttgat gcttcaccac agatgaggag acgtcctctt ttgcccttaa   2820
gcagagcctt gagggatttg ggtgtcgatc ttagacacga agaagctgaa ggtcatcacc   2880
ctctgactgt ccgtgctgct ggggttgaag gaggagaggt tactttggat gctggtcagt   2940
caagtcagta tctcactgcc ttgttgctcc ttggtcccct tacaagacaa ggactgagga   3000
taagggttac tgatttggtg tcagcaccat acgtggagat tacgcttgca atgatgaggg   3060
ctttcggagt tgaagtggca agggagggag atgtgttcgt tgttccacct ggtggatatc   3120
gtgcaactac gtatgctata gaacccgacg caagtactgc ttcttacttc ttcgcagctg   3180
ctgctttgac tcctggagct gaagtgactg tacctgggtt aggcacggga gcacttcaag   3240
gagatttggg atttgtagat gtcttaagga gaatgggagc cgaggtgtcc gtaggagctg   3300
atgcaaccac tgttagagga actggtgaat tgcgtggcct tacagccaac atgagagaca   3360
taagtgatac gatgccgacc ctcgctgcaa tagcaccctt tgctagtgct ccagttagaa   3420
tcgaggatgt tgccaacact cgtgtcaaag aatgtgacag acttgaggct tgtgcagaga   3480
accttaggag gttgggagta agggttgcaa cgggtccgga ctggattgag atacaccctg   3540
gtccagctac tggtgctcaa gtcacaagct atggtgatca cagaattgtg atgtcatttg   3600
cagtgactgg acttcgtgtg cctgggatca gcttcgacga ccctggctgt gttcgtaaga   3660
cttttcctgg gtttcacgag gctttcgcag aattgaggcg tggcattggg agctgatgag   3720
tagttagctt aatcacctaa gatcggcggc aatagcttct tagcgccatc ccgggttgat   3780
cctatctgtg ttgaaatagt tgcggtgggc aaggctctct ttcagaaaga caggcggcca   3840
aaggaaccca aggtgaggtg ggctatggct ctcagttcct tgtggaagcg cttggtctaa   3900
ggtgcagagg tgttagcggg atgaagcaaa agtgtccgat tgtaacaaga tatgttgatc   3960
ctacgtaagg atattaaagt atgtattcat cactaatata atcagtgtat tccaatatgt   4020
actacgattt ccaatgtctt tattgtcgcc gtatgtaatc ggcgtcacaa aataatcccc   4080
ggtgactttc ttttaatcca ggatgaaata atatgttatt ataatttttg cgatttggtc   4140
cgttatagga attgaagtgt gcttgcggtc gccaccactc ccatttcata attttacatg   4200
tatttgaaaa ataaaaattt atggtattca atttaaacac gtatacttgt aaagaatgat   4260
atcttgaaag aaatatagtt taaatattta ttgataaaat aacaagtcag gtattatagt   4320
ccaagcaaaa acataaattt attgatgcaa gtttaaattc agaaatattt caataactga   4380
ttatatcagc tggtacattg ccgtagatga aagactgagt gcgatattat ggtgtaatac   4440
atacggccgc cagaaggtaa ttatccaaga tgtagcatca agaatccaat gtttacggga   4500
aaaactatgg aagtattatg taagctcagc aagaagcaga tcaatatgcg gcacatatgc   4560
aacctatgtt caaaaatgaa gaatgtacag atacaagatc ctatactgcc agaatacgaa   4620
gaagaatacg tagaaattga aaaagaagaa ccaggcgaag aaaagaatct tgaagacgta   4680
agcactgacg acaacaatga aaagaagaag ataaggtcgg tgattgtgaa agagacatag   4740
aggacacatg taaggtggaa aatgtaaggg cggaaagtaa ccttatcaca aaggaatctt   4800
atcccccact acttatcctt ttatattttt ccgtgtcatt tttgcccttg agttttccta   4860
tataaggaac caagttcggc atttgtgaaa acaagaaaaa atttggtgta agctattttc   4920
```

```
tttgaagtac tgaggataca acttcagaga aatttgtaag tttgtaatgt ctccggagag   4980
gagaccagtt gagattaggc cagctacagc agctgatatg gccgcggttt gtgatatcgt   5040
taaccattac attgagacgt ctacagtgaa ctttaggaca gagccacaaa caccacaaga   5100
gtggattgat gatctcgaga ggttgcaaga tagataccct tggttggttg ctgaggttga   5160
gggtgttgtg gctggtattg cttacgctgg gccctggaag gctaggaacg cttacgattg   5220
gacagttgag agtactgttt acgtgtcaca taggcatcaa aggtcagttt tacttccctt   5280
aattttctat gtactttcat aattacttat gttattttct tcatgagttt taatgcaaat   5340
tactatatgg actctagtga aaacgttcag aatcctataa acatgactac tgagacgaac   5400
ttgagagtag ttttgatcat acacacgttt catgtggtac ttgagagtta ctaatttttg   5460
tcatcttcgt ataagtagta aaagatacta caagaatagt ttagtagaaa atactagcgg   5520
taggtgaaga tttgtcgcta tgtactatta ttgtctagta acttgagtaa caatttcgtg   5580
gtctaaatat caaataaaaa tggatgagtg gttcaccaaa tctaggcatc aaaactatta   5640
atgtcattgt ctagatctta ggtgacacca catttcgaat atttattggt aattgagatg   5700
ttaaagtacc aatatttgac ttaataaact aaaagatttt ggctttatca aatgtagaca   5760
ttgatgacat atcgttgtca ttatcttgag tatatacaag tcgatcaatt aggtgaaagt   5820
ttagtgtctc gtggttggta aacgattaat acagtagtat attttatcca aagacaaaat   5880
ccaaatcatt tcaccagtat gaatagtatt attttatctt aaaagctaaa atcttaaaaa   5940
ccaaggtagc acccacgttg agctagacga tcaaatcgat ttctgctttg tccaatttac   6000
caagctattt aaagccaaat aattgaaata taggtaggtc gttatattag gctaagattt   6060
atctcaaatg cttaactaaa ggaataacaa gggattctag ttgtgtggtt ttataagatt   6120
ggtccaattt cacttaagtt tgtttattgt agaattttat atgtgaataa tttgaattcc   6180
aattgaaaag atattatagt aaaagaaaaa atagtgcgaa caaaaaactt taatcccata   6240
aaaagaaaaa gaaaaatgaa aagttcttct aacatccata ttttgcatca tatcataaag   6300
ataagaaaga tacatatcat agacgtacag ataaacaaac atatcatcat ttgtgaaata   6360
catagtacaa taatttgctt ttaaatagag tttaagtcac acacactgac acacacgata   6420
aaacgataat gtctgcaaaa acactttaat cccattgcct agaggacagc ttctccactt   6480
tgtctttaag gttggttttg ccgtgttgtt tttatcttta tataatgatc tattttttgg   6540
attatgaaat gaattcacac attttaatta tttaagaaga tccatataca ggtttataac   6600
agtactaagt gatgattatt ttttgttttt gcatagttta gtttattggg taaacattca   6660
ttacgtgtct ctttatacga atcacccatc caaaatttca agtagtcttt tagttcattt   6720
attatttcat aactatttga cttattgatt tgacaagaaa caacaaaagt gttgacttat   6780
tgatagattg tgggatcata aaagtaatta agcgtcaacc acgacccaca acaacaaagc   6840
acatgttata cattaatatc tcgtttactt aattacagtt ttcagaatgc cgtttcatgt   6900
cttgtcactg gcgatgttat tatcatgttg gacaatattc gactgttgtc gtttttacat   6960
tttcgtattg actaaaacta aaaaaacaaa actctgtttc aggttgggcc taggatccac   7020
attgtacaca catttgctta agtctatgga ggcgcaaggt tttaagtctg tggttgctgt   7080
tataggcctt ccaaacgatc catctgttag gttgcatgag gctttgggat acacagcccg   7140
gggtacattg cgcgcagctg gatacaagca tggtggatgg catgatgttg gtttttggca   7200
aagggatttt gagttgccag ctcctccaag gccagttagg ccagttaccc agatctaata   7260
tcaaaatcta tttagaaata cacaatattt tgttgcaggc ttgctggaga atcgatctgc   7320
```

```
tatcataaaa attacaaaaa aattttattt gcctcaatta ttttaggatt ggtattaagg   7380
acgcttaaat tatttgtcgg gtcactacgc atcattgtga ttgagaagat cagcgatacg   7440
aaatattcgt agtactatcg ataatttatt tgaaaattca taagaaaagc aaacgttaca   7500
tgaattgatg aaacaataca aagacagata aagccacgca catttaggat attggccgag   7560
attactgaat attgagtaag atcacggaat ttctgacagg agcatgtctt caattcagcc   7620
caaatggcag ttgaaatact caaaccgccc catatgcagg agcggatcat tcattgtttg   7680
tttggttgcc tttgccaaca tgggagtcca aggttgcatg ccagggctgc gtcctaaccg   7740
gcgtctgggt catagcccac gagtgcggcc accacgcctt cagcgactac cagtggctgg   7800
acgacaccgt cggcctcatc ttccactcct tcctcctcgt cccttacttc tcctggaagt   7860
acagtcatcg acgccaccat tccaacactg gctccctcga gagagacgaa gtgtttgtcc   7920
ccaagaagaa gtcagacatc aagtggtacg gcaagtacct caacaaccct ttgggacgca   7980
ccgtgatgtt aacggttcag ttcactctcg gctggccttt gtacttagcc ttcaacgtct   8040
cggggagacc ttacgacggc ggcttcgctt gccatttcca ccccaacgct cccatctaca   8100
acgaccgtga gcgtctccag atatacatct ccgacgctgg catcctcgcc gtctgctacg   8160
gtctctaccg ctacgctgct gtccaaggag ttgcctcgat ggtctgcttc tacggagttc   8220
ctcttctgat tgtcaacggg ttcttagttt tgatcactta cttgcagcac acgcatcctt   8280
ccctgcctca ctatgactcg tctgagtggg attggttgag gggagctttg gccaccgttg   8340
acagagacta cggaatcttg aacaaggtct tccacaatat cacggacacg cacgtggcgc   8400
atcacctgtt ctcgaccatg ccgcattatc acgcgatgga agctacgaag gcgataaagc   8460
cgatactggg agagtattat cagttcgatg ggacgccggt ggttaaggcg atgtggaggg   8520
aggcgaagga gtgtatctat gtggaaccgg acaggcaagg tgagaagaaa ggtgtgttct   8580
ggtacaacaa taagttatga agcaaagaag aaactgaacc tttctcatct atgattgtct   8640
ttgttttaag aagctatgtt tctgtttcaa taatctttaa ttatccattt tgttgtgttt   8700
tctgacattt tggctaaaat ggcgccaccc agctttcttg tacaaagtgg tccccttaat   8760
taactgggcc tcatgggcct tccgctcact gcccgctttc cagtcgggaa acctgtcgtg   8820
ccagctgcat taacatggtc atagctgttt ccttgcgtat tgggcgctct ccgcttcctc   8880
gctcactgac tcgctgcgct cggtcgttcg ggtaaagcct ggggtgccta atgagcaaaa   8940
ggccagcaaa aggccaggaa ccgtaaaaag gccgcgttgc tggcgttttt ccataggctc   9000
cgcccccctg acgagcatca caaaaatcga cgctcaagtc agaggtggcg aaacccgaca   9060
ggactataaa gataccaggc gtttccccct ggaagctccc tcgtgcgctc tcctgttccg   9120
accctgccgc ttaccggata cctgtccgcc tttctccctt cgggaagcgt ggcgctttct   9180
catagctcac gctgtaggta tctcagttcg gtgtaggtcg ttcgctccaa gctgggctgt   9240
gtgcacgaac cccccgttca gcccgaccgc tgcgccttat ccggtaacta tcgtcttgag   9300
tccaacccgg taagacacga cttatcgcca ctggcagcag ccactggtaa caggattagc   9360
agagcgaggt atgtaggcgg tgctacagag ttcttgaagt ggtggcctaa ctacggctac   9420
actagaagaa cagtatttgg tatctgcgct ctgctgaagc cagttacctt cggaaaaaga   9480
gttggtagct cttgatccgg caaacaaacc accgctggta gcggtggttt ttttgtttgc   9540
aagcagcaga ttacgcgcag aaaaaaagga tctcaagaag atcctttgat cttttctacg   9600
gggtctgacg ctcagtggaa cgaaaactca cgttaaggga ttttggtcat gagattatca   9660
```

aaaaggatct tcacctagat ccttttaaat taaaaatgaa gttttaaatc aatctaaagt 9720
atatatgagt aaacttggtc tgacagttac caatgcttaa tcagtgaggc acctatctca 9780
gcgatctgtc tatttcgttc atccatagtt gcctgactcc ccgtcgtgta gataactacg 9840
atacgggagg gcttaccatc tggccccagt gctgcaatga taccgcgaga accacgctca 9900
ccggctccag atttatcagc aataaaccag ccagccggaa gggccgagcg cagaagtggt 9960
cctgcaactt tatccgcctc catccagtct attaattgtt gccgggaagc tagagtaagt 10020
agttcgccag ttaatagttt gcgcaacgtt gttgccattg ctacaggcat cgtggtgtca 10080
cgctcgtcgt ttggtatggc ttcattcagc tccggttccc aacgatcaag gcgagttaca 10140
tgatccccca tgttgtgcaa aaaagcggtt agctccttcg gtcctccgat cgttgtcaga 10200
agtaagttgg ccgcagtgtt atcactcatg gttatggcag cactgcataa ttctcttact 10260
gtcatgccat ccgtaagatg cttttctgtg actggtgagt actcaaccaa gtcattctga 10320
gaatagtgta tgcggcgacc gagttgctct tgcccggcgt caatacggga taataccgcg 10380
ccacatagca gaactttaaa agtgctcatc attggaaaac gttcttcggg gcgaaaactc 10440
tcaaggatct taccgctgtt gagatccagt tcgatgtaac ccactcgtgc acccaactga 10500
tcttcagcat cttttacttt caccagcgtt tctgggtgag caaaaacagg aaggcaaaat 10560
gccgcaaaaa agggaataag ggcgacacgg aaatgttgaa tactcatact cttccttttt 10620
caatattatt gaagcattta tcagggttat tgtctcatga gcggatacat atttgaatgt 10680
atttagaaaa ataaacaaat aggggttccg cgcacatttc cccgaaaagt gccac 10735

<210> SEQ ID NO 93
<211> LENGTH: 10421
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 93
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtggccgct acagggcgct cccattcgcc attcaggctg cgcaactgtt 180
gggaagggcg tttcggtgcg ggcctcttcg ctattacgcc agctggcgaa agggggatgt 240
gctgcaaggc gattaagttg ggtaacgcca gggttttccc agtcacgacg ttgtaaaacg 300
acggccagtg agcgcgacgt aatacgactc actatagggc gaattggcgg aaggccgtca 360
aggccgcatg gcgcgccggg gacaagtttg tacaaaaaag caggctgcgg ccgcgaaata 420
tccttcctat tcaaagttat atatatttgt ttacttttgt tttagatctg gacctgagac 480
atgtaagtac atatttgttg aatctttggg taaaaactta tgtctctggg taaaatttgc 540
tgagagattt gaccgattcc tattggctct ggattctgta gttacctaat acatgaaaaa 600
gtttcatttg gcctatgctc acttcatgct tataaacttt ttcttgcaaa ttaattggat 660
tagatgctcc ttcatagatt cagatgcaat agatttgcat gaagaaaata ataggattca 720
tgatagtaaa aagattgtat ttttgtttgt ttgtttatgt ttaaaagtct atatgttgac 780
aatagagttg ctatcaactg tttcatttag gtttatgttt ttgtcaagtt gcttattcta 840
agagacattg tgattatgac ttgtcttctc taacgtagtt tagtaataaa agacgaaaga 900
aattgatatc cacaagaaag agatgtaagc tgtaacgtat caaatctcat taataactag 960

```
tagtattctc aacgctatcg tttatttctt tctttggttt gccactatat gccgcttctc   1020
tgctctttat cccacgtact atccattttt tttgtggtag tccatttttt tgaaacttta   1080
ataacgtaac actgaatatt aatttgttgg tttaattaac tttgagtctt tgcttttggt   1140
ttatgcagaa acatgggtgc aggtggaaga atgcaagtgt ctcctccctc caaaaagtct   1200
gaaaccgaca acatcaagcg cgtaccctgc gagacaccgc ccttcactgt cggagaactc   1260
aagaaagcaa tcccaccgca ctgtttcaaa cgctcgatcc ctcgctcttt ctcctacctc   1320
atctgggaca tcatcatagc ctcctgcttc tactacgtcg ccaccactta cttccctctc   1380
ctccctcacc ctctctccta cttcgcctgg cctctctact gggccggtac cgtcgacgag   1440
atttttcaaa tcagtgcgct agacgtgacg taagtatccg agtcagtttt tatttttcta   1500
ctaatttggt cgtttatttc ggcgtgtagg acatggcaac cgggcctgaa tttcgcgggt   1560
attctgtttc tattccaact tttcttgat ccgcagccat taacgacttt tgaatagata   1620
cgtctagggt cgaggggga tccgtcgagg gggtccacca aaaacgtaag cgcttacgta   1680
catggtcgag ggggtccacc aaaaaacgtaa gcgcttacgt acatggtcga gggggtccac   1740
caaaaacgta agcgcttacg tacatggtcg agggggtcca ccaaaaaacgt aagcgcttac   1800
gtacatgctc gactagagcg tgacgctcgc ggtgacgcca tttcgccttt tcagaaatgg   1860
ataaatagcc ttgcttccta ttatatcttc ccaaattacc aatacattac actagcatct   1920
gaatttcata accaatctcg atacaccaaa tcgatggctc aatctagcag aatctgccac   1980
ggtgtgcaga acccatgtgt gatcatttcc aatctctcca aatccaacca gaacaaatct   2040
cctttctcag tcagcctcaa gactcaccag cagcagcgtc gtgcttacca gatatctagc   2100
tggggattga agaagtcaaa caacgggtcc gtgattcgtc cggttaaggc agctgcaaga   2160
gggatgccag ccttgtcttt acctggatca aagagtatca cagctagggc actctttctt   2220
gctgctgctg ctgatggggt tactactttg gtgaggccat tgagaagtga cgacacagaa   2280
ggattcgctg aggggttagt tcgtttaggc tatcgtgtag ggaggacacc cgatacttgg   2340
caagtcgatg gcagaccaca aggaccagca gtggctgagg ctgacgtcta ctgtagagac   2400
ggagcaacca ccgctagatt cttgccaacc ttagcagctg ctggtcacgg aacatacaga   2460
tttgatgctt caccacagat gaggagacgt cctcttttgc ccttaagcag agccttgagg   2520
gatttgggtg tcgatcttag acacgaagaa gctgaaggtc atcaccctct gactgtccgt   2580
gctgctgggg ttgaaggagg agaggttact ttggatgctg gtcagtcaag tcagtatctc   2640
actgccttgt tgctccttgg tcccttaca agacaaggac tgaggataag ggttactgat   2700
ttggtgtcag caccatacgt ggagattacg cttgcaatga tgagggcttt cggagttgaa   2760
gtggcaaggg agggagatgt gttcgttgtt ccacctggtg gatatcgtgc aactacgtat   2820
gctatagaac ccgacgcaag tactgcttct tacttcttcg cagctgctgc tttgactcct   2880
ggagctgaag tgactgtacc tgggttaggc acgggagcac ttcaaggaga tttgggattt   2940
gtagatgtct taaggagaat gggagccgag gtgtccgtag gagctgatgc aaccactgtt   3000
agaggaactg gtgaattgcg tggccttaca gccaacatga gagacataag tgatacgatg   3060
ccgaccctcg ctgcaatagc acccttttgct agtgctccag ttagaatcga ggatgttgcc   3120
aacactcgtg tcaaagaatg tgacagactt gaggcttgtg cagagaacct taggaggttg   3180
ggagtaaggg ttgcaacggg tccggactgg attgagatac accctggtcc agctactggt   3240
gctcaagtca caagctatgg tgatcacaga attgtgatgt catttgcagt gactggactt   3300
cgtgtgcctg ggatcagctt cgacgaccct ggctgtgttc gtaagacttt tcctgggttt   3360
```

```
cacgaggctt tcgcagaatt gaggcgtggc attgggagct gatgagtagt tagcttaatc   3420
acctaagatc ggcggcaata gcttcttagc gccatcccgg gttgatccta tctgtgttga   3480
aatagttgcg gtgggcaagg ctctctttca gaaagacagg cggccaaagg aacccaaggt   3540
gaggtgggct atggctctca gttccttgtg gaagcgcttg gtctaaggtg cagaggtgtt   3600
agcgggatga agcaaaagtg tccgattgta acaagatatg ttgatcctac gtaaggatat   3660
taaagtatgt attcatcact aatataatca gtgtattcca atatgtacta cgatttccaa   3720
tgtctttatt gtcgccgtat gtaatcggcg tcacaaaata atccccggtg actttctttt   3780
aatccaggat gaaataatat gttattataa tttttgcgat ttggtccgtt ataggaattg   3840
aagtgtgctt gcggtcgcca ccactcccat ttcataattt tacatgtatt tgaaaaataa   3900
aaatttatgg tattcaattt aaacacgtat acttgtaaag aatgatatct tgaaagaaat   3960
atagtttaaa tatttattga taaaataaca agtcaggtat tatagtccaa gcaaaaacat   4020
aaatttattg atgcaagttt aaattcagaa atatttcaat aactgattat atcagctggt   4080
acattgccgt agatgaaaga ctgagtgcga tattatggtg taatacatac ggccgccaga   4140
aggtaattat ccaagatgta gcatcaagaa tccaatgttt acgggaaaaa ctatggaagt   4200
attatgtaag ctcagcaaga agcagatcaa tatgcggcac atatgcaacc tatgttcaaa   4260
aatgaagaat gtacagatac aagatcctat actgccagaa tacgaagaag aatacgtaga   4320
aattgaaaaa gaagaaccag gcgaagaaaa gaatcttgaa gacgtaagca ctgacgacaa   4380
caatgaaaag aagaagataa ggtcggtgat tgtgaaagag acatagagga cacatgtaag   4440
gtggaaaatg taagggcgga aagtaacctt atcacaaagg aatcttatcc cccactactt   4500
atccttttat atttttccgt gtcatttttg cccttgagtt ttcctatata aggaaccaag   4560
ttcggcattt gtgaaaacaa gaaaaaattt ggtgtaagct attttctttg aagtactgag   4620
gatacaactt cagagaaatt tgtaagtttg taatgtctcc ggagaggaga ccagttgaga   4680
ttaggccagc tacagcagct gatatggccg cggtttgtga tatcgttaac cattacattg   4740
agacgtctac agtgaacttt aggacagagc cacaaacacc acaagagtgg attgatgatc   4800
tcgagaggtt gcaagataga tacccttggt tggttgctga ggttgagggt gttgtggctg   4860
gtattgctta cgctgggccc tggaaggcta ggaacgctta cgattggaca gttgagagta   4920
ctgtttacgt gtcacatagg catcaaaggt cagttttact tcccttaatt ttctatgtac   4980
tttcataatt acttatgtta ttttcttcat gagttttaat gcaaattact atatggactc   5040
tagtgaaaac gttcagaatc ctataaacat gactactgag acgaacttga gagtagtttt   5100
gatcatacac acgtttcatg tggtacttga gagttactaa tttttgtcat cttcgtataa   5160
gtagtaaaag atactacaag aatagtttag tagaaaatac tagcggtagg tgaagatttg   5220
tcgctatgta ctattattgt ctagtaactt gagtaacaat ttcgtggtct aaatatcaaa   5280
taaaaatgga tgagtggttc accaaatcta ggcatcaaaa ctattaatgt cattgtctag   5340
atcttaggtg acaccacatt tcgaatattt attggtaatt gagatgttaa agtaccaata   5400
tttgacttaa taaactaaaa gattttggct ttatcaaatg tagacattga tgacatatcg   5460
ttgtcattat cttgagtata tacaagtcga tcaattaggt gaaagtttag tgtctcgtgg   5520
ttggtaaacg attaatacag tagtatattt tatccaaaga caaaatccaa atcatttcac   5580
cagtatgaat agtattattt tatcttaaaa gctaaaatct taaaaaccaa ggtagcaccc   5640
acgttgagct agacgatcaa atcgatttct gctttgtcca atttaccaag ctatttaaag   5700
```

-continued

```
ccaaataatt gaaatatagg taggtcgtta tattaggcta agatttatct caaatgctta   5760
actaaaggaa taacaaggga ttctagttgt gtggttttat aagattggtc caatttcact   5820
taagtttgtt tattgtagaa ttttatatgt gaataatttg aattccaatt gaaaagatat   5880
tatagtaaaa gaaaaaatag tgcgaacaaa aaactttaat cccataaaaa gaaaaagaaa   5940
aatgaaaagt tcttctaaca tccatatttt gcatcatatc ataaagataa gaaagataca   6000
tatcatagac gtacagataa acaaacatat catcatttgt gaaatacata gtacaataat   6060
ttgcttttaa atagagttta agtcacacac actgacacac acgataaaac gataatgtct   6120
gcaaaaacac tttaatccca ttgcctagag gacagcttct ccactttgtc tttaaggttg   6180
gttttgccgt gttgttttta tctttatata atgatctatt ttttggatta tgaaatgaat   6240
tcacacattt taattattta agaagatcca tatacaggtt tataacagta ctaagtgatg   6300
attatttttt gtttttgcat agtttagttt attgggtaaa cattcattac gtgtctcttt   6360
atacgaatca cccatccaaa atttcaagta gtcttttagt tcatttatta tttcataact   6420
atttgactta ttgatttgac aagaaacaac aaaagtgttg acttattgat agattgtggg   6480
atcataaaag taattaagcg tcaaccacga cccacaacaa caaagcacat gttatacatt   6540
aatatctcgt ttacttaatt acagttttca gaatgccgtt tcatgtcttg tcactggcga   6600
tgttattatc atgttggaca atattcgact gttgtcgttt ttacattttc gtattgacta   6660
aaactaaaaa aacaaaactc tgtttcaggt tgggcctagg atccacattg tacacacatt   6720
tgcttaagtc tatggaggcg caaggtttta agtctgtggt tgctgttata ggccttccaa   6780
acgatccatc tgttaggttg catgaggctt tgggatacac agcccggggt acattgcgcg   6840
cagctggata caagcatggt ggatggcatg atgttggttt ttggcaaagg gattttgagt   6900
tgccagctcc tccaaggcca gttaggccag ttacccagat ctaatatcaa aatctattta   6960
gaaatacaca atattttgtt gcaggcttgc tggagaatcg atctgctatc ataaaaatta   7020
caaaaaaatt ttatttgcct caattatttt aggattggta ttaaggacgc ttaaattatt   7080
tgtcgggtca ctacgcatca ttgtgattga gaagatcagc gatacgaaat attcgtagta   7140
ctatcgataa tttatttgaa aattcataag aaaagcaaac gttacatgaa ttgatgaaac   7200
aatacaaaga cagataaagc cacgcacatt taggatattg gccgagatta ctgaatattg   7260
agtaagatca cggaatttct gacaggagca tgtcttcaat tcagcccaaa tggcagttga   7320
aatactcaaa ccgccccata tgcaggagcg gatcattcat tgtttgtttg gttgcctttg   7380
ccaacatggg agtccaaggt tgcatgccag ggctgcgtcc taaccggcgt ctgggtcata   7440
gcccacgagt gcggccacca cgccttcagc gactaccagt ggctggacga caccgtcggc   7500
ctcatcttcc actccttcct cctcgtccct tacttctcct ggaagtacag tcatcgacgc   7560
caccattcca acactggctc cctcgagaga gacgaagtgt ttgtccccaa gaagaagtca   7620
gacatcaagt ggtacggcaa gtacctcaac aaccctttgg gacgcaccgt gatgttaacg   7680
gttcagttca ctctcggctg gcctttgtac ttagccttca acgtctcggg gagaccttac   7740
gacggcggct tcgcttgcca tttccacccc aacgctccca tctacaacga ccgtgagcgt   7800
ctccagatat acatctccga cgctggcatc ctcgccgtct gctacggtct ctaccgctac   7860
gctgctgtcc aaggagttgc ctcgatggtc tgcttctacg gagttcctct tctgattgtc   7920
aacgggttct tagttttgat cacttacttg cagcacacgc atccttccct gcctcactat   7980
gactcgtctg agtgggattg gttgagggga gctttggcca ccgttgacag agactacgga   8040
atcttgaaca aggtcttcca caatatcacg gacacgcacg tggcgcatca cctgttctcg   8100
```

```
accatgccgc attatcacgc gatggaagct acgaaggcga taaagccgat actgggagag   8160
tattatcagt tcgatgggac gccggtggtt aaggcgatgt ggagggaggc gaaggagtgt   8220
atctatgtgg aaccggacag gcaaggtgag aagaaaggtg tgttctggta caacaataag   8280
ttatgaagca aagaagaaac tgaacctttc tcatctatga ttgtctttgt tttaagaagc   8340
tatgtttctg tttcaataat ctttaattat ccattttgtt gtgttttctg acattttggc   8400
taaaatggcg ccacccagct ttcttgtaca aagtggtccc cttaattaac tgggcctcat   8460
gggccttccg ctcactgccc gctttccagt cgggaaacct gtcgtgccag ctgcattaac   8520
atggtcatag ctgtttcctt gcgtattggg cgctctccgc ttcctcgctc actgactcgc   8580
tgcgctcggt cgttcgggta aagcctgggg tgcctaatga gcaaaaggcc agcaaaaggc   8640
caggaaccgt aaaaaggccg cgttgctggc gtttttccat aggctccgcc cccctgacga   8700
gcatcacaaa aatcgacgct caagtcagag gtggcgaaac ccgacaggac tataaagata   8760
ccaggcgttt ccccctggaa gctccctcgt gcgctctcct gttccgaccc tgccgcttac   8820
cggatacctg tccgcctttc tcccttcggg aagcgtggcg ctttctcata gctcacgctg   8880
taggtatctc agttcggtgt aggtcgttcg ctccaagctg ggctgtgtgc acgaaccccc   8940
cgttcagccc gaccgctgcg ccttatccgg taactatcgt cttgagtcca acccggtaag   9000
acacgactta tcgccactgg cagcagccac tggtaacagg attagcagag cgaggtatgt   9060
aggcggtgct acagagttct tgaagtggtg gcctaactac ggctacacta gaagaacagt   9120
atttggtatc tgcgctctgc tgaagccagt taccttcgga aaaagagttg gtagctcttg   9180
atccggcaaa caaaccaccg ctggtagcgg tggttttttt gtttgcaagc agcagattac   9240
gcgcagaaaa aaaggatctc aagaagatcc tttgatcttt tctacggggt ctgacgctca   9300
gtggaacgaa aactcacgtt aagggatttt ggtcatgaga ttatcaaaaa ggatcttcac   9360
ctagatcctt ttaaattaaa aatgaagttt taaatcaatc taaagtatat atgagtaaac   9420
ttggtctgac agttaccaat gcttaatcag tgaggcacct atctcagcga tctgtctatt   9480
tcgttcatcc atagttgcct gactccccgt cgtgtagata actacgatac gggagggctt   9540
accatctggc cccagtgctg caatgatacc gcgagaacca cgctcaccgg ctccagattt   9600
atcagcaata aaccagccag ccggaagggc cgagcgcaga agtggtcctg caactttatc   9660
cgcctccatc cagtctatta attgttgccg ggaagctaga gtaagtagtt cgccagttaa   9720
tagtttgcgc aacgttgttg ccattgctac aggcatcgtg gtgtcacgct cgtcgtttgg   9780
tatggcttca ttcagctccg gttcccaacg atcaaggcga gttacatgat cccccatgtt   9840
gtgcaaaaaa gcggttagct ccttcggtcc tccgatcgtt gtcagaagta agttggccgc   9900
agtgttatca ctcatggtta tggcagcact gcataattct cttactgtca tgccatccgt   9960
aagatgcttt tctgtgactg gtgagtactc aaccaagtca ttctgagaat agtgtatgcg   10020
gcgaccgagt tgctcttgcc cggcgtcaat acgggataat accgcgccac atagcagaac   10080
tttaaaagtg ctcatcattg gaaaacgttc ttcggggcga aaactctcaa ggatcttacc   10140
gctgttgaga tccagttcga tgtaacccac tcgtgcaccc aactgatctt cagcatcttt   10200
tactttcacc agcgtttctg ggtgagcaaa aacaggaagg caaaatgccg caaaaaaggg   10260
aataagggcg acacggaaat gttgaatact catactcttc ctttttcaat attattgaag   10320
catttatcag ggttattgtc tcatgagcgg atacatattt gaatgtattt agaaaaataa   10380
acaaataggg gttccgcgca catttccccg aaaagtgcca c                        10421
```

```
<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Arg Ser Asp Asn Leu Ser Thr
1               5


<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

His Ser His Ala Arg Ile Lys
1               5


<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

His Arg Ser Ser Leu Arg Arg
1               5


<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Arg Ser Asp His Leu Ser Glu
1               5


<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gln Asn Ala Asn Arg Ile Thr
1               5


<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 99

Asp Arg Ser Asn Leu Ser Arg
1               5

<210> SEQ ID NO 100

<400> SEQUENCE: 100

000

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 101

Thr Ser Gly Asn Leu Thr Arg
1               5

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 102

Met Ser His His Leu Arg Asp
1               5

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 103

Asp Gln Ser Asn Leu Arg Ala
1               5

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 104

Gln Ser Gly Asn Leu Ala Arg
1               5

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 105

Arg Ser Asp Asn Leu Ser Arg
1 5

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 106

Asp Asn Asn Ala Arg Ile Asn
1 5

<210> SEQ ID NO 107

<400> SEQUENCE: 107

000

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 108

Arg Ser Asp His Leu Thr Gln
1 5

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 109

Arg Ser Asp Asn Leu Arg Glu
1 5

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 110

Gln Ser Gly Ala Leu Ala Arg
1 5

<210> SEQ ID NO 111

<400> SEQUENCE: 111

000

<210> SEQ ID NO 112
<211> LENGTH: 7
<212> TYPE: PRT
<213> ORGANISM: Artificial Sequence
<220> FEATURE:

<223> OTHER INFORMATION: Description of Artificial Sequence: Synthetic peptide

<400> SEQUENCE: 112

Arg Ser Asp Val Leu Ser Glu
1               5

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 113

Ser Pro Ser Ser Arg Arg Thr
1               5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 114

Arg Ser Asp Ser Leu Ser Arg
1               5

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 115

Arg Lys Asp Ala Arg Ile Thr
1               5

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 116

Arg Ser Asp His Leu Ser Ala
1               5

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 117

Trp Ser Ser Ser Leu Tyr Tyr
1               5

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 118

Asn Ser Arg Asn Leu Arg Asn
1 5

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 119

Asp Gln Ser Thr Leu Arg Asn
1 5

<210> SEQ ID NO 120

<400> SEQUENCE: 120

000

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 121

Asp Arg Ser Asn Leu Trp Arg
1 5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 122

Asp Arg Ser Ala Leu Ser Arg
1 5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 123

Arg Ser Asp Ala Leu Ala Arg
1 5

<210> SEQ ID NO 124
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Arg Ser Asp Ala Leu Ser Arg
1               5


<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Asp Arg Ser Asp Leu Ser Arg
1               5


<210> SEQ ID NO 126

<400> SEQUENCE: 126

000


<210> SEQ ID NO 127

<400> SEQUENCE: 127

000


<210> SEQ ID NO 128

<400> SEQUENCE: 128

000


<210> SEQ ID NO 129

<400> SEQUENCE: 129

000


<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Asp Ser Ser Ala Arg Asn Thr
1               5


<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Asp Arg Ser Ser Arg Lys Arg
```

1 5

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 132

Gln Ser Gly Asp Leu Thr Arg
1 5

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 133

Leu Ala His His Leu Val Gln
1 5

<210> SEQ ID NO 134

<400> SEQUENCE: 134

000

<210> SEQ ID NO 135

<400> SEQUENCE: 135

000

<210> SEQ ID NO 136
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 136

Thr Ser Gly His Leu Ser Arg
1 5

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 137

Arg Ser Asp Asn Leu Ser Val
1 5

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 138

Ile Arg Ser Thr Leu Arg Asp
1 5

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 149

Arg Ser Ala Val Leu Ser Glu
1               5

<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 150

Thr Asn Ser Asn Arg Ile Thr
1               5

<210> SEQ ID NO 151
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 151

Leu Lys Gln His Leu Asn Glu
1               5

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 158

Gln Arg Thr His Leu Thr Gln
1 5

<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 159

Arg Ser Asp Asn Leu Ser Asn
1 5

<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 160

Thr Asn Ser Asn Arg Ile Lys
1 5

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 161

Gln Ser Ser Asp Leu Ser Arg
1 5

<210> SEQ ID NO 162
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 162

Gln Ser Ser Asp Leu Arg Arg
1 5

<210> SEQ ID NO 163
<211> LENGTH: 7
<212> TYPE: PRT
<213> ORGANISM: Artificial Sequence
<220> FEATURE:

<223> OTHER INFORMATION: Description of Artificial Sequence: Synthetic peptide

<400> SEQUENCE: 163

Asp Arg Ser Asn Arg Ile Lys
1 5

<210> SEQ ID NO 164
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 164

Arg Ser Ala Asn Leu Ala Arg
1 5

<210> SEQ ID NO 165
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 165

Arg Ser Asp Asn Leu Thr Thr
1 5

<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 166

Gln Ser Gly Glu Leu Ile Asn
1 5

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 167

Arg Ser Ala Asp Leu Ser Arg
1 5

<210> SEQ ID NO 168
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 168

Arg Ser Asp Asn Leu Ser Glu
1 5

<210> SEQ ID NO 169
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 169

Asp Arg Ser His Leu Ala Arg
1 5

<210> SEQ ID NO 170

<400> SEQUENCE: 170

000

<210> SEQ ID NO 171

<400> SEQUENCE: 171

000

<210> SEQ ID NO 172
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 172

Ser Lys Gln Tyr Leu Ile Lys
1 5

<210> SEQ ID NO 173
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 173

Glu Arg Gly Thr Leu Ala Arg
1 5

<210> SEQ ID NO 174
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 174

Arg Ser Asp His Leu Thr Thr
1 5

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 179

```
Arg Ser Asp Asn Leu Thr Arg
1               5
```

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 189

Ala Ser Lys Thr Arg Lys Asn
1 5

<210> SEQ ID NO 190
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 190

Arg Ser Asp Thr Leu Ser Glu
1 5

<210> SEQ ID NO 191
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 191

Gln Ser His Asn Arg Thr Lys
1 5

<210> SEQ ID NO 192
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 192

Gln Ser Asp His Leu Thr Gln
1 5

<210> SEQ ID NO 193
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 193

Arg Ser Ser Asp Leu Ser Arg
1 5

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 198

Asp Arg Ser His Leu Ser Arg
1 5

<210> SEQ ID NO 199

<400> SEQUENCE: 199

000

<210> SEQ ID NO 200

<400> SEQUENCE: 200

000

<210> SEQ ID NO 201
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 201

Asp Arg Ser Ala Leu Ala Arg
1 5

<210> SEQ ID NO 202

<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 202

Arg Ser Asp Asp Leu Ser Lys
1 5

<210> SEQ ID NO 203
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 203

Arg Ser Asp Thr Arg Lys Thr
1 5

<210> SEQ ID NO 204

<400> SEQUENCE: 204

000

<210> SEQ ID NO 205

<400> SEQUENCE: 205

000

<210> SEQ ID NO 206

<400> SEQUENCE: 206

000

<210> SEQ ID NO 207
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 207

Asn Asn Asp His Arg Lys Thr
1 5

<210> SEQ ID NO 208
<211> LENGTH: 10272
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 208
acaagtttgt acaaaaaagc aggctgtaag tttgtggatt cttcgtccat gtgatctttg 60
agtttcttta gagcttgtga gggattagta agtaacaatg cttgagtttt ttgctgctgg 120
gcttcgaaaa gtttgtcact tgttggtttg atccacaagg tcttcttctc catagctact 180
agacatgttt tagcttaaga ttcaagttta tatatgcctt gtggattaat cattgcctga 240

```
ttcttccgtg tcatctctga gtttatttag agcttggaag tggtgtagta ataactaaca    300
atactcttga taagttgtag caatgctctt gattagtgga tgtaatatga tgttgataag    360
atatatgagg cacagaacca aaagtggtgc ttccactaga cccgttttta gcctaaggtt    420
caagtttata ccttgtagat gtttctgtat tgtctgattc ttccctgtga tatttgaatt    480
tcttagagct ttggaagtga tataggaaca atgctcttgt gtgtttgtct ctatgaagat    540
tatcgctgtc gtgtttcatc cgagtgtgcg ggatttttg ctgctgggtt tagcctttct    600
tcaaaaagtt attacttgtt agttttattg ttttggtctt gataagagat gttaggacag    660
acatggtgct tcttgtctat agccactaga cctattttag cataaggtta acgaaattct    720
ctctacatac cttgtggatt tgtttacatt gcctgatctt tcctgtgatc gctgtcatgt    780
ttctttggaa tgattgatgt ttataaatgg aaaaatcttt gtgcaggttt aaacgtttac    840
gttaagcacc ctgctgatat ccctgattac aagaagcttt cattccctga gggattcaag    900
tgggagagag ttatgaactt cgaggatggt ggtgttgcta ctgttactca ggattcttca    960
cttcaggacg gatgcttcat ctacaaggtt aagttcatcg gagtgaactt cccttctgat   1020
ggacctgtta tgcagaaaaa gactatggga tgggaggctt ctaccgagag actttaccct   1080
agagatggtg ttcttaaggg tgagactcac aaggctctta agcttaaaga tggtggacac   1140
tacctcgtcg agttcaagtc tatctacatg gctaagaagc ctgttcagct tcctggttac   1200
tactacgttg acgctaagct tgatatcacc tctcacaacg aggactacac tatcgttgag   1260
caatacgaga gaactgaggg tagacatcac ttgttcctct gatatcaaaa tctatttaga   1320
aatacacaat attttgttgc aggcttgctg gagaatcgat ctgctatcat aaaaattaca   1380
aaaaaatttt atttgcctca attattttag gattggtatt aaggacgctt aaattatttg   1440
tcgggtcact acgcatcatt gtgattgaga agatcagcga tacgaaatat tcgtagtact   1500
atcgataatt tatttgaaaa ttcataagaa aagcaaacgt tacatgaatt gatgaaacaa   1560
tacaaagaca gataaagcca cgcacattta ggatattggc cgagattact gaatattgag   1620
taagatcacg gaatttctga caggagcatg tcttcaattc agcccaaatg gcagttgaaa   1680
tactcaaacc gccccatatg caggagcgga tcattcattg tttgtttggt tgcctttgcc   1740
aacatgggag tccaaggttg ccttttgcag tttatctcta tgcccgggac aagtgaagac   1800
tcccgcccat ctcactaggg acaggattgg agtccatgct caacaccgtg caggatgagg   1860
atgaccaaca actttgtata caaaagttgt atccgaagta aataaaacca tcggactctc   1920
gtataagact gtcgacaagc ttcttgcctc aattccggag gtgtttctag tgttcaacat   1980
gacaaacaaa acccatctct ttcagtatat gtctctcagt tgtgcttaat tcaaatttca   2040
actcagagaa cttcttggca tacttatcca gattatctaa tgatctcatc taatggtaat   2100
tcaactttca gtatatgtct cgcagcaaac tatctttaca tcaaattttt aacaactcaa   2160
tgcacaaaat acttttcctc aacctaaaaa taaggcaatt agccaaaaac aactttgcgt   2220
gtgaacaacg cgttacacgt ccctacacat acgtgtcaat ttataattgg ctattgcttc   2280
cacgccttag ctttctcgtg accgaccgag tcgtcctcgt cttttttgct tctataaatc   2340
aaatacccaa agagctcttc ttcttcacaa ttcagattcc aattttctca aactctaaaa   2400
tcaatctctc aaatctctca accgtgatca aggtagattt ctgagttctt attgtatttc   2460
ttcgatttgt ttcgttcgat cgcaatttag gctctgttct ttgattttga tctcgttaat   2520
ctctgatcgg aggcaaatta catagtttca tcgttagatc tcttcttatt tctcgattag   2580
```

```
ggttcgtatt tttcgcagat ctgtttattt tcttgttgtt tccttgtatt tgatccgatt   2640
tgttgaaaga atttgtgtgt tctcgattat ttacgctttg atctgtgatt tttatctaga   2700
tttggtgtta gtttcttgtt tgtgcgatcg aatttgtcga ttaatctcgg tttttctgat   2760
taacagatgg ctcaatctag cagaatctgc cacggtgtgc agaacccatg tgtgatcatt   2820
tccaatctct ccaaatccaa ccagaacaaa tctcctttct cagtcagcct caagactcac   2880
cagcagcagc gtcgtgctta ccagatatct agctggggat tgaagaagtc aaacaacggg   2940
tccgtgattc gtccggttaa ggcagctgca agagggatgc cagccttgtc tttacctgga   3000
tcaaagagta tcacagctag ggcactcttt cttgctgctg ctgctgatgg ggttactact   3060
ttggtgaggc cattgagaag tgacgacaca gaaggattcg ctgaggggtt agttcgttta   3120
ggctatcgtg tagggaggac acccgatact tggcaagtcg atggcagacc acaaggacca   3180
gcagtggctg aggctgacgt ctactgtaga gacggagcaa ccaccgctag attcttgcca   3240
accttagcag ctgctggtca cggaacatac agatttgatg cttcaccaca gatgaggaga   3300
cgtcctcttt tgcccttaag cagagccttg agggatttgg gtgtcgatct tagacacgaa   3360
gaagctgaag gtcatcaccc tctgactgtc cgtgctgctg ggttgaagg aggagaggtt    3420
actttggatg ctggtcagtc aagtcagtat ctcactgcct tgttgctcct tggtcccctt   3480
acaagacaag gactgaggat aagggttact gatttggtgt cagcaccata cgtggagatt   3540
acgcttgcaa tgatgagggc tttcggagtt gaagtggcaa gggagggaga tgtgttcgtt   3600
gttccacctg gtggatatcg tgcaactacg tatgctatag aacccgacgc aagtactgct   3660
tcttacttct tcgcagctgc tgctttgact cctggagctg aagtgactgt acctgggtta   3720
ggcacgggag cacttcaagg agatttggga tttgtagatg tcttaaggag aatgggagcc   3780
gaggtgtccg taggagctga tgcaaccact gttagaggaa ctggtgaatt gcgtggcctt   3840
acagccaaca tgagagacat aagtgatacg atgccgaccc tcgctgcaat agcacccttt   3900
gctagtgctc cagttagaat cgaggatgtt gccaacactc gtgtcaaaga atgtgacaga   3960
cttgaggctt gtgcagagaa ccttaggagg ttgggagtaa gggttgcaac gggtccggac   4020
tggattgaga tacaccctgg tccagctact ggtgctcaag tcacaagcta tggtgatcac   4080
agaattgtga tgtcatttgc agtgactgga cttcgtgtgc ctgggatcag cttcgacgac   4140
cctggctgtg ttcgtaagac ttttcctggg tttcacgagg ctttcgcaga attgaggcgt   4200
ggcattggga gctgatgagt agttagctta atcacctaag atcggcggca atagcttctt   4260
agcgccatcc cgggttgatc ctatctgtgt tgaaatagtt gcggtgggca aggctctctt   4320
tcagaaagac aggcggccaa aggaacccaa ggtgaggtgg gctatggctc tcagttcctt   4380
gtggaagcgc ttggtctaag gtgcagaggt gttagcggga tgaagcaaaa gtgtccgatt   4440
gtaacaagat atgttgatcc tacgtaagga tattaaagta tgtattcatc actaatataa   4500
tcagtgtatt ccaatatgta ctacgatttc caatgtcttt attgtcgccg tatgtaatcg   4560
gcgtcacaaa ataatccccg gtgactttct tttaatccag gatgaaataa tatgttatta   4620
taatttttgc gatttggtcc gttataggaa ttgaagtgtg cttgcggtcg ccaccactcc   4680
catttcataa ttttacatgt atttgaaaaa taaaaattta tggtattcaa tttaaacacg   4740
tatacttgta aagaatgata tcttgaaaga aatatagttt aaatatttat tgataaaata   4800
acaagtcagg tattatagtc caagcaaaaa cataaattta ttgatgcaag tttaaattca   4860
gaaatatttc aataactgat tatatcagct ggtacattgc cgtagatgaa agactgagtg   4920
cgatattatg gtgtaataca tacggccgac gcataggttc atttgaagct gctattctat   4980
```

```
ttagattgaa gtttaaaccc agaaggtaat tatccaagat gtagcatcaa gaatccaatg   5040
tttacgggaa aaactatgga agtattatgt aagctcagca agaagcagat caatatgcgg   5100
cacatatgca acctatgttc aaaaatgaag aatgtacaga tacaagatcc tatactgcca   5160
gaatacgaag aagaatacgt agaaattgaa aaagaagaac caggcgaaga aaagaatctt   5220
gaagacgtaa gcactgacga caacaatgaa aagaagaaga taaggtcggt gattgtgaaa   5280
gagacataga ggacacatgt aaggtggaaa atgtaagggc ggaaagtaac cttatcacaa   5340
aggaatctta tcccccacta cttatccttt tatatttttc cgtgtcattt ttgcccttga   5400
gttttcctat ataaggaacc aagttcggca tttgtgaaaa caagaaaaaa tttggtgtaa   5460
gctattttct ttgaagtact gaggatacaa cttcagagaa atttgtaagt ttgtaatgtc   5520
tccggagagg agaccagttg agattaggcc agctacagca gctgatatgg ccgcggtttg   5580
tgatatcgtt aaccattaca ttgagacgtc tacagtgaac tttaggacag agccacaaac   5640
accacaagag tggattgatg atctcgagag gttgcaagat agataccctt ggttggttgc   5700
tgaggttgag ggtgttgtgg ctggtattgc ttacgctggg ccctggaagg ctaggaacgc   5760
ttacgattgg acagttgaga gtactgttta cgtgtcacat aggcatcaaa ggtcagtttt   5820
acttccctta attttctatg tactttcata attacttatg ttattttctt catgagtttt   5880
aatgcaaatt actatatgga ctctagtgaa aacgttcaga atcctataaa catgactact   5940
gagacgaact tgagagtagt tttgatcata cacacgtttc atgtggtact tgagagttac   6000
taatttttgt catcttcgta taagtagtaa aagatactac aagaatagtt tagtagaaaa   6060
tactagcggt aggtgaagat ttgtcgctat gtactattat tgtctagtaa cttgagtaac   6120
aatttcgtgg tctaaatatc aaataaaaat ggatgagtgg ttcaccaaat ctaggcatca   6180
aaactattaa tgtcattgtc tagatcttag gtgacaccac atttcgaata tttattggta   6240
attgagatgt taaagtacca atatttgact taataaacta aaagattttg gctttatcaa   6300
atgtagacat tgatgacata tcgttgtcat tatcttgagt atatacaagt cgatcaatta   6360
ggtgaaagtt tagtgtctcg tggttggtaa acgattaata cagtagtata ttttatccaa   6420
agacaaaatc caaatcattt caccagtatg aatagtatta ttttatctta aaagctaaaa   6480
tcttaaaaac caaggtagca cccacgttga gctagacgat caaatcgatt tctgctttgt   6540
ccaatttacc aagctattta aagccaaata attgaaatat aggtaggtcg ttatattagg   6600
ctaagattta tctcaaatgc ttaactaaag gaataacaag ggattctagt tgtgtggttt   6660
tataagattg gtccaatttc acttaagttt gtttattgta gaattttata tgtgaataat   6720
ttgaattcca attgaaaaga tattatagta aaagaaaaaa tagtgcgaac aaaaaacttt   6780
aatcccataa aaagaaaaag aaaaatgaaa agttcttcta acatccatat tttgcatcat   6840
atcataaaga taagaaagat acatatcata gacgtacaga taaacaaaca tatcatcatt   6900
tgtgaaatac atagtacaat aatttgcttt taaatagagt ttaagtcaca cacactgaca   6960
cacacgataa aacgataatg tctgcaaaaa cactttaatc ccattgccta gaggacagct   7020
tctccacttt gtctttaagg ttggttttgc cgtgttgttt ttatctttat ataatgatct   7080
attttttgga ttatgaaatg aattcacaca ttttaattat ttaagaagat ccatatacag   7140
gtttataaca gtactaagtg atgattattt tttgtttttg catagtttag tttattgggt   7200
aaacattcat tacgtgtctc tttatacgaa tcacccatcc aaaatttcaa gtagtctttt   7260
agttcattta ttatttcata actatttgac ttattgattt gacaagaaac aacaaaagtg   7320
```

```
ttgacttatt gatagattgt gggatcataa aagtaattaa gcgtcaacca cgacccacaa   7380
caacaaagca catgttatac attaatatct cgtttactta attacagttt tcagaatgcc   7440
gtttcatgtc ttgtcactgg cgatgttatt atcatgttgg acaatattcg actgttgtcg   7500
tttttacatt ttcgtattga ctaaaactaa aaaaacaaaa ctctgtttca gacccagctt   7560
tcttgtacaa agtggtgatt cgacctgcag gcatgcaagc ttggcgtaat catggtcata   7620
gctgtttcct gtgtgaaatt gttatccgct cacaattcca cacaacatac gagccggaag   7680
cataaagtgt aaagcctggg gtgcctaatg agtgagctaa ctcacattaa ttgcgttgcg   7740
ctcactgccc gctttccagt cgggaaacct gtcgtgccag ctgcattaat gaatcggcca   7800
acgcgcgggg agaggcggtt tgcgtattgg gcgctcttcc gcttcctcgc tcactgactc   7860
gctgcgctcg gtcgttcggc tgcggcgagc ggtatcagct cactcaaagg cggtaatacg   7920
gttatccaca gaatcagggg ataacgcagg aaagaacatg tgagcaaaag gccagcaaaa   7980
ggccaggaac cgtaaaaagg ccgcgttgct ggcgtttttc cataggctcc gcccccctga   8040
cgagcatcac aaaaatcgac gctcaagtca gaggtggcga aacccgacag gactataaag   8100
ataccaggcg tttccccctg gaagctccct cgtgcgctct cctgttccga ccctgccgct   8160
taccggatac ctgtccgcct ttctcccttc gggaagcgtg gcgctttctc atagctcacg   8220
ctgtaggtat ctcagttcgg tgtaggtcgt tcgctccaag ctgggctgtg tgcacgaacc   8280
ccccgttcag cccgaccgct gcgccttatc cggtaactat cgtcttgagt ccaacccggt   8340
aagacacgac ttatcgccac tggcagcagc cactggtaac aggattagca gagcgaggta   8400
tgtaggcggt gctacagagt tcttgaagtg gtggcctaac tacggctaca ctagaaggac   8460
agtatttggt atctgcgctc tgctgaagcc agttaccttc ggaaaaagag ttggtagctc   8520
ttgatccggc aaacaaacca ccgctggtag cggtggtttt tttgtttgca agcagcagat   8580
tacgcgcaga aaaaaaggat ctcaagaaga tcctttgatc ttttctacgg ggtctgacgc   8640
tcagtggaac gaaaactcac gttaagggat tttggtcatg agattatcaa aaaggatctt   8700
cacctagatc cttttaaatt aaaaatgaag ttttaaatca atctaaagta tatatgagta   8760
aacttggtct gacagttacc aatgcttaat cagtgaggca cctatctcag cgatctgtct   8820
atttcgttca tccatagttg cctgactccc cgtcgtgtag ataactacga tacgggaggg   8880
cttaccatct ggccccagtg ctgcaatgat accgcgagac ccacgctcac cggctccaga   8940
tttatcagca ataaaccagc cagccggaag ggccgagcgc agaagtggtc ctgcaacttt   9000
atccgcctcc atccagtcta ttaattgttg ccgggaagct agagtaagta gttcgccagt   9060
taatagtttg cgcaacgttg ttgccattgc tacaggcatc gtggtgtcac gctcgtcgtt   9120
tggtatggct tcattcagct ccggttccca acgatcaagg cgagttacat gatcccccat   9180
gttgtgcaaa aaagcggtta gctccttcgg tcctccgatc gttgtcagaa gtaagttggc   9240
cgcagtgtta tcactcatgg ttatggcagc actgcataat tctcttactg tcatgccatc   9300
cgtaagatgc ttttctgtga ctggtgagta ctcaaccaag tcattctgag aatagtgtat   9360
gcggcgaccg agttgctctt gcccggcgtc aatacgggat aataccgcgc cacatagcag   9420
aactttaaaa gtgctcatca ttggaaaacg ttcttcgggg cgaaaactct caaggatctt   9480
accgctgttg agatccagtt cgatgtaacc cactcgtgca cccaactgat cttcagcatc   9540
ttttactttc accagcgttt ctgggtgagc aaaaacagga aggcaaaatg ccgcaaaaaa   9600
gggaataagg gcgacacgga aatgttgaat actcatactc ttcctttttc aatattattg   9660
aagcatttat cagggttatt gtctcatgag cggatacata tttgaatgta tttagaaaaa   9720
```

```
taaacaaata ggggttccgc gcacatttcc ccgaaaagtg ccacctgacg tctaagaaac   9780

cattattatc atgacattaa cctataaaaa taggcgtatc acgaggccct ttcgtctcgc   9840

gcgtttcggt gatgacggtg aaaacctctg acacatgcag ctcccggaga cggtcacagc   9900

ttgtctgtaa gcggatgccg ggagcagaca agcccgtcag ggcgcgtcag cgggtgttgg   9960

cgggtgtcgg ggctggctta actatgcggc atcagagcag attgtactga gagtgcacca  10020

tatgcggtgt gaaataccgc acagatgcgt aaggagaaaa taccgcatca ggcgccattc  10080

gccattcagg ctgcgcaact gttgggaagg gcgatcggtg cgggcctctt cgctattacg  10140

ccagctggcg aaagggggat gtgctgcaag gcgattaagt tgggtaacgc cagggttttc  10200

ccagtcacga cgttgtaaaa cgacggccag tgaattcgag ctcggtaccc ggggatcctc  10260

tagagtcgaa tc                                                      10272
```

<210> SEQ ID NO 209
<211> LENGTH: 8774
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 209

```
ggggacaagt ttgtacaaaa aagcaggctg cggccgcgaa atatccttcc tattcaaagt     60

tatatatatt tgtttacttt tgttttagat ctggacctga gacatgtaag tacatatttg    120

ttgaatcttt gggtaaaaac ttatgtctct gggtaaaatt tgctgagaga tttgaccgat    180

tcctattggc tctggattct gtagttacct aatacatgaa aaagtttcat ttggcctatg    240

ctcacttcat gcttataaac tttttcttgc aaattaattg gattagatgc tccttcatag    300

attcagatgc aatagatttg catgaagaaa ataataggat tcatgatagt aaaaagattg    360

tatttttgtt tgtttgttta tgtttaaaag tctatatgtt gacaatagag ttgctatcaa    420

ctgtttcatt taggtttatg tttttgtcaa gttgcttatt ctaagagaca ttgtgattat    480

gacttgtctt ctctaacgta gtttagtaat aaaagacgaa agaaattgat atccacaaga    540

aagagatgta agctgtaacg tatcaaatct cattaataac tagtagtatt ctcaacgcta    600

tcgtttattt ctttctttgg tttgccacta tatgccgctt ctctgctctt tatcccacgt    660

actatccatt ttttttgtgg tagtccattt ttttgaaact ttaataacgt aacactgaat    720

attaatttgt tggtttaatt aactttgagt ctttgctttt ggtttatgca gaaacatggg    780

tgcaggtgga agaatgcaag tgtctcctcc ctccaaaaag tctgaaaccg acaacatcaa    840

gcgcgtaccc tgcgagacac cgcccttcac tgtcggagaa ctcaagaaag caatcccacc    900

gcactgtttc aaacgctcga tccctcgctc tttctcctac ctcatctggg acatcatcat    960

agcctcctgc ttctactacg tcgccaccac ttacttccct ctcctccctc accctctctc   1020

ctacttcgcc tggcctctct actgggccgg taccgtcgac tgactgactg aatctcgagg   1080

ggtgtggaag atatgaattt ttttgagaaa ctagataaga ttaatgaata tcggtgtttt   1140

ggtttttttct tgtggccgtc tttgtttata ttgagatttt tcaaatcagt gcgcaagacg   1200

tgacgtaagt atccgagtca gtttttattt ttctactaat ttggtcgttt atttcggcgt   1260

gtaggacatg gcaaccgggc ctgaatttcg cgggtattct gtttctattc caactttttc   1320

ttgatccgca gccattaacg acttttgaat agatacgtct agggtcgagg ggggatccgt   1380

cgaggggggtc caccaaaaac gtaagcgctt acgtacatgg tcgagggggt ccaccaaaaa   1440
```

```
cgtaagcgct tacgtacatg gtcgaggggg tccaccaaaa acgtaagcgc ttacgtacat   1500
ggtcgagggt agagcgtgac gctcgcggtg acgccatttc gccttttcag aaatggataa   1560
atagccttgc ttcctattat atcttcccaa attaccaata cattacacta gcatctgaat   1620
ttcataacca atctcgatac accaaatcgc ggatcagatc ttagtagcca tggctcaatc   1680
tagcagaatc tgccacggtg tgcagaaccc atgtgtgatc atttccaatc tctccaaatc   1740
caaccagaac aaatctcctt tctcagtcag cctcaagact caccagcagc agcgtcgtgc   1800
ttaccagata tctagctggg gattgaagaa gtcaaacaac gggtccgtga ttcgtccggt   1860
taaggcagct gcaagaggga tgccagcctt gtctttacct ggatcaaaga gtatcacagc   1920
tagggcactc tttcttgctg ctgctgctga tggggttact actttggtga ggccattgag   1980
aagtgacgac acagaaggat tcgctgaggg gttagttcgt ttaggctatc gtgtagggag   2040
gacacccgat acttggcaag tcgatggcag accacaagga ccagcagtgg ctgaggctga   2100
cgtctactgt agagacggag caaccaccgc tagattcttg ccaaccttag cagctgctgg   2160
tcacggaaca tacagatttg atgcttcacc acagatgagg agacgtcctc ttttgccctt   2220
aagcagagcc ttgagggatt tgggtgtcga tcttagacac gaagaagctg aaggtcatca   2280
ccctctgact gtccgtgctg ctggggttga aggaggagag gttactttgg atgctggtca   2340
gtcaagtcag tatctcactg ccttgttgct ccttggtccc cttacaagac aaggactgag   2400
gataagggtt actgatttgg tgtcagcacc atacgtggag attacgcttg caatgatgag   2460
ggctttcgga gttgaagtgg caagggaggg agatgtgttc gttgttccac ctggtggata   2520
tcgtgcaact acgtatgcta tagaacccga cgcaagtact gcttcttact tcttcgcagc   2580
tgctgctttg actcctggag ctgaagtgac tgtacctggg ttaggcacgg gagcacttca   2640
aggagatttg ggatttgtag atgtcttaag gagaatggga gccgaggtgt ccgtaggagc   2700
tgatgcaacc actgttagag gaactggtga attgcgtggc cttacagcca acatgagaga   2760
cataagtgat acgatgccga ccctcgctgc aatagcaccc tttgctagtg ctccagttag   2820
aatcgaggat gttgccaaca ctcgtgtcaa agaatgtgac agacttgagg cttgtgcaga   2880
gaaccttagg aggttgggag taagggttgc aacgggtccg gactggattg agatacaccc   2940
tggtccagct actggtgctc aagtcacaag ctatggtgat cacagaattg tgatgtcatt   3000
tgcagtgact ggacttcgtg tgcctgggat cagcttcgac gaccctggct gtgttcgtaa   3060
gacttttcct gggtttcacg aggctttcgc agaattgagg cgtggcattg ggagctgatg   3120
agtagttagc ttaatcacct aagatcggcg gcaatagctt cttagcgcca tcccgggttg   3180
atcctatctg tgttgaaata gttgcggtgg gcaaggctct ctttcagaaa gacaggcggc   3240
caaaggaacc caaggtgagg tgggctatgg ctctcagttc cttgtggaag cgcttggtct   3300
aaggtgcaga ggtgttagcg ggatgaagca aaagtgtccg attgtaacaa gatatgttga   3360
tcctacgtaa ggatattaaa gtatgtattc atcactaata taatcagtgt attccaatat   3420
gtactacgat ttccaatgtc tttattgtcg ccgtatgtaa tcggcgtcac aaaataatcc   3480
ccggtgactt tcttttaatc caggatgaaa taatatgtta ttataatttt tgcgatttgg   3540
tccgttatag gaattgaagt gtgcttgcgg tcgccaccac tcccatttca taattttaca   3600
tgtatttgaa aaataaaaat ttatggtatt caatttaaac acgtatactt gtaaagaatg   3660
atatcttgaa agaaatatag tttaaatatt tattgataaa ataacaagtc aggtattata   3720
gtccaagcaa aaacataaat ttattgatgc aagtttaaat tcagaaatat ttcaataact   3780
```

```
gattatatca gctggtacat tgccgtagat gaaagactga gtgcgatatt atggtgtaat   3840
acatacggcc gccagaaggt aattatccaa gatgtagcat caagaatcca atgtttacgg   3900
gaaaaactat ggaagtatta tgtaagctca gcaagaagca gatcaatatg cggcacatat   3960
gcaacctatg ttcaaaaatg aagaatgtac agatacaaga tcctatactg ccagaatacg   4020
aagaagaata cgtagaaatt gaaaaagaag aaccaggcga agaaaagaat cttgaagacg   4080
taagcactga cgacaacaat gaaaagaaga agataaggtc ggtgattgtg aaagagacat   4140
agaggacaca tgtaaggtgg aaaatgtaag ggcggaaagt aaccttatca caaaggaatc   4200
ttatccccca ctacttatcc ttttatattt ttccgtgtca tttttgccct tgagttttcc   4260
tatataagga accaagttcg gcatttgtga aaacaagaaa aaatttggtg taagctattt   4320
tctttgaagt actgaggata caacttcaga gaaatttgta agtttgtaat gtctccggag   4380
aggagaccag ttgagattag gccagctaca gcagctgata tggccgcggt ttgtgatatc   4440
gttaaccatt acattgagac gtctacagtg aactttagga cagagccaca aacaccacaa   4500
gagtggattg atgatctcga gaggttgcaa gatagatacc cttggttggt tgctgaggtt   4560
gagggtgttg tggctggtat tgcttacgct gggccctgga aggctaggaa cgcttacgat   4620
tggacagttg agagtactgt ttacgtgtca cataggcatc aaaggttggg cctaggatcc   4680
acattgtaca cacatttgct taagtctatg gaggcgcaag gttttaagtc tgtggttgct   4740
gttataggcc ttccaaacga tccatctgtt aggttgcatg aggctttggg atacacagcc   4800
cggggtacat tgcgcgcagc tggatacaag catggtggat ggcatgatgt tggtttttgg   4860
caaagggatt ttgagttgcc agctcctcca aggccagtta ggccagttac ccagatctaa   4920
tatcaaaatc tatttagaaa tacacaatat tttgttgcag gcttgctgga gaatcgatct   4980
gctatcataa aaattacaaa aaaattttat ttgcctcaat tattttagga ttggtattaa   5040
ggacgcttaa attatttgtc gggtcactac gcatcattgt gattgagaag atcagcgata   5100
cgaaatattc gtagtactat cgataattta tttgaaaatt cataagaaaa gcaaacgtta   5160
catgaattga tgaaacaata caaagacaga taaagccacg cacatttagg atattggccg   5220
agattactga atattgagta agatcacgga atttctgaca ggagcatgtc ttcaattcag   5280
cccaaatggc agttgaaata ctcaaaccgc cccatatgca ggagcggatc attcattgtt   5340
tgtttggttg cctttgccaa catgggagtc caaggttgca tgccagggct gcgtcctaac   5400
cggcgtctgg gtcatagccc acgagtgcgg ccaccacgcc ttcagcgact accagtggct   5460
ggacgacacc gtcggcctca tcttccactc cttcctcctc gtcccttact tctcctggaa   5520
gtacagtcat cgacgccacc attccaacac tggctccctc gagagagacg aagtgtttgt   5580
ccccaagaag aagtcagaca tcaagtggta cggcaagtac ctcaacaacc ctttgggacg   5640
caccgtgatg ttaacggttc agttcactct cggctggcct ttgtacttag ccttcaacgt   5700
ctcggggaga ccttacgacg gcggcttcgc ttgccatttc caccccaacg ctcccatcta   5760
caacgaccgt gagcgtctcc agatatacat ctccgacgct ggcatcctcg ccgtctgcta   5820
cggtctctac cgctacgctg ctgtccaagg agttgcctcg atggtctgct tctacggagt   5880
tcctcttctg attgtcaacg ggttcttagt tttgatcact tacttgcagc acacgcatcc   5940
ttccctgcct cactatgact cgtctgagtg ggattggttg aggggagctt tggccaccgt   6000
tgacagagac tacggaatct tgaacaaggt cttccacaat atcacggaca cgcacgtggc   6060
gcatcacctg ttctcgacca tgccgcatta tcacgcgatg gaagctacga aggcgataaa   6120
gccgatactg ggagagtatt atcagttcga tgggacgccg gtggttaagg cgatgtggag   6180
```

```
ggaggcgaag gagtgtatct atgtggaacc ggacaggcaa ggtgagaaga aaggtgtgtt   6240
ctggtacaac aataagttat gaagcaaaga agaaactgaa cctttctcat ctatgattgt   6300
ctttgtttta agaagctatg tttctgtttc aataatcttt aattatccat tttgttgtgt   6360
tttctgacat tttggctaaa atggcgccac ccagctttct tgtacaaagt ggtcccctta   6420
attaactggg cctcatgggc cttccgctca ctgcccgctt tccagtcggg aaacctgtcg   6480
tgccagctgc attaacatgg tcatagctgt ttccttgcgt attgggcgct ctccgcttcc   6540
tcgctcactg actcgctgcg ctcggtcgtt cgggtaaagc ctggggtgcc taatgagcaa   6600
aaggccagca aaaggccagg aaccgtaaaa aggccgcgtt gctggcgttt ttccataggc   6660
tccgcccccc tgacgagcat cacaaaaatc gacgctcaag tcagaggtgg cgaaacccga   6720
caggactata aagataccag gcgtttcccc ctggaagctc cctcgtgcgc tctcctgttc   6780
cgaccctgcc gcttaccgga tacctgtccg cctttctccc ttcgggaagc gtggcgcttt   6840
ctcatagctc acgctgtagg tatctcagtt cggtgtaggt cgttcgctcc aagctgggct   6900
gtgtgcacga accccccgtt cagcccgacc gctgcgcctt atccggtaac tatcgtcttg   6960
agtccaaccc ggtaagacac gacttatcgc cactggcagc agccactggt aacaggatta   7020
gcagagcgag gtatgtaggc ggtgctacag agttcttgaa gtggtggcct aactacggct   7080
acactagaag aacagtattt ggtatctgcg ctctgctgaa gccagttacc ttcggaaaaa   7140
gagttggtag ctcttgatcc ggcaaacaaa ccaccgctgg tagcggtggt ttttttgttt   7200
gcaagcagca gattacgcgc agaaaaaaag gatctcaaga agatcctttg atcttttcta   7260
cggggtctga cgctcagtgg aacgaaaact cacgttaagg gattttggtc atgagattat   7320
caaaaaggat cttcacctag atccttttaa attaaaaatg aagttttaaa tcaatctaaa   7380
gtatatatga gtaaacttgg tctgacagtt accaatgctt aatcagtgag gcacctatct   7440
cagcgatctg tctatttcgt tcatccatag ttgcctgact ccccgtcgtg tagataacta   7500
cgatacggga gggcttacca tctggcccca gtgctgcaat gataccgcga gaaccacgct   7560
caccggctcc agatttatca gcaataaacc agccagccgg aagggccgag cgcagaagtg   7620
gtcctgcaac tttatccgcc tccatccagt ctattaattg ttgccgggaa gctagagtaa   7680
gtagttcgcc agttaatagt ttgcgcaacg ttgttgccat tgctacaggc atcgtggtgt   7740
cacgctcgtc gtttggtatg gcttcattca gctccggttc ccaacgatca aggcgagtta   7800
catgatcccc catgttgtgc aaaaaagcgg ttagctcctt cggtcctccg atcgttgtca   7860
gaagtaagtt ggccgcagtg ttatcactca tggttatggc agcactgcat aattctctta   7920
ctgtcatgcc atccgtaaga tgcttttctg tgactggtga gtactcaacc aagtcattct   7980
gagaatagtg tatgcggcga ccgagttgct cttgcccggc gtcaatacgg gataataccg   8040
cgccacatag cagaacttta aaagtgctca tcattggaaa acgttcttcg gggcgaaaac   8100
tctcaaggat cttaccgctg ttgagatcca gttcgatgta acccactcgt gcacccaact   8160
gatcttcagc atcttttact ttcaccagcg tttctgggtg agcaaaaaca ggaaggcaaa   8220
atgccgcaaa aaagggaata agggcgacac ggaaatgttg aatactcata ctcttccttt   8280
ttcaatatta ttgaagcatt tatcagggtt attgtctcat gagcggatac atatttgaat   8340
gtatttagaa aaataaacaa ataggggttc cgcgcacatt tccccgaaaa gtgccaccta   8400
aattgtaagc gttaatattt tgttaaaatt cgcgttaaat ttttgttaaa tcagctcatt   8460
ttttaaccaa taggccgaaa tcggcaaaat cccttataaa tcaaaagaat agaccgagat   8520
```

```
agggttgagt ggccgctaca gggcgctccc attcgccatt caggctgcgc aactgttggg   8580

aagggcgttt cggtgcgggc ctcttcgcta ttacgccagc tggcgaaagg gggatgtgct   8640

gcaaggcgat taagttgggt aacgccaggg ttttcccagt cacgacgttg taaaacgacg   8700

gccagtgagc gcgacgtaat acgactcact atagggcgaa ttggcggaag gccgtcaagg   8760

ccgcatggcg cgcc                                                     8774


<210> SEQ ID NO 210
<211> LENGTH: 9491
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 210

ggggacaagt ttgtacaaaa aagcaggctg cggccgcgaa atatccttcc tattcaaagt     60

tatatatatt tgtttacttt tgttttagat ctggacctga gacatgtaag tacatatttg    120

ttgaatcttt gggtaaaaac ttatgtctct gggtaaaatt tgctgagaga tttgaccgat    180

tcctattggc tctggattct gtagttacct aatacatgaa aaagtttcat ttggcctatg    240

ctcacttcat gcttataaac tttttcttgc aaattaattg gattagatgc tccttcatag    300

attcagatgc aatagatttg catgaagaaa ataataggat tcatgatagt aaaaagattg    360

tatttttgtt tgtttgttta tgtttaaaag tctatatgtt gacaatagag ttgctatcaa    420

ctgtttcatt taggtttatg tttttgtcaa gttgcttatt ctaagagaca ttgtgattat    480

gacttgtctt ctctaacgta gtttagtaat aaaagacgaa agaaattgat atccacaaga    540

aagagatgta agctgtaacg tatcaaatct cattaataac tagtagtatt ctcaacgcta    600

tcgtttattt ctttctttgg tttgccacta tatgccgctt ctctgctctt tatcccacgt    660

actatccatt ttttttgtgg tagtccattt ttttgaaact ttaataacgt aacactgaat    720

attaatttgt tggtttaatt aactttgagt ctttgctttt ggtttatgca gaaacatggg    780

tgcaggtgga agaatgcaag tgtctcctcc ctccaaaaag tctgaaaccg acaacatcaa    840

gcgcgtaccc tgcgagacac cgcccttcac tgtcggagaa ctcaagaaag caatccccac    900

gcactgtttc aaacgctcga tccctcgctc tttctcctac ctcatctggg acatcatcat    960

agcctcctgc ttctactacg tcgccaccac ttacttccct ctcctccctc accctctctc   1020

ctacttcgcc tggcctctct actgggccgg taccgtcgac gacgacctgc aggtcaacgg   1080

atcaggatat tcttgtttaa gatgttgaac tctatggagg tttgtatgaa ctgatgatct   1140

aggaccggat aagttccctt cttcatagcg aacttattca aagaatgttt tgtgtatcat   1200

tcttgttaca ttgttattaa tgaaaaaata ttattggtca ttggactgaa cacgagtgtt   1260

aaatatggac caggccccaa ataagatcca ttgatatatg aattaaataa caagaataaa   1320

tcgagtcacc aaaccacttg cctttttttaa cgagacttgt tcaccaactt gatacaaaag   1380

tcattatcct atgcaaatca ataatcatac aaaaatatcc aataacacta aaaaattaaa   1440

agaaatggat aatttcacaa tatgttatac gataaagaag ttacttttcc aagaaattca   1500

ctgattttat aagcccactt gcattagata aatggcaaaa aaaaacaaaa aggaaaagaa   1560

ataaagcacg aagaattcta gaaaatacga aatacgcttc aatgcagtgg gacccacggt   1620

tcaattattg ccaattttca gctccaccgt atatttaaaa aataaaacga taatgctaaa   1680

aaaatataaa tcgtaacgat cgttaaatct caacggctgg atcttatgac gaccgttaga   1740
```

```
aattgtggtt gacgacgagt cagtaataaa cggcgtcaaa gtggttgcag ccggcacaca   1800
cgagtcgtgt ttatcaactc aaagcacaaa tacttttcct caacctaaaa ataaggcaat   1860
tagccaaaaa caactttgcg tgtaaacaac gctcaataca cgtgtcattt tattattagc   1920
tattgcttca ccgccttagc tttctcgtga cctagtcgtc ctcgtctttt cttcttcttc   1980
ttctataaaa caatacccaa agagctcttc ttcttcacaa ttcagatttc aatttctcaa   2040
aatcttaaaa actttctctc aattctctct accgtgatca aggtaaattt ctgtgttcct   2100
tattctctca aaatcttcga ttttgttttc gttcgatccc aatttcgtat atgttctttg   2160
gtttagattc tgttaatctt agatcgaaga cgattttctg ggtttgatcg ttagatatca   2220
tcttaattct cgattagggt ttcatagata tcatccgatt tgttcaaata atttgagttt   2280
tgtcgaataa ttactcttcg atttgtgatt tctatctaga tctggtgtta gtttctagtt   2340
tgtgcgatcg aatttgtcga ttaatctgag tttttctgat taacagatgg ctcaatctag   2400
cagaatctgc cacggtgtgc agaacccatg tgtgatcatt tccaatctct ccaaatccaa   2460
ccagaacaaa tctcctttct cagtcagcct caagactcac cagcagcagc gtcgtgctta   2520
ccagatatct agctggggat tgaagaagtc aaacaacggg tccgtgattc gtccggttaa   2580
ggcagctgca agagggatgc cagccttgtc tttacctgga tcaaagagta tcacagctag   2640
ggcactcttt cttgctgctg ctgctgatgg ggttactact ttggtgaggc cattgagaag   2700
tgacgacaca gaaggattcg ctgaggggtt agttcgttta ggctatcgtg tagggaggac   2760
acccgatact tggcaagtcg atggcagacc acaaggacca gcagtggctg aggctgacgt   2820
ctactgtaga gacggagcaa ccaccgctag attcttgcca accttagcag ctgctggtca   2880
cggaacatac agatttgatg cttcaccaca gatgaggaga cgtcctcttt tgcccttaag   2940
cagagccttg agggatttgg gtgtcgatct tagacacgaa gaagctgaag gtcatcaccc   3000
tctgactgtc cgtgctgctg ggttgaagg aggagaggtt actttggatg ctggtcagtc   3060
aagtcagtat ctcactgcct tgttgctcct tggtcccctt acaagacaag gactgaggat   3120
aagggttact gatttggtgt cagcaccata cgtggagatt acgcttgcaa tgatgagggc   3180
tttcggagtt gaagtggcaa gggagggaga tgtgttcgtt gttccacctg gtggatatcg   3240
tgcaactacg tatgctatag aacccgacgc aagtactgct tcttacttct tcgcagctgc   3300
tgctttgact cctggagctg aagtgactgt acctgggtta ggcacgggag cacttcaagg   3360
agatttggga tttgtagatg tcttaaggag aatgggagcc gaggtgtccg taggagctga   3420
tgcaaccact gttagaggaa ctggtgaatt gcgtggcctt acagccaaca tgagagacat   3480
aagtgatacg atgccgaccc tcgctgcaat agcacccttt gctagtgctc cagttagaat   3540
cgaggatgtt gccaacactc gtgtcaaaga atgtgacaga cttgaggctt gtgcagagaa   3600
ccttaggagg ttgggagtaa gggttgcaac gggtccggac tggattgaga tacaccctgg   3660
tccagctact ggtgctcaag tcacaagcta tggtgatcac agaattgtga tgtcatttgc   3720
agtgactgga cttcgtgtgc ctgggatcag cttcgacgac cctggctgtg ttcgtaagac   3780
ttttcctggg tttcacgagg ctttcgcaga attgaggcgt ggcattggga gctgatgagt   3840
agttagctta atcacctaag atcggcggca atagcttctt agcgccatcc cgggttgatc   3900
ctatctgtgt tgaaatagtt gcggtgggca aggctctctt tcagaaagac aggcggccaa   3960
aggaacccaa ggtgaggtgg gctatggctc tcagttcctt gtggaagcgc ttggtctaag   4020
gtgcagaggt gttagcggga tgaagcaaaa gtgtccgatt gtaacaagat atgttgatcc   4080
tacgtaagga tattaaagta tgtattcatc actaatataa tcagtgtatt ccaatatgta   4140
```

```
ctacgatttc caatgtcttt attgtcgccg tatgtaatcg gcgtcacaaa ataatccccg   4200
gtgactttct tttaatccag gatgaaataa tatgttatta taatttttgc gatttggtcc   4260
gttataggaa ttgaagtgtg cttgcggtcg ccaccactcc catttcataa ttttacatgt   4320
atttgaaaaa taaaaattta tggtattcaa tttaaacacg tatacttgta aagaatgata   4380
tcttgaaaga aatatagttt aaatatttat tgataaaata acaagtcagg tattatagtc   4440
caagcaaaaa cataaattta ttgatgcaag tttaaattca gaaatatttc aataactgat   4500
tatatcagct ggtacattgc cgtagatgaa agactgagtg cgatattatg gtgtaataca   4560
tacggccgcc agaaggtaat tatccaagat gtagcatcaa gaatccaatg tttacgggaa   4620
aaactatgga agtattatgt aagctcagca agaagcagat caatatgcgg cacatatgca   4680
acctatgttc aaaaatgaag aatgtacaga tacaagatcc tatactgcca gaatacgaag   4740
aagaatacgt agaaattgaa aaagaagaac caggcgaaga aaagaatctt gaagacgtaa   4800
gcactgacga caacaatgaa aagaagaaga taaggtcggt gattgtgaaa gagacataga   4860
ggacacatgt aaggtggaaa atgtaagggc ggaaagtaac cttatcacaa aggaatctta   4920
tcccccacta cttatccttt tatatttttc cgtgtcattt ttgcccttga gttttcctat   4980
ataaggaacc aagttcggca tttgtgaaaa caagaaaaaa tttggtgtaa gctattttct   5040
ttgaagtact gaggatacaa cttcagagaa atttgtaagt ttgtaatgtc tccggagagg   5100
agaccagttg agattaggcc agctacagca gctgatatgg ccgcggtttg tgatatcgtt   5160
aaccattaca ttgagacgtc tacagtgaac tttaggacag agccacaaac accacaagag   5220
tggattgatg atctcgagag gttgcaagat agataccctt ggttggttgc tgaggttgag   5280
ggtgttgtgg ctggtattgc ttacgctggg ccctggaagg ctaggaacgc ttacgattgg   5340
acagttgaga gtactgttta cgtgtcacat aggcatcaaa ggttgggcct aggatccaca   5400
ttgtacacac atttgcttaa gtctatggag gcgcaaggtt ttaagtctgt ggttgctgtt   5460
ataggccttc caaacgatcc atctgttagg ttgcatgagg ctttgggata cacagcccgg   5520
ggtacattgc gcgcagctgg atacaagcat ggtggatggc atgatgttgg tttttggcaa   5580
agggattttg agttgccagc tcctccaagg ccagttaggc cagttaccca gatctaatat   5640
caaaatctat ttagaaatac acaatatttt gttgcaggct tgctggagaa tcgatctgct   5700
atcataaaaa ttacaaaaaa attttatttg cctcaattat tttaggattg gtattaagga   5760
cgcttaaatt atttgtcggg tcactacgca tcattgtgat tgagaagatc agcgatacga   5820
aatattcgta gtactatcga taatttattt gaaaattcat aagaaaagca aacgttacat   5880
gaattgatga aacaatacaa agacagataa agccacgcac atttaggata ttggccgaga   5940
ttactgaata ttgagtaaga tcacggaatt tctgacagga gcatgtcttc aattcagccc   6000
aaatggcagt tgaaatactc aaaccgcccc atatgcagga gcggatcatt cattgtttgt   6060
ttggttgcct ttgccaacat gggagtccaa ggttgcatgc cagggctgcg tcctaaccgg   6120
cgtctgggtc atagcccacg agtgcggcca ccacgccttc agcgactacc agtggctgga   6180
cgacaccgtc ggcctcatct tccactcctt cctcctcgtc ccttacttct cctggaagta   6240
cagtcatcga cgccaccatt ccaacactgg ctccctcgag agagacgaag tgtttgtccc   6300
caagaagaag tcagacatca agtggtacgg caagtacctc aacaaccctt tgggacgcac   6360
cgtgatgtta acggttcagt tcactctcgg ctggcctttg tacttagcct tcaacgtctc   6420
ggggagacct tacgacggcg gcttcgcttg ccatttccac cccaacgctc ccatctacaa   6480
```

```
cgaccgtgag cgtctccaga tatacatctc cgacgctggc atcctcgccg tctgctacgg   6540
tctctaccgc tacgctgctg tccaaggagt tgcctcgatg gtctgcttct acggagttcc   6600
tcttctgatt gtcaacgggt tcttagtttt gatcacttac ttgcagcaca cgcatccttc   6660
cctgcctcac tatgactcgt ctgagtggga ttggttgagg ggagctttgg ccaccgttga   6720
cagagactac ggaatcttga acaaggtctt ccacaatatc acggacacgc acgtggcgca   6780
tcacctgttc tcgaccatgc cgcattatca cgcgatggaa gctacgaagg cgataaagcc   6840
gatactggga gagtattatc agttcgatgg gacgccggtg gttaaggcga tgtggaggga   6900
ggcgaaggag tgtatctatg tggaaccgga caggcaaggt gagaagaaag gtgtgttctg   6960
gtacaacaat aagttatgaa gcaaagaaga aactgaacct ttctcatcta tgattgtctt   7020
tgttttaaga agctatgttt ctgtttcaat aatctttaat tatccatttt gttgtgtttt   7080
ctgacatttt ggctaaaatg gcgccaccca gctttcttgt acaaagtggt ccccttaatt   7140
aactgggcct catgggcctt ccgctcactg cccgctttcc agtcgggaaa cctgtcgtgc   7200
cagctgcatt aacatggtca tagctgtttc cttgcgtatt gggcgctctc cgcttcctcg   7260
ctcactgact cgctgcgctc ggtcgttcgg gtaaagcctg gggtgcctaa tgagcaaaag   7320
gccagcaaaa ggccaggaac cgtaaaaagg ccgcgttgct ggcgtttttc cataggctcc   7380
gcccccctga cgagcatcac aaaaatcgac gctcaagtca gaggtggcga aacccgacag   7440
gactataaag ataccaggcg tttccccctg gaagctccct cgtgcgctct cctgttccga   7500
ccctgccgct taccggatac ctgtccgcct ttctcccttc gggaagcgtg gcgctttctc   7560
atagctcacg ctgtaggtat ctcagttcgg tgtaggtcgt tcgctccaag ctgggctgtg   7620
tgcacgaacc ccccgttcag cccgaccgct gcgccttatc cggtaactat cgtcttgagt   7680
ccaacccggt aagacacgac ttatcgccac tggcagcagc cactggtaac aggattagca   7740
gagcgaggta tgtaggcggt gctacagagt tcttgaagtg gtggcctaac tacggctaca   7800
ctagaagaac agtatttggt atctgcgctc tgctgaagcc agttaccttc ggaaaaagag   7860
ttggtagctc ttgatccggc aaacaaacca ccgctggtag cggtggtttt tttgtttgca   7920
agcagcagat tacgcgcaga aaaaaaggat ctcaagaaga tcctttgatc ttttctacgg   7980
ggtctgacgc tcagtggaac gaaaactcac gttaagggat tttggtcatg agattatcaa   8040
aaaggatctt cacctagatc cttttaaatt aaaaatgaag ttttaaatca atctaaagta   8100
tatatgagta aacttggtct gacagttacc aatgcttaat cagtgaggca cctatctcag   8160
cgatctgtct atttcgttca tccatagttg cctgactccc cgtcgtgtag ataactacga   8220
tacgggaggg cttaccatct ggccccagtg ctgcaatgat accgcgagaa ccacgctcac   8280
cggctccaga tttatcagca ataaaccagc cagccggaag ggccgagcgc agaagtggtc   8340
ctgcaacttt atccgcctcc atccagtcta ttaattgttg ccgggaagct agagtaagta   8400
gttcgccagt taatagtttg cgcaacgttg ttgccattgc tacaggcatc gtggtgtcac   8460
gctcgtcgtt tggtatggct tcattcagct ccggttccca acgatcaagg cgagttacat   8520
gatcccccat gttgtgcaaa aaagcggtta gctccttcgg tcctccgatc gttgtcagaa   8580
gtaagttggc cgcagtgtta tcactcatgg ttatggcagc actgcataat tctcttactg   8640
tcatgccatc cgtaagatgc ttttctgtga ctggtgagta ctcaaccaag tcattctgag   8700
aatagtgtat gcggcgaccg agttgctctt gcccggcgtc aatacgggat aataccgcgc   8760
cacatagcag aactttaaaa gtgctcatca ttggaaaacg ttcttcgggg cgaaaactct   8820
caaggatctt accgctgttg agatccagtt cgatgtaacc cactcgtgca cccaactgat   8880
```

```
cttcagcatc ttttactttc accagcgttt ctgggtgagc aaaaacagga aggcaaaatg   8940

ccgcaaaaaa gggaataagg gcgacacgga aatgttgaat actcatactc ttcctttttc   9000

aatattattg aagcatttat cagggttatt gtctcatgag cggatacata tttgaatgta   9060

tttagaaaaa taaacaaata ggggttccgc gcacatttcc ccgaaaagtg ccacctaaat   9120

tgtaagcgtt aatattttgt taaaattcgc gttaaatttt tgttaaatca gctcattttt   9180

taaccaatag gccgaaatcg gcaaaatccc ttataaatca aaagaataga ccgagatagg   9240

gttgagtggc cgctacaggg cgctcccatt cgccattcag gctgcgcaac tgttgggaag   9300

ggcgtttcgg tgcgggcctc ttcgctatta cgccagctgg cgaaaggggg atgtgctgca   9360

aggcgattaa gttgggtaac gccagggttt tcccagtcac gacgttgtaa aacgacggcc   9420

agtgagcgcg acgtaatacg actcactata gggcgaattg gcggaaggcc gtcaaggccg   9480

catggcgcgc c                                                        9491
```

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300

<400> SEQUENCE: 300

000

<210> SEQ ID NO 301

<400> SEQUENCE: 301

000

<210> SEQ ID NO 302

<400> SEQUENCE: 302

000

<210> SEQ ID NO 303

<400> SEQUENCE: 303

000

<210> SEQ ID NO 304

<400> SEQUENCE: 304

000

<210> SEQ ID NO 305

<400> SEQUENCE: 305

000

<210> SEQ ID NO 306

<400> SEQUENCE: 306

000

<210> SEQ ID NO 307

<400> SEQUENCE: 307

000

<210> SEQ ID NO 308

<400> SEQUENCE: 308

000

<210> SEQ ID NO 309

<400> SEQUENCE: 309

000

<210> SEQ ID NO 310

<400> SEQUENCE: 310

000

<210> SEQ ID NO 311

<400> SEQUENCE: 311

000

<210> SEQ ID NO 312

<400> SEQUENCE: 312

000

<210> SEQ ID NO 313

<400> SEQUENCE: 313

000

<210> SEQ ID NO 314

<400> SEQUENCE: 314

000

<210> SEQ ID NO 315

<400> SEQUENCE: 315

000

<210> SEQ ID NO 316

<400> SEQUENCE: 316

000

<210> SEQ ID NO 317

<400> SEQUENCE: 317

000

<210> SEQ ID NO 318

<400> SEQUENCE: 318

000

<210> SEQ ID NO 319

<400> SEQUENCE: 319

000

<210> SEQ ID NO 320

<400> SEQUENCE: 320

000

<210> SEQ ID NO 321

<400> SEQUENCE: 321

000

<210> SEQ ID NO 322

<400> SEQUENCE: 322

000

<210> SEQ ID NO 323

<400> SEQUENCE: 323

000

<210> SEQ ID NO 324

<400> SEQUENCE: 324

000

<210> SEQ ID NO 325

<400> SEQUENCE: 325

000

<210> SEQ ID NO 326

<400> SEQUENCE: 326

000

<210> SEQ ID NO 327

<400> SEQUENCE: 327

000

<210> SEQ ID NO 328

<400> SEQUENCE: 328

000

<210> SEQ ID NO 329

<400> SEQUENCE: 329

000

<210> SEQ ID NO 330

<400> SEQUENCE: 330

000

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

<210> SEQ ID NO 348

<400> SEQUENCE: 348

000

<210> SEQ ID NO 349

<400> SEQUENCE: 349

000

<210> SEQ ID NO 350

<400> SEQUENCE: 350

000

<210> SEQ ID NO 351

<400> SEQUENCE: 351

000

<210> SEQ ID NO 352

<400> SEQUENCE: 352

000

<210> SEQ ID NO 353

<400> SEQUENCE: 353

000

<210> SEQ ID NO 354

<400> SEQUENCE: 354

000

<210> SEQ ID NO 355

<400> SEQUENCE: 355

000

<210> SEQ ID NO 356

<400> SEQUENCE: 356

000

<210> SEQ ID NO 357

<400> SEQUENCE: 357

000

<210> SEQ ID NO 358

<400> SEQUENCE: 358

000

<210> SEQ ID NO 359

<400> SEQUENCE: 359

000

<210> SEQ ID NO 360

<400> SEQUENCE: 360

000

<210> SEQ ID NO 361

<400> SEQUENCE: 361

000

<210> SEQ ID NO 362

<400> SEQUENCE: 362

000

<210> SEQ ID NO 363

<400> SEQUENCE: 363

000

<210> SEQ ID NO 364

<400> SEQUENCE: 364

000

<210> SEQ ID NO 365

<400> SEQUENCE: 365

000

<210> SEQ ID NO 366

<400> SEQUENCE: 366

000

<210> SEQ ID NO 367

<400> SEQUENCE: 367

000

<210> SEQ ID NO 368

<400> SEQUENCE: 368

000

<210> SEQ ID NO 369

<400> SEQUENCE: 369

000

<210> SEQ ID NO 370

<400> SEQUENCE: 370

000

<210> SEQ ID NO 371

<400> SEQUENCE: 371

000

<210> SEQ ID NO 372

<400> SEQUENCE: 372

000

<210> SEQ ID NO 373

<400> SEQUENCE: 373

000

<210> SEQ ID NO 374

<400> SEQUENCE: 374

000

<210> SEQ ID NO 375

<400> SEQUENCE: 375

000

<210> SEQ ID NO 376

<400> SEQUENCE: 376

000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000

<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

<210> SEQ ID NO 393

<400> SEQUENCE: 393

000

<210> SEQ ID NO 394

<400> SEQUENCE: 394

000

<210> SEQ ID NO 395

<400> SEQUENCE: 395

000

<210> SEQ ID NO 396

<400> SEQUENCE: 396

000

<210> SEQ ID NO 397

<400> SEQUENCE: 397

000

<210> SEQ ID NO 398

<400> SEQUENCE: 398

000

<210> SEQ ID NO 399

<400> SEQUENCE: 399

000

<210> SEQ ID NO 400
<400> SEQUENCE: 400
000

<210> SEQ ID NO 401
<400> SEQUENCE: 401
000

<210> SEQ ID NO 402
<400> SEQUENCE: 402
000

<210> SEQ ID NO 403
<400> SEQUENCE: 403
000

<210> SEQ ID NO 404
<400> SEQUENCE: 404
000

<210> SEQ ID NO 405
<400> SEQUENCE: 405
000

<210> SEQ ID NO 406
<400> SEQUENCE: 406
000

<210> SEQ ID NO 407
<400> SEQUENCE: 407
000

<210> SEQ ID NO 408
<400> SEQUENCE: 408
000

<210> SEQ ID NO 409
<400> SEQUENCE: 409
000

<210> SEQ ID NO 410
<400> SEQUENCE: 410
000

<210> SEQ ID NO 411

<400> SEQUENCE: 411

000

<210> SEQ ID NO 412

<400> SEQUENCE: 412

000

<210> SEQ ID NO 413

<400> SEQUENCE: 413

000

<210> SEQ ID NO 414

<400> SEQUENCE: 414

000

<210> SEQ ID NO 415

<400> SEQUENCE: 415

000

<210> SEQ ID NO 416

<400> SEQUENCE: 416

000

<210> SEQ ID NO 417

<400> SEQUENCE: 417

000

<210> SEQ ID NO 418

<400> SEQUENCE: 418

000

<210> SEQ ID NO 419

<400> SEQUENCE: 419

000

<210> SEQ ID NO 420

<400> SEQUENCE: 420

000

<210> SEQ ID NO 421

<400> SEQUENCE: 421

000

<210> SEQ ID NO 422

<400> SEQUENCE: 422

000

<210> SEQ ID NO 423

<400> SEQUENCE: 423

000

<210> SEQ ID NO 424

<400> SEQUENCE: 424

000

<210> SEQ ID NO 425

<400> SEQUENCE: 425

000

<210> SEQ ID NO 426

<400> SEQUENCE: 426

000

<210> SEQ ID NO 427

<400> SEQUENCE: 427

000

<210> SEQ ID NO 428

<400> SEQUENCE: 428

000

<210> SEQ ID NO 429

<400> SEQUENCE: 429

000

<210> SEQ ID NO 430

<400> SEQUENCE: 430

000

<210> SEQ ID NO 431

<400> SEQUENCE: 431

000

<210> SEQ ID NO 432

<400> SEQUENCE: 432

000

<210> SEQ ID NO 433

<400> SEQUENCE: 433

000

<210> SEQ ID NO 434

<400> SEQUENCE: 434

000

<210> SEQ ID NO 435

<400> SEQUENCE: 435

000

<210> SEQ ID NO 436

<400> SEQUENCE: 436

000

<210> SEQ ID NO 437

<400> SEQUENCE: 437

000

<210> SEQ ID NO 438

<400> SEQUENCE: 438

000

<210> SEQ ID NO 439

<400> SEQUENCE: 439

000

<210> SEQ ID NO 440

<400> SEQUENCE: 440

000

<210> SEQ ID NO 441

<400> SEQUENCE: 441

000

<210> SEQ ID NO 442

<400> SEQUENCE: 442

000

<210> SEQ ID NO 443

<400> SEQUENCE: 443

000

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000

<210> SEQ ID NO 447

<400> SEQUENCE: 447

000

<210> SEQ ID NO 448

<400> SEQUENCE: 448

000

<210> SEQ ID NO 449

<400> SEQUENCE: 449

000

<210> SEQ ID NO 450

<400> SEQUENCE: 450

000

<210> SEQ ID NO 451

<400> SEQUENCE: 451

000

<210> SEQ ID NO 452

<400> SEQUENCE: 452

000

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

000

<210> SEQ ID NO 461

<400> SEQUENCE: 461

000

<210> SEQ ID NO 462

<400> SEQUENCE: 462

000

<210> SEQ ID NO 463

<400> SEQUENCE: 463

000

<210> SEQ ID NO 464

<400> SEQUENCE: 464

000

<210> SEQ ID NO 465

<400> SEQUENCE: 465

000

<210> SEQ ID NO 466

<400> SEQUENCE: 466

000

<210> SEQ ID NO 467

<400> SEQUENCE: 467

000

<210> SEQ ID NO 468

<400> SEQUENCE: 468

000

<210> SEQ ID NO 469

<400> SEQUENCE: 469

000

<210> SEQ ID NO 470

<400> SEQUENCE: 470

000

<210> SEQ ID NO 471
<211> LENGTH: 119
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 471
gacatcaagt ggtacggcaa gtacctcaac aacccgctag gacgcacggt gatgctaacc 60
gtccagttca agctcggctg gccgttgtac ttagccttca acgtctcggg aagacctta 119

<210> SEQ ID NO 472
<211> LENGTH: 119
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 472
gacatcaagt ggtacggaaa gtacctcaac aacccgctag gacgcacggt gatgctaacc 60
gtccagttca cgctcggctg gccgttgtac ttagccttca acgtctctgg aagacctta 119

<210> SEQ ID NO 473
<211> LENGTH: 119
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 473
gacatcaagt ggtacggcaa gtacctcaac aaccctttgg gacgcaccgt gatgttaacg 60
gttcagttca ctctcggctg gcctttgtac ttagccttca acgtctcggg gagacctta 119

<210> SEQ ID NO 474
<211> LENGTH: 119
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 474
gacatcaagt ggtacggcaa gtacctcaac aaccctttgg gacgcaccgt gatgttaacg 60
gttcagttca ctctcggctg gccgttgtac ttagccttca acgtctcggg aagacctta 119

<210> SEQ ID NO 475
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 475
cagacatcaa gtggtacggc 20

<210> SEQ ID NO 476
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 476
acggcaagta cctcaacaac cctttggg 28

<210> SEQ ID NO 477
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 477
cgcaccgtga tgttaacggt tcagttca 28

<210> SEQ ID NO 478
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 478
cggcaagtac ctcaacaacc ctttggga 28

<210> SEQ ID NO 479
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 479
accgtgatgt taacggttca gttcactc 28

<210> SEQ ID NO 480
<211> LENGTH: 21
<212> TYPE: DNA
<213> ORGANISM: Artificial Sequence
<220> FEATURE:
<223> OTHER INFORMATION: Description of Artificial Sequence: Synthetic

```
      oligonucleotide

<400> SEQUENCE: 480

cttagccttc aacgtctcgg g                                          21
```